(12) United States Patent
Montgomery et al.

(10) Patent No.: US 11,752,468 B2
(45) Date of Patent: Sep. 12, 2023

(54) MATERIALS AND METHODS FOR PRODUCING BLOOD PRODUCTS

(71) Applicant: Cellphire, Inc., Rockville, MD (US)

(72) Inventors: Joshua Donald Montgomery, Silver Spring, MD (US); Braden Carl Ishler, Montgomery Village, MD (US); Stephen Edward Amos, Buckeystown, MD (US); Keith Andrew Moskowitz, Westfield, IN (US); Amber Nicole Lee, Montgomery Village, MD (US); Rafael Jorda, Merignac (FR); Glen Michael Fitzpatrick, North Potomac, MD (US); Michael Alexander Mathews, Arlington, VA (US)

(73) Assignee: Cellphire, Inc., Rockville, MD (US)

( * ) Notice: Subject to any disclaimer, the term of this patent is extended or adjusted under 35 U.S.C. 154(b) by 0 days.

(21) Appl. No.: 18/056,220

(22) Filed: Nov. 16, 2022

(65) Prior Publication Data

US 2023/0226493 A1 Jul. 20, 2023

Related U.S. Application Data

(63) Continuation of application No. 16/865,215, filed on May 1, 2020, now Pat. No. 11,529,587.
(Continued)

(51) Int. Cl.
*B01D 61/14* (2006.01)
*C12N 5/078* (2010.01)
*A01N 1/00* (2006.01)

(52) U.S. Cl.
CPC .......... *B01D 61/14* (2013.01); *C12N 5/0644* (2013.01); *B01D 2311/12* (2013.01); *B01D 2315/10* (2013.01); *B01D 2315/16* (2013.01)

(58) Field of Classification Search
CPC ........ A61K 35/14; A61K 35/15; A61K 35/16; A61K 35/19; A61K 31/10; A61K 31/336;
(Continued)

(56) References Cited

U.S. PATENT DOCUMENTS 3,932,943 A 1/1976 Briggs et al.
4,157,383 A 6/1979 Sedlacek et al.
(Continued)

FOREIGN PATENT DOCUMENTS

CA 1261259 A 9/1989
CA 2097063 C 6/1992
(Continued)

OTHER PUBLICATIONS

Alquwaizani, et.al., "Anticoagulants: A Review of the Pharmacology, Dosing, and Complications", Current Emergency and Hospital Medicine Reports, vol. 1, No. 2, Apr. 21, 2013, pp. 83-97, DOI: 10.1007/s40138-013-0014-6.
(Continued)

*Primary Examiner* — Allison G Fitzsimmons
(74) *Attorney, Agent, or Firm* — DOUBLE HELIX LAW; Emanuel Vacchiano

(57) ABSTRACT

Provided herein are materials and methods for the preparation of blood products. In one aspect, provided herein is a composition including platelets or platelet derivatives and an aqueous medium, wherein the aqueous medium has a protein concentration less than 50% of the protein concentration of donor apheresis plasma.

25 Claims, 53 Drawing Sheets

Related U.S. Application Data

(60) Provisional application No. 62/936,122, filed on Nov. 15, 2019, provisional application No. 62/843,061, filed on May 3, 2019.

(58) Field of Classification Search
CPC .............. A61K 31/7016; A61K 31/715; A61K 31/045; A61K 31/047; A61K 31/70; A61K 31/7004; A01N 1/00; B01D 12/00; B01D 37/00; B01D 37/04; B01D 39/00; B01D 39/14; B01D 61/00; B01D 61/14; B01D 61/147; B01D 61/24; B01D 61/243; B01D 63/08
See application file for complete search history.

(56) References Cited

U.S. PATENT DOCUMENTS

| | | |
|---|---|---|
| 4,455,299 A | 6/1984 | Grode |
| 4,670,013 A | 6/1987 | Barnes et al. |
| 4,865,871 A | 9/1989 | Livesey et al. |
| 4,994,367 A | 2/1991 | Bode |
| 5,059,518 A | 10/1991 | Kortright et al. |
| 5,213,814 A | 5/1993 | Goodrich |
| 5,332,578 A | 7/1994 | Chao |
| 5,364,756 A | 11/1994 | Livesey et al. |
| 5,423,738 A | 6/1995 | Robinson |
| 5,571,801 A | 11/1996 | Segall |
| 5,622,867 A | 4/1997 | Livesy |
| 5,656,498 A | 8/1997 | Iijima |
| 5,656,598 A | 8/1997 | Dunstan et al. |
| 5,723,281 A | 3/1998 | Segall et al. |
| 5,736,313 A | 4/1998 | Spargo |
| 5,759,542 A | 6/1998 | Gurewich |
| 5,800,978 A | 9/1998 | Goodrich |
| 5,817,381 A | 10/1998 | Chen |
| 5,827,741 A | 10/1998 | Beattie |
| 5,919,614 A | 7/1999 | Livesey |
| 5,958,670 A | 9/1999 | Goodrich |
| 5,993,804 A | 11/1999 | Read |
| 6,127,111 A | 10/2000 | Braun |
| 6,211,575 B1 | 4/2001 | Hansford |
| 6,221,575 B1 | 4/2001 | Roser |
| 6,372,423 B1 | 4/2002 | Braun |
| 6,596,296 B1 | 7/2003 | Nelson |
| 6,653,062 B1 | 11/2003 | DePablo |
| 6,723,497 B2 | 4/2004 | Wolkers |
| 6,770,478 B2 | 8/2004 | Crowe |
| 6,833,236 B1 | 12/2004 | Stienstra |
| 6,858,222 B2 | 2/2005 | Nelson |
| 7,033,603 B2 | 4/2006 | Nelson |
| 7,169,606 B2 | 1/2007 | DePablo |
| 7,514,095 B2 | 4/2009 | Nelson |
| 7,811,558 B2 | 10/2010 | Ho |
| 8,097,403 B2 | 1/2012 | Ho |
| 8,486,617 B2 | 7/2013 | Ho |
| 8,486,619 B2 | 7/2013 | Miller |
| 8,529,961 B2 | 9/2013 | Campbell |
| 8,877,060 B2 | 11/2014 | Sehgal |
| 8,900,209 B2 | 12/2014 | Rosati |
| 9,402,866 B2 | 8/2016 | Radwanski et al. |
| 9,545,379 B2 | 1/2017 | Liu et al. |
| 9,863,699 B2 | 1/2018 | Corbin et al. |
| 9,878,011 B2 | 1/2018 | Landrigan et al. |
| 9,950,035 B2 | 4/2018 | Binder et al. |
| 10,400,017 B2 | 9/2019 | Higgins et al. |
| 10,441,634 B2 | 10/2019 | Landrigan et al. |
| 10,539,367 B2 | 1/2020 | Corbin et al. |
| 10,793,327 B2 | 10/2020 | Weimer et al. |
| 10,843,100 B2 | 11/2020 | Khan et al. |
| 10,969,171 B2 | 4/2021 | Corbin et al. |
| 10,976,105 B2 | 4/2021 | Corbin et al. |
| 11,052,045 B2 | 7/2021 | Liu et al. |
| 11,529,587 B2 | 12/2022 | Montgomery et al. |
| 2001/0019819 A1 | 9/2001 | Wolkers et al. |
| 2001/0028880 A1 | 10/2001 | Fisher |
| 2001/0046487 A1 | 11/2001 | Roser et al. |
| 2002/0009500 A1 | 1/2002 | Wolkers et al. |
| 2002/0076445 A1 | 6/2002 | Crowe |
| 2003/0022333 A1 | 1/2003 | Bronshtein |
| 2003/0073238 A1 | 4/2003 | Dzekunov et al. |
| 2003/0148449 A1 | 8/2003 | Kuliopulos et al. |
| 2003/0157475 A1 | 8/2003 | Schenk |
| 2004/0136974 A1 | 7/2004 | Crowe |
| 2004/0147024 A1 | 7/2004 | Crowe |
| 2004/0152964 A1 | 8/2004 | Crowe |
| 2004/0185524 A1 | 9/2004 | Crowe |
| 2004/0265293 A1 | 12/2004 | Crowe et al. |
| 2005/0028559 A1 | 2/2005 | Hiromatsu |
| 2005/0048460 A1 | 3/2005 | Crowe |
| 2005/0074402 A1 | 4/2005 | Cagnolini |
| 2005/0181978 A1 | 8/2005 | Rojkjaer et al. |
| 2005/0191286 A1 | 9/2005 | Gandy |
| 2006/0034809 A1 | 2/2006 | Ho et al. |
| 2006/0035383 A1 | 2/2006 | Ho |
| 2006/0051731 A1 | 3/2006 | Ho |
| 2006/0223050 A1 | 10/2006 | Crowe et al. |
| 2007/0087061 A1 | 4/2007 | Drake |
| 2007/0166389 A1 | 7/2007 | Bakaltcheva |
| 2007/0178104 A1 | 8/2007 | Awdalla |
| 2007/0243178 A1 | 10/2007 | Ho et al. |
| 2007/0248612 A1 | 10/2007 | Wilson |
| 2007/0249047 A1 | 10/2007 | McKenna, Jr. |
| 2008/0064628 A1 | 3/2008 | Goodall et al. |
| 2008/0145834 A1 | 6/2008 | Ho et al. |
| 2008/0286366 A1 | 11/2008 | Fischer et al. |
| 2008/0299212 A1 | 12/2008 | Kim |
| 2009/0035289 A1 | 2/2009 | Wagner et al. |
| 2009/0111118 A1 | 4/2009 | Mylvaganam et al. |
| 2009/0175905 A1 | 7/2009 | Tseng et al. |
| 2009/0299212 A1 | 12/2009 | Principe et al. |
| 2010/0055067 A1 | 3/2010 | Park |
| 2010/0135969 A1 | 6/2010 | Mishra |
| 2010/0190717 A1 | 7/2010 | Bevec |
| 2010/0196461 A1 | 8/2010 | Simpkins |
| 2010/0267928 A1 | 10/2010 | Heckl |
| 2011/0008804 A1 | 1/2011 | Kain et al. |
| 2011/0020107 A1 | 1/2011 | Presz, Jr. et al. |
| 2011/0027257 A1 | 2/2011 | Burnouf et al. |
| 2011/0183311 A1 | 7/2011 | Ho |
| 2011/0189151 A1 | 8/2011 | Stossel et al. |
| 2012/0009221 A1 | 1/2012 | Hoerr et al. |
| 2012/0028236 A1 | 2/2012 | Sehgal |
| 2012/0095085 A1 | 4/2012 | Layzer et al. |
| 2012/0141434 A1 | 6/2012 | Peled et al. |
| 2012/0156306 A1* | 6/2012 | Weissman ............... A61P 29/00 514/8.1 |
| 2012/0264815 A1 | 10/2012 | Sullenger et al. |
| 2012/0276581 A1 | 11/2012 | Arav et al. |
| 2012/0321722 A1 | 12/2012 | Liu |
| 2013/0059380 A1 | 3/2013 | Ho et al. |
| 2013/0061849 A1 | 3/2013 | Lemper |
| 2013/0122107 A1 | 5/2013 | Bakaltcheva |
| 2013/0195959 A1 | 8/2013 | Patel |
| 2013/0210903 A1 | 8/2013 | Sullenger et al. |
| 2014/0065120 A1 | 3/2014 | Nichols |
| 2014/0329323 A1 | 11/2014 | Nygaard et al. |
| 2014/0330226 A1 | 11/2014 | Coffey |
| 2014/0356948 A1 | 12/2014 | Jeon et al. |
| 2015/0064259 A1 | 3/2015 | Simpkins et al. |
| 2015/0306212 A1 | 10/2015 | Kahvejian et al. |
| 2015/0313943 A1 | 11/2015 | Kishikawa et al. |
| 2015/0361453 A1 | 12/2015 | Gresele et al. |
| 2016/0082044 A1 | 3/2016 | Liu et al. |
| 2016/0206783 A1 | 7/2016 | Dietz |
| 2016/0219870 A1 | 8/2016 | Wang et al. |
| 2016/0231338 A1 | 8/2016 | Aster et al. |
| 2016/0235781 A1 | 8/2016 | Emanuele |
| 2016/0324897 A1 | 11/2016 | Ingber et al. |
| 2017/0198335 A1 | 7/2017 | Muller |
| 2017/0333593 A1 | 11/2017 | Willard |
| 2018/0009874 A1 | 1/2018 | Wilcox et al. |
| 2018/0070581 A1 | 3/2018 | Tarrand et al. |
| 2018/0092348 A1 | 4/2018 | She et al. |

(56) References Cited

U.S. PATENT DOCUMENTS

| | | |
|---|---|---|
| 2018/0169027 A1 | 6/2018 | Zhang et al. |
| 2018/0169139 A1 | 6/2018 | Feuerstein |
| 2018/0235894 A1 | 8/2018 | Gu et al. |
| 2018/0311176 A1 | 11/2018 | Ozsolak |
| 2018/0312903 A1 | 11/2018 | Grölz |
| 2019/0008143 A1 | 1/2019 | Dee |
| 2019/0076478 A1 | 3/2019 | Hale et al. |
| 2020/0046771 A1 | 2/2020 | Kuhn et al. |
| 2020/0060262 A1 | 2/2020 | Stolla |
| 2020/0076455 A1 | 3/2020 | Sharf |
| 2020/0078407 A1 | 3/2020 | Bhattacharya et al. |
| 2020/0093853 A1 | 3/2020 | Feuerstein |
| 2020/0206143 A1 | 7/2020 | Moskowitz et al. |
| 2020/0208109 A1 | 7/2020 | Moskowitz et al. |
| 2020/0208110 A1 | 7/2020 | Lee et al. |
| 2020/0224164 A1 | 7/2020 | Moskowitz et al. |
| 2020/0281980 A1 | 9/2020 | Willard et al. |
| 2020/0291356 A1 | 9/2020 | Jorda et al. |
| 2020/0346167 A1 | 11/2020 | Montgomery et al. |
| 2021/0046120 A1 | 2/2021 | Moskowitz et al. |
| 2021/0046121 A1 | 2/2021 | Moskowitz et al. |
| 2021/0069240 A1 | 3/2021 | Jorda et al. |
| 2021/0100846 A1 | 4/2021 | Lee et al. |
| 2021/0180016 A1 | 6/2021 | Moskowitz et al. |
| 2021/0189341 A1 | 6/2021 | Sheik et al. |
| 2021/0299179 A1 | 9/2021 | Moskowitz et al. |
| 2021/0308066 A1 | 10/2021 | Moskowitz et al. |
| 2021/0308185 A1 | 10/2021 | Moskowitz et al. |
| 2021/0315935 A1 | 10/2021 | Moskowitz et al. |
| 2021/0353680 A1 | 11/2021 | Bhattacharya et al. |
| 2021/0368782 A1 | 12/2021 | Dee et al. |
| 2022/0168353 A1 | 6/2022 | Moskowitz et al. |
| 2022/0211029 A1 | 7/2022 | Moskowitz et al. |
| 2022/0273724 A1 | 9/2022 | Moskowitz et al. |
| 2022/0279777 A1 | 9/2022 | Moskowitz et al. |

FOREIGN PATENT DOCUMENTS

| | | |
|---|---|---|
| CA | 2136848 A1 | 12/1993 |
| CA | 2393315 A1 | 6/2001 |
| CA | 2840568 A1 | 1/2013 |
| CA | 3053041 A1 | 2/2020 |
| CN | 103524613 | 1/2014 |
| CN | 103907595 | 7/2014 |
| CN | 108715834 A | 10/2018 |
| EP | 0397890 A1 | 11/1990 |
| EP | 0967862 | 1/2003 |
| EP | 1374890 A2 | 1/2004 |
| EP | 1652538 | 5/2006 |
| EP | 1784639 A2 | 5/2007 |
| EP | 3307283 B1 | 12/2018 |
| EP | 3681518 A1 | 7/2020 |
| EP | 3551198 B1 | 2/2022 |
| JP | H08109136 | 4/1996 |
| JP | 2005053841 | 3/2005 |
| JP | 2012143554 A | 8/2012 |
| WO | WO 1990/005461 | 5/1990 |
| WO | 9012581 A1 | 11/1990 |
| WO | 1991017655 A1 | 11/1991 |
| WO | WO 1992008349 | 5/1992 |
| WO | WO 1993000806 | 1/1993 |
| WO | 1993023997 A1 | 12/1993 |
| WO | 9428950 A1 | 12/1994 |
| WO | 1998034478 A1 | 8/1998 |
| WO | 1999055346 A1 | 11/1999 |
| WO | 2001058266 A1 | 8/2001 |
| WO | 2003014305 A2 | 2/2003 |
| WO | 2003090839 A1 | 11/2003 |
| WO | WO 2004050896 | 6/2004 |
| WO | 2005002499 A2 | 1/2005 |
| WO | 2005020893 A2 | 3/2005 |
| WO | 2005021706 A2 | 3/2005 |
| WO | WO 2005/077299 | 8/2005 |
| WO | 2005002499 A3 | 11/2005 |
| WO | WO 2006020773 | 2/2006 |
| WO | 2006059329 A1 | 6/2006 |
| WO | 2004050896 A3 | 12/2006 |
| WO | 2006020773 A2 | 7/2007 |
| WO | 2010046949 A1 | 4/2010 |
| WO | WO 2011/020107 | 2/2011 |
| WO | 2011020107 A3 | 10/2011 |
| WO | 2012018484 A2 | 4/2012 |
| WO | 2012074637 A2 | 7/2012 |
| WO | 2014051537 A1 | 4/2014 |
| WO | WO 2014055949 | 4/2014 |
| WO | 2014066142 A1 | 5/2014 |
| WO | WO 2014118817 | 8/2014 |
| WO | 2014118817 A2 | 10/2014 |
| WO | 2014118817 A3 | 10/2014 |
| WO | 2015073587 A2 | 5/2015 |
| WO | 2015191632 A1 | 12/2015 |
| WO | WO 2016014854 | 1/2016 |
| WO | WO 2016057041 | 4/2016 |
| WO | 2016077682 A1 | 5/2016 |
| WO | 2016141325 A1 | 9/2016 |
| WO | WO 2016201081 | 12/2016 |
| WO | WO 2017040238 | 3/2017 |
| WO | 2017123539 A1 | 7/2017 |
| WO | WO 2018106250 | 6/2018 |
| WO | 2019055683 A1 | 3/2019 |
| WO | WO 2020/023905 | 1/2020 |
| WO | 2020056009 A1 | 3/2020 |
| WO | WO 2020112963 | 6/2020 |
| WO | WO 2020113035 | 6/2020 |
| WO | WO 2020113090 | 6/2020 |
| WO | WO 2020113101 | 6/2020 |
| WO | 2020165152 A1 | 8/2020 |
| WO | 2020186193 A1 | 9/2020 |
| WO | 2020227149 A1 | 11/2020 |
| WO | 2021011857 A1 | 1/2021 |
| WO | 2021034716 A1 | 2/2021 |
| WO | 2021034719 A1 | 2/2021 |
| WO | 2021046409 A1 | 3/2021 |
| WO | 2021108538 A1 | 6/2021 |
| WO | 2021108539 A1 | 6/2021 |
| WO | 2021158622 A1 | 8/2021 |
| WO | 2021158625 A1 | 8/2021 |
| WO | 2021158641 A1 | 8/2021 |
| WO | 2021158645 A1 | 8/2021 |
| WO | 2021158646 A1 | 8/2021 |
| WO | 2021232015 A1 | 11/2021 |
| WO | 2022103861 A1 | 5/2022 |
| WO | 2022178177 A1 | 8/2022 |
| WO | 2022178191 A1 | 8/2022 |
| WO | 2022178177 A4 | 10/2022 |

OTHER PUBLICATIONS

Barroso, et. al., "Safety Evaluation of a Lyophilized Platelet Derived Hemostatic Product", Transfusion, vol. 58 (12), Dec. 2018, pp. 2969-2977, DOI: 10.1111/trf.14972.
Cap, et. al., "Trauma Induced Coagulopathy", Chapter 22: Platelet Transfusion, Springer International Publishing, 2016, pp. 347-376.
Colman, "Are hemostasis and thrombosis two sides of the same coin?", Journal of Experimental Medicine, Mar. 20, 2006, vol. 203, No. 3, pp. 493-495, doi: 10.1084/jem.20060217.
Cowles, "Anticoagulant effect of aspirin goes beyond platelet aggregation", Hematology/Oncology, May 1, 2007, 3 pages.
Crowe, et. al., "Stabilization of membranes in human platelets freeze-dried with trehalose", Chemistry and Physics of Lipids, vol. 122, Issues 1-2, Jan. 2003, pp. 41-52, https://doi.org/10.1016/S0009-3084(02)00177-9.
Dickerson, "Lyophilized Human Platelets Restore Hemostasis in the Presence of the P2Y12 Inhibitors Cangrelor, Ticagrelor and Clopidogrel", Cellphire Therapeutics Inc., Rockville, MD, 7 pages.
Dickerson, "Lyophilized Human Platelets Restore Hemostasis in the Presence of the P2Y12 Inhibitors Cangrelor, Ticagrelor and Clopidogre", American Society of Hematology, Blood,3.22 Disorders of Coagulation or Fibrinolysis, Nov. 5, 2020, 6 pages.
Dickerson, "Lyophilized human platelets support thrombosis unlike normal platelets in the presence of GPIIb/IIIa antagonists", Cellphire Therapeutics Inc., Rockville, MD, 1 page.

(56) References Cited

OTHER PUBLICATIONS

Dickerson, et. al., "Lyophilized human platelets support thrombosis unlike normal platelets in the presence of GPIIb/IIIa antagonists", Cellphire Therapeutics, ISth Virtual Congress, Jul. 2021, 1 page.

Eikelboom, et. al., "Combined antiplatelet and anticoagulant therapy clinical benefits and risks", Journal of Thrombosis and Haemostasis, vol. 5, Suppl 1, Jul. 2007, pp. 255-263, DOI: 10.1111/j.1538-7836.2007.02499.x.

Etchill, et. al., "Platelet Transfusion in Critical Care and Surgery: Evidence-Based Review of Contemporary Practice and Future Directions", SHOCK, vol. 47, No. 5, May 1, 2017, pp. 537-549.

Extended European Search Report in EP Appln. No. 19840600.1 dated Mar. 25, 2022, 8 pages.

Goggs, et. al., "Lyophilized Platelets Versus Cryopreserved Platelets for Management of Bleeding in Thrombocytopenic Dogs: A Multicenter Randomized Clinical Trial", Journal Of Veterinary Internal Medicine, Nov. 2020, vol. 34, Issue 6, pp. 2384-2397, doi: 10.1111/jvim.15922.

Hagedorn, et. al., "Factor XIIa Inhibitor Recombinant Human Albumin Infestin-4 Abolishes Occlusive Arterial Thrombus Formation Without Affecting Bleeding", Circulation, vol. 121, Issue 13, Apr. 6, 2010, pp. 1510-1517, DOI: 10.1161/CIRCULATIONAHA.109.924761.

Hale, et.al., "A Novel Use of the NOD SCID Mouse Model for Hemostatic Efficacy", Cellphire, Inc., 2019, 1 page.

Heitmeier, et. al., "Pharmacological profile of asundexian, a novel, orally bioavailable inhibitor of factor XIa", Journal of Thrombosis and Haemostasis, vol. 20, No. 6, Jun. 2022, pp. 1400-1411, https://doi.org/10.1111/jth.15700.

Holmes, et. al., "Combining Antiplatelet and Anticoagulant Therapies", Journal of The American College of Cardiology, vol. 54, No. 2, Jul. 7, 2009, pp. 95-109.

Huebner, et. al., "Freeze-dried plasma enhances clot formation and inhibits fibrinolysis in the presence of tissue plasminogen activator similar to pooled liquid plasma", Transfusion, vol. 57, Issue 8, Aug. 2017, pp. 2007-2015, DOI:10.1111/trf.14149.

International Partial Search Report in International Appln No. PCT/US2022/016866, dated May 11, 2022, 13 pages.

International Search Report and Written Opinion in International Appln. No. PCT/US2021/032783, dated Aug. 24, 2021, 13 pages.

International Search Report and Written Opinion in International Appln. No. PCT/US2021/058814, dated Mar. 17, 2020, 14 pages.

International Search Report and Written Opinion in International Appln. No. PCT/US2022/016866, dated Jul. 4, 2022, 18 pages.

International Search Report and Written Opinion in International Appln. No. PCT/US2022/016883, dated May 11, 2022.

Jennings, et. al., "Antiplatelet and anticoagulant agents: Key differences in mechanisms of action, clinical application, and therapeutic benefit in patients with non-ST-segment-elevation acute coronary syndromes", Current Opinion in Cardiology vol. 23, No. 4, Jul. 2008, pp. 302-308, DOI: 10.1097/HCO.0b013e3283021ad9.

Jennings, et. al., "The pharmacodynamics of parenteral glycoprotein IIb/IIIa inhibitors", Journal of Interventional Cardiology, vol. 15, No. 1, Feb. 2002, pp. 45-60, DOI: 10.1111/j.1540-8183.2002.tb01034.x.

Joshi, et. al., "Lyophilised Reconstituted Human Platelets Increase Thrombus Formation in a Clinical Ex Vivo Model of Deep Arterial Injury", Thrombosis and Haemostasis, vol. 108, No. 1, 2012, pp. 176-182, DOI: 10.1160/TH12-02-0059.

Li, et.al., "Extended antiplatelet therapy with clopidogrel alone versus clopidogrel plus aspirin after completion of 9- to 12-month dual antiplatelet therapy for acute coronary syndrome patients with both high bleeding and ischemic risk. Rationale and design of the OPT-BIRISK double-blinded, placebo-controlled randomized trial", American Hear Journal, vol. 228, Oct. 2020, pp. 1-7, https://doi.org/10.1016/j.ahj.2020.07.005.

Machine Language Translation of Chinese Patent No. CN 108715834, 10 pages.

Mailer, et. al., "Commentary on "Pharmacological profile of asundexian, a novel, orally bioavailable inhibitor of factor XIa": Small molecule factor XIa inhibitor asundexian allows for safer anticoagulation", Journal of Thrombosis and Haemostasis, vol. 20, Issue 6, Jun. 2022, pp. 1309-1311, https://doi.org/10.1111/jth.15722.

Marder, "Bleeding Complications of Thrombolytic Treatment", American Journal of Hospital Pharmacy, vol. 47, Suppl 2, Sep. 1990, pp. S15-S19.

Mehendale, et. at., "Platelet Enrichment in a Continuous and Clog-Free Microfluidic Filter With Sunflower Head Geometry", 20th International Conference on Miniaturized Systems for Chemistry and Life Sciences, Dublin, Ireland, Oct. 9-13, 2016, pp. 272-273.

Mihatov, et. al., "Individualizing Dual Antiplatelet Therapy (DAPT) Duration Based on Bleeding Risk, Ischemic Risk, ar Both: An Analysis From the DAPT Study", Cardiovascular Revascularization Medicine, vol. 41, Aug. 2022, pp. 105-112, https://doi.org/10.1016/j.carrev.2022.01.006.

Montague, "Strategies to Improve Haemostasis in Trauma: Evaluation of Thrombosomes in the Presence of Native Platelet Dysfunction", vol. 100, Issue Suppl 3, 2014, pp. A91-A92, DOI:10.1136/heartjnl-2014-306118.158.

Mullin, et.al., "Doxorubicin chemotherapy for presumptive cardiac hemangiosarcoma in dogs", Veterinary and Comparative Oncology, vol. 14, Issue 4, Dec. 18, 2014, 13 pages, doi:10.1111/vco.12131.

NasrEldin, "Effect of cold storage on platelets quality stored in a small containers: Implications for pediatric transfusion", Pediatric Hematology Oncology Journal, vol. 2, Issue 2, Aug. 2017, pp. 29-34, doi.org/10.1016/j.phoj.20 17.07.001.

Ohanian, et. al., "Freeze-Dried Platelets Are a Promising Alternative in Bleeding Thrombocytopenic Patients with Hematological Malignancies", American Journal of Hematology, vol. 97, Issue 3, Mar. 1, 2022, pp. 256-266, doi: 10.1002/ajh.26403.

Powner, et. al., "Counteracting the Effects of Anticoagulants and Antiplatelet Agents During Neurosurgical Emergencies", Neurosurgery, vol. 57, No. 5, Nov. 2005 pp. 823-831.

Read, et. al., "Preservation of hemostatic and structural properties of rehydrated lyophilized platelets: potential for long-term storage of dried platelets for transfusion", Proceedings of the National Academy of Sciences of the USA, vol. 92, Jan. 1995, pp. 397-401, DOI: 10.1073/pnas.92.2.397.

Sane, et. al., "Bleeding During Thrombolytic Therapy for Acute Myocardial Infarction: Mechanisms and Management", Annals of Internal Medicine, vol. 111, No. 12, Dec. 15, 1989, pp. 1010-1022.

Sibbing, et. al., "Antiplatelet effects of clopidogrel and bleeding in patients undergoing coronary stent placement", Journal of Thrombosis and Haemostasis, vol. 8, Issue 2, pp. 250-256, DOI: 10.1111/j.1538-7836.2009.03709.x.

Srivastava, et. al., "The rebirth of the contact pathway: a new therapeutic target", Current Opinion in Hematology, vol. 27, No. 5, Sep. 2020, pp. 311-319, doi: 10.1097/MOH.0000000000000603.

Swami, et.al., "von Willebrand Disease: A Concise Review and Update for the Practicing Physician", Clinical and Applied Thrombosis/Hemostasis, vol. 23 (8), Nov. 2017, pp. 900-910, DOI: 10.1177/1076029616675969.

Tang, et al., "Targeted repair of heart injury by stem cells fused with platelet nanovesicles", Nature Biomedical Engineering, vol. 2, No. 1, May 30, 2018, pp. 17-26, DOI:10.1038/s41551-017-0182-x.

Trivedi, et. al., "Freeze-Dried Platelets Promote Clot Formation, Attenuate Endothelial Cell Permeability, and Decrease Pulmonary Vascular Leak in a Murine Model of Hemorrhagic Shock", The Journal of Trauma and Acute Care Surgery, vol. 90, Issue 2, Feb. 1, 2021, pp. 203-214, doi: 10.1097/TA.0000000000002984.

Tsai, et.al, "Increased risk of bleeding in patients on clopidogrel therapy after drug-eluting stents implantation: insights from the HMO Research Network-Stent Registry (HMORN-stent)", Circulation Cardiovascular Interventions, vol. 3, Issue 3, Jun. 1, 2010, pp. 230-235, Doi: 10.1161/Circinterventions.109.919001.

Undas, et. al., "Antithrombotic properties of aspirin and resistance to aspirin: beyond strictly antiplatelet actions", Blood, vol. 109, No. 6, Mar. 15, 2007, pp. 2285-2292, DOI: 10.1182/blood-2006-01-010645.

Van Der Meer, et.al, Platelet preservation: Agitation and containers, Transfusion and Apheresis Science, vol. 44, Issue 3, Jun. 2011, pp. 297-304, //doi.org/10.1016/j.transci.2011.03.005.

(56) References Cited

OTHER PUBLICATIONS

Van Der Meijden, et al., "Platelet- and erythrocyte-derived microparticles trigger thrombin generation via factor XIIa", Journal of Thrombosis and Haemostasis, vol. 10, Issue 7, Apr. 26, 2012, pp. 1355-1362, doi.org/10.1111/i.1538-7836.2012.04758.x.
Xu, et.al., "Thrombosomes as a Treatment Option for Low-Dose Heparin Reversal", Cellphire Therapeutics, Inc., Rockville, MD, 2020 Annual Meeting, 3 pages.
Bohoněk, Miloš. "Cryopreservation of platelets: advances and current practice." Cryopreservation Biotechnology in Biomedical and Biological Sciences. IntechOpen, 2018.
Crowe et. al., Stabilization of Dry Mammalian Cells: Lessons from Nature, Integr. Comp. Biol., 45:810-820 (2005).
Dickson, Mary Nora et al. "A scalable, micropore, platelet rich plasma separation device." Biomedical microdevices vol. 14,6 (2012): 1095-102. doi:10.1007/s10544-012-9675-2.
Dumont, Larry J., et al. "A randomized controlled trial evaluating recovery and survival of 6% dimethyl sulfoxide-frozen autologous platelets in healthy volunteers." Transfusion 53.1 (2013): 128-137.
Fischer, Thomas H et al. "The interaction of factor VIIa with rehydrated, lyophilized platelets." Platelets vol. 19,3 (2008): 182-91. doi:10.1080/09537100701493794.
Fischer, Thomas H et al. "Thrombus formation with rehydrated, lyophilized platelets." Hematology (Amsterdam, Netherlands) vol. 7,6 (2002): 359-69. doi:10.1080/1024533021000047954.
Gao, D. Y., et al. "Development of optimal techniques for cryopreservation of human platelets: I. Platelet activation during cold storage (at 22 and 8° C.) and cryopreservation." Cryobiology 38.3 (1999): 225-235.
Human Translation of Chinese patent No. CN103907595 Published Jul. 9, 2014, Trehalose-containing platelet low temperature preservation solution and application thereof, First Inventor Zhao Shuming.
Lo, Meng-chen, and Jeffrey D. Zahn. "Development of a multi-compartment microfiltration device for particle fractionation." 16th international conference on miniaturized systems for chemistry and life sciences, Okinawa, Japan. 2012.
Machine translation of Japanese Patent JP2012143554 Titled "Polysulfone-Based Hollow Fiber Membrane, Hollow Fiber Membrane Module for Cleaning Platelet Suspension, and Cleaning Method of Platelet Suspension."
Mccarrel, Taralyn, and Lisa Fortier. "Temporal growth factor release from platelet-rich plasma, trehalose lyophilized platelets, and bone marrow aspirate and their effect on tendon and ligament gene expression." Journal of orthopaedic research : official publication of the Orthopaedic Research Society vol. 27,8 (2009): 1033-42. doi:10.1002/jor.20853.
Mehendale, Ninad, et al. "Platelet enrichment from whole blood in a clog-free microfluidic radial pillar device (RAPID)." bioRxiv (2017): 197749.
Pietramaggiori, Giorgio et al. "Trehalose lyophilized platelets for wound healing." Wound repair and regeneration : official publication of the Wound Healing Society [and] the European Tissue Repair Society vol. 15,2 (2007): 213-20. doi:1 0.1111/j.1524-475X.2007.00207.x.
Schoug et. al: "Differential effects of polymers PVP90 and Ficoll400 on storage stability and viability of Lactobacillus coryniformis Si3 freeze-dried in sucrose", Journal of Applied Microbiology, vol. 108, No. 3, pp. 1032-1040, Feb. 8, 2010.
Valeri, C. Robert, Gina Ragno, and Shukri Khuri. "Freezing human platelets with 6 percent dimethyl sulfoxide with removal of the supernatant solution before freezing and storage at −80° C. without postthaw processing." Transfusion 45.12 (2005): 1890-1898.
Wickramasinghe, S. R. "Washing cryopreserved blood products using hollow fibres." Food and bioproducts processing 77.4 (1999): 287-292.
Ishler B et al. "Lyophilized Human Platelets Show Hemostatic Function Independent of von Willebrand Factor", Abstract No. PB1533, ISTH 2020 Virtual Congress presentation. Res Pract Thromb Haemost. 2020; 4 (Suppl 1).

2.palomar.edu [online], "The Five Kingdoms of Life," Feb. 1998, retrieved on May 17, 2021, retrieved from URL <https://www2.palomar.edu/users/warmstrong/trfeb98.htm>; 18 pages.
Appleman et al., "Cryopreservation of canine platelets," Journal of veterinary internal medicine, Jan. 2009, 23(1):138-145.
Clemmons et al., "Acquisition and aggregation of canine blood platelets: basic mechanisms of function and differences because of breed origin," American journal of veterinary research, Jan. 1, 1984, 45(1):137-144.
Extended European Search report in EP Appln. No. 18856149.2, dated May 26, 2021, 9 pages.
Healthline.com [online], "How Many Cells Are in the Human Body? Fast Facts," Jul. 18, 2018, retrieved on May 17, 2021, retrieved from URL<https://www.https://www.healthline.com/health/number-of-cells-in-body>, 11 pages.
Lee et al., "Novel treatment modalities: New platelet preparations and subsititutes," British journal of haematology, Sep. 2001, 114(3):496-505.
Microbenotes.com [online], "Types of Plant Cell—Definition, Structure, Functions, Diagrams," Feb. 25, 2020, retrieved May 17, 2021, retrieved from URL<microbenotes.com/types-of-plant-cell/>, 31 pages.
PCT International Preliminary Report on Patentability in PCT Appln. No. PCT/US2019/063549, dated Jun. 10, 2021, 9 pages.
PCT International Preliminary Report on Patentability in PCT Appln. No. PCT/US2019/063650, dated Jun. 10, 2021, 9 pages.
PCT International Preliminary Report on Patentability in PCT Appln. No. PCT/US2019/063750, dated Jun. 10, 2021, 8 pages.
PCT International Preliminary Report on Patentability in PCT Appln. No. PCT/US2019/063736, dated Jun. 10, 2021, 8 pages.
PCT International Search Report and Written Opinion in PCT Appln. No. PCT/US2021/016390, dated May 18, 2021, 13 pages.
PCT International Search Report and Written Opinion in PCT Appln. No. PCT/US2021/016360, dated May 21, 2021, 13 pages.
PCT International Search Report and Written Opinion in PCT Appln. No. PCT/US2021/016363, dated May 18, 2021, 15 pages.
PCT International Search Report and Written Opinion in PCT Appln. No. PCT/US2021/016389, dated May 18, 2021, 15 pages.
Scheinkönig et al., "Adoption of long-term cultures to evaluate the cryoprotective potential of trehalose for freezing hematopoietic stem cells," Bone marrow transplantation, Sep. 2004, 34(6):531-536.
PCT International Preliminary Report on Patentability in International Appln. No. PCT/US2019/050624, dated Mar. 25, 2021, 10 pages.
Chen et al., "Modifying murine von Willebrand factor A1 domain for in vivo assessment of human platelet therapies," Nature biotechnology, Jan. 2008, 26(1):114-119.
diapharma.com [online], "DiaPharmaProductList," retrieved on Feb. 18, 2021, retrieved from URL<http://diapharma.com/wp-content/uploads/2016/03/DiaPharmaProductList_ML-00-00002REV7.pdf>, 4 pages.
helena.com [online], "Ristocetin Cofactor Assay," retrieved on Feb. 18, 2021, retrieved from URL <https://www.helena.com/Procedures/Pro064Rev5.pdf>, 2 pages.
Homepage.haemonetics.com [online], "TEG® 5000 Thrombelastograph® Hemostasis Analyzer System," retrieved Feb. 18, 2021, retrieved from URL<http://homepage.haemonetics.com/en/products/devices/surgical-and-diagnostic-devices/teg-5000>, 3 pages.
Luo et al., "Construction and in vitro studies of magnetic-apoferritin nanocages conjugated with KGDS peptide targeted at activated platelets for the MRI diagnosis of thrombus," Journal of Nanoparticle Research, Aug. 2019, 21(8):1-12.
PCT International Preliminary Report on Patentability in International Appln. No. PCT/US2019/043723, dated Feb. 11, 2021, 14 pages.
PCT International Search Report and Written Opinion for International Appln. No. PCT/US2020/62214, dated Mar. 17, 2021, 9 pages.
PCT International Search Report and Written Opinion in International Appln. No. PCT/US2020/049489, dated Feb. 16, 2021, 8 Pages.

(56) References Cited

OTHER PUBLICATIONS

PCT International Search Report and Written Opinion in International Appln. No. PCT/US2020/062216, dated Feb. 9, 2021, 9 pages.
thrombinoscope.com [online], "Thrombin Calibrator," retrieved on Feb. 18, 2021, retrieved from URL <https://www.thrombinoscope.com/method-products/products/>, 2 pages.
Whitney et al. "Ratiometric Activatable Cell-Penetrating Peptides Provide Rapid In Vivo Readout of Thrombin Activation," Angewandte Chemie International Edition, 2013, 52:325-330.
Gaertner et al., "Migrating platelets are mechano-scavengers that collect and bundle bacteria," Cell, Nov. 30, 2017, 171(6):1368-1382.
Kishbaugh et al., "Intervening with Platelet Therapies," NEHL at the National Zoo, 2017, vol. 4 #2, 4 Pages.
PCT International Search Report and Written Opinion in International Appln. No. PCT/US2020/046522, dated Nov. 10, 2020, 10 Pages.
PCT International Search Report and Written Opinion in International Appln. No. PCT/US2020/046525, dated Nov. 10, 2020, 11 Pages.
PCT International Search Report and Written Opinion in PCT Appln. No. PCT/US2020/042492, dated Nov. 24, 2020, 9 pages.
Robson et al., "Coronavirus RNA proofreading: molecular basis and therapeutic targeting," Molecular Cell, Aug. 4, 2020, 18 Pages.
Ullah et al., "A Review on Malarial Parasite," World Journal of Zoology, 2015, 10(4):285-290.
International Search Report and Written Opinion in PCT Appln. No. PCT/US2020/022705, dated Jul. 29, 2020, 12 pages.
International Search Report and Written Opinion in PCT Appln. No. PCT/US2020/031172, dated Aug. 12, 2020, 9 pages.
Morrison et al. "Storage of apheresis platelet concentrates after manual replacement of >95% of plasma with PAS 5," Vox Sangtmis, May 2014,107(3):247-253.
"Cryoprotein." The American Heritage® Stedman's Medical Dictionary. Houghton Mifflin Company. Mar. 24, 2010. <Dictionary.com http://dictionary.reference.conVbrowse/cryoprotein>.
"Expose", http://dictionary.reference.com/browse/expose, accessed Jul. 18, 2009.
"Platelet." The American Heritage® Dictionary of the English Language, Fourth Edition. Houghton Mifflin Company, 2004. Mar. 23, 2010. <Dictionary.com http://dictionary.reference.com/browse/platelet>.
"Rounding". Dictionary.com. Dictionary.com Unabridged (v 1.1). Random House, Inc. http://dictionary.reference.com/browse/rounding (accessed: Oct. 27, 2008).
Abdelgawwad, et al., "Transfusion of plateletes loaded with recombinant ADAMTS13 is efficacious for inhibiting arterial thrombosis in mice and in human," Arterioscler. Thromb. Vas. Biol., 2018, 38(11):2731-2743.
Adams, ed., Ducry, et al., "The principles of freeze-drying," DNA Repair Protocols, Methods in Molecular Biology, Humana Press, US, 2007, Chapter 2, 368:15-38.
Agam et al. "Passive Participation of Fixed Platelets in Aggregation Facilitated by Covalently Bound Fibrinogen" Blood 61:1, pp. 186-191, 1983.
Ahmadzada, et al., "Fundamentals of siRNA and miRNA therapeutics and a review of targeted nanoparticle delivery systems in breast cancer," Biophysical Reviews, 2018, 10:69-86.
Al Ghaithi, "Evaluation of the total Thrombus-Formation System (T-TAS)," Platelets, 2018, 1-8.
Arav, et al., "Freeze drying (lyophilization) of red blood cells," Journal of Trauma, 2011, 70:S61-S64.
Arnold P., et al., "The preparation and clinical administration of lyophilized platelet material to children with acute leukemia and aplastic anemia," The Journal of Pediatrics, 1956, 49(5):517-522.
Bynum, et al., "Evaluation of a lyophilized platelet-derived hemostatic product," Transfusion, 2019, 49:1490-1498.
Cellphire, "Loading Platelets with Biological Agents for Enhanced Local Delivery," 2006, 14 pages.

Chen, et al., "Advance of molecular imaging technology and targeted imaging agent in imaging and therapy," Biomed. Res. Int., 2014, 819324, 12 pages.
Chen, et al., "Stabilizaton of peptides against proteolysis through disulfide-bridged conjugation with synthetic aromatics," Org. Biomol. Chem., 2017, 15(8):1921-1929.
Christenson et al., "Autologous fibrin glue reinforced by platelets in surgery of ascending aorta", Thorac. Cardiovasc. Surg., vol. 52, p. 225-229, 2004.
Christopher, et al., "MicroRNA therapeutics: discovering novel targets and developing specific therapy," Perspect. Clin. Res., 2016, 7(2):68-74.
Cox, et al., "Platelets and the innate immune system: mechanisms of bacterial-induced platelet activation," Journal of Thrombosis and Haemostasis, 2011, 9:1097-1107.
Daidone, "Usefulness of the Total Thrombus-formation Analysis System (T-TAS) in the diagnosis and characterization of von Willebrand disease," Haemophillia, 2016, 22:949-956.
Daly, et al., "Hemostatic regulators of tumor angiogenesis: a source of antiangiogenic agents for cancer treatment?" Journal of the National Cancer Institute, 2003, 95(22):1660-1673.
Dennison, "A simple and universal method for making up buffer solutions," Biochem. Edu., 1988, 16(4):210-211.
Dielis, et al., "Coagulation factors and the protein C system as determinants of thrombin generation in a normal population," J. Thromb. Haemost., 2008, 6:125-131.
Diener, "Antiplatelet agents and randomized trials," Review in Neurological Diseases, 2007, 4(4):177-183.
Dong, et al., "Ristocetin-dependent, but not botrocetin-dependent, binding of von Willebrand factor to the platelet glycoprotein Ib-IX-V complex correlates with shear-dependent interactions," Blood, 2001,97:162-+168.
European Search Report in EP Appln. No. 05784165.2, dated Mar. 26, 2008.
European Search Report in EP Appln. No. 16808270.9, dated Nov. 22, 2018.
European Search Report in EP Appln. No. 16842662.5, dated Jul. 26, 2019.
European Search Report in EP Appln. No. 17738796.6, dated Jul. 23, 2019.
Extended European Search report in EP Appln. No. 16923314.5, dated Jun. 18, 2020, 7 pages.
Fijnheer et al., "Platelet activation during preparation of platelet concentrates: a comparison of the platelet-rich plasma and the buffy coat methods," Transfiision, 1990, 30(7):634-638.
Fischer et al., "Primary and secondary hemostatic functionalities of rehydrated, lyophilized platelets," 2006, Transfusion, 46:1943-1950.
Fitzpatrick, et al., "Thrombosomes: a platelet-derived hemostatic agent for control of noncompressible hemorrhage," Transfusion, 2013, 53:100S-106S.
Gilbert et al., "Platelet-derived microparticles express high affinity receptors for factor VIII.", J.Biol.Chem., 1991, 266:17261-17268.
Giles et al., "A combination of factor Xa and phosphatidylcholine-phosphatidylserine vesicles bypasses factor VIII in vivo", Br. J., Haematol., 1988, 69(4):491-497.
Greene, et al., "Chapter 9: Component Preparation and Manufacturing," Transfusion Medicine and Hemostasis, Elsevier Science, 2009, pp. 45-50.
Heitz, et al., "Twenty years of cell-penetrating peptides: from molecular mechanisms to therapeutics," British Journal of Pharmacology, 2009, 157:195-206.
Hemker, et al., "Calibrated automated thrombin generation measurement in clotting plasma," Pathophysiol. Haemost. Thromb., 2003, 33:4-15.
Hoffman et al., "Coagulation Factor IXa Binding to Activated Platelets and Platelet-Derived Microparticles: A Flow Cytometric Study," Thromb. Haemost., 1992, 68:74-78.
Holcomb, et al., "Optimal fluid therapy for traumatic hemorrhagic shock," Crit. Care Clin., 2017, 33(1):15-36.
Holme et al., "Platelet-derived microvesicles and activated platelets express factor Xa activity," Blood Coagul. Fibrinolysis, 1995, 6:302-310.

(56) References Cited

OTHER PUBLICATIONS

Hong, et al., "Transfection of human platelets with short interfering RNA," Clin. Transl. Sci., 2011, 4(3):180-182.
Hrachovinova et al., "Interaction of P-selectin and PSGL-1 generates microparticles that correct hemostasis in a mouse model of hemophilia A," Nat Med., 2003, 9(8): 1020-1025.
International Preliminary Report on Patentability in International Appln. No. PCT/US2017/012836, dated Jul. 17, 2018.
International Preliminary Report on Patentability in International Appln. No. PCT/US2005/28559, dated May 8, 2007.
International Preliminary Report on Patentability in International Appln. No. PCT/US2015/060533, dated May 16, 2017.
International Preliminary Report on Patentability in International Appln. No. PCT/US2016/036657, dated Dec. 12, 2017.
International Preliminary Report on Patentability in International Appln. No. PCT/US2016/048846, dated Mar. 6, 2018.
International Preliminary Report on Patentability in International Appln. No. PCT/US2016/065681, dated Jun. 11, 2019.
International Preliminary Report on Patentability in PCT Appln. No. PCT/US2018/050924, dated Mar. 17, 2020, 17 pages.
International Search Report and Written Opinion in International Appln. No. PCT/US2005/28559, dated Mar. 23, 2007.
International Search Report and Written Opinion in International Appln. No. PCT/US2015/060533, dated Jan. 28, 2016.
International Search Report and Written opinion in International Appln. No. PCT/US2016/036657, dated Aug. 29, 2016.
International Search Report and Written Opinion in International Appln. No. PCT/US2016/048846, dated Nov. 16, 2016.
International Search Report and Written Opinion in International Appln. No. PCT/US2016/065681, dated Feb. 17, 2017.
International Search Report and Written Opinion in International Appln. No. PCT/US2017/012836, dated Apr. 7, 2017.
International Search Report and Written Opinion in International Appln. No. PCT/US2018/050924, dated Nov. 20, 2018.
International Search Report and Written Opinion in PCT Appln. No. PCT/US2019/043723, dated Oct. 9, 2019, 16 pages.
International Search Report and Written Opinion in PCT Appln. No. PCT/US2019/050624, dated Nov. 20, 2019, 23 pages.
International Search Report and Written Opinion in PCT Appln. No. PCT/US2019/063549, dated Feb. 4, 2020, 10 pages.
International Search Report and Written Opinion in PCT Appln. No. PCT/US2019/063650, dated Feb. 27, 2020, 11 pages.
International Search Report and Written Opinion in PCT Appln. No. PCT/US2019/063736, dated Feb. 20, 2020, 10 pages.
International Search Report and Written Opinion in PCT Appln. No. PCT/US2019/063750, dated Feb. 19, 2020, 10 pages.
Invitation to Pay Additional Fees in PCT Appln. No. PCT/US2020/022705, dated May 18, 2020, 2 pages.
Ishler, "StablePlate RX Canine Promotes in vitro Thromblin Generation and Thrombus Formation Under High Shear," Journal of Veterinary Internal Medicine, 2019 ACVIM Forum Research Abstract Program, p. 2483, Abstract Only.
Ito, et al., "Total Thrombus-formation Analysis System (T-TAS) can predict periprocedural bleeding events in patients undergoing catheter ablation for atrial fibrillation," Journal of American Heart Association, 2015, 5(1):e002744, 12 pages.
Kariko, et al., "Phosphate-enhanced transfection of cationic lipid-complexed mRNA and plasmid DNA," Biochim. Biophys. Acta, 1998, 1369(2):320-334.
Kerrigan, "Platelet interactions with bacteria," The non-thrombotic role of platelets in health and disease; Chapter 4, 2015, 65-84.
Kerrigan, et al., "Molecular basis for *Staphylococcus aureus* mediated platelet aggregate formation under arterial shear in vitro," Arteriosclerosis Thrombosis and Vascular Biology, 2008, 28(2):334-340.
Kirby et al., "Preparation of liposomes containing Factor VIII for oral treatment of haemophilia," 1984, J. Microencapsul. 1(1): 33-45.
Lam, et al., "siRNA versus miRNA as therapeutics for gene silencing," Molecular Therapy—Nucleic Acids, 2015, 4:e252.

Lannan, et al., "Breaking the Mold: Transcription Factors in the Anuceleate Platelet and Platelet-Derived Microparticles," Front ImunnoL, 2015, 6:48, 17 pages.
Makielski, et al., "Development and implementation of a novel immune thrombocytopenia bleeding score for dogs," J. Vet. Intern. Med., 2018, 32(3):1-10.
Mazzucco et al., "The use of autologous platelet gel to treat difficult-to-heal wounds: a pilot study," Transfusion, 2004, 44:1013-1018.
MedWow, "Manufacturer Specifications—CS-2000 Plus, Baxter," Apr. 19, 2011, retrieved on Sep. 26, 2019 from http://www.medwow.com/med/apheresis-machine/baxter/cs-3000-plus/5782.model-spec, 2 pages.
Merten et al., "Platelet Microparticles Promote Platelet Interaction with Subendothelial Matrix in a Glycoprotein IIb/IIIa Dependent Mechanism", Circulation, 1999, 99:2577-2582.
Miajlovic, et al., "Both complement- and fibrinogen-dependent mechanisms contribute to platelet aggregation mediated by *Staphylococcus aureus* clumping factor B," Infection and Immunity, 2007, 75(7):3335-3343.
Mishra, et al., "Cell-penetrating peptides and peptide nucleic acid-coupled MRI contrast agents evaluation of cellular delivery and target binding," Bioconjugate Chem., 2009, 20:1860-1868.
Montecinos, et al., "Selective targeting of bioengineered platelets to prostate cancer vasculature: new paradigm for the therapeutic modalities," 2015, 19(7):1530-1537.
Morris, et al., "A peptide carrier for the delivery of biologically active proteins into mammalian cells," Nature Biotechnology, 2001, 19:1173-1176.
Natan, et al., "Freeze-drying of mononuclear cells derived from umbilical cord blood followed by colony formation," PLoS One, 2009, 4(4):e5240.
Nieuwland et al., "Cell-derived microparticles generated in patients during cardiopulmonary bypass are highly procoagulant", Circulation, 1997, 96:3534-3541.
Novakowski, et al., "Delivery of mRNA to platelets using lipid nanoparticles," Scientific Reports, 2019, 9:552, 11 pages.
O'Brien, et al., "Multiple mechanisms for the activation of human platelet aggregation by *Staphylococcus aureus*: roles for the clumping factors ClfA and ClfB, the serine-aspartate repeat protein SdrE and protein A," Molecular Microbiology, 2002, 44(4):1033-1044.
Oikarinen et al., "Augmentation of the narrow traumatized anterior alveolar ridge to facilitate dental implant placement," Dent. Traumatol., 2003, 19:19-29.
Oliver, "Dry state preservation of nucleated cells: progress and challenge," Cryobiology, 2011, 63(3):307, abstract.
Pierce et al., "Platelet-derived growth factor and transforming growth factor-beta enhance tissue repair activities by unique mechanisms", J. Cell Biol., 1989, 109:429-440.
Prior et al., "A Sprayable Hemostat Containing Fibrillar Collagen, Bovine Thrombin, and Autologous Plasma ", Ann.Thorac.Surg., 1999, 68:479-485.
Rosing et al., "Impaired factor X and prothrombin activation associated with decreased phospholipid exposure in platelets from a patient with a bleeding disorder", Blood, 1985, 65:1557-1561.
Rowley, et. al., "Platelet mRNA: the meaning behind the message," Curr. Opin. Hematol., 2012, 19(5):385-391.
scbcinfo.org [online], Strong, ed., "Indications for platelet transfusion therapy," available on or before Dec. 25, 2005, via Internet Archive: Wayback Machine URL <https://web.archive.org/web/20051225110714/http://www.scbcinfo.org/publications/bulletin_v2_n2.htm>, 7 pages.
Serebruany, et al., "Crossreactivity of Human versus Swine Platelet Surface Antigens Is Similar for Glycoproteins Ib and IIIa, but Not for the Glycoprotein IIb/IIIa Complex," J.Thromb. and Thromb., 1998, 5:37-41.
Sims et al., "Complement Proteins C5b-9 Cause Release of Membrane Vesicles from the Platelet Surface That Are Enriched in the Membrane Receptor for Coagulation Factor Va and Express Prothrombinase Activiy", J. Biol Chem., 1988, 263:18205-18212.

(56) References Cited

OTHER PUBLICATIONS

Sims et al., "Regulatory control of complement on blood platelets. Modulation of platelet procoagulant responses by a membrane inhibitor of the C5b-9 complex", J Biol. Chem., 1989, 264:19228-19235.
Steed, "The role of growth factors in wound healing," Surg. Clin. North Am., 1997, 77:575-586.
Strober, "Trypan blue exclusion test of cell viability," Current Protocols in Immunology, 1997, A.3B.1-A.3B.2.
Szekely and Lex, "Antifibrinolytics," Heart, Lung and Vessels, 2014, 6(1):5-7.
Tacar, et al., "Doxorubicin: an update on anticancer molecular action, toxicity and novel drug delivery systems," The Journal of Pharmacy and Pharmacology, 2013, 65(2):157-170.
Tans et al., "Comparison of anticoagulant and procoagulant activities of stimulated platelets and platelet-derived microparticles", Blood, 1991, 77:2641-2648.
Taune, et al., "Whole blood coagulation assays ROTEM and T-TAS to monitor dabigatran t dabigatran treatment," Thrombosis Research, 2017, 153(30):76-82.
Tsegaye et al., "Platelet activation suppresses HIV-1 infection of T cells," Retrovirology, 2013, 10:48.
T-TAS.info [online], Publications, 2019, retrieved on Aug. 28, 2019, retrieved from URL<https://www.t-tas.info/pub/>, 8 pages.
Valentini, et al., "Use of CD9 and CD61 for the characterization of AML-M7 by flow cytometry in a dog," Vet. Comp. Oncol., 2011, 10:312-318.
Valeri, et al., "Survival of baboon biotin-X-N-hydroxysuccinimide and 111In-oxine-labelled autologous fresh and lyophilized reconstituted platelets," Vox Sanguinis, 2005, 88:122-129.
Vlieghe, et al., "Synthetic therapeutic peptides: science and market," Drug Discovery Today, 2010, 15:40-56.
Volz, et al., "Inhibition of platelet GPVI induces intratumor hemorrhage and increases efficacy of chemotherapy in mice," Blood, 2019, 133(25):2696-2706.
Wajon et al., "Intraoperative Plateletpheresis and Autologous Platelet Gel Do Not Reduce Chest Tube Drainage or Allogeneic Blood Transfusion After Reoperative Coronary Artery Bypass Graft", Anesth. Analg., 2001, 93:536-542.
Wang, et al., "Commonly used dietary supplements on coagulation function during surgery," Medicines, 2015, 2:157-185.
Wilkerson, M.J., et al., "Platelet size, platelet surface-associated IgG, and reticulated platelets in dogs with immune-mediated thrombocytopenia," Veterinary Clinical Pathology, 2001, 30(3):141-149.
Wilson, et al., "A simple rapid method for layering blood on Ficoll-Isopaque gradients," Journal of Immunological Methods, 1975, 9(1): 67-68.
Wolkers et al., "Human Platelets Loaded with Trehalose Survive Freeze-Drying", Cryobiology 42:79-87, 2001.
WPI Database No. AN 2014-E98028 / CN103524613, Jan. 22, 2014: 2 pages.
Xu, et al., "Doxorubicin-loaded platelets as a smart drug delivery system: an improved therapy for lymphoma," Scientific Reports, 2017, 7:42632.
Yarovoi et al., "Factor VIII ectopically expressed in platelets: efficacy in hemophilia A treatment", Blood 102(12): 4006-4013, 2003.
Zhou, et al., "Loading Trehalose into Red Blood Cells by Improved Hypotonic Method," Cell Preservation Technology, 2008, 6(2):119-122.
Vibhudutta et al., "Trehalose Stabilized Freeze Dried Human Platelets, Thrombosomes, Persist In Circulation 24 Hours After Infusion and Are Non-Immunogenic in New Zealand White Rabbits", Cellphire, Inc. P-0454, 1 page, Poster.
Vibhudutta et al., "Trehalose Stabilized Freeze Dried Human Platelets, Thrombosomes, Reduce Blood Loss in Thrombocytopenic Rabbit Ear Bleed Model by as Much as 89.5%", International Society of Blood Transfusion Vox Sanguinis, vol. 99, Suppl. 1, P-0452, 2010, p. 261, Abstract.
Viswanathan et al., "Clopidogrel Alters Thrombus Quantity and Quality in Patients With Type II Diabetes Mellitus and Stable Coronary Artery Disease", Journal of the American College of Cardiology, vol. 61, No. 10, Mar. 2013, E1154, 1 page.
Wei et al., "ICAM-5/Telencephalin Is a Functional Entry Receptor for Enterovirus D68", Cell Host Microbe, vol. 20, Issue 5, Nov. 9, 2016, pp. 631-641, doi: 10.1016/j.chom.2016.09.013.
Whitman et al., "Design of the CRYPTICS Trail: A Randomized Controlled Trial Comparing Cryopreserved to Liquid Stored Platelets in Patients Undergoing Cardiac Surgery", Journal of Thoracic and Cardiovascular Surgery, 2022, doi. org/10.1016/j.xjon.2022.11.003.
Wright et al., "Doxorubicin delivery via novel lyophilized/reconstituted platelet-product has anti-cancer activity", Hematology & Transfusion International Journal, vol. 9, Issue 3, 2021, pp. 41-51.
Xu et al., "EACA Loaded Platelets Sustain Clots More Efficiently Than Free EACA", Cellphire, Inc., Jul. 2021, 1 page, Poster.
Xu et al., "EACA Loaded Platelets Sustain Clots More Efficiently Then Free EACA", Cellphire, Inc., 2021. 2 page.
Xu et al., "Human Platelet Derived Lyophilized Hemostatic Retains Hemostatic Properties Heparin Complexation with Protamine", Cellphire, Inc. Jul. 2022, 1 page, Poster.
Zafar et. al., "Badimon Perfusion Chamber: An Ex Vivo Model of Thrombosis", Methods Molecular Biology, vol. 1816, 2018, pp. 161-171, doi: 10.1007/978-1-4939-8597-5_12.
Zhou et al., "Hemostatic and Thrombogenic Properties of Lyophilized Human Platelets", CellPhire, Inc. Jul. 2021, 1 page, Poster.
Zhou et al., "Lyophilized Human Platelets Promote Coagulation in Humanized Mouse VWF Transgenic Models of Hemostasisand Thrombosis", Cellphire, Inc., 2021, 1 page.
Ghaithi et al., "Evaluation of the Total Thrombus-Formation System (T-TAS): application to human and mouse blood analysis", Platelets, vol. 30, Issue 7, 2019, pp. 893-900, doi: 10.1080/09537104.2018.1535704.
International Partial Search Report in International Appln No. PCT/US2022/079280, dated Feb. 20, 2023, 14 pages.
Wang et al., "Solubility and Molecular Interactions of Trimetazidine Hydrochloride in 12 Monosolvents and Solvent Mixtures of Methanol + (Ethanol, N,N-Dimethylfomnamide or Ethyl Acetate)", Journal of Chemical Engineering Data, Folume 63, Sep. 6, 2018, pp. 3704-3714, doi.org/10.1021/acs.jced.8b00235.
Zhang et al., "Coupling of liquid chromatography with mass spectrometry by desorption electrospray ionization (DESI)", Chemical Communications, Issue 14, Feb. 28, 2011, pp. 4171-4173, doi.org/10.1039/C0CC05736C.
Bannai et al., "The effects of pH and agitation on platelet preservation", The Journal of AABB Transfusion, vol. 25, Jan.-Feb. 1985, pp. 57-59, https://doi.org/10.1046/j.1537-2995.1985.25185116505.x.
Böck et al., "Cryopreservation of human platelets with dimethyl sulfoxide: changes in biochemistry and cell function", Transfusion, vol. 35, No. 11, Nov.-Dec. 1995, pp. 921-924, doi: 10.1046/.1537-2995.1995.351196110896.x.
Booth et al., "Lyophilized human platelets are superior to apheresis or fresh-drawn platelets in their ability to accelerate thrombin production", Cellphire, Inc. Jul. 2022, 1 page, Poster.
Charkhkar et al., "Amyloid beta modulation of neuronal network activity in vitro", Brain Research, vol. 1629, Dec. 2015, pp. 1-9, doi: 10.1016/j.brainres.2015.09.036.
Chelliah et. al., "P-selectin antagonism reduces thrombus formation in humans", Journal of Thrombosis and Haemostasis, vol. 7, No. 11, Nov. 2009, pp. 1915-1919. doi: 10.1111/j.1538-7836.2009.03587.x.
Crowe et al., "Freeze-dried platelets: Moving towards clinical use", Cryobiology, vol. 66, Issue 3, Jun. 2013, p. 348, Abstract, doi.org/10.1016/j.cryobiol.2013.02.028.
Dee et al., Trehalose Stabilized Freeze Dried Human Platelets, Thrombosomes, Express Surface Markers, Thromboelastogram (TEG) Values and Size Distribution Similar to Two to Three Day Old Stored Platelets, Cllphire, Inc., P-0453, 2019, 1 page, Poster.
Dee et al., "Trehalose Stabilized Freeze Dried Human Platelets, Thrombosomes, Express Surface Markers, Thromboelastogram (TEG) Values and Size Distribution Similar to Two to Three Day Old

(56) References Cited

OTHER PUBLICATIONS

Stored Platelets", International Society of Blood Transfusion Vox Sanguinis, vol. 99, Suppl. 1, P-0453, 2010, p. 262, Abstract.
Dickerson et al., "Lyophilized Human Platelets Restore Hemostasis in the Presence of the P2Y12 Inhibitors Dangrelor, Ticagrelor and Clopidogrel", Cellphire, Inc., 2020, 6 pages, Poster.
Dickerson et al., "Thrombosomes as a Treatment Option for Low-Dose Heparin Reversal", Cellphire, Inc, Oct. 2020. 1 page, Poster.
Dinçer et al., "Effect of taurine on wound healing", Amino Acids, vol. 10, Issue 1, Mar. 1996, pp. 59-71, doi 10.1007/BF00806093.
Extended European Search Report in EP Appln. No. 19888909.9 dated Sep. 28, 2022.
Extended European Search Report in EP Appln. No. 19888994.1 dated Nov. 7, 2022.
Extended European Search Report in EP Appln. No. 19891082.0 dated Sep. 30, 2022.
Extended European Search Report in EP Appln. No. 20769409.2 dated Dec. 6, 2022.
Extended European Search Report in EP Appln. No. 20802506.4 dated Jan. 4, 2023.
Fitzpatrick et al., "A Novel Lyophilized Platelet Derivative Produces Effective Hemostasis in Uncontrolled Bleeding/Shock Model without Systemic Thrombosis", Blood, vol. 118, Issue 21, Nov. 18, 2011, pp. 719-722, doi.org/10.1182/blood.V118.21.719.719.
Fitzpatrick et al., "Freeze-dried platelets: Advancing towards clinical use", Cryobiology, vol. 67, Issue 3, Dec. 2013, p. 420, Abstract, doi.org/10.1016/j.cryobiol.2013.09.086.
Fitzpatrick et al., "Stabilization and preservation of a platelet derived hemostatic agent, Thrombosomes", Cryobiology, vol. 63, Issue 3, Dec. 2011, p. 306, Abstract, doi:10.1016/j.cryobiol.2011.09.005.
Fitzpatrick, "Novel platelet products under development for the treatment of thrombocytopenia or acute hemorrhage". Transfusion and Apheresis Science, vol. 58, Issue 1, Feb. 2019, pp. 7-11, doi: 10.1016/j.transci.2018.12.010.
Godier et al., "Management of antiplatelet therapy for non elective invasive procedures of bleeding complications: proposals from the French working group on perioperative haemostasis (GIHP), in collaboration with the French Society of Anaesthesia and Intensive Care Medicine (SFAR)" Anaesthesia, Critical Care and Pain Medicine, vol. 38, Issue 3, Jun. 2019, pp. 289-302, doi: 10.1016/j.accpm.2018.10.004.
Grosset et al., "Rapid presymptomatic detection of PrPSc via conformationally responsive palindromic PrP peptides", Peptides, vol. 26, Issue 11, Nov. 2005, pp. 2193-2200, doi: 10.1016/j.peptides.2005.03.006.
Inaba et al., "Dried platelets in a swine model of liver injury", Shock, vol. 41, Issue 5, May 2014, pp. 429-434, doi: 10 1097/SHK.0000000000000141.
Ishler et al., "Lyophilized Human Platelets Interact with Fresh Platelets to Promote Hemostasis Under Shear In Vitro", Cellphire, Inc., 2021, 2 page, Abstract.
Ishler et al., "Lyophilized Human Platelets Interact with Fresh Platelets to Promote Hemostasis Under Shear In Vitro", Cellphire, Inc., PB0990, Jul. 2021, 1 page, Poster.
Ishler et al., "Lyophilized Human Platelets Show Hemostatic Function Independent of von Willebrand Factor", Abstract No. PB1533, ISth 2020 Virtual Congress Presentation, Jul. 2020, Res Pract Thromb Haemost. 2020; 4 (Suppl 1). https://abstracts.isth.org/abstract/lyophilized-human-platelets-show-hemostatic-function-independent-of-von-willebrand-factor/.
Ishler et al., "Lyophilized Platelets Show Hemostatic Function Independent of von Willebrand Factor", Cellphire, Inc., Department of Discovery and Research, ISth 2020 Virtual Congress, PB1533, Jul. 2020, 1 page, Poster.
Ishler et al., "StablePlate RX® Canine Promotes In Vitro Thrombin Generation and Thrombus Formation Under High Shear", Cellphire, Inc., 2019, 1 page, Poster1.

Ushler et al., "StablePlate RX® Canine Promotes In Vitro Thrombin Generation and Thrombus Formation Under High Shear", Cellphire, Inc., 2019, 1 page, Poster2.
Joshi et al., "Thrombosomes Show Dose-Dependent Increase in Thrombus Formation in a Model of Deep Arterial Injury", Blood, vol. 118, Issue 21, Nov. 18, 2011, Abstract 2319, 8 pages, doi.org/10.1182/blood.V118.21.2319.2319.
Kuhn et al., "Assessing Circulation Persistence of Human Platelet Products in a NOD-SCID Mouse Model", Cellphire, Inc. Jul. 2022, 1 page, Poster.
Lassila et al., "Dynamic Monitoring of Platelet Deposition on Severely Damaged Vessel Wall in Flowing Blood. Effects of Different Stenoses on Thrombus Growth", Arteriosclerosis, vol. 10, No. 2, Mar.-Apr. 1990, pp. 306-315, doi: 10.1161/01.atv.10.2.306.
Lee et al., "High Efficiency Transfection and Preservation of Platelets with Tumor Suppressing Short RNA", Cellphire, Inc. Jul. 2020, 1 page, Poster.
Lee et al., "Lyophilized Human Platelets Exhibit Adhesive Interactions with *Staphylococcus aureus*", Cellphire, Inc. Jul. 2020, 1 page, Poster.
Lucking et. al., "Characterisation and reproducibility of a human ex vivo model of thrombosis", Thrombosis Research, vol. 126, No. 5, Nov. 2010, pp. 431-435, doi: 10.1016/j.thromres.2010.06.030.
Marris, "The war against wounds", Nature, Mar. 21, 2007, Issue 446, pp. 369-371.
Mathews et al., "Development of Lyophilized Platelet-Derived Extracellular Vesicles for Multiple Indications", Cellphire, Inc., Oct. 2020, 1 page, Poster.
Mathews et al., "Development of Lyophilized Platelet-Derived Extracellular Vesicles for Multiple Indications", Chellphire, Inc., 2020, 1 page, Abstract.
Meisel et al., "A Simplified Direct Lipid Mixing Lipoplex Preparation: Comparison of Liposomal-, Dimethylsulfoxide-, and Ethanol-Based Methods", Scientific Reports, vol. 6, Article 27662, Jun. 21, 2016, 12 pages, doi: 10.1038/srep27662.
Midgett et al., "Combination of freeze-dry microscopy, differential scanning calorimetry, and electron microscopy analysis as a guide for lyophilization cycle optimization to enhance Thrombosomes function", Cryobiology, vol. 63, Issue 3, 2011, p. 320, Abstract, doi:10.1016/j.cryobiol.2011.09.054.
Moskowitz et al., "Hemostatic Properties of Infusible Trehalose-Stabilized Lyophilized Platelet Derivatives", Blood, vol. 104, Issue 11, Nov. 16, 2004, p. 834, Abstract, doi.org/10.1182/blood.V104.11.834.834.
Moskowitz, "Thrombosomes for the Treatment of Bleeding Associated with Aggressive Anticoagulation", Cellphire, Inc., Dec. 2021, 40 pages, Posters.
Müller et al., "Factor XI and XII as antithrombotic targets", Current Opinion in Hematology, vol. 15, No. 5, Sep. 2011, pp. 349-355, doi: 10.1097/MOH.0b013e3283497e61.
Pati et al., "Targeting the Endotheliopathy of Trauma in Hemorrhagic Shock and Traumatic Brain Injury with Freeze-Dried Platelets", Defense Technical Information Center, U.S. Army Medical Research and Development Command, Medicine and Medical Research; Biology, Sep. 1, 2020, 22 pages.
Reddoch et al., "Extended Storage of Refrigerated Platelets in Isoplate and Intersol PAS: An Evaluation of Two FDA-Approved Methods of Collection", Blood, vol. 128, Issue 22, Dec. 2, 2016, 3 pages, doi.org/10.1182/blood.V128.22.2631.2631.
Samanbar et al., "Evaluation of the Hemostatic Ability of the New Device 'Total Thrombus Formation Analysis System' (T-TAS) for Thrombocytopenic Patients. Invitro effect of lyophilized human platelets", Cellphire, Inc. Jul. 2022, 1 page, Poster.
Sheik et al., "Stably Loading Human Platelets with Gadolinium Conjugates to Enhance Magnetic Resonance maging", Cellphire, Inc., 2020, 1 page.
Sum et al., "Wound-healing properties of trehalose-stabilized freeze-dried outdated platelets", Transfusion, vol. 47, Issue 4, Apr. 2007, pp. 672-679, doi: 10.1111/j.1537-2995.2007.01170.x.
Vibhudutta et al., "Trehalose Stabilized Freeze Dried Human Platelets, Thrombosomes, Reduce Blood Loss in Thrombocytopenic Rabbit Ear Bleed Model by as Much as 89.5%", Cellphire, Inc. P-0454, www.bodevet.com, Mar. 2017, 1 page, Poster.

(56) References Cited

OTHER PUBLICATIONS

Vibhudutta et al., "Trehalose Stabilized Freeze Dried Human Platelets, Thrombosomes, Persist in Circulation 24 Hours After Infusion and Are Non-Immunogenic in New Zealand White Rabbits", International Society of Blood Transfusion Vox Sanguinis, vol. 99, Suppl. 1, P-0454, 2010, p. 262, Abstract.

* cited by examiner

*Class II Background*

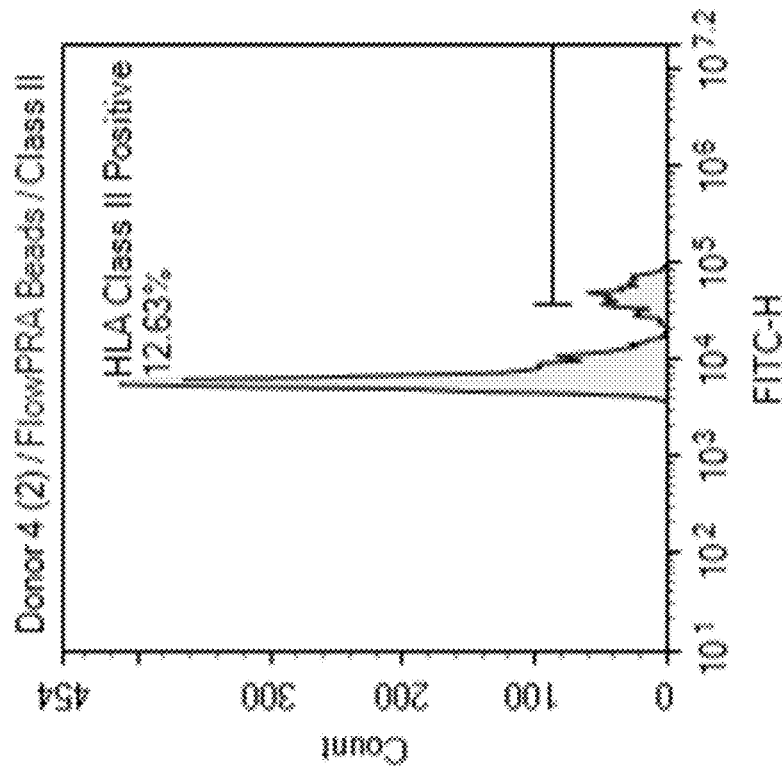
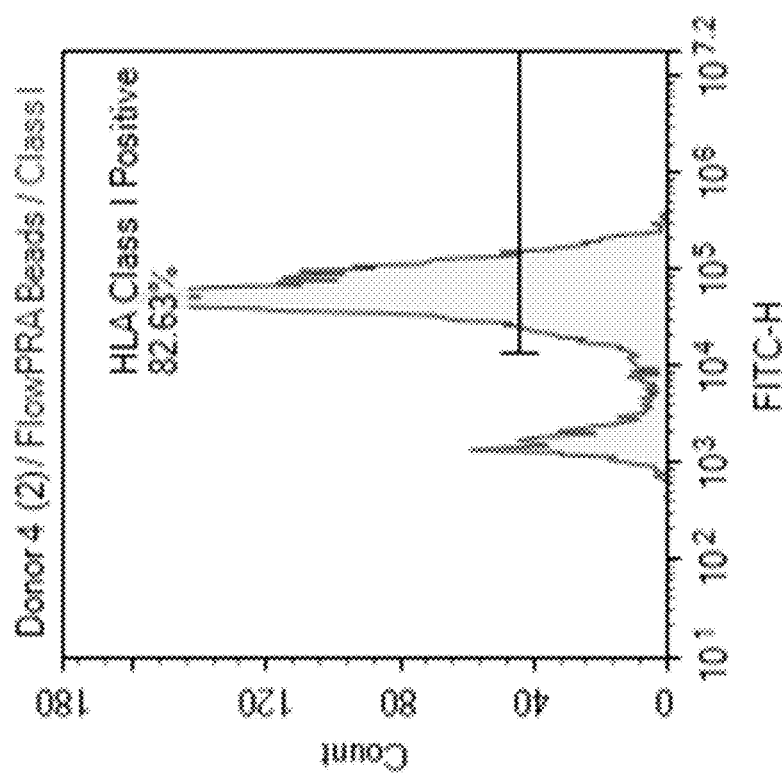
Fig. 7A
Fig. 7B

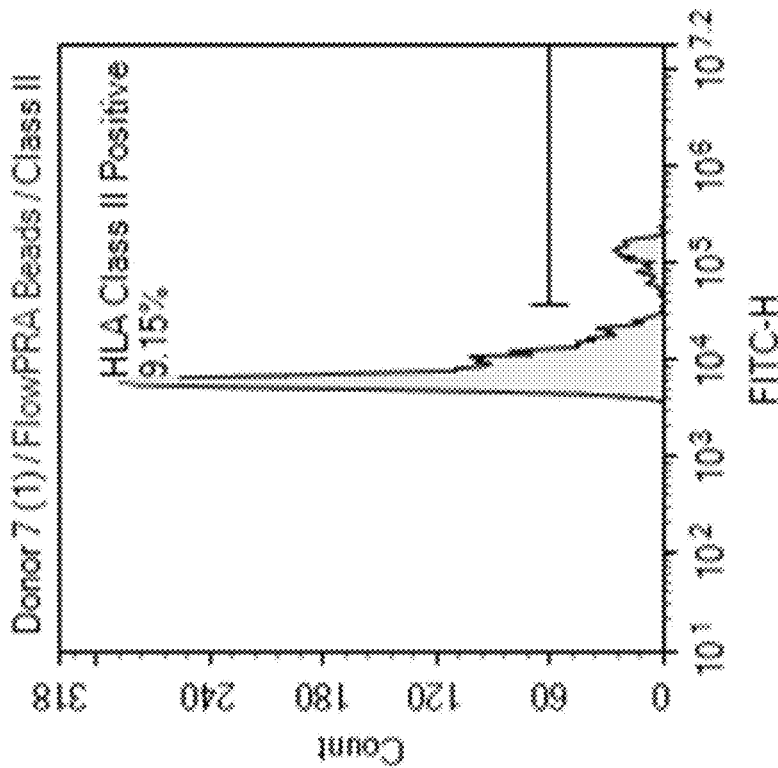
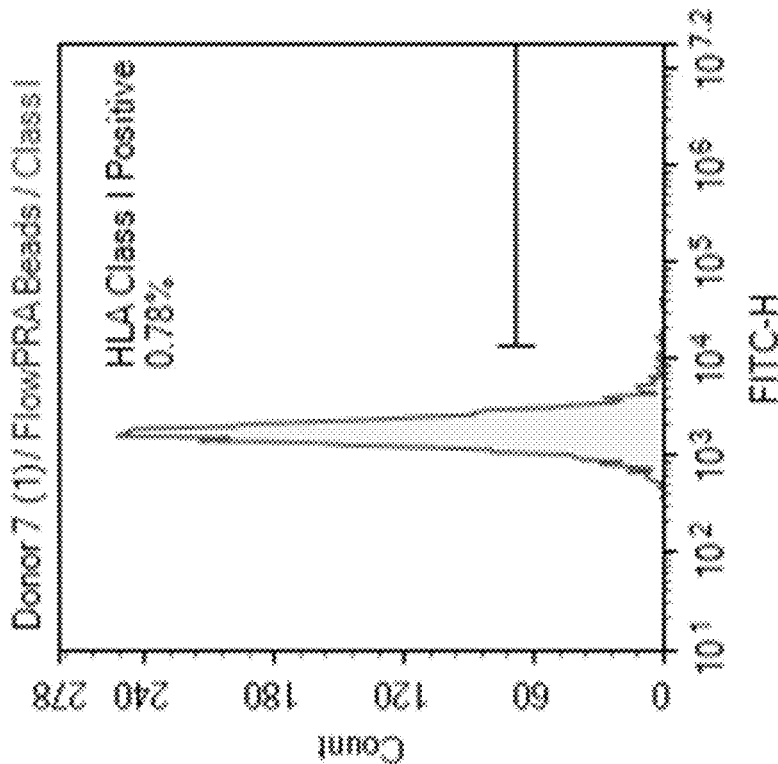
Fig. 10B
Fig. 10A

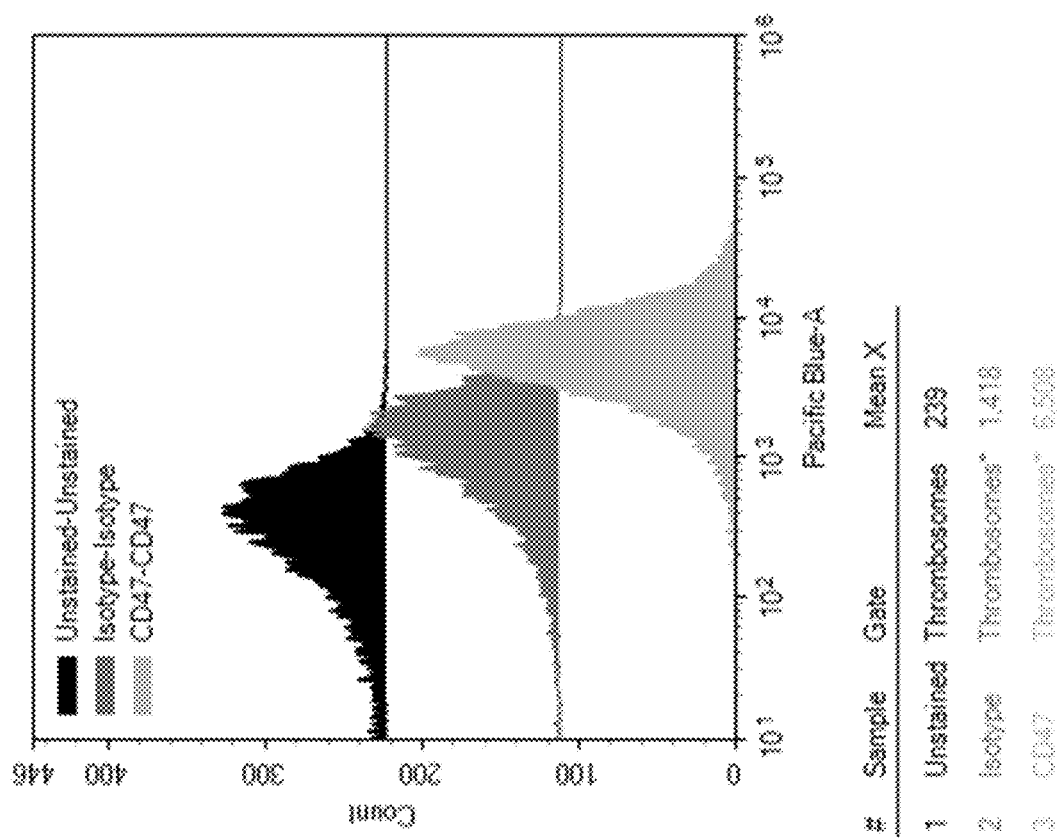

MATERIALS AND METHODS FOR PRODUCING BLOOD PRODUCTS

CROSS-REFERENCE TO RELATED APPLICATIONS

This application is a continuation of U.S. patent application Ser. No. 16/865,215, filed on May 1, 2020, which claims priority to U.S. Provisional Application Ser. No. 62/843,061, filed on May 3, 2019, and 62/936,122, filed on Nov. 15, 2019, each of which is herein incorporated by reference in its entirety.

STATEMENT OF GOVERNMENT INTEREST

This invention was made with government support under Contract No. HHS0100201300021 awarded by the Biomedical Advanced Research and Development Authority (BARDA) of the U.S. Department of Health and Human Services. The government has certain rights in the invention.

TECHNICAL FIELD

The present disclosure generally relates to blood products, such as blood products with reduced HLA antibody content, and methods of producing such blood products.

BACKGROUND

Blood is a complex mixture of numerous components. In general, blood can be described as comprising four main parts: red blood cells, white blood cells, platelets, and plasma. The first three are cellular or cell-like components, whereas the fourth (plasma) is a liquid component comprising a wide and variable mixture of salts, proteins, and other factors necessary for numerous bodily functions. The components of blood can be separated from each other by various methods. In general, differential centrifugation is most commonly used currently to separate the different components of blood based on size and, in some applications, density.

Inactivated platelets, which are also commonly referred to as thrombocytes, are small, often irregularly-shaped (e.g., discoidal or ovoidal) megakaryocyte-derived components of blood that are involved in the clotting process. They aid in protecting the body from excessive blood loss due not only to trauma or injury, but to normal physiological activity as well. Platelets are considered crucial in normal hemostasis, providing the first line of defense against blood escaping from injured blood vessels. Platelets generally function by adhering to the lining of broken blood vessels, in the process becoming activated, changing to an amorphous shape, and interacting with components of the clotting system that are present in plasma or are released by the platelets themselves or other components of the blood. Purified platelets have found use in treating subjects with low platelet count (thrombocytopenia) and abnormal platelet function (thrombasthenia). Concentrated platelets are often used to control bleeding after injury or during acquired platelet function defects or deficiencies, for example those occurring during surgery and those due to the presence of platelet inhibitors.

SUMMARY

This document is based, at least in part, on the production of blood products (e.g., a composition comprising platelets or platelet derivatives (e.g., thrombosomes)) with reduced levels of free protein (e.g., antibodies (e.g., Human Leukocyte Antigen (HLA) antibodies, or Human Neutrophil Antigen (HNA) antibodies)).

Provided herein is a composition including platelets and an aqueous medium, wherein the aqueous medium has a protein concentration less than 50% of the protein concentration of donor apheresis plasma.

Implementations can have one or more of the following features. The protein concentration of the aqueous medium can be less than 30% of the protein concentration of donor apheresis plasma. The aqueous medium can have a concentration of human leukocyte antigen (HLA) Class I antibodies that is less than 30% of the human leukocyte antigen (HLA) Class I antibody concentration in donor apheresis plasma. The aqueous medium can have a concentration of human leukocyte antigen (HLA) Class II antibodies that is less than 30% of the human leukocyte antigen (HLA) Class II antibody concentration in donor apheresis plasma. The aqueous medium can have a concentration of human neutrophil antigen (HNA) antibodies that is less than 30% of the HNA antibody concentration in donor apheresis plasma. The protein concentration can be less than 10% of the protein concentration of donor apheresis plasma. The aqueous medium can have a concentration of human HLA Class I antibodies that is less than 10% of the HLA Class I antibody concentration in donor apheresis plasma. The aqueous medium can have a concentration of human HLA Class II antibodies that is less than 10% of the HLA Class II antibody concentration in donor apheresis plasma. The aqueous medium can have a concentration of human HNA antibodies that is less than 10% of the HNA antibody concentration in donor apheresis plasma. The protein concentration can be less than 5% of the protein concentration of donor apheresis plasma. The aqueous medium can have a concentration of human HLA Class I antibodies that is less than 5% of the HLA Class I antibody concentration in donor apheresis plasma. The aqueous medium can have a concentration of human HLA Class II antibodies that is less than 5% of the HLA Class II antibody concentration in donor apheresis plasma. The aqueous medium can have a concentration of human HNA antibodies that is less than 5% of the HNA antibody concentration in donor apheresis plasma. The protein concentration can be less than 3% of the protein concentration of donor apheresis plasma. The aqueous medium can be a concentration of human HLA Class I antibodies that is less than 3% of the HLA Class I antibody concentration in donor apheresis plasma. The aqueous medium can have a concentration of human HLA Class II antibodies that is less than 3% of the HLA Class II antibody concentration in donor apheresis plasma. The aqueous medium can have a concentration of human HNA antibodies that is less than 3% of the HNA antibody concentration in donor apheresis plasma. The protein concentration can be less than 1% of the protein concentration of donor apheresis plasma. The aqueous medium can have a concentration of human HLA Class I antibodies that is less than 1% of the HLA Class I antibody concentration in donor apheresis plasma. The aqueous medium can have a concentration of human HLA Class II antibodies that is less than 1% of the HLA Class II antibody concentration in donor apheresis plasma. The aqueous medium can have a concentration of human HNA antibodies that is less than 1% of the HNA antibody concentration in donor apheresis plasma. The protein concentration can be determined by absorbance at 280 nanometers (nm) with a path length of 0.5 cm. In some embodiments, the absorbance at 280 nm can be less than 1.7 AU. In some embodiments, the absorbance at 280 nm can be less than 1.66 AU. In some embodiments, the absorbance at 280 nm can be less than 1.6 AU. In some embodiments, the platelet count can be at least $200 \times 10^3$ platelets/µL. In some embodiments, the platelet count can be at least $2250 \times 10^3$ platelets/µL. In some embodiments, the composition can have an erythrocyte count less than $0.2 \times 10^6$ erythrocytes/µL. In some embodiments, the composition can further include erythrocytes. In some embodiments, the erythrocyte count can be less than $0.2 \times 10^6$ erythrocytes/µL. The composition can be negative for HLA Class I antibodies based on a regulatory agency approved test. The composition can be negative for HLA Class II antibodies based on a regulatory agency approved test. The composition can be negative for HNA antibodies based on a regulatory agency approved test. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 5%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 3%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 1%. The percentage of beads positive for HLA Class I antibodies, as determined for the composition by flow cytometry using beads coated with Class I HLAs, can be less than 5%. The percentage of beads positive for HLA Class I antibodies, as determined for the composition by flow cytometry using beads coated with Class I HLAs, can be less than 3%. The percentage of beads positive for HLA Class I antibodies, as determined for the composition by flow cytometry using beads coated with Class I HLAs, can be less than 1%. The percentage of beads positive for HLA Class II antibodies, as determined for the composition by flow cytometry using beads coated with Class II HLAs can be less than 5%. The percentage of beads positive for HLA Class II antibodies, as determined for the composition by flow cytometry using beads coated with Class II HLAs, can be less than 3%. The percentage of beads positive for HLA Class II antibodies, as determined for the composition by flow cytometry using beads coated with Class II HLAs, can be less than 1%. The percentage of beads positive for HNA antibodies, as determined for the composition by flow cytometry using beads coated with HNAs can be less than 5%. The percentage of beads positive for HNA antibodies, as determined for the composition by flow cytometry using beads coated with HNAs, can be less than 3%. The percentage of beads positive for HNAs, as determined for the composition by flow cytometry using beads coated with HNAs, can be less than 1%. The aqueous medium can further include a buffering agent, a base, a loading agent, optionally a salt, and optionally at least one organic solvent. The buffering agent can be HEPES (4-(2-hydroxyethyl)-1-piperazineethane-sulfonic acid). The base can be sodium bicarbonate. The loading agent can be a monosaccharide, a polysaccharide, or a combination thereof. The monosaccharide can be selected from the group consisting of sucrose, maltose, trehalose, glucose, mannose, and xylose. The monosaccharide can be trehalose. The polysaccharide can be polysucrose. The salt can be sodium chloride, potassium chloride, or a combination thereof. The organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof. The composition can be prepared by a process including tangential flow filtration (TFF) of a starting material comprising platelets, centrifugation of a starting material comprising platelets, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 50% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 75% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 90% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 95% as compared to a similar composition not prepared by a process including tangential flow filtration of a blood product composition, centrifugation of a blood product composition, or a combination thereof. The starting material can be (a) positive for HLA Class I antibodies based on a regulatory agency approved test, (b) positive for HLA Class II antibodies based on a regulatory agency approved test, (c) positive for HNA antibodies based on a regulatory agency approved test, or (d) one or more of (a), (b), and (c). The starting material can have a protein concentration of about 60 to about 80 mg/ml. The starting material can include donor blood product. The donor blood product can be pooled donor blood product. The starting material can include donor apheresis material. The TFF can include concentrating. The TFF can include diafiltering. The diafiltering can include diafiltering with at least two diavolumes. The TFF can include buffer exchange. The TFF can be carried out using a membrane with pore size of about 0.2 µm to about 1 µm. The TFF can be carried out using a membrane with pore size of about 0.2 µm to about 0.45 µm. The TFF can be performed at a temperature of about 20° C. to about 37° C. The TFF can be carried out until the absorbance at 280 nm of the aqueous medium is less than 50% of the absorbance at 280 nm of the starting material, using a path length of 0.5 cm. The TFF can be carried out until the absorbance at 280 nm of the aqueous medium is less than 30% of the absorbance at 280 nm of the starting material, using a path length of 0.5 cm. The TFF can be carried out until the absorbance at 280 nm of the aqueous medium is less than 10% of the absorbance at 280 nm of the starting material, using a path length of 0.5 cm. The TFF can be carried out until the absorbance at 280 nm of the aqueous medium is less than 5% of the absorbance at 280 nm of the starting material, using a path length of 0.5 cm. The TFF can be carried out until the absorbance at 280 nm of the aqueous medium is less than 3% of the absorbance at 280 nm of the starting material, using a path length of 0.5 cm. The TFF can be carried out until the absorbance at 280 nm of the aqueous medium is less than 1% of the absorbance at 280 nm of the starting material, using a path length of 0.5 cm. The TFF can be carried out until the absorbance at 280 nm of the aqueous medium is less than 1.70 AU, using a path length of 0.5 cm. The TFF can be carried out until the absorbance at 280 nm of the aqueous medium is less than 1.66 AU, using a path length of 0.5 cm. The TFF can be carried out until the absorbance at 280 nm of the aqueous medium is less than 1.60 AU, using a path length of 0.5 cm. The TFF can be carried out until the platelet concentration is at least about $2000\times10^3$ platelets/μL. The TFF can be carried out until the platelet concentration is at least about $2250\times10^3$ platelets/μL. The TFF can include buffer exchange into a buffer comprising a buffering agent, a base, a loading agent, optionally a salt, and optionally at least one organic solvent. The buffering agent can be HEPES (4-(2-hydroxyethyl)-1-piperazineethanesulfonic acid). The base can be sodium bicarbonate. The loading agent can be a monosaccharide, a polysaccharide, or a combination thereof. The monosaccharide can be selected from the group consisting of sucrose, maltose, trehalose, glucose, mannose, and xylose. The monosaccharide can be trehalose. The polysaccharide can be polysucrose. The salt can be sodium chloride, potassium chloride, or a combination thereof. The organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof. The centrifugation can include centrifugation at 1400×g to about 1550×g. The centrifugation can include centrifugation at 1450×g to about 1500×g. The process can lack centrifugation of a composition comprising platelets. The composition can include less than 5.0% (by scattering intensity) microparticles. The composition can include less than 4.5% (by scattering intensity) microparticles. The composition can include less than 4.0% (by scattering intensity) microparticles. The composition can include less than 3.5% (by scattering intensity) microparticles. The platelets or platelet derivatives can have a CD41 percent positivity of at least 55%. The platelets or platelet derivatives can have a CD41 percent positivity of at least 60%. The platelets or platelet derivatives can have a CD41 percent positivity of at least 65%. The platelets or platelet derivatives can have a CD42 percent positivity of at least 80%. The platelets or platelet derivatives can have a CD42 percent positivity of at least 85%. The platelets or platelet derivatives can have a CD42 percent positivity of at least 90%. The platelets or platelet derivatives can retain at least about 10% of the lactate dehydrogenase activity of donor apheresis platelets. The platelets or platelet derivatives can retain at least about 15% of the lactate dehydrogenase activity of donor apheresis platelets. The platelets or platelet derivatives can retain at least about 20% of the lactate dehydrogenase activity of donor apheresis platelets. The platelets or platelet derivatives can have an annexin V percent positivity of at least 70%. The platelets or platelet derivatives can have an annexin V percent positivity of at least 75%. The platelets or platelet derivatives can have an annexin V percent positivity of at least 80%. The platelets or platelet derivatives can have CD47 percent positivity of at least 8%. The platelets or platelet derivatives can have CD47 percent positivity of at least 10%. The platelets or platelet derivatives can have CD47 percent positivity of at least 15%. The platelets or platelet derivatives can have CD47 percent positivity of at least 20%. The platelets or platelet derivatives can have CD62 percent positivity of at least 80%. The platelets or platelet derivatives can have CD62 percent positivity of at least 82%. The platelets or platelet derivatives can have CD62 percent positivity of at least 85%. The platelets or platelet derivatives can have CD62 percent positivity of at least 90%. The platelets or platelet derivatives can have fibrinogen associated with the cell membrane. The aqueous medium can have a lactate concentration of less than 2.0 mmol/L. The aqueous medium can have a lactate concentration of less than 1.5 mmol/L. The aqueous medium can have a lactate concentration of about 0.4 to about 1.3 mmol/L. The aqueous medium can have a lactate concentration of about 0.5 to about 1.0 mmol/L. The platelet derivatives can include thrombosomes.

Also provided herein is a process for preparing a composition comprising platelets and an aqueous medium, the process including tangential flow filtration (TFF) of a starting material comprising platelets, centrifugation of a starting material comprising platelets, or a combination thereof, wherein the aqueous medium has a protein concentration less than 50% of the protein concentration of donor apheresis plasma.

Implementations can include one or more of the following features. The starting material can be (a) positive for HLA Class I antibodies based on a regulatory agency approved test, (b) positive for HLA Class II antibodies based on a regulatory agency approved test, (c) positive for HNA antibodies based on a regulatory agency approved test, or (d) one or more of a), b), and c). The starting material can have a protein concentration of about 60 to about 80 mg/mL. The starting material can include donor blood product. The donor blood product can be pooled donor blood product. The starting material can include donor apheresis material. The TFF can include concentrating. The TFF can include diafiltering. The diafiltration can include diafiltering with at least two diavolumes. The TFF can include buffer exchange. The TFF can be carried out using a membrane with pore size of about 0.2 μm to about 1 μm. The TFF can be carried out using a membrane with pore size of about 0.2 μm to about 0.45 μm. The TFF can be performed at a temperature of about 20° C. to about 37° C. The TFF can be carried out until the absorbance at 280 nm of the aqueous medium is less than 50% of the absorbance at 280 nm of the starting material, using a path length of 0.5 cm. The TFF is carried out until the absorbance at 280 nm of the aqueous medium is less than 30% of the absorbance at 280 nm of the starting material, using a path length of 0.5 cm. The TFF can be carried out until the absorbance at 280 nm of the aqueous medium is less than 10% of the absorbance at 280 nm of the starting material, using a path length of 0.5 cm. The TFF can be carried out until the absorbance at 280 nm of the aqueous medium is less than 5% of the absorbance at 280 nm of the starting material, using a path length of 0.5 cm. The TFF can be carried out until the absorbance at 280 nm of the aqueous medium is less than 3% of the absorbance at 280 nm of the starting material, using a path length of 0.5 cm. The TFF can be carried out until the absorbance at 280 nm of the aqueous medium is less than 1% of the absorbance at 280 nm of the starting material, using a path length of 0.5 cm. The TFF can be carried out until the absorbance at 280 nm of the aqueous medium is less than 1.70 AU, using a path length of 0.5 cm. The TFF can be carried out until the absorbance at 280 nm of the aqueous medium is less than 1.66 AU, using a path length of 0.5 cm. The TFF can be carried out until the absorbance at 280 nm of the aqueous medium is less than 1.60 AU, using a path length of 0.5 cm. The TFF can be carried out until the platelet concentration is at least about $2000 \times 10^3$ platelets/µL. The TFF can be carried out until the platelet concentration is at least about $2250 \times 10^3$ platelets/µL. The TFF can include buffer exchange into a buffer comprising a buffering agent, a base, a loading agent, optionally a salt, and optionally at least one organic solvent. The buffering agent can be HEPES (4-(2-hydroxyethyl)-1-piperazineethanesulfonic acid). The base can be sodium bicarbonate. The loading agent can be a monosaccharide, a polysaccharide, or a combination thereof. The monosaccharide can be selected from the group consisting of sucrose, maltose, trehalose, glucose, mannose, and xylose. The monosaccharide can be trehalose. The polysaccharide can be polysucrose. The salt can be sodium chloride, potassium chloride, or a combination thereof. The organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof. The centrifugation can include centrifugation at 1400×g to about 1550×g. The centrifugation can include centrifugation at 1450×g to about 1500×g. The process can lack centrifugation of a composition comprising platelets. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 50% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 75% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 90% as compared to a similar composition not prepared by a process including tangential flow filtration of a blood product composition, centrifugation of a blood product composition, or a combination thereof. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be reduced by at least 95% as compared to a similar composition not prepared by a process including tangential flow filtration of a blood product composition, centrifugation of a blood product composition, or a combination thereof. The protein concentration can be less than 30% of the protein concentration of donor apheresis plasma. The aqueous medium can have a concentration of human leukocyte antigen (HLA) Class I antibodies that is less than 30% of the human leukocyte antigen (HLA) Class I antibody concentration in donor apheresis plasma. The aqueous medium can have a concentration of human leukocyte antigen (HLA) Class II antibodies that is less than 30% of the human leukocyte antigen (HLA) Class II antibody concentration in donor apheresis plasma. The aqueous medium can have a concentration of human neutrophil antigen (HNA) antibodies that is less than 30% of the HNA antibody concentration in donor apheresis plasma. The protein concentration can be less than 10% of the protein concentration of donor apheresis plasma. The aqueous medium can have a concentration of human HLA Class I antibodies that is less than 10% of the HLA Class I antibody concentration in donor apheresis plasma. The aqueous medium can have a concentration of human HLA Class II antibodies that is less than 10% of the HLA Class II antibody concentration in donor apheresis plasma. The aqueous medium can have a concentration of human HNA antibodies that is less than 10% of the HNA antibody concentration in donor apheresis plasma. The protein concentration can be less than 5% of the protein concentration of donor apheresis plasma. The aqueous medium can have a concentration of human HLA Class I antibodies that is less than 5% of the HLA Class I antibody concentration in donor apheresis plasma. The aqueous medium can have a concentration of human HLA Class II antibodies that is less than 5% of the HLA Class II antibody concentration in donor apheresis plasma. The aqueous medium can have a concentration of human HNA antibodies that is less than 5% of the HNA antibody concentration in donor apheresis plasma. The protein concentration can be less than 3% of the protein concentration of donor apheresis plasma. The aqueous medium can have a concentration of human HLA Class I antibodies that is less than 3% of the HLA Class I antibody concentration in donor apheresis plasma. The aqueous medium can have a concentration of human HLA Class II antibodies that is less than 3% of the HLA Class II antibody concentration in donor apheresis plasma. The aqueous medium can have a concentration of human HNA antibodies that is less than 3% of the HNA antibody concentration in donor apheresis plasma. The protein concentration can be less than 1% of the protein concentration of donor apheresis plasma. The aqueous medium can have a concentration of human HLA Class I antibodies that is less than 1% of the HLA Class I antibody concentration in donor apheresis plasma. The aqueous medium can have a concentration of human HLA Class II antibodies that is less than 1% of the HLA Class II antibody concentration in donor apheresis plasma. The aqueous medium can have a concentration of human HNA antibodies that is less than 1% of the HNA antibody concentration in donor apheresis plasma. The composition can be negative for HLA Class I antibodies based on a regulatory agency approved test. The composition can be negative for HLA Class II antibodies based on a regulatory agency approved test. The composition can be negative for HNA antibodies based on a regulatory agency approved test. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 5%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 3%. The percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, can be less than 1%. The percentage of beads positive for HLA Class I antibodies, as determined for the composition by flow cytometry using beads coated with Class I HLAs, can be less than 5%. The percentage of beads positive for HLA Class I antibodies, as determined for the composition by flow cytometry using beads coated with Class I HLAs, can be less than 3%. The percentage of beads positive for HLA Class I antibodies, as determined for the composition by flow cytometry using beads coated with Class I HLAs, can be less than 1%. The percentage of beads positive for HLA Class II antibodies, as determined for the composition by flow cytometry using beads coated with Class II HLAs can be less than 5%. The percentage of beads positive for HLA Class II antibodies, as determined for the composition by flow cytometry using beads coated with Class II HLAs, can be less than 3%. The percentage of beads positive for HLA Class II antibodies, as determined for the composition by flow cytometry using beads coated with Class II HLAs, can be less than 1%. The percentage of beads positive for HNA antibodies, as determined for the composition by flow cytometry using beads coated with HNAs, can be less than 5%. The percentage of beads positive for HNA antibodies, as determined for the composition by flow cytometry using beads coated with HNAs, can be less than 3%. The percentage of beads positive for HNAs, as determined for the composition by flow cytometry using beads coated with HNAs, can be less than 1%. The process of any one of claims 125-199, wherein the composition comprises less than 5.0% (by scattering intensity) microparticles. The composition can include less than 4.5% (by scattering intensity) microparticles. The composition can include less than 4.0% (by scattering intensity) microparticles. The composition can include less than 3.5% (by scattering intensity) microparticles. The platelets or platelet derivatives can have a CD41 percent positivity of at least 55%. The platelets or platelet derivatives can have a CD41 percent positivity of at least 60%. The platelets or platelet derivatives can have a CD41 percent positivity of at least 65%. The platelets or platelet derivatives can have a CD42 percent positivity of at least 80%. The platelets or platelet derivatives can have a CD42 percent positivity of at least 85%. The platelets or platelet derivatives can have a CD42 percent positivity of at least 90%. The platelets or platelet derivatives can retain at least about 10% of the lactate dehydrogenase activity of donor apheresis platelets. The platelets or platelet derivatives can retain at least about 15% of the lactate dehydrogenase activity of donor apheresis platelets. The platelets or platelet derivatives can retain at least about 20% of the lactate dehydrogenase activity of donor apheresis platelets. The platelets or platelet derivatives can have an annexin V percent positivity of at least 70%. The platelets or platelet derivatives can have an annexin V percent positivity of at least 75%. The platelets or platelet derivatives can have an annexin V percent positivity of at least 80%. The platelets or platelet derivatives can have CD47 percent positivity of at least 8%. The platelets or platelet derivatives can have CD47 percent positivity of at least 10%. The platelets or platelet derivatives can have CD47 percent positivity of at least 15%. The platelets or platelet derivatives can have CD47 percent positivity of at least 20%. The platelets or platelet derivatives can have CD62 percent positivity of at least 80%. The platelets or platelet derivatives can have CD62 percent positivity of at least 82%. The platelets or platelet derivatives can have CD62 percent positivity of at least 85%. The platelets or platelet derivatives can have CD62 percent positivity of at least 90%. The platelets or platelet derivatives can have fibrinogen associated with the cell membrane. The aqueous medium can have a lactate concentration of less than 2.0 mmol/L. The aqueous medium can have a lactate concentration of less than 1.5 mmol/L. The aqueous medium can have a lactate concentration of about 0.4 to about 1.3 mmol/L. The aqueous medium can have a lactate concentration of about 0.5 to about 1.0 mmol/L. The platelet derivatives can include thrombosomes. The process can further include a pathogen reduction step. The pathogen reduction step can precede TFF. The process can further include lyophilizing the composition comprising platelets or platelet derivatives. The process can further include thermally treating the composition comprising platelets or platelet derivatives.

Also provided herein is a composition including platelets and an aqueous medium prepared by any of the processes described herein.

Also provided herein is a process for preparing freeze-dried platelets, including (a) preparing a composition comprising platelets and an aqueous medium using any of the processes described herein and (b) freeze-drying the composition comprising platelets and the aqueous medium.

Also provided herein is a composition comprising freeze-dried platelets, prepared by any of the processes described herein.

Also provided herein is a method for preparing a composition comprising platelets or platelet derivatives and an aqueous medium, the method including diluting a starting material comprising platelets to form a diluted starting material, concentrating the platelets to about 2250×10³ cells/µL (±250×10³) to form a concentrated platelet composition, and washing the concentrated platelet composition with at least 2 diavolumes (DV) of the preparation agent to form a TFF-treated composition.

Implementations can include one or more of the following features. Diluting can include diluting with an approximately equal weight (±10%) of the preparation agent. The method can further include a pathogen reduction step. The pathogen reduction step can occur before diluting the starting material. The residual plasma percentage can be less than about 15% relative plasma (as determined by plasma protein content). Following washing, if the concentration of the cells in the TFF-treated composition is not about 2000× 10³ cells/µL (+300×10³), the method can further include diluting the preparation agent or can be concentrated to fall within this range. The method can further include lyophilizing the TFF-treated composition to form a lyophilized composition. The method can further include treating the lyophilized composition at about 80° C. for about 24 hours.

Also provided herein is a composition comprising platelets or platelet derivatives prepared by any of the methods described herein.

The materials and methods described herein can provide several advantages. First, they can allow for the collection of otherwise deferred donors and reduce the competition for apheresis materials.

DESCRIPTION OF THE DRAWINGS

FIG. 7A shows an exemplary FITC-H histogram of FLOWPRA™ beads in Donor 4 PPP gated on Class I HLA.

FIG. 7B shows an exemplary FITC-H histogram of FLOWPRA™ beads in Donor 4 PPP gated on Class II HLA.

FIG. 10A shows an exemplary FITC-H histogram of FLOWPRA™ beads in Donor 7 PPP gated on Class I HLA.

FIG. 10B shows an exemplary FITC-H histogram of FLOWPRA™ beads in Donor 7 PPP gated on Class II HLA.

FIG. 22D is an exemplary histogram of thrombosomes that were unstained (black), stained with an isotype control antibody (dark gray), or stained with an anti-CD47 antibody (light gray).

Figures 1A, 1B:
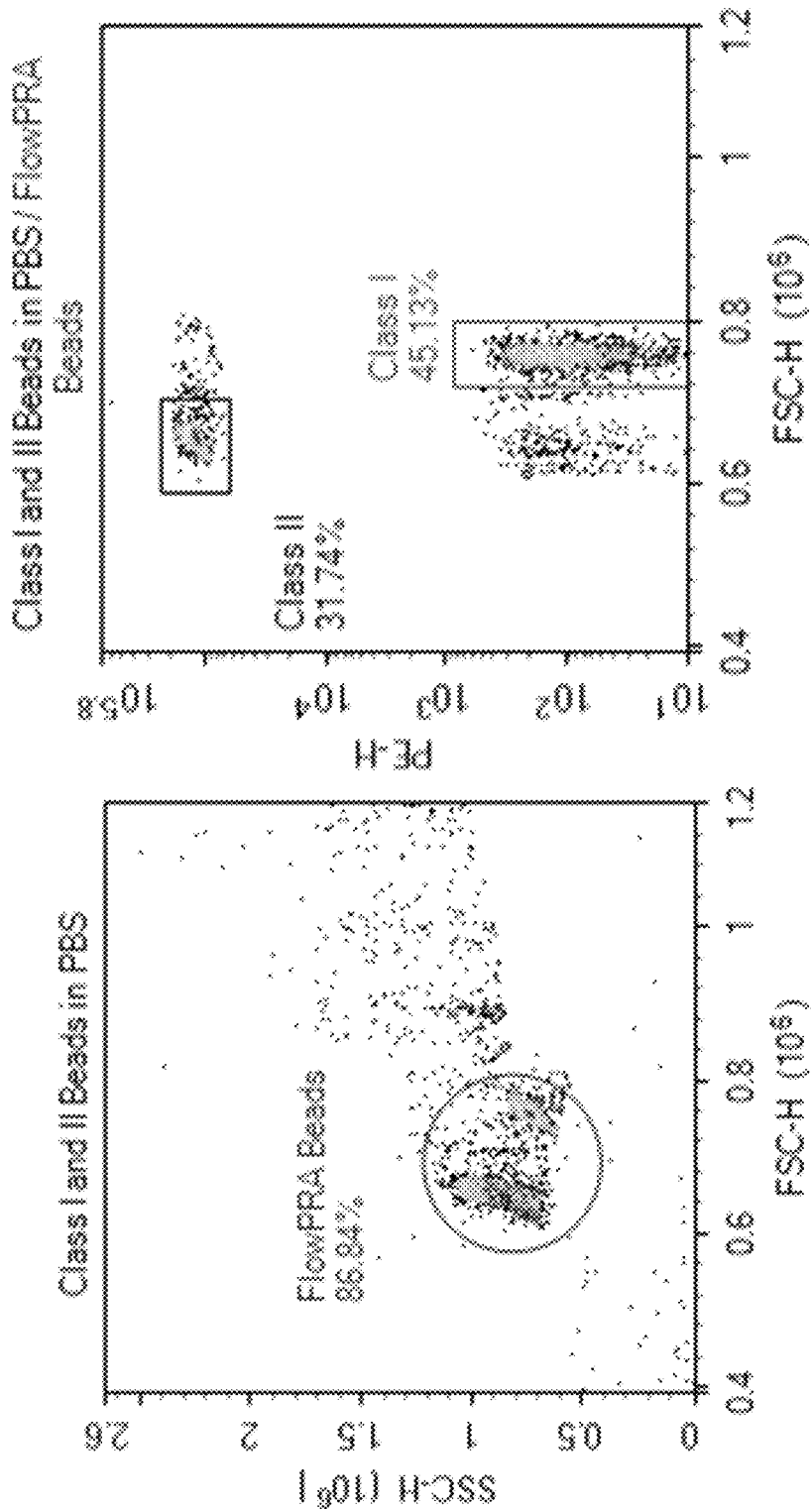
FIG. 1A shows initial gate placement for identification of Class I and Class II HLA FLOWPRA™ beads in PBS using side scattering vs. forward scattering.
FIG. 1B shows initial gate placement for identification of Class I and Class II HLA FLOWPRA™ beads in PBS using phycoerythrin fluorescence vs. forward scattering.
Figure 2A:
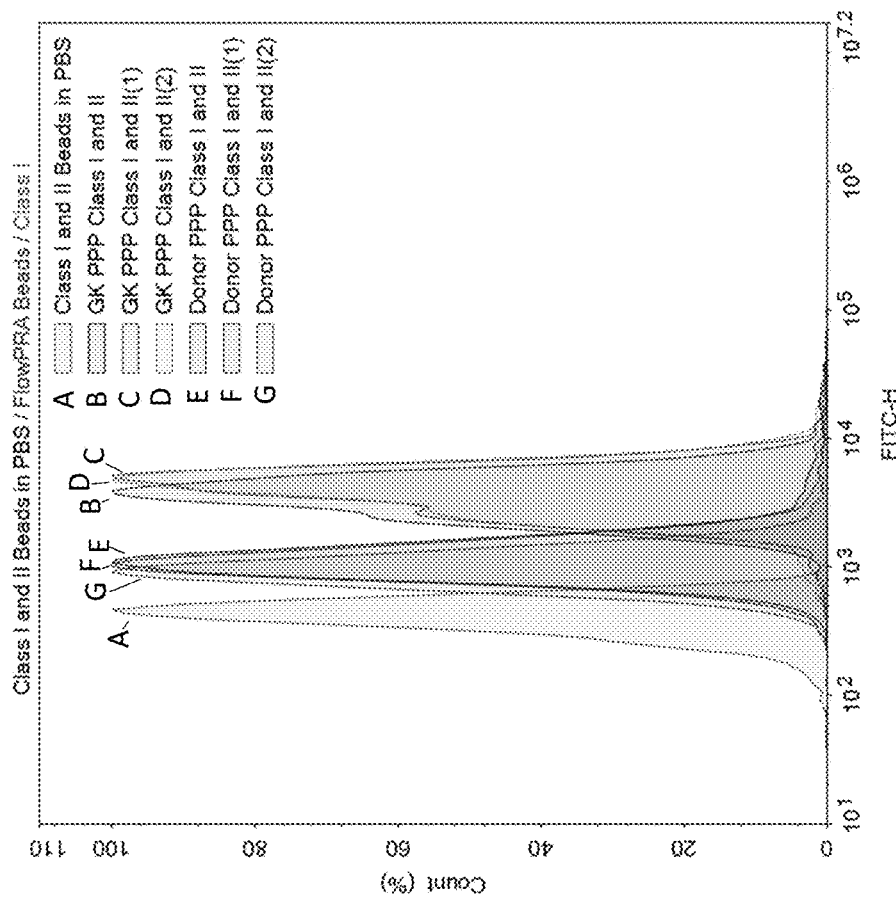
FIG. 2A shows an exemplary FITC-H histogram of FLOWPRA™ beads in PBS, supplier platelet-poor plasma (PPP) (in triplicate), and donor platelet-poor plasma gated on Class I HLA (in triplicate).
Figure 2B:
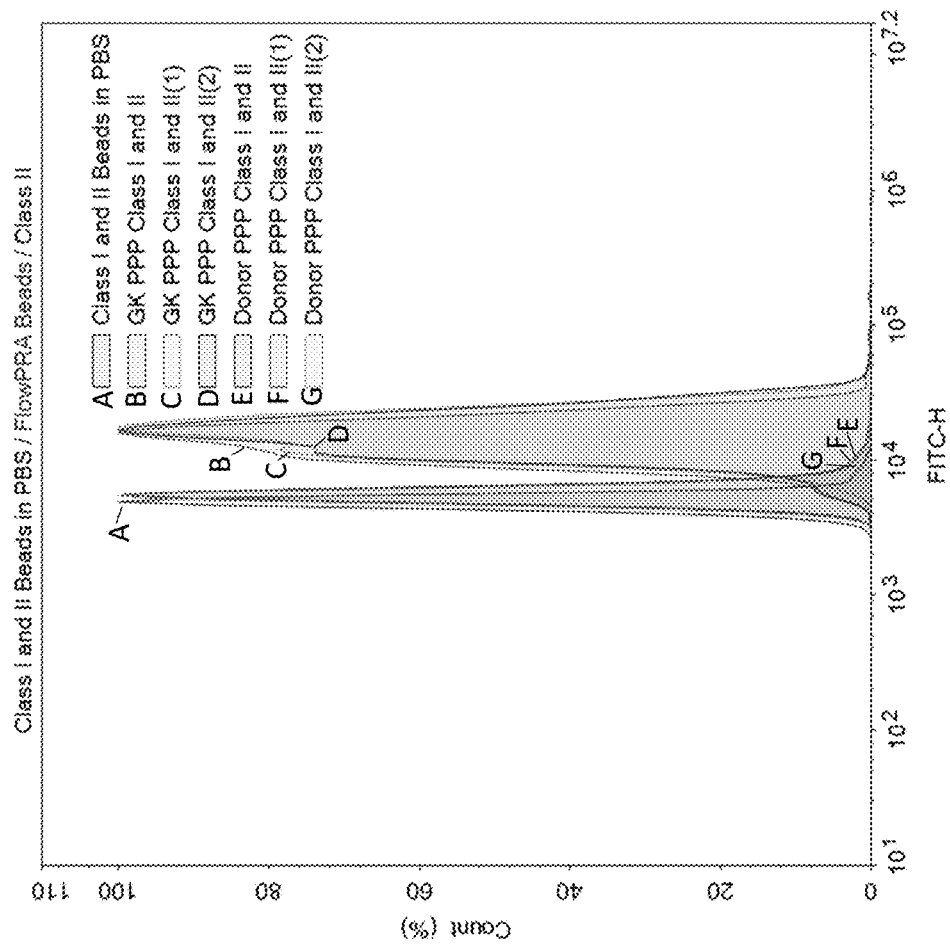
FIG. 2B shows an exemplary FITC-H histogram of FLOWPRA™ beads in PBS, supplier platelet-poor plasma (PPP) (in triplicate), and donor platelet-poor plasma gated on Class II HLA (in triplicate).
Figure 2C:
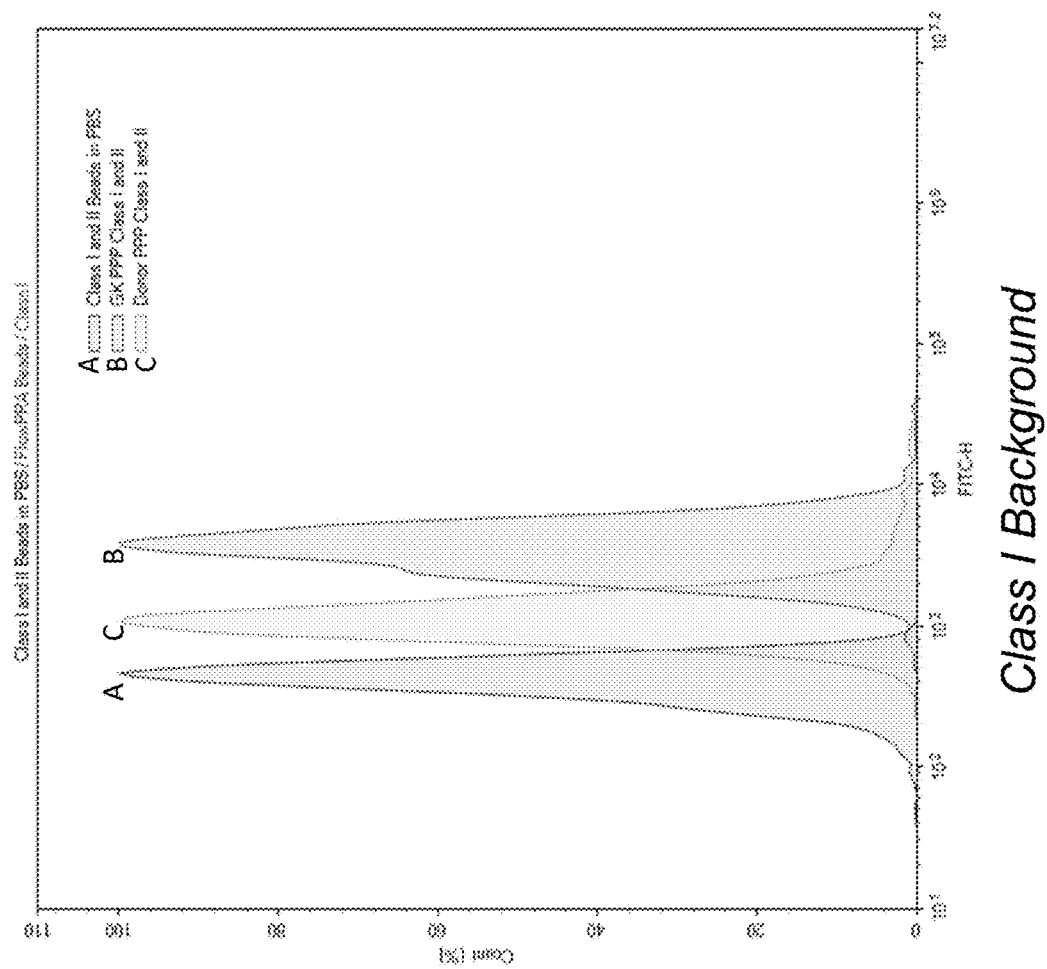
FIG. 2C shows an exemplary FITC-H histogram of FLOWPRA™ beads in PBS, supplier platelet-poor plasma (PPP) (single data set), and donor platelet-poor plasma gated on Class I HLA (single data set).
Figure 2D:
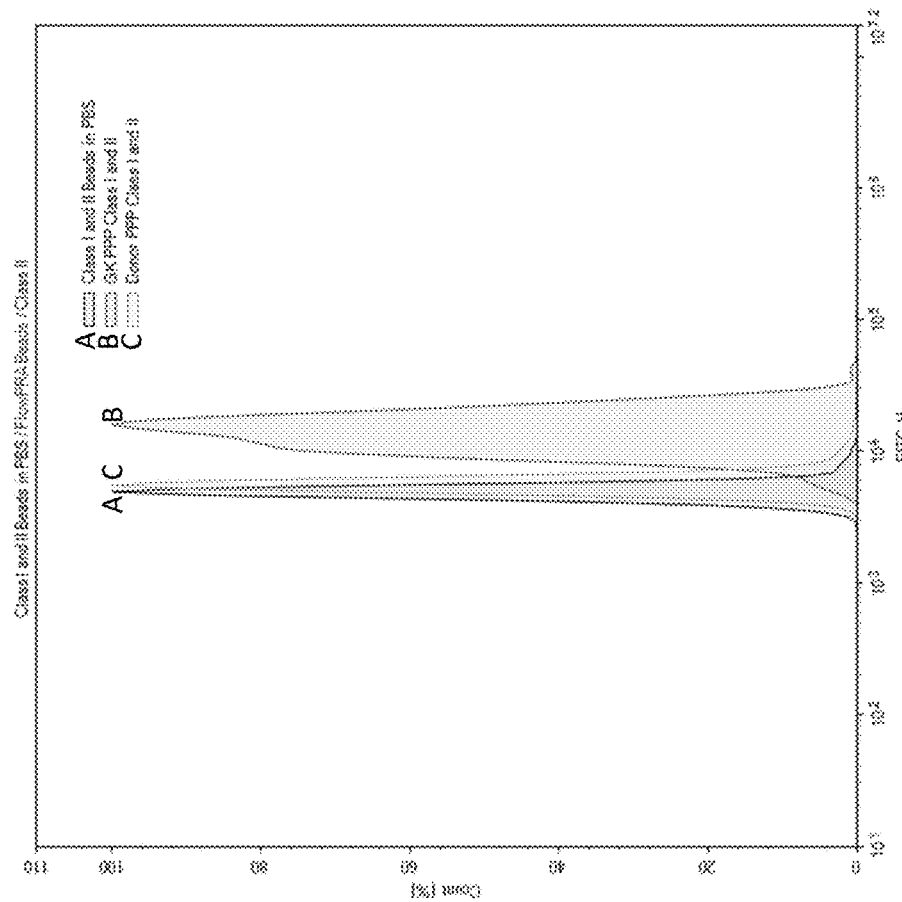
FIG. 2D shows an exemplary FITC-H histogram of FLOWPRA™ beads in PBS, supplier platelet-poor plasma (PPP) (single data set), and donor platelet-poor plasma gated on Class II HLA (single data set).
Figures 3A, 3B:
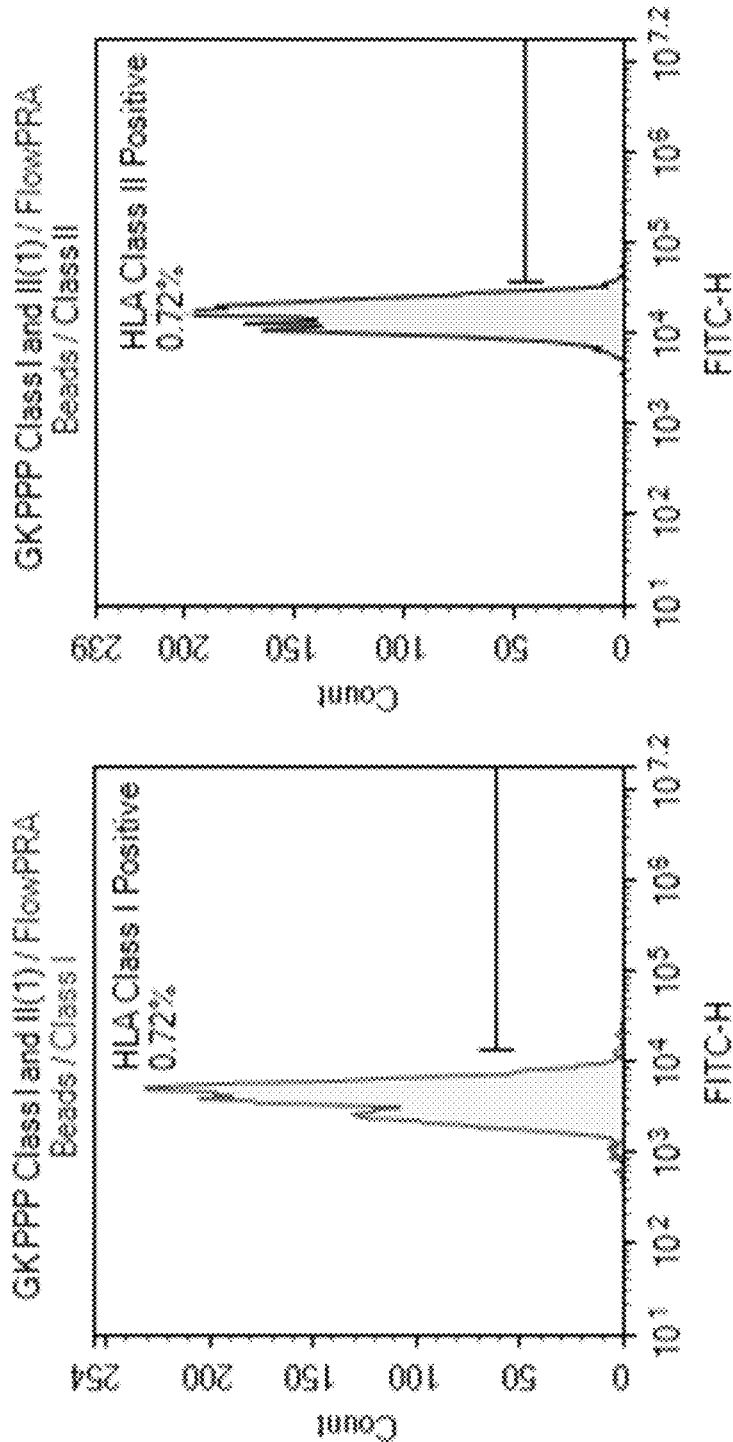
FIG. 3A shows an exemplary FITC-H histogram of FLOWPRA™ beads in George King PPP gated on Class I HLA.
FIG. 3B shows an exemplary FITC-H histogram of FLOWPRA™ beads in George King PPP gated on Class II HLA.

As used herein and in the appended claims, the term "platelet" can include whole platelets, fragmented platelets, and platelet derivatives.

As used herein and in the appended claims, the singular forms "a", "an", and "the" include plural referents unless the context clearly dictates otherwise. Thus, for example, reference to "a platelet" includes a plurality of such platelets. Furthermore, the use of terms that can be described using equivalent terms include the use of those equivalent terms. Thus, for example, the use of the term "subject" is to be understood to include the terms "patient", "individual" and other terms used in the art to indicate one who is subject to a treatment.

Unless defined otherwise, all technical and scientific terms used herein have the same meaning as commonly understood by one of ordinary skill in the art to which the term belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited. The present disclosure is controlling to the extent it conflicts with any incorporated publication.

DETAILED DESCRIPTION

It is to be understood that the terminology used herein is for the purpose of describing particular embodiments only, and is not intended to be limiting. Further, where a range of values is disclosed, the skilled artisan will understand that all other specific values within the disclosed range are inherently disclosed by these values and the ranges they represent without the need to disclose each specific value or range herein. For example, a disclosed range of 1-10 includes 1-9, 1-5, 2-10, 3.1-6, 1, 2, 3, 4, 5, and so forth. In addition, each disclosed range includes up to 5% lower for the lower value of the range and up to 5% higher for the higher value of the range. For example, a disclosed range of 4-10 includes 3.8-10.5. This concept is captured in this document by the term "about".

Unless defined otherwise, all technical and scientific terms used herein have the same meaning as commonly understood by one of ordinary skill in the art to which the term belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited. The present disclosure is controlling to the extent it conflicts with any incorporated publication.

As used herein and in the appended claims, the term "platelet" can include whole platelets, fragmented platelets, platelet derivatives, or thrombosomes. "Platelets" within the above definition may include, for example, platelets in whole blood, platelets in plasma, platelets in buffer optionally supplemented with select plasma proteins, cold stored platelets, dried platelets, cryopreserved platelets, thawed cryopreserved platelets, rehydrated dried platelets, rehydrated cryopreserved platelets, lyopreserved platelets, thawed lyopreserved platelets, or rehydrated lyopreserved platelets. "Platelets" may be "platelets" of mammals, such as of humans, or such as of non-human mammals.

As used herein, "thrombosomes" (sometimes also called Tsomes) are platelet derivatives that have been treated with a preparation agent (e.g., any of the preparation agents described herein) and lyopreserved (such as freeze-dried). In some cases, thrombosomes can be prepared from pooled platelets. Thrombosomes can have a shelf life of 2-3 years in dry form at ambient temperature and can be rehydrated with sterile water within minutes for immediate infusion. One example of thrombosomes are THROMBOSOMES®, which are in clinical trials for the treatment of acute hemorrhage in thrombocytopenic patients.

Transfusion-related acute lung injury (TRALI) is a condition believed to be caused by the presence of antibodies (e.g., Human Leukocyte Antigen (HLA), Human Neutrophil Antigen (HNA), or granulocyte antibodies) in a transfused blood product, which can react with antigens in a transfusion recipient.

The use of plasma-based blood products from donors considered to be high-risk or who test positive for Human Leukocyte Antigen (HLA) Class I, Class II, and neutrophil-specific antibodies are banned from use in transfusion or production of human-derived platelet products (e.g., compositions comprising platelets and/or platelet derivatives (e.g., thrombosomes)) and are therefore omitted from the donor pool.

The use of tangential flow filtration (TFF) or multi-pass centrifugation can reduce the amount of antibody in a blood product, for example, to limits not detectable by current, FDA-approved, testing methods. In some cases, reduction of certain plasma components (e.g., HLA antibodies) can allow for this donor population to be accepted for production of blood products (e.g., compositions comprising platelets and/or platelet derivatives (e.g., thrombosomes)). In some embodiments described herein, a blood product can be a composition that includes platelets and an aqueous medium.

Thrombosomes or cryopreserved platelet production can be limited by the availability of licensed apheresis collections performed at blood donor centers around the United States. Competition for these products can be fierce, and distribution for blood product manufacturing needs is usually prioritized below the needs of patient care. Blood product manufacturing (e.g., scale-up), could be aided by apheresis collections from otherwise deferred donors. One way this could be accomplished is by reducing free antibody levels in donor plasma to meet current, FDA approved, testing thresholds by utilizing tangential flow filtration (TFF) or centrifugation and plasma removal. Centrifugation of the raw materials (e.g., donor plasma), while typically more time consuming than TFF, can have a similar effect on the raw material. In some cases, removal of the donor plasma and replacement with buffer can allow the inventors to manufacture and characterize a final product (e.g., compositions comprising platelets and/or platelet derivatives (e.g., thrombosomes)) with a reduced protein (e.g., antibody (e.g., HLA antibody or HNA antibody)) content (e.g., as measured by absorbance at 280 nm). Such a product can increase the safety for a recipient of the product by reducing the transfusion related cause for TRALI.

In some embodiments, the materials and methods provided herein can allow previously deferred donors (such as those who screen positive for HLA antibodies or whose donor history presents a risk for positive HLA) to be allowed into the donor pool of raw materials used to manufacture blood products (e.g., compositions comprising platelets and/or platelet derivatives (e.g., thrombosomes)). In some embodiments described herein, a blood product can be a composition that includes platelets and an aqueous medium. Additionally, a reduction in HLA antibodies from the raw materials (e.g., donor apheresis material (e.g., platelets or pooled platelets)) can allow for a final product (e.g., compositions comprising platelets and/or platelet derivatives (e.g., thrombosomes)) to be labeled as HLA-reduced, increasing the safety of a product for a recipient.

In some embodiments, a blood product (e.g., compositions comprising platelets and/or platelet derivatives (e.g., thrombosomes)) as provided herein can have no detectable level of HLA antibodies. In some embodiments, a blood product (e.g., compositions comprising platelets and/or platelet derivatives (e.g., thrombosomes)) as provided herein can have no detectable level of an antibody selected from the group consisting of HLA Class I antibodies, HLA Class II antibodies, and HNA antibodies. In some embodiments, a blood product (e.g., compositions comprising platelets and/or platelet derivatives (e.g., thrombosomes)) as provided herein can have no detectable level of HLA Class I antibodies. In some embodiments, a blood product (e.g., compositions comprising platelets and/or platelet derivatives (e.g., thrombosomes)) as provided herein can have no detectable level of HLA Class II antibodies. In some embodiments, a blood product (e.g., compositions comprising platelets and/or platelet derivatives (e.g., thrombosomes)) as provided herein can have no detectable level of HNA antibodies. In some embodiments, detection of antibodies can be carried out using a regulatory agency approved (e.g., FDA cleared) assay. A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software. In some embodiments described herein, a blood product can be a composition that includes platelets and an aqueous medium.

In some embodiments, a blood product (e.g., compositions comprising platelets and/or platelet derivatives (e.g., thrombosomes)) as provided herein can have a level of an antibody selected from the group consisting of HLA Class I antibodies, HLA Class II antibodies, and HNA antibodies below a reference level. In some embodiments, a blood product (e.g., compositions comprising platelets and/or platelet derivatives (e.g., thrombosomes)) as provided herein can have a level of HLA Class I antibodies below a reference level. In some embodiments, a blood product (e.g., compositions comprising platelets and/or platelet derivatives (e.g., thrombosomes)) as provided herein can have a level of HLA Class II antibodies below a reference level. In some embodiments, a blood product (e.g., a composition comprising platelets and/or platelet derivatives (e.g., thrombosomes)) as provided herein can have a level of HNA antibodies below a reference level. A reference level can be any appropriate reference level. In some embodiments described herein, a blood product can be a composition that includes platelets and an aqueous medium.

In some embodiments, a blood product (e.g., a composition comprising platelets and/or platelet derivatives (e.g., thrombosomes)) as provided herein test negative for an antibody selected from the group consisting of HLA Class I antibodies, HLA Class II antibodies, and HNA antibodies in a regulatory agency approved assay (e.g., an FDA cleared assay). In some embodiments, a blood product (e.g., a composition comprising platelets and/or platelet derivatives (e.g., thrombosomes)) as provided herein can test negative for HLA Class I antibodies in a regulatory agency approved assay (e.g., an FDA cleared assay). In some embodiments, a blood product (e.g., a composition comprising platelets and/or platelet derivatives (e.g., thrombosomes)) as provided herein can test negative for HLA Class II antibodies a in regulatory agency approved assay (e.g., an FDA cleared assay). In some embodiments, a blood product (e.g., a composition comprising platelets and/or platelet derivatives (e.g., thrombosomes)) as provided herein can test negative for HNA antibodies in a regulatory agency approved assay (e.g., an FDA cleared assay). In some embodiments described herein, a blood product can be a composition that includes platelets and an aqueous medium. A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software.

Provided herein are compositions comprising platelets and/or platelet derivatives (e.g., thrombosomes) and an aqueous medium. In some embodiments, an aqueous medium can include a preparation agent (e.g., any of the preparation agents described herein). In some embodiments, an aqueous medium as provided herein can have a level of an antibody selected from the group consisting of HLA Class I antibodies, HLA Class II antibodies, and HNA antibodies below a reference level. In some embodiments, an aqueous medium as provided herein can have a level of HLA Class I antibodies below a reference level. In some embodiments, an aqueous medium as provided herein can have a level of HLA Class II antibodies below a reference level. In some embodiments, an aqueous medium as provided herein can have a level of HNA antibodies below a reference level. A reference level can be any appropriate reference level. In some embodiments, an aqueous medium as provided herein can test negative for an antibody selected from the group consisting of HLA Class I antibodies, HLA Class II antibodies, and HNA antibodies in a regulatory agency approved assay (e.g., an FDA cleared assay). In some embodiments, an aqueous medium as provided herein can test negative for HLA Class I antibodies in a regulatory agency approved assay (e.g., an FDA cleared assay). In some embodiments, an aqueous medium as provided herein can test negative for HLA Class II antibodies in a regulatory agency approved assay (e.g., an FDA cleared assay). In some embodiments, an aqueous medium as provided herein can test negative for HNA antibodies in a regulatory agency approved assay (e.g., an FDA cleared assay). A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software.

In some embodiments, an aqueous medium can have a reduced amount of residual plasma compared to donor apheresis plasma (e.g., single-donor apheresis plasma or pooled donor apheresis plasma) can be a percentage of residual plasma (e.g., less than or equal to about 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of residual plasma). In some embodiments, an aqueous medium can have a reduced amount of residual plasma compared to donor apheresis plasma (e.g., single-donor apheresis plasma or pooled donor apheresis plasma) can be a percentage range of residual plasma (e.g., about 5% to about 50%, about 5% to about 40%, about 5% to about 30%, about 5% to about 20%, about 5% to about 15%, about 5% to about 10%, about 10% to about 20%, about 7% to about 15%, about 7% to about 10%, about 8% to about 15%, about 8% to about 10%, about 0.1% to about 5%, about 0.1% to about 3%, about 0.1% to about 1%, about 0.5% to about 3%, about 0.5% to about 1%, or about 1% to about 3% of residual plasma). In some embodiments, an aqueous medium can have a protein concentration less than or equal to about 50% (e.g., less than or equal to about 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the protein concentration of donor apheresis plasma (e.g., single-donor apheresis plasma or pooled donor apheresis plasma). In some embodiments, an aqueous medium can have a protein concentration of about 5% to about 50% (e.g., about 5% to about 40%, about 5% to about 30%, about 5% to about 20%, about 5% to about 15%, about 5% to about 10%, about 10% to about 20%, about 7% to about 15%, about 7% to about 10%, about 8% to about 15%, or about 8% to about 10%) of the protein concentration of donor apheresis plasma (e.g., single-donor apheresis plasma or pooled donor apheresis plasma). In some embodiments, an aqueous medium can have a protein concentration of about 0.1% to about 5% (e.g., about 0.1% to about 3%, about 0.1% to about 1%, about 0.5% to about 3%, about 0.5% to about 1%, about 1% to about 2%, or about 1% to about 3%) of the protein concentration of donor apheresis plasma (e.g., single-donor apheresis plasma or pooled donor apheresis plasma). A protein concentration can be measured by any appropriate method. In some embodiments, a protein concentration can be measured by absorbance at 280 nm (A280). In some embodiments, an aqueous medium can have an A280 that is less that is less than 1.70 AU (e.g., less than 1.66, 1.6, 1.5, 1.4, 1.3, 1.2, 1.1, 1.0, 0.9, 0.8, 0.7, 0.6, 0.5, 0.4, 0.3, 0.2, or 0.1 AU) with a path length of 0.5 cm.

In some embodiments, an aqueous medium can have a HLA Class I antibody concentration less than about 70% (e.g., less than about 60%, 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the HLA Class I antibody concentration of donor apheresis plasma (e.g., single-donor apheresis plasma or pooled donor apheresis plasma). A HLA Class I antibody concentration can be measured by any appropriate method.

In some embodiments, an aqueous medium can have a HLA Class II antibody concentration less than about 50% (e.g., less than about 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%) of the HLA Class II antibody concentration of donor apheresis plasma (e.g., single-donor apheresis plasma or pooled donor apheresis plasma). A HLA Class II antibody concentration can be measured by any appropriate method.

In some embodiments, an aqueous medium can have a HNA antibody concentration less than about 50% (e.g., less than about 40%, 30%, 20%, 15%, 10%, 9%, 8%, 7%, 6%, 5% 4%, 3%, 2%, %, 0.9%, 0.8%, 0.7%, 0.6%, 0.5%, 0.4%, 0.3%, 0.2%, or 0.1%) of the HNA antibody concentration of donor apheresis plasma (e.g., single-donor apheresis plasma or pooled donor apheresis plasma). A HNA antibody concentration can be measured by any appropriate method.

In some embodiments, a composition as described herein can have a platelet count of at least $10^6$ (e.g., at least $5 \times 10^6$, $10^7$, $5 \times 10^7$, $10^8$, $5 \times 10^8$, $10^9$, $5 \times 10^9$, or $10^{10}$). In some embodiments, a composition as described herein can have a platelet count of at least about $200 \times 10^3$ platelets/µL (e.g., at least about $300 \times 10^3$, $400 \times 10^3$, $500 \times 10^3$, $750 \times 10^3$, $1000 \times 10^3$, $1500 \times 10^3$, $2000 \times 10^3$, or $2500 \times 10^3$ platelets/µL). In some embodiments, a composition as described herein can have a platelet count of at least about $2000 \times 10^3$ platelets/µL (e.g., at least about $2050 \times 10^3$, $2100 \times 10^3$, $2150 \times 10^3$, $2200 \times 10^3$, $2250 \times 10^3$, $2300 \times 10^3$, $2350 \times 10^3$, $2400 \times 10^3$, $2450 \times 10^3$, or $2500 \times 10^3$ platelets/µL). In some embodiments, a composition as described herein can have a platelet count less than or equal to $1000 \times 10^4$ platelets/µL.

In some embodiments, a composition as provided herein can include erythrocytes. In some embodiments, a composition as provided herein can have an erythrocyte count of less than about $10^{10}$ (e.g., less than $5 \times 10^9$, $10^9$, $5 \times 10^8$, $10^8$, $5 \times 10^7$, $10^7$, $5 \times 10^6$, or $10^6$). In some embodiments, the erythrocyte count can be less than $0.2 \times 10^6$/µL (e.g., less than $0.1 \times 10^6$/µL, $0.5 \times 10^5$/µL, or $0.1 \times 10^5$/µL).

In some cases, flow cytometry can be used to evaluate compositions as provided herein. In some embodiments, an antibody selected from the group consisting of HLA Class I antibodies, HLA Class II antibodies, and HNA antibodies, as determined for a composition comprising platelets and an aqueous medium by flow cytometry using beads coated with Class I HLAs, Class II HLAs, or HNAs, respectively, is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class I antibodies, as determined for a composition comprising platelets and an aqueous medium by flow cytometry using beads coated with Class I HLAs, is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class II antibodies, as determined for a composition comprising platelets and an aqueous medium by flow cytometry using beads coated with Class II HLAs is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HNA antibodies, as determined for a composition comprising platelets and an aqueous medium by flow cytometry using beads coated with HNAs is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%).

In some embodiments, an antibody selected from the group consisting of HLA Class I antibodies, HLA Class II antibodies, and HNA antibodies, as determined for an aqueous medium by flow cytometry using beads coated with Class I HLAs, Class II HLAs, or HNAs, respectively, is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class I antibodies, as determined for an aqueous medium by flow cytometry using beads coated with Class I HLAs, is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HLA Class II antibodies, as determined for an aqueous medium by flow cytometry using beads coated with Class II HLAs is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%). In some embodiments, the percentage of beads positive for HNA antibodies, as determined for an aqueous medium by flow cytometry using beads coated with HNAs is less than 10% (e.g., less than 9%, 8%, 7%, 6%, 5%, 4%, 3%, 2%, 1%, 0.9%, 0.8%, 0.7%, 0.6%, 0.5%, 0.4%, 0.3%, 0.2%, or 0.1%).

In some embodiments, a composition provided herein can include one or more additional components. In some embodiments, a composition provided herein can include a preparation agent (e.g., any of the preparation agents described herein). In some embodiments, the composition can include a buffering agent, a base, a loading agent, optionally a salt, and optionally at least one organic solvent. A buffering agent can be any appropriate buffering agent. In some embodiments, a buffering agent can be HEPES (4-(2-hydroxyethyl)-1-piperazineethanesulfonic acid). A base can be any appropriate base. In some embodiments, a base can be sodium bicarbonate. A loading agent can be any appropriate loading agent. In some embodiments, a loading agent can be a monosaccharide, a polysaccharide, or a combination thereof. In some embodiments, a loading agent can be selected from the group consisting of sucrose, maltose, trehalose, glucose, mannose, and xylose. In some embodiments, a loading agent can be trehalose. In some embodiments, a polysaccharide can be polysucrose. A salt can be any appropriate salt. In some embodiments, a salt can be sodium chloride, potassium chloride, or a combination thereof. An organic solvent can be any appropriate organic solvent. In some embodiments, an organic solvent can be selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

A preparation agent can include any appropriate components. In some embodiments, the preparation agent may comprise a liquid medium. In some embodiments the preparation agent may comprise one or more salts selected from phosphate salts, sodium salts, potassium salts, calcium salts, magnesium salts, and any other salt that can be found in blood or blood products, or that is known to be useful in drying platelets, or any combination of two or more of these.

In some embodiments, the preparation agent comprises one or more salts, such as phosphate salts, sodium salts, potassium salts, calcium salts, magnesium salts, and any other salt that can be found in blood or blood products. Exemplary salts include sodium chloride (NaCl), potassium chloride (KCl), and combinations thereof. In some embodiments, the preparation agent includes from about 0.5 mM to about 100 mM of the one or more salts. In some embodiments, the preparation agent includes from about 0.5 mM to about 100 mM (e.g., about 0.5 to about 2 mM, about 2 mM to about 90 mM, about 2 mM to about 6 mM, about 50 mM to about 100 mM, about 60 mM to about 90 mM, about 70 to about 85 mM) of the one or more salts. In some embodiments, the preparation agent includes about 5 mM, about 75 mM, or about 80 mM of the one or more salts. In some embodiments, the preparation agent comprises one or more salts selected from calcium salts, magnesium salts, and a combination of the two, in a concentration of about 0.5 mM to about 2 mM.

Preferably, these salts are present in the composition comprising platelets or platelet derivatives, such as freeze-dried platelets, at an amount that is about the same as is found in whole blood.

In some embodiments, the preparation agent further comprises a carrier protein. In some embodiments, the carrier protein comprises human serum albumin, bovine serum albumin, or a combination thereof. In some embodiments, the carrier protein is present in an amount of about 0.05% to about 1.0% (w/v).

The preparation agent may be any buffer that is non-toxic to the platelets and provides adequate buffering capacity to the solution at the temperatures at which the solution will be exposed during the process provided herein. Thus, the buffer may comprise any of the known biologically compatible buffers available commercially, such as phosphate buffers, such as phosphate buffered saline (PBS), bicarbonate/carbonic acid, such as sodium-bicarbonate buffer, N-2-hydroxyethylpiperazine-N'-2-ethanesulfonic acid (HEPES), and tris-based buffers, such as tris-buffered saline (TBS). Likewise, it may comprise one or more of the following buffers: propane-1,2,3-tricarboxylic (tricarballylic); benzenepentacarboxylic; maleic; 2,2-dimethylsuccinic; EDTA; 3,3-dimethylglutaric; bis(2-hydroxyethyl)imino-tris(hydroxymethyl)-methane (BIS-TRIS); benzenehexacarboxylic (mellitic); N-(2-acetamido)imino-diacetic acid (ADA); butane-1,2,3,4-tetracarboxylic; pyrophosphoric; 1,1-cyclopentanediacetic (3,3 tetramethylene-glutaric acid); piperazine-1,4-bis-(2-ethanesulfonic acid) (PIPES); N-(2-acetamido)-2-amnoethanesulfonic acid (ACES); 1,1-cyclohexanediacetic; 3,6-endomethylene-1,2,3,6-tetrahydrophthalic acid (EMTA; ENDCA); imidazole; 2-(aminoethyl)trimethylammonium chloride (CHOLAMINE); N,N-bis(2-hydroxyethyl)-2-aminoethanesulfonic acid (BES); 2-methylpropane-1,2,3-triscarboxylic (beta-methyltricarballylic); 2-(N-morpholino)propanesulfonic acid (MOPS); phosphoric; and N-tris(hydroxymethyl)methyl-2-aminoethane sulfonic acid (TES). In some embodiments, the preparation agent includes one or more buffers, e.g., N-2-hydroxyethylpiperazine-N'-2-ethanesulfonic acid (HEPES), or sodium-bicarbonate ($NaHCO_3$). In some embodiments, the preparation agent includes from about 5 to about 100 mM of the one or more buffers. In some embodiments, the preparation agent includes from about 5 to about 50 mM (e.g., from about 5 mM to about 40 mM, from about 8 mM to about 30 mM, about 10 mM to about 25 mM) about of the one or more buffers. In some embodiments, the preparation agent includes about 10 mM, about 20 mM, about 25 mM, or about 30 mM of the one or more buffers.

In some embodiments, the preparation agent includes one or more saccharides, such as monosaccharides and disaccharides, including sucrose, maltose, trehalose, glucose, mannose, dextrose, and xylose. In some embodiments, the saccharide is a monosaccharide. In some embodiments, the saccharide is a disaccharide. In some embodiments, the saccharide is a monosaccharide, a disaccharide, or a combination thereof. In some embodiments, the saccharide is a non-reducing disaccharide. In some embodiments, the saccharide is sucrose, maltose, trehalose, glucose (e.g., dextrose), mannose, or xylose. In some embodiments, the saccharide comprises trehalose. In some embodiments, the preparation agent comprises a starch. In some embodiments, the preparation agent includes polysucrose, a polymer of sucrose and epichlorohydrin. In some embodiments, the preparation agent includes from about 10 mM to about 1,000 mM of the one or more saccharides. In some embodiments, the preparation agent includes from about 50 to about 500 mM of the one or more saccharides. In some embodiments, one or more saccharides is present in an amount of from 10 mM 10 to 500 mM. In some embodiments, one or more saccharides is present in an amount of from 50 mM to 200 mM. In some embodiments, one or more saccharides is present in an amount from 100 mM to 150 mM. In some embodiments, the one or more saccharides are the lyophilizing agent; for example, in some embodiments, the lyophilizing agent comprises trehalose, polysucrose, or a combination thereof.

In some embodiments the composition comprising platelets or platelet derivatives, (e.g., thrombosomes), may comprise one or more of water or a saline solution. In some embodiments the composition comprising platelets or platelet derivatives, such as freeze-dried platelets, may comprise DMSO.

In some embodiments, the preparation agent comprises an organic solvent, such as an alcohol (e.g., ethanol). In such a preparation agent, the amount of solvent can range from 0.1% to 5.0% (v/v). In some embodiments, the organic solvent can range from about 0.1% (v/v) to about 5.0% (v/v), such as from about 0.3% (v/v) to about 3.0% (v/v), or from about 0.5% (v/v) to about 2% (v/v).

In some embodiments, suitable organic solvents include, but are not limited to alcohols, esters, ketones, ethers, halogenated solvents, hydrocarbons, nitriles, glycols, alkyl nitrates, water or mixtures thereof. In some embodiments, suitable organic solvents includes, but are not limited to methanol, ethanol, n-propanol, isopropanol, acetic acid, acetone, methyl ethyl ketone, methyl isobutyl ketone, methyl acetate, ethyl acetate, isopropyl acetate, tetrahydrofuran, isopropyl ether (IPE), tert-butyl methyl ether, dioxane (e.g., 1,4-dioxane), acetonitrile, propionitrile, methylene chloride, chloroform, toluene, anisole, cyclohexane, hexane, heptane, ethylene glycol, nitromethane, dimethylformamide, dimethyl sulfoxide, N-methyl pyrrolidone, dimethylacetamide, and combinations thereof. In some embodiments the organic solvent is selected from the group consisting of ethanol, acetic acid, acetone, acetonitrile, dimethylformamide, dimethyl sulfoxide (DMSO), dioxane, methanol, n-propanol, isopropanol, tetrahydrofuran (THF), N-methyl pyrrolidone, dimethylacetamide (DMAC), or combinations thereof. In some embodiments, the organic solvent comprises ethanol, DMSO, or a combination thereof. The presence of organic solvents, such as ethanol, can be beneficial in the processing of platelets, platelet derivatives, or thrombosomes (e.g., freeze-dried platelet derivatives).

In some embodiments the preparation agent does not include an organic solvent. In some embodiments, the preparation agent comprises an organic solvent. In some embodiments the preparation agent comprises DMSO.

A preparation agent can have any appropriate pH. For example, in some embodiments, a preparation agent can have a pH of about 6.0 to about 7.4 (e.g., about 6.5 to about 6.9, or about 6.6 to about 6.8).

In some embodiments, one or more other components may be combined with in the platelets (e.g., as part of a preparation agent). Exemplary components may include Prostaglandin E1 or Prostacyclin and or EDTA/EGTA to prevent platelet aggregation and activation.

In some embodiments, a preparation agent can be Buffer A, as shown in Example 1. In some embodiments, a preparation agent can comprise Buffer A, as shown in Example 1, wherein one or more components (e.g., ethanol) is present in an amount up to three times the amount shown in Example 1. Non-limiting examples of preparation agent compositions that may be used are shown in Tables P1-P6.

TABLE P1

Table P1. A preparation agent that can be used Buffer

| Component | Concentration (mM unless otherwise specified) |
| --- | --- |
| NaCl | 75.0 |
| KCl | 4.8 |
| HEPES | 9.5 |
| NaHCO$_3$ | 12.0 |
| Dextrose | 3 |
| Trehalose | 100 |
| Ethanol | 1% (v/v) |

TABLE P2

Table P2. A preparation agent that can be used Buffer

| Component | Concentration (mM unless otherwise specified) |
| --- | --- |
| NaCl | 75.0 |
| KCl | 4.8 |
| HEPES | 9.5 |
| NaHCO$_3$ | 12.0 |
| Dextrose | 3 |
| Trehalose | 100 |

TABLE P3

Table P3. A preparation agent that can be used. Buffer A1 (pH 6.5)

| Component | Concentration (mM unless specified otherwise) |
| --- | --- |
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |

TABLE P4

Table P4. Buffer B can be used when incubating platelets, e.g., for flow cytometry. Such an incubation can be done at room temperature in the dark. Albumin is an optional component of Buffer B. Buffer B

| Component | Concentration (mM unless otherwise specified) |
| --- | --- |
| Buffer and Salts | Table P5 (below) |
| BSA | 0.35% |
| Dextrose | 5 |
| pH | 7.4 |

TABLE P5

Concentration of HEPES and of Salts in Buffer B

| Component | Concentration (mM unless otherwise specified) |
| --- | --- |
| HEPES | 25 |
| NaCl | 119 |
| KCl | 5 |
| CaCl$_2$ | 2 |
| MgCl$_2$ | 2 |
| glucose | 6 g/l |

Table P5 shows the concentrations of HEPES and salts in Buffer B. The pH can be adjusted to 7.4 with NaOH. Albumin is an optional component of Buffer B.

TABLE P6

Tyrode's HEPES Buffer (plus PGE1)

| Component | Concentration (mM) |
| --- | --- |
| CaCl$_2$ | 1.8 |
| MgCl$_2$ | 1.1 |
| KCl | 2.7 |
| NaCl | 137 |
| NaH$_2$PO$_4$ | 0.4 |
| HEPES | 10 |
| D-glucose | 5.6 |
| pH | 6.5 |
| Prostaglandin E1 (PGE1) | 1 ug/ml |

Table P6 is another exemplary preparation agent.

In some embodiments, rehydrating the composition comprising platelets or platelet derivatives comprises adding to the platelets an aqueous liquid. In some embodiments, the aqueous liquid is water. In some embodiments, the aqueous liquid is an aqueous solution (e.g., a buffer). In some embodiments, the aqueous liquid is a saline solution. In some embodiments, the aqueous liquid is a suspension.

In some embodiments, the platelets or platelet derivatives (e.g., thrombosomes) have less than about 10%, such as less than about 8%, such as less than about 6%, such as less than about 4%, such as less than about 2%, such as less than about 0.5% crosslinking of platelet membranes via proteins and/or lipids present on the membranes. In some embodiments, the rehydrated platelets or platelet derivatives (e.g., thrombosomes), have less than about 10%, such as less than about 8%, such as less than about 6%, such as less than about 4%, such as less than about 2%, such as less than about 0.5% crosslinking of platelet membranes via proteins and/or lipids present on the membranes.

In some embodiments, the platelets or pooled platelets may be acidified to a pH of about 6.0 to about 7.4 prior to TFF or being diluted with the preparation agent. In some embodiments, the method comprises acidifying the platelets to a pH of about 6.5 to about 6.9. In some embodiments, the method comprises acidifying the platelets to a pH of about 6.6 to about 6.8. In some embodiments, the acidifying comprises adding to the pooled platelets a solution comprising Acid Citrate Dextrose (ACD).

In some embodiments, the platelets are isolated prior to the TFF or being diluted with the preparation agent. In some embodiments, the method further comprises isolating platelets by using centrifugation. In some embodiments, the centrifugation occurs at a relative centrifugal force (RCF) of about 1000×g to about 2000×g. In some embodiments, the centrifugation occurs at relative centrifugal force (RCF) of about 1300×g to about 1800×g. In some embodiments, the centrifugation occurs at relative centrifugal force (RCF) of about 1500×g. In some embodiments, the centrifugation occurs for about 1 minute to about 60 minutes. In some embodiments, the centrifugation occurs for about 10 minutes to about 30 minutes. In some embodiments, the centrifugation occurs for about 30 minutes.

In some embodiments, platelets are isolated, for example in a liquid medium, prior to treating a subject.

In some embodiments, platelets are donor-derived platelets. In some embodiments, platelets are obtained by a process that comprises an apheresis step. In some embodiments, platelets are pooled platelets.

In some embodiments, platelets are pooled from a plurality of donors. Such platelets pooled from a plurality of donors may be also referred herein to as pooled platelets. In some embodiments, the donors are more than 5, such as more than 10, such as more than 20, such as more than 50, such as up to about 100 donors. In some embodiments, the donors are from about 5 to about 100, such as from about 10 to about 50, such as from about 20 to about 40, such as from about 25 to about 35. Pooled platelets can be used to make any of the compositions described herein.

In some embodiments, platelets are derived in vitro. In some embodiments, platelets are derived or prepared in a culture. In some embodiments, preparing the platelets comprises deriving or growing the platelets from a culture of megakaryocytes. In some embodiments, preparing the platelets comprises deriving or growing the platelets (or megakaryocytes) from a culture of human pluripotent stem cells (PSCs), including embryonic stem cells (ESCs) and/or induced pluripotent stem cells (iPSCs).

Accordingly, in some embodiments, platelets or platelet derivatives (e.g., thrombosomes) are prepared prior to treating a subject as described herein. In some embodiments, the platelets or platelet derivatives (e.g., thrombosomes) are lyophilized. In some embodiments, the platelets or platelet derivatives (e.g., thrombosomes) are cryopreserved. For example, in some embodiments, the platelets or platelet derivatives can be cryopreserved in plasma and DMSO (e.g., 3-9% DMSO (e.g., 6% DMSO)). In some embodiments, the platelets or platelet derivatives are cryopreserved as described in U.S. Patent Application Publication No. 2020/0046771 A1, published on Feb. 13, 2020, incorporated herein by reference in its entirety.

In some embodiments, platelets (e.g., apheresis platelet, platelets isolated from whole blood, pooled platelets, or a combination thereof) form a suspension in a preparation agent comprising a liquid medium at a concentration from 10,000 platelets/μL to 10,000,000 platelets/μL, such as 50,000 platelets/μL to 2,000,000 platelets/μL, such as 100,000 platelets/μL to 500,000 platelets/μL, such as 150,000 platelets/μL to 300,000 platelets/μL, such as 200,000 platelets/μL.

In some embodiments, the method further comprises drying the platelets or platelet derivatives (e.g., thrombosomes). In some embodiments, the drying step comprises lyophilizing the platelets or platelet derivatives (e.g., thrombosomes). In some embodiments, the drying step comprises freeze-drying the platelets or platelet derivatives (e.g., thrombosomes). In some embodiments, the method further comprises rehydrating the platelets or platelet derivatives (e.g., thrombosomes) obtained from the drying step.

In some embodiments, the platelets or platelet derivatives (e.g., thrombosomes) are cold stored, cryopreserved, or lyophilized (e.g., to produce thrombosomes) prior to use in therapy or in functional assays.

Any known technique for drying platelets can be used in accordance with the present disclosure, as long as the technique can achieve a final residual moisture content of less than 5%. Preferably, the technique achieves a final residual moisture content of less than 2%, such as 1%, 0.5%, or 0.1%. Non-limiting examples of suitable techniques are freeze-drying (lyophilization) and spray-drying. A suitable lyophilization method is presented in Table LA. Additional exemplary lyophilization methods can be found in U.S. Pat. Nos. 7,811,558, 8,486,617, and 8,097,403. An exemplary spray-drying method includes: combining nitrogen, as a drying gas, with a preparation agent according to the present disclosure, then introducing the mixture into GEA Mobile Minor spray dryer from GEA Processing Engineering, Inc. (Columbia Md., USA), which has a Two-Fluid Nozzle configuration, spray drying the mixture at an inlet temperature in the range of 150° C. to 190° C., an outlet temperature in the range of 65° C. to 100° C., an atomic rate in the range of 0.5 to 2.0 bars, an atomic rate in the range of 5 to 13 kg/hr, a nitrogen use in the range of 60 to 100 kg/hr, and a run time of 10 to 35 minutes. The final step in spray drying is preferentially collecting the dried mixture. The dried composition in some embodiments is stable for at least six months at temperatures that range from −20° C. or lower to 90° C. or higher.

TABLE LA

Exemplary Lyophilization Protocol

| | Step | Temp. Set | Type | Duration | Pressure Set |
| --- | --- | --- | --- | --- | --- |
| Freezing Step | F1 | −50° C. | Ramp | Var | N/A |
| | F2 | −50° C. | Hold | 3 Hrs | N/A |
| Vacuum Pulldown | F3 | −50° | Hold | Var | N/A |
| Primary Dry | P1 | −40° | Hold | 1.5 Hrs | 0 mT |
| | P2 | −35° | Ramp | 2 Hrs | 0 mT |
| | P3 | −25° | Ramp | 2 Hrs | 0 mT |
| | P4 | −17° C. | Ramp | 2 Hrs | 0 mT |
| | P5 | 0° C. | Ramp | 1.5 Hrs | 0 mT |
| | P6 | 27° C. | Ramp | 1.5 Hrs | 0 mT |
| | P7 | 27° C. | Hold | 16 Hrs | 0 mT |
| Secondary Dry | S1 | 27° C. | Hold | >8 Hrs | 0 mT |

In some embodiments, the step of drying the platelets or platelet derivatives (e.g., thrombosomes) that are obtained as disclosed herein, such as the step of freeze-drying the platelets and/or platelet derivatives that are obtained as disclosed herein, comprises incubating the platelet and/or platelet derivatives with a lyophilizing agent (e.g., a non-reducing disaccharide). Accordingly, in some embodiments, the methods for preparing platelets and/or platelet derivatives further comprises incubating the platelets with a lyophilizing agent. In some embodiments the lyophilizing agent is a saccharide. In some embodiments the saccharide is a disaccharide, such as a non-reducing disaccharide.

In some embodiments, the platelets and/or platelet derivatives are incubated with a lyophilizing agent for a sufficient amount of time and at a suitable temperature to incubate the platelets with the lyophilizing agent. Non-limiting examples of suitable lyophilizing agents are saccharides, such as monosaccharides and disaccharides, including sucrose, maltose, trehalose, glucose (e.g., dextrose), mannose, and xylose. In some embodiments, non-limiting examples of lyophilizing agent include serum albumin, dextran, polyvinyl pyrrolidone (PVP), starch, and hydroxyethyl starch (HES). In some embodiments, exemplary lyophilizing agents can include a high molecular weight polymer. By "high molecular weight" it means a polymer having an average molecular weight of about or above 70 kDa and up to 1,000,000 kDa. Non-limiting examples are polymers of sucrose and epichlorohydrin (e.g., polysucrose). In some embodiments, the lyophilizing agent is polysucrose. Although any amount of high molecular weight polymer can be used as a lyophilizing agent, it is preferred that an amount be used that achieves a final concentration of about 3% to 10% (w/v), such as 3% to 7%, for example 6%.

An exemplary saccharide for use in the compositions disclosed herein is trehalose. Regardless of the identity of the saccharide, it can be present in the composition in any suitable amount. For example, it can be present in an amount of 1 mM to 1 M. In embodiments, it is present in an amount of from 10 mM 10 to 500 mM. In some embodiments, it is present in an amount of from 20 mM to 200 mM. In embodiments, it is present in an amount from 40 mM to 100 mM. In various embodiments, the saccharide is present in different specific concentrations within the ranges recited above, and one of skill in the art can immediately understand the various concentrations without the need to specifically recite each herein. Where more than one saccharide is present in the composition, each saccharide can be present in an amount according to the ranges and particular concentrations recited above.

In some cases, preparation of thrombosomes further comprises one or more of the procedures described in U.S. Pat. No. 8,486,617 (such as, e.g., Examples 1-5) and U.S. Pat. No. 8,097,403 (such as, e.g., Examples 1-3), incorporated herein by reference in their entirety. In some cases, a starting material (e.g., one or more donor platelet units) are initially pooled into a common vessel. In some embodiments, a starting material can comprise one or more donor platelet units. In some embodiments, a starting material can comprise donor plasma. The starting material may or may not be acidified with an anti-coagulation buffer (i.e. ACD-A) before centrifugation. Plasma can be aspirated off of the platelet pellet after centrifugation. Cell compatible buffer containing cryoprotectants (e.g., a loading buffer, which can be similar to or the same as a preparation agent) can be added to the platelet pellet before resuspending the cells into suspension. Platelets may or may not be diluted to a pre-determined concentration (e.g., 2200 k/ul to 2800 k/ul) with buffer if desired. Platelets in buffer may be incubated between 0 minutes and 240 minutes at an incubation temperature from 18° C. to 37° C. A lyoprotectant bulking agent (e.g., polysucrose) can be added to the platelets in buffer to achieve a final bulking agent concentration from 1% to 10% w/v (with preference at 6% w/v). The centrifuged processed platelets can then be filled into vials, lyophilized and thermally treated.

In some embodiments, the platelets or platelet derivatives (e.g., thrombosomes) have a particle size (e.g., diameter, max dimension) of at least about 0.5 µm (e.g., at least about at least about 0.6 µm, at least about 0.7 µm, at least about 0.8 µm, at least about 0.9 µm, at least about 1.0 µm, at least about 1.2 µm, at least about 1.5 µm, at least about 2.0 µm, at least about 2.5 µm, or at least about 5.0 µm). In some embodiments, the particle size is less than about 5.0 µm (e.g., less than about 2.5 µm, less than about 2.0 µm, less than about 1.5 µm, less than about 1.0 µm, less than about 0.9 µm, less than about 0.8 µm, less than about 0.7 µm, less than about 0.6 µm, less than about 0.5 µm, less than about 0.4 µm, or less than about 0.3 µm). In some embodiments, the particle size is from about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some embodiments, at least 50% (e.g., at least about 55%, at least about 60%, at least about 65%, at least about 70%, at least about 75%, at least about 80%, at least about 85%, at least about 90%, at least about 95%, or at least about 99%) of platelets or platelet derivatives (e.g., thrombosomes), have a particle size in the range of about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, at most 99% (e.g., at most about 95%, at most about 80%, at most about 75%, at most about 70%, at most about 65%, at most about 60%, at most about 55%, or at most about 50%) of the platelets or platelet derivatives (e.g., thrombosomes), are in the range of about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm). In some embodiments, about 50% to about 99% (e.g., about 55% to about 95%, about 60% to about 90%, about 65% to about 85, about 70% to about 80%) of the platelets or platelet derivatives (e.g., thrombosomes) are in the range of about 0.5 µm to about 5.0 µm (e.g., from about 0.5 µm to about 4.0 µm, from about 0.5 µm to about 2.5 µm, from about 0.6 µm to about 2.0 µm, from about 0.7 µm to about 1.0 µm, from about 0.5 µm to about 0.9 µm, or from about 0.6 µm to about 0.8 µm).

In some cases, a microparticle can be a particle having a particle size (e.g., diameter, max dimension) of less than about 0.5 µm (less than about 0.45 µm or 0.4 µm) In some cases, a microparticle can be a particle having a particle size of about 0.01 µm to about 0.5 µm (e.g., about 0.02 µm to about 0.5 µm).

Compositions comprising platelets or platelet derivatives (e.g., thrombosomes), such as those prepared according to methods described herein, can have a microparticle content that contributes to less than about 5.0% (e.g., less than about 4.5%, 4.0%, 3.5%, 3.0%, 2.5%, 2.0%, 1.5%, 1.0%, or 0.5%) of the total scattering intensity of all particles from about 1 nm to about 60,000 nm in radius in the composition. As used herein, a content of microparticles "by scattering intensity" refers to the microparticle content based on the scattering intensity of all particles from about 1 nm to about 60,000 nm in radius in the composition. The microparticle content can be measured by any appropriate method, for example, by dynamic light scattering (DLS). In some cases, the viscosity of a sample used for DLS can be at about 1.060 cP (or adjusted to be so), as this is the approximate viscosity of plasma.

Platelets or platelet derivatives (e.g., thrombosomes) as described herein can have cell surface markers. The presence of cell surface markers can be determined using any appropriate method. In some embodiments, the presence of cell surface markers can be determined using binding proteins (e.g., antibodies) specific for one or more cell surface markers and flow cytometry (e.g., as a percent positivity, e.g., using approximately $2.7 \times 10^5$ thrombosomes/μL; and about 4.8 μL of an anti-CD41 antibody, about 3.3 μL of an anti-CD42 antibody, about 1.3 μL of annexin V, or about 2.4 μL of an anti-CD62 antibody). Non-limiting examples of cell-surface markers include CD41 (also called glycoprotein IIb or GPIIb, which can be assayed using e.g., an anti-CD41 antibody), CD42 (which can be assayed using, e.g., an anti-CD42 antibody), CD62 (also called CD62P or P-selectin, which can be assayed using, e.g., an anti-CD62 antibody), phosphatidylserine (which can be assayed using, e.g., annexin V (AV)), and CD47 (which is used in self-recognition; absence of this marker, in some cases, can lead to phagocytosis). The percent positivity of any cell surface marker can be any appropriate percent positivity. For example, platelets or platelet derivatives (e.g., thrombosomes), such as those prepared by methods described herein, can have an average CD41 percent positivity of at least 55% (e.g., at least 60%, at least 65%, at least 67%, at least 70%, at least 75%, at least 80%, at least 85%, at least 90%, or at least 95%). As another example, platelets or platelet derivatives (e.g., thrombosomes), such as those described herein, can have an average CD42 percent positivity of at least 65% (e.g., at least 67%, at least 70%, at least 75%, at least 80%, at least 85%, at least 90%, or at least 95%). As another example, platelets or platelet derivatives (e.g., thrombosomes), such as those prepared by methods described herein, can have an average CD62 percent positivity of at least 10% (e.g., at least 15%, at least 20%, at least 25%, at least 30%, at least 35%, at least 40%, at least 45%, at least 50%, at least 55%, at least 60%, at least 65%, at least 70%, at least 75%, at least 80%, at least 82%, at least 83%, at least 84%, at least 85%, at least 90%, or at least 95%). As yet another example, platelets or platelet derivatives (e.g., thrombosomes), such as those prepared by methods described herein, can have an average annexin V positivity of at least 25% (e.g., at least 30%, at least 35%, at least 40%, at least 45%, at least 50%, at least 55%, at least 60%, at least 65%, at least 70%, at least 75%, at least 80%, at least 85%, at least 90%, at least 95%, at least 97%, or at least 99%). As another example, platelets or platelet derivatives (e.g., thrombosomes), such as those prepared by methods described herein, can have an average CD47 percent positivity of at least about 8% (e.g., at least about 10%, 15%, 20%, 25%, 30%, 35%, 40%, 45%, 50%, or 55%).

Glycoprotein VI (GPVI) is a platelet receptor for collagen, and the binding of collagen to GVPI activates the platelet. Receptor binding can be noticeably reduced in thrombosomes compared to fresh platelets. Without being bound by any particular theory, it is believed that the manufacturing process is blocking or destroying some copies of this receptor in thrombosomes, possibly to a reduction in collagen binding in thrombosomes relative to fresh platelets.

Platelets or platelet derivatives (e.g., thrombosomes) as described herein can have fibrinogen associated with the cell membrane. Aggregation of activated platelets is mediated by the formation of the GPIIb/IIIa complex, which can bind to fibrinogen (also called Factor 1) and form a clot. GPIIb/IIIa is a platelet fibrinogen receptor also known as CD41/CD61 complex. The GPIIb/IIIa clone PAC-1 binds to the active form of the GPIIb/IIIa. Without being bound by any particular theory, it is believed that the presence of fibrinogen on the cell membrane may be indicative of platelets or platelet derivatives (e.g., thrombosomes) capable of forming clots. Similarly without being bound by any particular theory, it is believed that a lack of binding by anti-PAC1 antibodies to the platelets or platelet derivatives (e.g., thrombosomes), such as those prepared by methods described herein, can be indicative of fibrinogen bound to the active form of GPIIb/GPIIIa, as PAC-1 binds to the same complex. In some cases, platelets or platelets derivatives (e.g., thrombosomes), such as those prepared by methods described herein, can have a greater amount of bound fibrinogen when they retain a higher amount of residual plasma.

Platelets or platelet derivatives (e.g., thrombosomes) as described herein can be capable of generating thrombin, for example, when in the presence of a reagent containing tissue factor and phospholipids. For example, in some cases, platelets or platelet derivatives (e.g., thrombosomes) (e.g., at a concentration of about $4.8 \times 10^3$ particles/μL) as described herein can generate a thrombin peak height (TPH) of at least 25 nM (e.g., at least 30 nM, 35 nM, 40 nM, 45 nM, 50 nM, 52 nM, 54 nM, 55 nM, 56 nM, 58 nM, 60 nM, 65 nM, 70 nM, 75 nM, or 80 nM) when in the presence of a reagent containing tissue factor (e.g., at 0.25 pM, 0.5 pM, 1 pM, 2 pM, 5 pM or 10 pM) and optionally phospholipids. For example, in some cases, platelets or platelet derivatives (e.g., thrombosomes) (e.g., at a concentration of about $4.8 \times 10^3$ particles/μL) as described herein can generate a TPH of about 25 nM to about 100 nM (e.g., about 25 nM to about 50 nM, about 25 to about 75 nM, about 50 to about 100 nM, about 75 to about 100 nM, about 35 nM to about 95 nM, about 45 to about 85 nM, about 55 to about 75 nM, or about 60 to about 70 nM) when in the presence of a reagent containing tissue factor and (e.g., at 0.25 pM, 0.5 pM, 1 pM, 2 pM, 5 pM or 10 pM) and optionally phospholipids. In some cases, platelets or platelet derivatives (e.g., thrombosomes) (e.g., at a concentration of about $4.8 \times 10^3$ particles/μL) as described herein can generate a TPH of at least 25 nM (e.g., at least 30 nM, 35 nM, 40 nM, 45 nM, 50 nM, 52 nM, 54 nM, 55 nM, 56 nM, 58 nM, 60 nM, 65 nM, 70 nM, 75 nM, or 80 nM) when in the presence of PRP Reagent (cat #TS30.00 from Thrombinoscope), for example, using conditions comprising 20 μL of PRP Reagent and 80 μL of a composition comprising about $4.8 \times 10^3$ particles/μL of platelets or platelet derivatives (e.g., thrombosomes). In some cases, platelets or platelet derivatives (e.g., thrombosomes) (e.g., at a concentration of about $4.8 \times 10^3$ particles/μL) as described herein can generate a TPH of about 25 nM to about 100 nM (e.g., about 25 nM to about 50 nM, about 25 to about 75 nM, about 50 to about 100 nM, about 75 to about 100 nM, about 35 nM to about 95 nM, about 45 to about 85 nM, about 55 to about 75 nM, or about 60 to about 70 nM) when in the presence of PRP Reagent (cat #TS30.00 from Thrombinoscope), for example, using conditions comprising 20 μL of PRP Reagent and 80 μL of a composition comprising about $4.8 \times 10^3$ particles/μL of platelets or platelet derivatives (e.g., thrombosomes).

Platelets or Platelet derivatives (e.g., thrombosomes) as described herein can be capable of generating thrombin, for example, when in the presence of a reagent containing tissue factor and phospholipids. For example, in some cases, platelets or platelet derivatives (e.g., thrombosomes) can have a potency of at least 1.2 (e.g., at least 1.3, 1.4, 1.5, 1.6, 1.7, 1.8, 1.9, 2.0, 2.1, 2.2, 2.3, 2.4, or 2.5) thrombin generation potency units (TGPU) per $10^6$ particles. For example, in some cases, platelets or platelet derivatives (e.g., thrombosomes) can have a potency of between 1.2 and 2.5 TPGU per $10^6$ particles (e.g., between 1.2 and 2.0, between 1.3 and 1.5, between 1.5 and 2.25, between 1.5 and 2.0, between 1.5 and 1.75, between 1.75 and 2.5, between 2.0 and 2.5, or between 2.25 and 2.5 TPGU per $10^6$ particles). TPGU can be calculated as follows: TGPU/million particles=[TPH in nM]*[Potency Coefficient in IU/(nM)]/[0.576 million particles in the well]. Similarly, the Potency Coefficient for a sample of thrombin can be calculated as follows: Potency Coefficient=Calculated Calibrator Activity (IU)/Effective Calibrator Activity (nM). In some cases, the calibrator activity can be based on a WHO international thrombin standard.

Platelets or platelet derivatives (e.g., thrombosomes) as described herein can be capable of aggregating, as determined, for example, by using a total thrombus-formation analysis system (T-TAS®). In some cases, platelets or platelet derivatives as described herein, when at a concentration of at least $70 \times 10^3$ particles/µL (e.g., at least $73 \times 10^3$, $100 \times 10^3$, $150 \times 10^3$, $173 \times 10^3$, $200 \times 10^3$, $250 \times 10^3$, or $255 \times 10^3$ particles/µL) can result in a T-TAS occlusion time (e.g., time to reach kPa of 80) of less than 14 minutes (e.g., less than 13.5, 13, 12.5, 12, 11.5, or 11 minutes), for example, in platelet-reduced citrated whole blood. In some cases, platelets or platelet derivatives as described herein, when at a concentration of at least $70 \times 10^3$ particles/µL (e.g., at least $73 \times 10^3$, $100 \times 10^3$, $150 \times 10^3$, $173 \times 10^3$, $200 \times 10^3$, $250 \times 10^3$, or $255 \times 10^3$ particles/µL) can result in an area under the curve (AUC) of at least 1300 (e.g., at least 1380, 1400, 1500, 1600, or 1700), for example, in platelet-reduced citrated whole blood.

Platelets or platelet derivatives (e.g., thrombosomes) as described herein can be capable of aggregating, for example, in the presence of an aggregation agonist. Non-limiting examples of aggregation agonists include thrombin and collagen. In some cases, platelets or platelet derivatives (e.g., thrombosomes) as described herein can have a percent aggregation of at least 5% (e.g., at least 10%, 15%, 20%, 25%, 30%, 35%, 40%, 45%, 50%, 55%, 60%, 65%, 67%, 70%, 75%, 85%, 90%, or 99%) in the presence of an aggregation agonist. In some cases, platelets or platelet derivatives (e.g., thrombosomes) as described herein can have a percent aggregation of about 25% to about 100% (e.g., about 25% to about 50%, about 25% to about 75%, about 50% to about 100%, about 75% to about 100%, about 40% to about 95%, about 55% to about 80%, or about 65% to about 75%) in the presence of an aggregation agonist. Percent aggregation can be determined by any appropriate method, for example, light transmission aggregometry.

Compositions comprising platelets or platelet derivatives (e.g., thrombosomes) as described herein can have appropriate conditions and amounts of cellular substrates and/or metabolites, such as pH, $pCO_2$, $pO_2$, $HCO_3$ concentration, total carbon dioxide ($TCO_2$), $sO_2$, and lactate concentration. Lactate can be the products of glycolysis. Without being bound by any particular theory, a starting material can have high lactate concentration because it has been stored ex vivo, respirating and performing glycolysis, for a period of time (e.g., about 3 days) by the time of manufacturing. For example, in some cases, the pH can be about 6.0 to about 7.5 (e.g., about 6.0 to about 7.4, about 6.9 to about 7.5, or about 7.0 to about 7.3). As another example, the $pCO_2$ can be about 10 to about 20 mmHg (e.g., about 10 to about 15 mmHg, about 15 to about 20 mmHg, or about 17 to about 19 mmHg). The $pO_2$ can be about 140 to about 165 mmHg (e.g., about 140 to about 150 mmHg, about 150 to about 160 mmgH, or about 160 to about 165 mmHg). The $HCO_3$ concentration can be about 4.5 to about 6.5 mmol/L (e.g., about 5.0 to about 6.0 mmol/L). The total carbon dioxide can be about 4 to about 8 mmol/L (e.g., about 5 to about 7 mmol/L). The $sO_2$ can be at least about 98% (e.g., at least about 99%). The lactate concentration can be less than about 2.0 mmol/L (e.g., less than 1.5 mmol/L or 1.0 mmol/L). The lactate concentration can be about 0.4 to about 1.3 mmol/L (e.g., about 0.5 to about 0.6 mmol/L, about 0.5 to about 1.0 mmol/L, or about 0.8 to about 1.3 mmol/L).

Platelet or platelet derivatives (e.g., thrombosomes) as described herein can retain some metabolic activity, for example, as evidenced by lactate dehydrogenase (LDH) activity. In some cases, platelets or platelet derivatives (e.g., thrombosomes) as described herein can retain at least about 10% (e.g., at least about 12%, 15%, 20%, 25%, 30%, 35%, 40%, or 45%) of the LDH activity of donor apheresis platelets. Without being bound by any particular theory, it is believed that the addition of increasing amounts of polysucrose increases the amount of LDH activity remained (e.g., products of a preparation agent with 8% polysucrose have more retained LDH activity than products of a preparation agent with 4% polysucrose). Similarly unbound by any particular theory, it is believed that thermal treatment of a lyophilized composition comprising platelets or platelet derivatives (e.g., thrombosomes) increases the amount of LDH activity retained. As another example, metabolic activity can be evidenced by retained esterase activity, such as the ability of the cells to cleave the acetate groups on carboxyfluorescein diacetate succinimidyl ester (CFDASE) to unmask a fluorophore.

The reduction of pathogens is generally desirable in blood products. Without being bound by any particular theory, it is believed that some methods of pathogen reduction can cause the formation of microparticles in the treated blood product. One method of pathogen reduction involves the use of a photosensitive nucleic acid-intercalating compound to alter the nucleic acids of pathogens upon illumination with an appropriate wavelength. The INTERCEPT® system (made by Cerus) uses amotosalen, a nucleic acid intercalating compound that forms cross-links in nucleic acid upon illumination with UVA.

A final blood product (e.g., platelets, cryopreserved platelets, freeze-dried platelets (e.g., thrombosomes)) as described herein can be prepared by any appropriate method. A final blood product (e.g., platelets, cryopreserved platelets, freeze-dried platelets (e.g., thrombosomes)) as described herein can be prepared by a method as disclosed herein. In some embodiments described herein, a final blood product can be a composition that includes platelets and an aqueous medium. In some embodiments, a final blood product can be the result of freeze-drying a composition that includes platelets and an aqueous medium, as described herein. In some embodiments, a final blood product can be prepared using tangential flow filtration (TFF) of a starting material (e.g., an unprocessed blood product (e.g., donor apheresis material (e.g., pooled donor apheresis material)), or a partially processed blood product (e.g., a blood product that has undergone filtration)). In some embodiments, a final blood product can be prepared using centrifugation of a starting material (e.g., an unprocessed blood product (e.g., donor apheresis material (e.g., pooled donor apheresis material)), or a partially processed blood product (e.g., a blood product that has undergone filtration)). It will be appreciated that while the methods described herein are generally described in the context of a starting material being apheresis material, other materials, such as platelets cultured in vitro, or whole blood, may be used. In some cases, platelets may be isolated from whole blood (e.g. pooled whole blood).

A starting material can be any appropriate starting material. In some embodiments, a starting material can have a protein concentration of about 60 to about 80 mg/mL. In some embodiments, a protein concentration can be based on the protein concentration in the plasma of whole blood. In some embodiments, a protein concentration can be based on the protein concentration of donor apheresis plasma. In some embodiments, a starting material can be donor blood product (e.g., whole blood or fractionated blood). In some embodiments, the starting material can be pooled donor blood product (e.g., pooled whole blood or pooled fractionated blood). In some embodiments, a starting material can include donor apheresis plasma. In some embodiments, a starting material can be derived from donor apheresis plasma. As used herein, "donor apheresis plasma" can refer to the plasma component of apheresis material, whether or not the material contains platelets or other blood cells.

In some embodiments, a starting material can be donor apheresis material (e.g., donor platelets or a pool of donor platelets). In some embodiments, a starting material is positive for one or more of: HLA Class I antibodies, HLA Class II antibodies, and HNA antibodies based on a regulatory agency-approved assay (e.g., an FDA cleared assay). In some embodiments, starting material can test positive for HLA Class I antibodies in a regulatory agency approved assay (e.g., an FDA cleared assay). In some embodiments, a starting material can test positive for HLA Class II antibodies in a regulatory agency approved assay (e.g., an FDA cleared assay). In some embodiments, starting material can test positive for HNA antibodies in a regulatory agency approved assay (e.g., an FDA cleared assay). A regulatory agency approved assay can be any appropriate regulatory agency approved assay. In some embodiments, a regulatory agency approved test can be the LABSCREEN™ Mixed by One Lambda. In some implementations, a regulatory agency approved test can be carried out using a LUMINEX® 100/200 or a LUMINEX® XY and the HLA FUSION™ software.

In some embodiments, a starting material can undergo a pathogen reduction step, for example, a nucleic acid intercalating compound that forms cross-links in nucleic acid upon illumination with UVA.

In some embodiments, a starting material (e.g., one or more units of donor platelets) can be initially pooled into a common vessel. The starting material may or may not be initially diluted with an acidified washing buffer (e.g., a control buffer). Without being bound by any particular theory, it is believed that washing with an acidified washing buffer can reduce platelet activation during processing. In some cases, a starting material can undergo two general processing pathways; either washed with control buffer (e.g. using TFF) until a desired residual component is reached (e.g., a percentage of residual donor plasma) before being concentrated to a final concentration; or the starting material can be concentrated to a final concentration before being washed with control buffer (e.g., using TFF) until a desired residual component is reached (e.g., a percentage of residual donor plasma). TFF processed material can then be filled into vials, lyophilized and thermally treated.

In some embodiments, the method can include an initial dilution step, for example, a starting material (e.g., an unprocessed blood product (e.g., donor apheresis material (e.g., pooled donor apheresis material)) can be diluted with a preparation agent (e.g., any of the preparation agents described herein) to form a diluted starting material. In some cases, the initial dilution step can include dilution with a preparation agent with a mass of preparation agent equal to at least about 10% of the mass of the starting material (e.g., at least about 15%, 25%, 50%, 75%, 100%, 150%, or 200% of the mass of the starting material. In some embodiments, an initial dilution step can be carried out using the TFF apparatus.

In some embodiments, the method can include concentrating (e.g., concentrating platelets) (e.g., concentrating a starting material or a diluted starting material) to form a concentrated platelet composition. For example, concentrated can include concentrating to a about $1000 \times 10^3$ to about $4000 \times 10^3$ platelets/μL (e.g., about $1000 \times 10^3$ to about $2000 \times 10^3$, about $2000 \times 10^3$ to about $3000 \times 10^3$, or about $4000 \times 10^3$ platelets/μL). In some embodiments, a concentration step can be carried out using the TFF apparatus.

The concentration of platelets or platelet derivatives (e.g., thrombosomes) can be determined by any appropriate method. For example, a counter can be used to quantitate concentration of blood cells in suspension using impedance (e.g., a Beckman Coulter AcT 10 or an AcT diff 2).

In some embodiments, TFF can include diafiltering (sometimes called "washing") of a starting material, a diluted starting material, a concentrated platelet composition, or a combination thereof. In some embodiments, diafiltering can include washing with at least 2 (e.g., at least 3, 4, 5, 6, 7, 8, 9, 10, or more) diavolumes. In some embodiments, TFF can include buffer exchange. In some embodiments, a buffer can be used in TFF. A buffer can be any appropriate buffer. In some embodiments, the buffer can be a preparation agent (e.g., any of the preparation agents described herein). In some embodiments, the buffer can be the same preparation agent as was used for dilution. In some embodiments, the buffer can be a different preparation than was used for dilution. In some embodiments, a buffer can include a lyophilizing agent, including a buffering agent, a base, a loading agent, optionally a salt, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof. A buffering agent can be any appropriate buffering agent. In some embodiments, a buffering agent can be HEPES ((4-(2-hydroxyethyl)-1-piperazineethanesulfonic acid). A base can be any appropriate base. In some embodiments, a base can be sodium bicarbonate. In some embodiments, a saccharide can be a monosaccharide. In some embodiments, a loading agent can be a saccharide. In some embodiments, a saccharide can include sucrose, maltose, trehalose, glucose (e.g., dextrose), mannose, or xylose. In some embodiments, a monosaccharide can be trehalose. In some embodiments, the loading agent can include polysucrose. A salt can be any appropriate salt. In some embodiments, a salt can be selected from the group consisting of sodium chloride (NaCl), potassium chloride (KCl), or a combination thereof.

In some embodiments, a membrane with a pore size of about 0.1 μm to about 1 μm (e.g., about 0.1 μm to about 1 μm, about 0.1 μm to about 0.5 μm, about 0.2 μm to about 0.45 μm, about 0.45 μm to about 1 μm, about 0.1 μm, about 0.2 μm, about 0.45 μm, about 0.65 μm, or about 1 μm) can be used in TFF. A membrane can be made from any appropriate material. In some cases, a membrane can be a hydrophilic membrane. In some embodiments, a membrane can be a hydrophobic membrane. In some embodiments, a membrane with a nominal molecular weight cutoff (NMWCO) of at least about 100 kDa (e.g., at least about 200, 300 kDa, 500 kDa, or 1000 kDa) can be used in TFF.

TFF can be performed at any appropriate temperature. In some embodiments, TFF can be performed at a temperature of about 20° C. to about 37° C. (e.g., about 20° C. to about 25° C., about 20° C. to about 30° C., about 25° C. to about 30° C., about 30° C. to about 35° C., about 30° C. to about 37° C., about 25° C. to about 35° C., or about 25° C. to about 37° C.). In some embodiments, TFF can be carried out at a flow rate (e.g., a circulating flow rate) of about 100 ml/min to about 800 ml/min (e.g., about 100 to about 200 ml/min, about 100 to about 400 ml/min, about 100 to about 600 ml/min, about 200 to about 400 ml/min, about 200 to about 600 ml/min, about 200 to about 800 ml/min, about 400 to about 600 ml/min, about 400 to about 800 ml/min, about 600 to about 800 ml/min, about 100 ml/min, about 200 ml/min, about 300 ml/min, about 400 ml/min, about 500 ml/min, about 600 ml/min, about 700 ml/min, or about 800 ml/min).

In some embodiments, TFF can be performed until a particular endpoint is reached, forming a TFF-treated composition. An endpoint can be any appropriate endpoint. In some embodiments, an endpoint can be a percentage of residual plasma (e.g., less than or equal to about 50%, 40%, 30%, 20%, 15%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% of residual plasma). In some embodiments, an endpoint can be a relative absorbance at 280 nm (A280). For example, an endpoint can be an A280 (e.g., using a path length of 0.5 cm) that is less than or equal to about 50% (e.g., less than or equal to about 40%, 30%, 20%, 15%, 10%, 9% 8%, 7% 6%, 5%, 4%, 3%, 2%, 1%, 0.9%, 0.8%, 0.7%, 0.6%, 0.5%, 0.4%, 0.3%, 0.2%, or 0.1%) of the A280 (e.g., using a path length of 0.5 cm) prior to TFF (e.g., of a starting material or of a diluted starting material). In some embodiments, an A280 can be relative to a system that measures 7.5% plasma=1.66 AU. In some embodiments, an instrument to measure A280 can be configured as follows: a 0.5 cm gap flow cell can be attached to the filtrate line of the TFF system. The flow cell can be connected to a photometer with fiber optics cables attached to each side of the flow cell (light source cable and light detector cable). The flow cell can be made with a silica glass lens on each side of the fiber optic cables. In some embodiments, an endpoint can be an absolute A280 (e.g., using a path length of 0.5 cm). For example, an endpoint can be an A280 that is less than or equal to 1.70 AU (e.g., less than or equal to 1.66, 1.6, 1.5, 1.4, 1.3, 1.2, 1.1, 1.0, 0.9, 0.8, 0.7, 0.6, 0.5, 0.4, 0.3, 0.2, or 0.1 AU) (e.g., using a path length of 0.5 cm). In some embodiments, a percentage of residual plasma, a relative A280, or an A280 can be determined based on the aqueous medium of a composition comprising platelets and an aqueous medium. In some embodiments, a percentage of residual plasma can be determined based on a known correlation to an A280. In some embodiments, an endpoint can be a platelet concentration, as TFF can include concentration or dilution of a sample (e.g., using a preparation agent). For example, an endpoint can be a platelet concentration of at least about $2000 \times 10^3$ platelets/μL (e.g., at least about $2050 \times 10^3$, $2100 \times 10^3$, $2150 \times 10^3$, $2200 \times 10^3$, $2250 \times 10^3$, $2300 \times 10^3$, $2350 \times 10^3$, $2400 \times 10^3$, $2450 \times 10^3$, or $2500 \times 10^3$ platelets/μL). As another example, an endpoint can be a platelet concentration of about $1000 \times 10^3$ to about $2500$ platelets/μL (e.g., about $1000 \times 10^3$ to about $2000 \times 10^3$, about $1500 \times 10^3$ to about $2300 \times 10^3$, or about $1700 \times 10^3$ to about $2300 \times 10^3$ platelets/μL) In some embodiments, an endpoint can include more than one criterion (e.g., a percentage of residual plasma and a platelet concentration, a relative A280 and a platelet concentration, or an absolute A280 and a platelet concentration).

Typically, a TFF-treated composition is subsequently lyophilized, optionally with a thermal treatment step, to form a final blood product (e.g., platelets, cryopreserved platelets, freeze-dried platelets (e.g., thrombosomes)). However, in some cases, a TFF-treated composition can be considered to be a final blood product.

In some embodiments, a blood product can be prepared using centrifugation of a blood product (e.g., an unprocessed blood product (e.g., donor apheresis material (e.g., pooled donor apheresis material)), or a partially processed blood product (e.g., a blood product that has undergone TFF)). In some embodiments, a blood product can be prepared without centrifugation of a blood product (e.g., an unprocessed blood product (e.g., donor apheresis material), or a partially processed blood product (e.g., a blood product that has undergone TFF)). Centrifugation can include any appropriate steps. In some embodiments, centrifugation can include a slow acceleration, a slow deceleration, or a combination thereof. In some embodiments, centrifugation can include centrifugation at about 1400×g to about 1550×g (e.g., about 1400 to about 1450×g, about 1450 to about 1500×g, or 1500 to about 1550×g, about 1400×g, about 1410×g, about 1430× g, about 1450×g, about 1470×g, about 1490×g, about 1500× g, about 1510×g, about 1530×g, or about 1550×g). In some embodiments, the duration of centrifugation can be about 10 min to about 30 min (e.g., about 10 to about 20 min, about 20 to about 30 min, about 10 min, about 20 min, or about 30 min).

In some embodiments, a final blood product can be prepared using both TFF and centrifugation (e.g., TFF followed by centrifugation or centrifugation followed by TFF).

Also provided herein are compositions prepared by any of the methods described herein.

In some embodiments, a composition as described herein can be analyzed at multiple points during processing. In some embodiments, a starting material (e.g., donor apheresis material (e.g., pooled donor apheresis material)) can be analyzed for antibody content (e.g., HLA or HNA antibody content). In some embodiments, a starting material (e.g., donor apheresis material (e.g., pooled donor apheresis material)) can be analyzed for protein concentration (e.g., by absorbance at 280 nm (e.g., using a path length of 0.5 cm)). In some embodiments, a composition in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of an unprocessed blood product) can be analyzed for antibody content (e.g., HLA or HNA antibody content). In some embodiments, the antibody content (e.g., HLA or HNA antibody content) of a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of the starting material. In some embodiments, a final blood product (e.g., (e.g., platelets, cryopreserved platelets, freeze-dried platelets (e.g., thrombosomes)) can be analyzed for antibody content (e.g., HLA or HNA antibody content). In some embodiments described herein, a final blood product can be a composition that includes platelets and an aqueous medium. In some embodiments, the antibody content (e.g., HLA or HNA antibody content) of a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of the starting material. In some embodiments, a final blood product can have no detectable level of an antibody selected from the group consisting of HLA Class I antibodies, HLA Class II antibodies, and HNA antibodies. In some embodiments, the aqueous medium of a composition as described herein can be analyzed as described herein.

In some embodiments, a composition as described herein can be analyzed at multiple points during processing. In some embodiments, donor apheresis plasma can be analyzed for antibody content (e.g., HLA or HNA antibody content). In some embodiments, donor apheresis plasma can be analyzed for protein concentration (e.g., by absorbance at 280 nm). In some embodiments, a composition in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of an unprocessed blood product) can be analyzed for antibody content (e.g., HLA or HNA antibody content). In some embodiments, the antibody content (e.g., HLA or HNA antibody content) of a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of donor apheresis plasma. In some embodiments, a final blood product (e.g., (e.g., platelets, cryopreserved platelets, freeze-dried platelets (e.g., thrombosomes)) can be analyzed for antibody content (e.g., HLA or HNA antibody content). In some embodiments described herein, a final blood product can be a composition that includes platelets and an aqueous medium. In some embodiments, the antibody content (e.g., HLA or HNA antibody content) of a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the antibody content of donor apheresis plasma. In some embodiments, a final blood product can have no detectable level of an antibody selected from the group consisting of HLA Class I antibodies, HLA Class II antibodies, and HNA antibodies. In some embodiments, the aqueous medium of a composition as described herein can be analyzed as described herein.

The protein concentration of a blood product can be measured by any appropriate method. In some embodiments, the protein concentration of a blood product can be measured using absorbance at 280 nm.

The antibody content (e.g., HLA or HNA antibody content) of a blood product can be measured by any appropriate method.

In some embodiments, a FLOWPRA™ Screening or a LABScreen Multi test kits from One Lambda, Thermo Fisher Scientific can be used as a method of HLA detection. Raw materials can be tested prior to the TFF or centrifugation processes to determine a baseline level of class I and II antibodies for Human Leukocyte Antigen (HLA) and Human Neutrophil Antigens (HNA). Testing can be repeated after processing by centrifugation or TFF to measure the removal of HLA and HNA. Additional testing points can be performed throughout the TFF procedure to maintain in-process control. Post-lyophilization and annealing, random samples can be selected from a batch and qualitative HLA/ HNA antibody testing can be performed to ensure reduction and compliance with current FDA testing and acceptance requirements.

In some embodiments, the antibody content (e.g., HLA or HNA antibody content) of two blood products can be compared by determining the percentage of beads positive for a marker (e.g., HLA or HNA coated beads bound to HLA or HNA antibodies, respectively). Any appropriate comparative method can be used. In some embodiments, the antibody content of two blood products can be compared using a method as described herein. In some embodiments, such a method can be carried out as follows. An aliquot of plasma (e.g., about 1 mL) platelet-poor plasma can be obtained. In some embodiments, an aliquot of filtered (e.g., using a 0.2 µm filter) platelet-poor plasma (PPP) (e.g., about 1 mL) can be obtained. Beads coated with Class I HLA and/or beads coated with Class II HLA can be added to the plasma (e.g., about 5 µL of each type of bead to about 20 µL of PPP) to form a mixture of PPP and beads. The mixture of PPP and beads can be vortexed. The mixture of PPP and beads can be incubated to form an incubated mixture. Any appropriate incubation conditions can be used. For example, in some embodiments, incubation can occur for a time (e.g., for about 30 minutes) at a temperature (e.g., at room temperature) with other conditions (e.g., in the dark) to form an incubated mixture. In some embodiments, incubation can include agitation (e.g., gentle rocking). The beads in the incubated mixture can be washed using any appropriate conditions. In some embodiments, the beads in the incubated mixture can be washed with a wash buffer. Washed beads can be separated from the incubated mixture by any appropriate method. In some embodiments, the washed beads can be separated by centrifugation (e.g., at 9,000×g for 2 minutes) to obtain pelleted beads. In some embodiments, the washing step can be repeated. The beads can be resuspended to form a bead solution. An antibody (e.g., an antibody that will bind to the assayed antibody content (e.g., HLA or HNA antibody content)) conjugated to a detectable moiety can be added to the bead solution (e.g., an αIgG conjugated to a fluorescent reporter, such as FITC). The antibody can be incubated with the bead solution under any appropriate conditions. In some embodiments, the antibody can be incubated for a time (e.g., for about 30 minutes) at a temperature (e.g., at room temperature) with other conditions (e.g., in the dark) to form labeled beads. Labeled beads can be washed to remove unbound antibody conjugated to a detectable moiety. The labeled beads can be washed using any appropriate conditions. In some embodiments, the labeled beads can be washed with a wash buffer. Washed labeled beads can be separated by any appropriate method. In some embodiments, the washed labeled beads can be separated by centrifugation (e.g., at 9,000 g for 2 minutes) to obtain pelleted labeled beads. In some embodiments, the washing step can be repeated. Labeled beads can be detected by any appropriate method. In some embodiments, labeled beads can be detected by flow cytometry. In some embodiments, detection can include measurement of the percentage of beads that are positive for the detectable moiety as compared to a negative control. In some embodiments, a negative control can be prepared as above, using a PPP sample that is known to be negative for antibodies (e.g. HLA Class I, HLA Class II, or HNA antibodies).

In some embodiments, a blood product (e.g., platelets, cryopreserved platelets, freeze-dried platelets (e.g., thrombosomes)) can be analyzed at multiple points during processing. In some embodiments, a starting material (e.g., donor apheresis material) can be analyzed to determine the percent of positive beads (e.g., HLA or HNA coated beads). In some embodiments, a starting material (e.g., donor apheresis material) can be analyzed for protein concentration (e.g., by absorbance at 280 nm). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, the percent of positive beads (e.g., HLA or HNA coated beads) from a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from a starting material. In some embodiments, the percent of positive beads (e.g., HLA or HNA coated beads) from a blood product in an intermediate step of processing can be less than or equal to 75% (e.g., less than or equal to 70%, 65%, 60%, 55%, 50%, 45%, 40%, 35%, 30%, 25%, 20%1, 5%, 10%, 9%, 8%, 7%, 6%, 5%, 4%, 3%, 2%, 1%, or less) of the total amount of beads. In some embodiments, a final blood product (e.g., (e.g., platelets, cryopreserved platelets, freeze-dried platelets (e.g., thrombosomes)) can be analyzed to determine the percent of positive beads (e.g., HLA or HNA coated beads). In some embodiments, the percent of positive beads (e.g., HLA or HNA coated beads) from a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from a starting material. In some embodiments, the percent of positive beads (e.g., HLA or HNA coated beads) from a final blood product can be less than or equal to 75% (e.g., less than or equal to 70%, 65%0, 60%, 55%, 50%4, 45%, 40%, 35%, 30%, 25%, 20%, 15%, 10%, 9%, 8%, 7%, 6%, 5%, 4%, 3%, 2%, 1%, or less) of the total amount of beads. In some embodiments, the aqueous medium of a composition as described herein can be analyzed as described herein.

In some embodiments, a blood product (e.g., platelets, cryopreserved platelets, freeze-dried platelets (e.g., thrombosomes)) can be analyzed at multiple points during processing. In some embodiments, donor apheresis plasma can be analyzed to determine the percent of positive beads (e.g., HLA or HNA coated beads). In some embodiments, donor apheresis plasma can be analyzed for protein concentration (e.g., by absorbance at 280 nm). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%°, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, a blood product in an intermediate step of processing (e.g., when protein concentration reduced to less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the protein concentration of a starting material) can be analyzed to determine the percent of positive beads (e.g., HLA or HNA coated beads). In some embodiments, the percent of positive beads (e.g., HLA or HNA coated beads) from a blood product in an intermediate step of processing can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from donor apheresis plasma. In some embodiments, the percent of positive beads (e.g., HLA or HNA coated beads) from a blood product in an intermediate step of processing can be less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less) of the total amount of beads. In some embodiments, a final blood product (e.g., (e.g., platelets, cryopreserved platelets, freeze-dried platelets (e.g., thrombosomes)) can be analyzed to determine the percent of positive beads (e.g., HLA or HNA coated beads). In some embodiments, the percent of positive beads (e.g., HLA or HNA coated beads) from a final blood product (e.g., (e.g., platelets, cryopreserved platelets, freeze-dried platelets (e.g., thrombosomes)) can be at least 5% reduced (e.g., 10%, 20%, 30%, 40%, 50%, 60%, 70%, 75%, 80%, 85%, 90%, 95%, 96%, 97%, 98%, 99%, or more, reduced) compared to the percent of positive beads from donor apheresis material. In some embodiments, the percent of positive beads (e.g., HLA or HNA coated beads) from a final blood product can be less than or equal to 75% (e.g., less than or equal to 70%, 65%, 60%, 55%, 50%, 45%, 40%, 35%, 30%, 25%, 20%, 15%, 10%, 9%, 8%, 7%, 6%, 5%, 4%, 3% 2%, 1%, or less) of the total amount of beads. In some embodiments, the aqueous medium of a composition as described herein can be analyzed as described herein.

A percentage of positive beads can be determined using any appropriate method. In some embodiments, positive beads can be determined compared to a negative control sample. A negative control sample can be any appropriate negative control sample. In some embodiments, a negative control sample can be used to determine positivity gating such that less than a certain percentage (e.g., between about 0.01% and about 1% (e.g., about 0.01% to about 0.05%, about 0.05% to about 0.1%, about 0.1% to about 0.5%, about 0.5% to about 1%, about 0.01%, about 0.05%, about 0.1%, about 0.5%, or about 1%)) of the negative control sample is present within the positivity gate. In some embodiments, a negative control sample can be a buffer (e.g., PBS). In some embodiments, a negative control sample can be a synthetic plasma composition. In some embodiments, a negative control sample can be a blood product known to be negative for the assayed antibodies (e.g., HLA or HNA antibodies).

Also provided herein is a method of reducing the percentage of an antibody (e.g., a HLA antibody (e.g., a HLA Class I antibody or a HLA Class II antibody) or a HNA antibody) in a composition (e.g., a blood product) comprising platelets, the method comprising filtering the composition by tangential flow filtration. Also provided herein is a method of reducing the amount of an antibody (e.g., a HLA antibody (e.g., a HLA Class I antibody or a HLA Class II antibody) or a HNA antibody) in a composition (e.g., a blood product) comprising platelets, the method comprising filtering the composition by tangential flow filtration. Also provided herein is a method of reducing the percentage of beads positive for an antibody (e.g., a HLA antibody (e.g., a HLA Class I antibody or a HLA Class II antibody) or a HNA antibody) in a composition (e.g., a blood product) comprising platelets, the method comprising filtering the composition by tangential flow filtration.

Also provided herein is a method of reducing the percentage of an antibody (e.g., a HLA antibody (e.g., a HLA Class I antibody or a HLA Class II antibody) or a HNA antibody) in a composition (e.g., a blood product) comprising platelets, the method comprising filtering the composition by centrifugation. Also provided herein is a method of reducing the amount of an antibody (e.g., a HLA antibody (e.g., a HLA Class I antibody or a HLA Class II antibody) or a HNA antibody) in a composition (e.g., a blood product) comprising platelets, the method comprising filtering the composition by centrifugation. Also provided herein is a method of reducing the percentage of beads positive for an antibody (e.g., a HLA antibody (e.g., a HLA Class I antibody or a HLA Class II antibody) or a HNA antibody) in a composition (e.g., a blood product) comprising platelets, the method comprising filtering the composition by centrifugation.

In some embodiments of any of the methods described herein, the amount of an antibody (e.g., a HLA antibody (e.g., a HLA Class I antibody or a HLA Class II antibody) or a HNA antibody) in a composition (e.g., a blood product) can be reduced to below a reference level. A reference level can be any appropriate reference level. In some embodiments of any of the methods described herein, the percentage of beads positive an antibody (e.g., a HLA antibody (e.g., a HLA Class I antibody or a HLA Class II antibody) or a HNA antibody) in a composition (e.g., a blood product) can be reduced as compared to the blood product before undergoing the methods described herein. A percentage of beads positive for an antibody can be reduced by any appropriate amount. In some embodiments, a percentage of beads positive for an antibody can be reduced by at least 5% (e.g., reduced by at least 10%, 20%, 30%, 40%, 50%, 60%, 70%, 75%, 80%, 85%, 90%, 95%, 96%, 97%, 98%, 99%, or more) compared to the blood product before undergoing any of the methods described herein.

In some embodiments, a composition as described herein can undergo any appropriate additional processing steps. In some embodiments, a composition as described herein can be freeze-dried. In some embodiments, freeze-dried platelets can be thermally treated (e.g., at about 80° C. for about 24 hours).

For example, in some embodiments, a composition can be cryopreserved or freeze-dried. In some embodiments, a first composition (e.g., a composition comprising platelets and an aqueous medium as described herein) can be treated with a mixture. In some embodiments, a mixture can include a lyophilizing agent, including a base, a loading agent, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof, to form a second composition comprising platelets. In some embodiments, a loading agent can be a saccharide. In some embodiments, a saccharide can be a monosaccharide. In some embodiments, a saccharide can be sucrose, maltose, trehalose, glucose (e.g., dextrose), mannose, or xylose. In some embodiments, the loading agent can be polysucrose.

In some embodiments, a first composition or a second composition can be dried. In some embodiments, a first composition or a second composition can be dried with a cryoprotectant. In some embodiments, a cryoprotectant can include a saccharide, optionally a base, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof to form a third composition. In some embodiments, a cryoprotectant can be polysucrose.

In some embodiments, a first composition or a second composition can be freeze-dried. In some embodiments, a first composition or a second composition can be freeze-dried with a cryoprotectant. In some embodiments, a cryoprotectant can include a saccharide, optionally a base, and optionally at least one organic solvent such as an organic solvent selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), or combinations thereof to form a fourth composition. In some embodiments freeze-drying can occur at a temperature of about −40° C. to about 5° C. In some embodiments, freeze-drying can occur over a gradient (e.g., about −40° C. to about 5° C.). In some embodiments, a secondary drying step can be carried out (e.g., at about 20° C. to about 40° C.).

Also provided herein are blood products (e.g., platelets, cryopreserved platelets, freeze-dried platelets (e.g., thrombosomes)) produced by any of the methods described herein.

In some embodiments, the percentage of beads positive for an antibody selected from the group consisting of HLA Class I antibodies, HLA Class II antibodies, and HNA antibodies, as determined for a composition as described herein by flow cytometry using beads coated with Class I HLAs, Class II HLAs, or HNAs, respectively, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

In some embodiments, the percentage of beads positive for HLA Class I antibodies, as determined for a composition as described herein by flow cytometry using beads coated with Class I HLAs, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

In some embodiments, the percentage of beads positive for HLA Class II antibodies, as determined for a composition as described herein by flow cytometry using beads coated with Class II HLAs, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

In some embodiments, the percentage of beads positive for HNA antibodies, as determined for a composition as described herein by flow cytometry using beads coated with HNAs, is reduced by at least 10% (e.g., at least 20%, 30%, 40%, 50%, 60%, 70%, 75%, 80%, 85%, 90%, 95%, or 99%) as compared to a similar composition not prepared by a process comprising tangential flow filtration of a composition comprising platelets, centrifugation of a composition comprising platelets, or a combination thereof.

Within the process provided herein for making the compositions provided herein, optional addition of a lyophilizing agent can be the last step prior to drying. However, in some embodiments, the lyophilizing agent can be added at the same time or before other components of the composition, such as a salt, a buffer, optionally a cryoprotectant, or other components. In some embodiments, the lyophilizing agent is added to a preparation agent, thoroughly mixed to form a drying solution, dispensed into a drying vessel (e.g., a glass or plastic serum vial, a lyophilization bag), and subjected to conditions that allow for drying of a TFF-treated composition to form a dried composition.

In various embodiments, the lyophilization bag is a gas-permeable bag configured to allow gases to pass through at least a portion or all portions of the bag during the processing. The gas-permeable bag can allow for the exchange of gas within the interior of the bag with atmospheric gas present in the surrounding environment. The gas-permeable bag can be permeable to gases, such as oxygen, nitrogen, water, air, hydrogen, and carbon dioxide, allowing gas exchange to occur in the compositions provided herein. In some embodiments, the gas-permeable bag allows for the removal of some of the carbon dioxide present within an interior of the bag by allowing the carbon dioxide to permeate through its wall. In some embodiments, the release of carbon dioxide from the bag can be advantageous to maintaining a desired pH level of the composition contained within the bag.

In some embodiments, the container of the process herein is a gas-permeable container that is closed or sealed. In some embodiments, the container is a container that is closed or sealed and a portion of which is gas-permeable. In some embodiments, the surface area of a gas-permeable portion of a closed or sealed container (e.g., bag) relative to the volume of the product being contained in the container (hereinafter referred to as the "SA/V ratio") can be adjusted to improve pH maintenance of the compositions provided herein. For example, in some embodiments, the SA/V ratio of the container can be at least about 2.0 $cm^2/mL$ (e.g., at least about 2.1 $cm^2/mL$, at least about 2.2 $cm^2/mL$, at least about 2.3 $cm^2/mL$, at least about 2.4 $cm^2/mL$, at least about 2.5 $cm^2/mL$, at least about 2.6 $cm^2/mL$, at least about 2.7 $cm^2/mL$, at least about 2.8 $cm^2/mL$, at least about 2.9 $cm^2/mL$, at least about 3.0 $cm^2/mL$, at least about 3.1 $cm^2/mL$, at least about 3.2 $cm^2/mL$, at least about 3.3 $cm^2/mL$, at least about 3.4 $cm^2/mL$, at least about 3.5 $cm^2/mL$, at least about 3.6 $cm^2/mL$, at least about 3.7 $cm^2/mL$, at least about 3.8 $cm^2/mL$, at least about 3.9 $cm^2/mL$, at least about 4.0 $cm^2/mL$, at least about 4.1 $cm^2/mL$, at least about 4.2 $cm^2/mL$, at least about 4.3 $cm^2/mL$, at least about 4.4 $cm^2/mL$, at least about 4.5 $cm^2/mL$, at least about 4.6 $cm^2/mL$, at least about 4.7 $cm^2/mL$, at least about 4.8 $cm^2/mL$, at least about 4.9 $cm^2/mL$, or at least about 5.0 $cm^2/mL$. In some embodiments, the SA/V ratio of the container can be at most about 10.0 $cm^2/mL$ (e.g., at most about 9.9 $cm^2/mL$, at most about 9.8 $cm^2/mL$, at most about 9.7 $cm^2/mL$, at most about 9.6 $cm^2/mL$, at most about 9.5 $cm^2/mL$, at most about 9.4 $cm^2/mL$, at most about 9.3 $cm^2/mL$, at most about 9.2 $cm^2/mL$, at most about 9.1 $cm^2/mL$, at most about 9.0 $cm^2/mL$, at most about 8.9 $cm^2/mL$, at most about 8.8 $cm^2/mL$, at most about 8.7 $cm^2/mL$, at most about 8.6, at most about 8.5 $cm^2/mL$, at most about 8.4 $cm^2/mL$, at most about 8.3 $cm^2/mL$, at most about 8.2 $cm^2/mL$, at most about 8.1 $cm^2/mL$, at most about 8.0 $cm^2/mL$, at most about 7.9 $cm^2/mL$, at most about 7.8 $cm^2/mL$, at most about 7.7 $cm^2/mL$, at most about 7.6 $cm^2/mL$, at most about 7.5 $cm^2/mL$, at most about 7.4 $cm^2/mL$, at most about 7.3 $cm^2/mL$, at most about 7.2 $cm^2/mL$, at most about 7.1 $cm^2/mL$, at most about 6.9 $cm^2/mL$, at most about 6.8 $cm^2/mL$, at most about 6.7 $cm^2/mL$, at most about 6.6 $cm^2/mL$, at most about 6.5 $cm^2/mL$, at most about 6.4 $cm^2/mL$, at most about 6.3 $cm^2/mL$, at most about 6.2 $cm^2/mL$, at most about 6.1 $cm^2/mL$, at most about 6.0 $cm^2/mL$, at most about 5.9 $cm^2/mL$, at most about 5.8 $cm^2/mL$, at most about 5.7 $cm^2/mL$, at most about 5.6 $cm^2/mL$, at most about 5.5 $cm^2/mL$, at most about 5.4 $cm^2/mL$, at most about 5.3 $cm^2/mL$, at most about 5.2 $cm^2/mL$, at most about 5.1 $cm^2/mL$, at most about 5.0 $cm^2/mL$, at most about 4.9 $cm^2/mL$, at most about 4.8 $cm^2/mL$, at most about 4.7 $cm^2/mL$, at most about 4.6 $cm^2/mL$, at most about 4.5 $cm^2/mL$, at most about 4.4 $cm^2/mL$, at most about 4.3 $cm^2/mL$, at most about 4.2 $cm^2/mL$, at most about 4.1 $cm^2/mL$, or at most about 4.0 $cm^2/mL$. In some embodiments, the SA/V ratio of the container can range from about 2.0 to about 10.0 $cm^2/mL$ (e.g., from about 2.1 $cm^2/mL$ to about 9.9 $cm^2/mL$, from about 2.2 $cm^2/mL$ to about 9.8 $cm^2/mL$, from about 2.3 $cm^2/mL$ to about 9.7 $cm^2/mL$, from about 2.4 $cm^2/mL$ to about 9.6 $cm^2/mL$, from about 2.5 $cm^2/mL$ to about 9.5 $cm^2/mL$, from about 2.6 $cm^2/mL$ to about 9.4 $cm^2/mL$, from about 2.7 $cm^2/mL$ to about 9.3 $cm^2/mL$, from about 2.8 $cm^2/mL$ to about 9.2 $cm^2/mL$, from about 2.9 $cm^2/mL$ to about 9.1 $cm^2/mL$, from about 3.0 $cm^2/mL$ to about 9.0 $cm^2/mL$, from about 3.1 $cm^2/mL$ to about 8.9 $cm^2/mL$, from about 3.2 $cm^2/mL$ to about 8.8 $cm^2/mL$, from about 3.3 $cm^2/mL$ to about 8.7 $cm^2/mL$, from about 3.4 $cm^2/mL$ to about 8.6 $cm^2/mL$, from about 3.5 $cm^2/mL$ to about 8.5 $cm^2/mL$, from about 3.6 $cm^2/mL$ to about 8.4 $cm^2/mL$, from about 3.7 $cm^2/mL$ to about 8.3 $cm^2/mL$, from about 3.8 $cm^2/mL$ to about 8.2 $cm^2/mL$, from about 3.9 $cm^2/mL$ to about 8.1 $cm^2/mL$, from about 4.0 $cm^2/mL$ to about 8.0 $cm^2/mL$, from about 4.1 $cm^2/mL$ to about 7.9 $cm^2/mL$, from about 4.2 $cm^2/mL$ to about 7.8 $cm^2/mL$, from about 4.3 $cm^2/mL$ to about 7.7 $cm^2/mL$, from about 4.4 $cm^2/mL$ to about 7.6 $cm^2/mL$, from about 4.5 $cm^2/mL$ to about 7.5 $cm^2/mL$, from about 4.6 $cm^2/mL$ to about 7.4 $cm^2/mL$, from about 4.7 $cm^2/mL$ to about 7.3 $cm^2/mL$, from about 4.8 $cm^2/mL$ to about 7.2 $cm^2/mL$, from about 4.9 $cm^2/mL$ to about 7.1 $cm^2/mL$, from about 5.0 $cm^2/mL$ to about 6.9 $cm^2/mL$, from about 5.1 $cm^2/mL$ to about 6.8 $cm^2/mL$, from about 5.2 $cm^2/mL$ to about 6.7 $cm^2/mL$, from about 5.3 $cm^2/mL$ to about 6.6 $cm^2/mL$, from about 5.4 $cm^2/mL$ to about 6.5 $cm^2/mL$, from about 5.5 $cm^2/mL$ to about 6.4 $cm^2/mL$, from about 5.6 $cm^2/mL$ to about 6.3 $cm^2/mL$, from about 5.7 $cm^2/mL$ to about 6.2 $cm^2/mL$, or from about 5.8 $cm^2/mL$ to about 6.1 $cm^2/mL$.

Gas-permeable closed containers (e.g., bags) or portions thereof can be made of one or more various gas-permeable materials. In some embodiments, the gas-permeable bag can be made of one or more polymers including fluoropolymers (such as polytetrafluoroethylene (PTFE) and perfluoroalkoxy (PFA) polymers), polyolefins (such as low-density polyethylene (LDPE), high-density polyethylene (HDPE)), fluorinated ethylene propylene (FEP), polystyrene, polyvinylchloride (PVC), silicone, and any combinations thereof.

In some embodiments, dried platelets or platelet derivatives (e.g., thrombosomes) can undergo heat treatment. Heating can be performed at a temperature above about 25° C. (e.g., greater than about 40° C., 50° C., 60° C., 70° C., 80° C. or higher). In some embodiments, heating is conducted between about 70° C. and about 85° C. (e.g., between about 75° C. and about 85° C., or at about 75° C. or 80° C.). The temperature for heating can be selected in conjunction with the length of time that heating is to be performed. Although any suitable time can be used, typically, the lyophilized platelets are heated for at least 1 hour, but not more than 36 hours. Thus, in embodiments, heating is performed for at least 2 hours, at least 6 hours, at least 12 hours, at least 18 hours, at least 20 hours, at least 24 hours, or at least 30 hours. For example, the lyophilized platelets can be heated for 18 hours, 19 hours, 20 hours, 21 hours, 22 hours, 23 hours, 24 hours, 25 hours, 26 hours, 27 hours, 28 hours, 29 hours, or 30 hours. Non-limiting exemplary combinations include: heating the dried platelets or platelet derivatives (e.g., thrombosomes) for at least 30 minutes at a temperature higher than 30° C.; heating the dried platelets or platelet derivatives (e.g., thrombosomes) for at least 10 hours at a temperature higher than 50° C.; heating the dried platelets or platelet derivatives (e.g., thrombosomes) for at least 18 hours at a temperature higher than 75° C.; and heating the dried platelets or platelet derivatives (e.g., thrombosomes) for 24 hours at 80° C. In some embodiments, heating can be performed in sealed container, such as a capped vial. In some embodiments, a sealed container be subjected to a vacuum prior to heating. The heat treatment step, particularly in the presence of a cryoprotectant such as albumin or polysucrose, has been found to improve the stability and shelf-life of the freeze-dried platelets. Indeed, advantageous results have been obtained with the particular combination of serum albumin or polysucrose and a post-lyophilization heat treatment step, as compared to those cryoprotectants without a heat treatment step. A cryoprotectant (e.g., sucrose) can be present in any appropriate amount (e.g. about 3% to about 10% by mass or by volume of the platelets or platelet derivatives (e.g., thrombosomes).

In some cases, compositions comprising platelets or platelet derivatives (e.g., thrombosomes) can be rehydrated with water (e.g., sterile water for injection) over about 10 minutes at about room temperature. In general, the rehydration volume is about equal to the volume used to fill each vial of thrombosomes prior to drying.

In some embodiments, the platelets or platelet derivatives (e.g., thrombosomes) prepared as disclosed herein have a storage stability that is at least about equal to that of the platelets prior to the preparation.

In some embodiments, the method further comprises cryopreserving the platelets or platelet derivatives prior to administering the platelets or platelet derivatives (e.g., with a preparation agent, e.g., a preparation agent described herein).

In some embodiments, the method further comprises drying a composition comprising platelets or platelet derivatives, (e.g., with a preparation agent e.g., a preparation agent described herein) prior to administering the platelets or platelet derivatives (e.g., thrombosomes). In some embodiments, the method may further comprise heating the composition following the drying step. In some embodiments, the method may further comprise rehydrating the composition following the freeze-drying step or the heating step.

In some embodiments, the method further comprises freeze-drying a composition comprising platelets or platelet derivatives (e.g., with a preparation agent e.g., a preparation agent described herein) prior to administering the platelets or platelet derivatives (e.g., thrombosomes) In some embodiments, the method may further comprise heating the composition following the freeze-drying step. In some embodiments, the method may further comprise rehydrating the composition following the freeze-drying step or the heating step.

In some embodiments, the method further comprises cold storing the platelets, platelet derivatives, or the thrombosomes prior to administering the platelets, platelet derivatives, or thrombosomes (e.g., with a preparation agent, e.g., a preparation agent described herein).

Storing conditions include, for example, standard room temperature storing (e.g., storing at a temperature ranging from about 20 to about 30° C.) or cold storing (e.g., storing at a temperature ranging from about 1 to about 10° C.). In some embodiments, the method further comprises cryopreserving, freeze-drying, thawing, rehydrating, and combinations thereof, a composition comprising platelets or platelet derivatives (e.g., thrombosomes) (e.g., with a preparation agent e.g., a preparation agent described herein) prior to administering the platelets or platelet derivatives (e.g., thrombosomes). For example, in some embodiments, the method further comprises drying (e.g., freeze-drying) a composition comprising platelets or platelet derivatives (e.g., with a preparation agent e.g., a preparation agent described herein) (e.g., to form thrombosomes) prior to administering the platelets or platelet derivatives (e.g., thrombosomes). In some embodiments, the method may further comprise rehydrating the composition obtained from the drying step.

In some embodiments, provided herein is a method for preparing a composition comprising platelets or platelet derivatives (e.g., thrombosomes). The method can include diluting a starting material comprising platelets with an approximately equal weight (±10%) of a preparation agent (e.g., Buffer A, as provided in Example 1), concentrating the platelets to about 2250×10³ cells/μL (+250×10³) and then washed with 2-4 diavolumes (DV) (e.g., about 2 diavolumes) of the preparation agent to form a TFF-treated composition. The residual plasma percentage can be less than about 15% relative plasma (as determined by plasma protein content). Following washing, if the concentration of the cells in the TFF-treated composition is not about 2000×10³ cells/μL (+300×10³), the cells can be diluted with the preparation agent or can be concentrated to fall within this range. The method can further include lyophilizing the TFF-treated composition and subsequently treating the lyophilized composition comprising platelets or platelet derivatives (e.g., thrombosomes) at about 80° C. for about 24 hours. In some embodiments, the method can further include a pathogen reduction step, for example, before diluting the starting material.

Also provided herein are compositions produced by any of the methods described herein.

In some embodiments, any of the compositions provided herein can be made by the methods described herein.

Specific embodiments disclosed herein may be further limited in the claims using "consisting of" or "consisting essentially of" language.

Exemplary Embodiments

Embodiment 1 is a composition comprising platelets or platelet derivatives and an aqueous medium, wherein the aqueous medium has a protein concentration less than or equal to 50% of the protein concentration of donor apheresis plasma.

Embodiment 2 is the composition of embodiment 1, wherein the protein concentration of the aqueous medium is less than or equal to 30% of the protein concentration of donor apheresis plasma.

Embodiment 3 is the composition of embodiment 1 or 2, wherein the aqueous medium has a concentration of human leukocyte antigen (HLA) Class I antibodies that is less than 30% of the human leukocyte antigen (HLA) Class I antibody concentration in donor apheresis plasma.

Embodiment 4 is the composition of any one of embodiments 1-3, wherein the aqueous medium has a concentration of human leukocyte antigen (HLA) Class II antibodies that is less than 30% of the human leukocyte antigen (HLA) Class II antibody concentration in donor apheresis plasma.

Embodiment 5 is the composition of any one of embodiments 1-4, wherein the aqueous medium has a concentration of human neutrophil antigen (HNA) antibodies that is less than 30% of the HNA antibody concentration in donor apheresis plasma.

Embodiment 6 is the composition of any one of embodiments 1-5, wherein the protein concentration is less than or equal to 10% of the protein concentration of donor apheresis plasma.

Embodiment 7 is the composition of any one of embodiments 1-6, wherein the aqueous medium has a concentration of human HLA Class I antibodies that is less than 10% of the HLA Class I antibody concentration in donor apheresis plasma.

Embodiment 8 is the composition of any one of embodiments 1-7, wherein the aqueous medium has a concentration of human HLA Class II antibodies that is less than 10% of the HLA Class II antibody concentration in donor apheresis plasma.

Embodiment 9 is the composition of any one of embodiments 1-8, wherein the aqueous medium has a concentration of human HNA antibodies that is less than 10% of the HNA antibody concentration in donor apheresis plasma.

Embodiment 10 is the composition of any one of embodiments 1-9, wherein the protein concentration is less than or equal to 5% of the protein concentration of donor apheresis plasma.

Embodiment 11 is the composition of any one of embodiments 1-10, wherein the aqueous medium has a concentration of human HLA Class I antibodies that is less than 5% of the HLA Class I antibody concentration in donor apheresis plasma.

Embodiment 12 is the composition of any one of embodiments 1-11, wherein the aqueous medium has a concentration of human HLA Class II antibodies that is less than 5% of the HLA Class II antibody concentration in donor apheresis plasma.

Embodiment 13 is the composition of any one of embodiments 1-12, wherein the aqueous medium has a concentration of human HNA antibodies that is less than 5% of the HNA antibody concentration in donor apheresis plasma.

Embodiment 14 is the composition of any one of embodiments 1-13, wherein the protein concentration is less than or equal to 3% of the protein concentration of donor apheresis plasma.

Embodiment 15 is the composition of any one of embodiments 1-14, wherein the aqueous medium has a concentration of human HLA Class I antibodies that is less than 3% of the HLA Class I antibody concentration in donor apheresis plasma.

Embodiment 16 is the composition of any one of embodiments 1-15, wherein the aqueous medium has a concentration of human HLA Class II antibodies that is less than 3% of the HLA Class II antibody concentration in donor apheresis plasma.

Embodiment 17 is the composition of any one of embodiments 1-16, wherein the aqueous medium has a concentration of human HNA antibodies that is less than 3% of the HNA antibody concentration in donor apheresis plasma.

Embodiment 18 is the composition of any one of embodiments 1-17, wherein the protein concentration is less than or equal to 1% of the protein concentration of donor apheresis plasma.

Embodiment 19 is the composition of any one of embodiments 1-18, wherein the aqueous medium has a concentration of human HLA Class I antibodies that is less than 1% of the HLA Class I antibody concentration in donor apheresis plasma.

Embodiment 20 is the composition of any one of embodiments 1-19, wherein the aqueous medium has a concentration of human HLA Class II antibodies that is less than 1% of the HLA Class II antibody concentration in donor apheresis plasma.

Embodiment 21 is the composition of any one of embodiments 1-20, wherein the aqueous medium has a concentration of human HNA antibodies that is less than 1% of the HNA antibody concentration in donor apheresis plasma.

Embodiment 22 is the composition of any one of embodiments 1-21, wherein protein concentration is determined by absorbance at 280 nanometers (nm) with a path length of 0.5 cm.

Embodiment 23 is the composition of embodiment 22, wherein the absorbance at 280 nm is less than or equal to 1.7 AU.

Embodiment 24 is the composition of embodiment 22, wherein the absorbance at 280 nm is less than or equal to 1.66 AU.

Embodiment 25 is the composition of embodiment 22, wherein the absorbance at 280 nm is less than or equal to 1.6 AU.

Embodiment 26 is the composition of any one of embodiments 1-25, wherein the platelet count is at least $200 \times 10^3$ platelets/μL.

Embodiment 27 is the composition of embodiment 26, wherein the platelet count is at least $2250 \times 10^3$ platelets/μL.

Embodiment 28 is the composition of any one of embodiments 1-27, wherein the composition has an erythrocyte count less than $0.2 \times 10^6$ erythrocytes/μL.

Embodiment 29 is the composition of any one of embodiments 1-27, wherein the composition further comprises erythrocytes.

Embodiment 30 is the composition embodiment 29, wherein the erythrocyte count is less than $0.2 \times 10^6$ erythrocytes/μL.

Embodiment 31 is the composition of any one of embodiments 1-30, wherein the composition is negative for HLA Class I antibodies based on a regulatory agency approved test.

Embodiment 32 is the composition of any one of embodiments 1-31, wherein the composition is negative for HLA Class II antibodies based on a regulatory agency approved test.

Embodiment 33 is the composition of any one of embodiments 1-32, wherein the composition is negative for HNA antibodies based on a regulatory agency approved test.

Embodiment 34 is the composition of any one of embodiments 1-33, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 5%.

Embodiment 35 is the composition of any one of embodiments 1-34, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 3%.

Embodiment 36 is the composition of any one of embodiments 1-35, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 1%.

Embodiment 37 is the composition of any one of embodiments 1-33, wherein a percentage of beads positive for HLA Class I antibodies, as determined for the composition by flow cytometry using beads coated with Class I HLAs, is less than 5%.

Embodiment 38 is the composition of any one of embodiments 1-33, wherein a percentage of beads positive for HLA Class I antibodies, as determined for the composition by flow cytometry using beads coated with Class I HLAs, is less than 3%.

Embodiment 39 is the composition of any one of embodiments 1-33, wherein a percentage of beads positive for HLA Class I antibodies, as determined for the composition by flow cytometry using beads coated with Class I HLAs, is less than 1%.

Embodiment 40 is the composition of any one of embodiments 1-33, wherein a percentage of beads positive for HLA Class II antibodies, as determined for the composition by flow cytometry using beads coated with Class II HLAs is less than 5%.

Embodiment 41 is the composition of any one of embodiments 1-33, wherein a percentage of beads positive for HLA Class II antibodies, as determined for the composition by flow cytometry using beads coated with Class II HLAs, is less than 3%.

Embodiment 42 is the composition of any one of embodiments 1-33, wherein a percentage of beads positive for HLA Class II antibodies, as determined for the composition by flow cytometry using beads coated with Class II HLAs, is less than 1%.

Embodiment 43 is the composition of any one of embodiments 1-33, wherein a percentage of beads positive for HNA antibodies, as determined for the composition by flow cytometry using beads coated with HNAs is less than 5%.

Embodiment 44 is the composition of any one of embodiments 1-33, wherein a percentage of beads positive for HNA antibodies, as determined for the composition by flow cytometry using beads coated with HNAs, is less than 3%.

Embodiment 45 is the composition of any one of embodiments 1-33, wherein a percentage of beads positive for HNAs, as determined for the composition by flow cytometry using beads coated with HNAs, is less than 1%.

Embodiment 46 is the composition of any one of embodiments 1-45, wherein the aqueous medium further comprises a buffering agent, a base, a loading agent, optionally a salt, and optionally at least one organic solvent.

Embodiment 47 is the composition of embodiment 46, wherein the buffering agent is HEPES (4-(2-hydroxyethyl)-1-piperazineethanesulfonic acid).

Embodiment 48 is the composition of any one of embodiments 46-47, wherein the base is sodium bicarbonate.

Embodiment 49 is the composition of any one of embodiments 46-48, wherein the loading agent is a monosaccharide, a polysaccharide, or a combination thereof.

Embodiment 50 is the composition of embodiment 49, wherein the monosaccharide is selected from the group consisting of sucrose, maltose, trehalose, glucose, mannose, and xylose.

Embodiment 51 is the composition of embodiment 49, wherein the monosaccharide is trehalose.

Embodiment 52 is the composition of any one of embodiments 49-51, wherein the polysaccharide is polysucrose.

Embodiment 53 is the composition of any one of embodiments 46-52, wherein the salt is sodium chloride, potassium chloride, or a combination thereof.

Embodiment 54 is the composition of any one of embodiments 46-53, wherein the organic solvent is selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

Embodiment 55 is the composition of any one of embodiments 1-54, wherein the composition is prepared by a process comprising tangential flow filtration (TFF) of a starting material comprising platelets, centrifugation of a starting material comprising platelets, or a combination thereof.

Embodiment 56 is the composition of embodiment 55, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 50% as compared to a similar composition not prepared by a process comprising tangential flow filtration of a blood product composition, centrifugation of a blood product composition, or a combination thereof.

Embodiment 57 is the composition of embodiment 55, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 75% as compared to a similar composition not prepared by a process comprising tangential flow filtration of a blood product composition, centrifugation of a blood product composition, or a combination thereof.

Embodiment 58 is the composition of embodiment 55, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 90% as compared to a similar composition not prepared by a process comprising tangential flow filtration of a blood product composition, centrifugation of a blood product composition, or a combination thereof.

Embodiment 59 is the composition of embodiment 55, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 95% as compared to a similar composition not prepared by a process comprising tangential flow filtration of a blood product composition, centrifugation of a blood product composition, or a combination thereof.

Embodiment 60 is the composition of any one of embodiments 55-59, wherein the starting material is:

a) positive for HLA Class I antibodies based on a regulatory agency approved test;

b) positive for HLA Class II antibodies based on a regulatory agency approved test;

c) positive for HNA antibodies based on a regulatory agency approved test; or d) one or more of a), b), or c).

Embodiment 61 is the composition of any one of embodiments 55-60, wherein the starting material has a protein concentration of about 60 to about 80 mg/ml.

Embodiment 62 is the composition of any one of embodiments 55-61, wherein the starting material comprises donor blood product.

Embodiment 63 is the composition of embodiment 62, wherein the donor blood product is pooled donor blood product.

Embodiment 64 is the composition of any one of embodiments 62-63, wherein the starting material comprises donor apheresis material.

Embodiment 65 is the composition of any one of embodiments 55-64, wherein TFF comprises concentrating.

Embodiment 66 is the composition of any one of embodiments 55-65, wherein TFF comprises diafiltering.

Embodiment 67 is the composition of embodiment 66, wherein diafiltering comprises diafiltering with at least two diavolumes.

Embodiment 68 is the composition of any one of embodiments 55-67, wherein TFF comprises buffer exchange.

Embodiment 69 is the composition of any one of embodiments 55-68, wherein TFF is carried out using a membrane with pore size of about 0.2 μm to about 1 μm.

Embodiment 70 is the composition of any one of embodiments 55-68, wherein TFF is carried out using a membrane with pore size of about 0.2 μm to about 0.45 μm.

Embodiment 71 is the composition of any one of embodiments 55-70, wherein TFF is performed at a temperature of about 20° C. to about 37° C.

Embodiment 72 is the composition of any one of embodiments 55-71, wherein TFF is carried out until the absorbance at 280 nm of the aqueous medium is less than or equal to 50% of the absorbance at 280 nm of the starting material, using a path length of 0.5 cm.

Embodiment 73 is the composition of any one of embodiments 55-71, wherein TFF is carried out until the absorbance at 280 nm of the aqueous medium is less than or equal to 30% of the absorbance at 280 nm of the starting material, using a path length of 0.5 cm.

Embodiment 74 is the composition of any one of embodiments 55-71, wherein TFF is carried out until the absorbance at 280 nm of the aqueous medium is less than or equal to 10% of the absorbance at 280 nm of the starting material, using a path length of 0.5 cm.

Embodiment 75 is the composition of any one of embodiments 55-71, wherein TFF is carried out until the absorbance at 280 nm of the aqueous medium is less than or equal to 5% of the absorbance at 280 nm of the starting material, using a path length of 0.5 cm.

Embodiment 76 is the composition of any one of embodiments 55-71, wherein TFF is carried out until the absorbance at 280 nm of the aqueous medium is less than or equal to 3% of the absorbance at 280 nm of the starting material, using a path length of 0.5 cm.

Embodiment 77 is the composition of any one of embodiments 55-71, wherein TFF is carried out until the absorbance at 280 nm of the aqueous medium is less than or equal to 1% of the absorbance at 280 nm of the starting material, using a path length of 0.5 cm.

Embodiment 78 is the composition of any one of embodiments 55-77, wherein TFF is carried out until the absorbance at 280 nm of the aqueous medium is less than or equal to 1.70 AU, using a path length of 0.5 cm.

Embodiment 79 is the composition of any one of embodiments 55-77, wherein TFF is carried out until the absorbance at 280 nm of the aqueous medium is less than or equal to 1.66 AU, using a path length of 0.5 cm.

Embodiment 80 is the composition of any one of embodiments 55-77, wherein TFF is carried out until the absorbance at 280 nm of the aqueous medium is less than or equal to 1.60 AU, using a path length of 0.5 cm.

Embodiment 81 is the composition of any one of embodiments 55-80, wherein TFF is carried out until the platelet concentration is at least about $2000 \times 10^3$ platelets/μL.

Embodiment 82 is the composition of any one of embodiments 55-80, wherein TFF is carried out until the platelet concentration is at least about $2250 \times 10^3$ platelets/μL.

Embodiment 83 is the composition of any one of embodiments 55-82, wherein TFF comprises buffer exchange into a preparation agent comprising a buffering agent, a base, a loading agent, optionally a salt, and optionally at least one organic solvent.

Embodiment 84 is the composition of embodiment 83, wherein the buffering agent is HEPES (4-(2-hydroxyethyl)-1-piperazineethanesulfonic acid).

Embodiment 85 is the composition of any one of embodiments 83-84, wherein the base is sodium bicarbonate.

Embodiment 86 is the composition of any one of embodiments 83-85, wherein the loading agent is a monosaccharide, a polysaccharide, or a combination thereof.

Embodiment 87 is the composition of embodiment 86, wherein the monosaccharide is selected from the group consisting of sucrose, maltose, trehalose, glucose, mannose, and xylose.

Embodiment 88 is the composition of embodiment 86, wherein the monosaccharide is trehalose.

Embodiment 89 is the composition of any one of embodiments 86-88, wherein the polysaccharide is polysucrose.

Embodiment 90 is the composition of any one of embodiments 83-89, wherein the salt is sodium chloride, potassium chloride, or a combination thereof.

Embodiment 91 is the composition of any one of embodiments 83-90, wherein the organic solvent is selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

Embodiment 92 is the composition of any one of embodiments 55-91, wherein centrifugation comprises centrifugation at 1400×g to about 1550×g.

Embodiment 93 is the composition of any one of embodiments 55-91, wherein centrifugation comprises centrifugation at 1450×g to about 1500×g.

Embodiment 94 is the composition of any one of embodiments 55-91, wherein the process does not comprise centrifugation of a composition comprising platelets.

Embodiment 95 is the composition of any one of embodiments 1-94, wherein the composition comprises less than 5.0% (by scattering intensity) microparticles.

Embodiment 96 is the composition of any one of embodiments 1-94, wherein the composition comprises less than 4.5% (by scattering intensity) microparticles.

Embodiment 97 is the composition of any one of embodiments 1-94, wherein the composition comprises less than 4.0% (by scattering intensity) microparticles.

Embodiment 98 is the composition of any one of embodiments 1-94, wherein the composition comprises less than 3.5% (by scattering intensity) microparticles.

Embodiment 99 is the composition of any one of embodiments 1-98, wherein the platelets or platelet derivatives have a CD41 percent positivity of at least 55%.

Embodiment 100 is the composition of any one of embodiments 1-98, wherein the platelets or platelet derivatives have a CD41 percent positivity of at least 60%.

Embodiment 101 is the composition of any one of embodiments 1-98, wherein the platelets or platelet derivatives have a CD41 percent positivity of at least 65%.

Embodiment 102 is the composition of any one of embodiments 1-101, wherein the platelets or platelet derivatives have a CD42 percent positivity of at least 65%.

Embodiment 103 is the composition of any one of embodiments 1-101, wherein the platelets or platelet derivatives have a CD42 percent positivity of at least 80%.

Embodiment 104 is the composition of any one of embodiments 1-101, wherein the platelets or platelet derivatives have a CD42 percent positivity of at least 90%.

Embodiment 105 is the composition of any one of embodiments 1-104, wherein the platelets or platelet derivatives retain at least about 10% of the lactate dehydrogenase activity of donor apheresis platelets.

Embodiment 106 is the composition of any one of embodiments 1-104, wherein the platelets or platelet derivatives retain at least about 15% of the lactate dehydrogenase activity of donor apheresis platelets.

Embodiment 107 is the composition of any one of embodiments 1-104, wherein the platelets or platelet derivatives retain at least about 20% of the lactate dehydrogenase activity of donor apheresis platelets.

Embodiment 108 is the composition of any one of embodiments 1-107, wherein the platelets or platelet derivatives have an annexin V percent positivity of at least 25%.

Embodiment 109 is the composition of any one of embodiments 1-107, wherein the platelets or platelet derivatives have an annexin V percent positivity of at least 50%.

Embodiment 110 is the composition of any one of embodiments 1-107, wherein the platelets or platelet derivatives have an annexin V percent positivity of at least 70%.

Embodiment 111 is the composition of any one of embodiments 1-110, wherein the platelets or platelet derivatives have CD47 percent positivity of at least 8%.

Embodiment 112 is the composition of any one of embodiments 1-110, wherein the platelets or platelet derivatives have CD47 percent positivity of at least 10%.

Embodiment 113 is the composition of any one of embodiments 1-110, wherein the platelets or platelet derivatives have CD47 percent positivity of at least 15%.

Embodiment 114 is the composition of any one of embodiments 1-110, wherein the platelets or platelet derivatives have CD47 percent positivity of at least 20%.

Embodiment 115 is the composition of any one of embodiments 1-114, wherein the platelets or platelet derivatives have CD62 percent positivity of at least 10%.

Embodiment 116 is the composition of any one of embodiments 1-114, wherein the platelets or platelet derivatives have CD62 percent positivity of at least 50%.

Embodiment 117 is the composition of any one of embodiments 1-114, wherein the platelets or platelet derivatives have CD62 percent positivity of at least 80%.

Embodiment 118 is the composition of any one of embodiments 1-114, wherein the platelets or platelet derivatives have CD62 percent positivity of at least 90%.

Embodiment 119 is the composition of any one of embodiments 1-118, wherein the platelets or platelet derivatives have fibrinogen associated with the cell membrane.

Embodiment 120 is the composition of any one of embodiments 1-119, wherein the aqueous medium has a lactate concentration of less than 2.0 mmol/L.

Embodiment 121 is the composition of any one of embodiments 1-119, wherein the aqueous medium has a lactate concentration of less than 1.5 mmol/L.

Embodiment 122 is the composition of any one of embodiments 1-121, wherein the aqueous medium has a lactate concentration of about 0.4 to about 1.3 mmol/L.

Embodiment 123 is the composition of any one of embodiments 1-121, wherein the aqueous medium has a lactate concentration of about 0.5 to about 1.0 mmol/L.

Embodiment 124 is the composition of any one of embodiments 1-123, wherein the platelet derivatives comprise thrombosomes.

Embodiment 125 is the composition of any one of embodiments 1 or 22-124, wherein the protein concentration is about 5% to about 50% of the protein concentration of donor apheresis plasma.

Embodiment 126 is the composition of any one of embodiments 1-5 or 22-125, wherein the protein concentration is about 5% to about 30% of the protein concentration of donor apheresis plasma.

Embodiment 127 is the composition of any one of embodiments 1-5 or 22-126, wherein the protein concentration is about 5% to about 15% of the protein concentration of donor apheresis plasma.

Embodiment 128 is the composition of any one of embodiments 1-9 or 22-127, wherein the protein concentration is about 8% to about 10% of the protein concentration of donor apheresis plasma.

Embodiment 129 is the composition of any one of embodiments 1-9 or 22-128, wherein the protein concentration is about 7% to about 10% of the protein concentration of donor apheresis plasma.

Embodiment 130 is the composition of any one of embodiments 1-129, wherein the platelets or platelet derivatives, when at a concentration of about $4.8 \times 10^3$ particles/µL generate a thrombin peak height (TPH) of at least 25 nM when in the presence of a reagent containing tissue factor and phospholipids.

Embodiment 131 is the composition of any one of embodiments 1-129, wherein the platelets or platelet derivatives, when at a concentration of about $4.8 \times 10^3$ particles/µL generate a thrombin peak height (TPH) of at least 50 nM when in the presence of a reagent containing tissue factor and phospholipids.

Embodiment 132 is the composition of any one of embodiments 1-129, wherein the platelets or platelet derivatives have a potency of at least 1.5 thrombin generation potency units (TGPU) per $10^6$ particles.

Embodiment 133 is the composition of any one of embodiments 1-129, wherein the platelets or platelet derivatives, when at a concentration of at least about $70 \times 10^3$ particles/μL, produce an occlusion time of less than 14 minutes in a total thrombus-formation analysis system (T-TAS) assay.

Embodiment 134 is the composition of any one of embodiments 1-129, wherein the platelets or platelet derivatives, when at a concentration of about 70×10' particles/μL produce an occlusion time of less than 12 minutes in a total thrombus-formation analysis system (T-TAS) assay.

Embodiment 135 is a process for preparing a composition comprising platelets or platelet derivatives and an aqueous medium, the process comprising:

tangential flow filtration (TFF) of a starting material comprising platelets, a diluted starting material comprising platelets, a concentrated platelet composition, or a combination thereof, thereby preparing a composition comprising platelets or platelet derivatives and aqueous medium, wherein the aqueous medium has a protein concentration less than or equal to 50% of the protein concentration of donor apheresis plasma.

Embodiment 136 is the process of embodiment 125, wherein the starting material is:
a) positive for HLA Class I antibodies based on a regulatory agency approved test;
b) positive for HLA Class II antibodies based on a regulatory agency approved test;
c) positive for HNA antibodies based on a regulatory agency approved test; or
d) one or more of a), b), and c).

Embodiment 137 is the process of any one of embodiments 135-136, wherein the starting material has a protein concentration of about 60 to about 80 mg/mL.

Embodiment 138 is the process of any one of embodiments 135-137, wherein the starting material comprises donor blood product.

Embodiment 139 is the process of embodiment 138, wherein the donor blood product is pooled donor blood product.

Embodiment 140 is the process of any one of embodiments 135-139, wherein the starting material comprises donor apheresis material.

Embodiment 141 is the process of any one of embodiments 135-140, wherein TFF comprises concentrating.

Embodiment 142 is the process of any one of embodiments 135-141, wherein TFF comprises diafiltering.

Embodiment 143 is the process of embodiment 142, wherein diafiltering comprises diafiltering with at least two diavolumes.

Embodiment 144 is the process of any one of embodiments 135-143, wherein TFF comprises buffer exchange.

Embodiment 145 is the process of any one of embodiments 135-144, wherein TFF is carried out using a membrane with pore size of about 0.2 μm to about 1 μm.

Embodiment 146 is the process of any one of embodiments 135-145, wherein TFF is carried out using a membrane with pore size of about 0.2 μm to about 0.45 μm.

Embodiment 147 is the process of any one of embodiments 135-146, wherein TFF is performed at a temperature of about 20° C. to about 37° C.

Embodiment 148 is the process of any one of embodiments 135-147, wherein TFF is carried out until the absorbance at 280 nm of the aqueous medium is less than or equal to 50% of the absorbance at 280 nm of the starting material, using a path length of 0.5 cm.

Embodiment 149 is the process of any one of embodiments 135-148, wherein TFF is carried out until the absorbance at 280 nm of the aqueous medium is less than or equal to 30% of the absorbance at 280 nm of the starting material, using a path length of 0.5 cm.

Embodiment 150 is the process of any one of embodiments 135-149, wherein TFF is carried out until the absorbance at 280 nm of the aqueous medium is less than or equal to 10% of the absorbance at 280 nm of the starting material, using a path length of 0.5 cm.

Embodiment 151 is the process of any one of embodiments 135-150, wherein TFF is carried out until the absorbance at 280 nm of the aqueous medium is less than or equal to 5% of the absorbance at 280 nm of the starting material, using a path length of 0.5 cm.

Embodiment 152 is the process of any one of embodiments 135-151, wherein TFF is carried out until the absorbance at 280 nm of the aqueous medium is less than or equal to 3% of the absorbance at 280 nm of the starting material, using a path length of 0.5 cm.

Embodiment 153 is the process of any one of embodiments 135-152, wherein TFF is carried out until the absorbance at 280 nm of the aqueous medium is less than or equal to 1% of the absorbance at 280 nm of the starting material, using a path length of 0.5 cm.

Embodiment 154 is the process of any one of embodiments 135-153, wherein TFF is carried out until the absorbance at 280 nm of the aqueous medium is less than or equal to 1.70 AU, using a path length of 0.5 cm.

Embodiment 155 is the process of any one of embodiments 135-154, wherein TFF is carried out until the absorbance at 280 nm of the aqueous medium is less than or equal to 1.66 AU, using a path length of 0.5 cm.

Embodiment 156 is the process of any one of embodiments 135-155, wherein TFF is carried out until the absorbance at 280 nm of the aqueous medium is less than or equal to 1.60 AU, using a path length of 0.5 cm.

Embodiment 157 is the process of any one of embodiments 135-156, wherein TFF is carried out until the platelet concentration is at least about $2000 \times 10^3$ platelets/μL.

Embodiment 158 is the process of any one of embodiments 135-156, wherein TFF is carried out until the platelet concentration is at least about $2250 \times 10^3$ platelets/μL.

Embodiment 159 is the process of any one of embodiments 135-158, wherein TFF comprises diafiltering with a preparation agent comprising a buffering agent, a base, a loading agent, optionally a salt, and optionally at least one organic solvent.

Embodiment 160 is the process of any one of embodiments 135-159, wherein TFF comprises buffer exchange into a preparation agent comprising a buffering agent, a base, a loading agent, optionally a salt, and optionally at least one organic solvent.

Embodiment 161 is the process of any one of embodiments 149-160, wherein the buffering agent is HEPES (4-(2-hydroxyethyl)-1-piperazineethanesulfonic acid).

Embodiment 162 is the process of any one of embodiments 149-161, wherein the base is sodium bicarbonate.

Embodiment 163 is the process of any one of embodiments 149-162, wherein the loading agent is a monosaccharide, a polysaccharide, or a combination thereof.

Embodiment 164 is the process of embodiment 163, wherein the monosaccharide is selected from the group consisting of sucrose, maltose, trehalose, glucose, mannose, xylose, and combinations thereof.

Embodiment 165 is the process of embodiment 163, wherein the monosaccharide is trehalose.

Embodiment 166 is the process of any one of embodiments 163-165, wherein the polysaccharide is polysucrose.

Embodiment 167 is the process of any one of embodiments 159-166, wherein the salt is sodium chloride, potassium chloride, or a combination thereof.

Embodiment 168 is the process of any one of embodiments 159-167, wherein the organic solvent is selected from the group consisting of ethanol, acetic acid, acetone, acetonitrile, dimethylformamide, dimethyl sulfoxide, dioxane, methanol, n-propanol, isopropanol, tetrahydrofuran (THF), N-methyl pyrrolidone, dimethylacetamide (DMAC), and combinations thereof.

Embodiment 169 is the process of any one of embodiments 135-168, wherein the process does not comprise centrifugation of the starting material comprising platelets, the diluted starting material comprising platelets, the concentrated platelet composition, or the combination thereof.

Embodiment 170 is the process of any one of embodiments 135-169, wherein the process does not comprise centrifugation of a composition comprising platelets.

Embodiment 171 is the process of any one of embodiments 135-170, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 50% as compared to a similar composition not prepared by a process comprising tangential flow filtration of a blood product composition, centrifugation of a blood product composition, or a combination thereof.

Embodiment 172 is the process of any one of embodiments 135-170, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 75% as compared to a similar composition not prepared by a process comprising tangential flow filtration of a blood product composition, centrifugation of a blood product composition, or a combination thereof.

Embodiment 173 is the process of any one of embodiments 135-170, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 90% as compared to a similar composition not prepared by a process comprising tangential flow filtration of a blood product composition, centrifugation of a blood product composition, or a combination thereof.

Embodiment 174 is the process of any one of embodiments 135-170, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is reduced by at least 95% as compared to a similar composition not prepared by a process comprising tangential flow filtration of a blood product composition, centrifugation of a blood product composition, or a combination thereof.

Embodiment 175 is the process of any one of embodiments 135-174, wherein the protein concentration is less than or equal to 30% of the protein concentration of donor apheresis plasma.

Embodiment 176 is the process of any one of embodiments 135-175, wherein the aqueous medium has a concentration of human leukocyte antigen (HLA) Class I antibodies that is less than 30% of the human leukocyte antigen (HLA) Class I antibody concentration in donor apheresis plasma.

Embodiment 177 is the process of any one of embodiments 135-176, wherein the aqueous medium has a concentration of human leukocyte antigen (HLA) Class II antibodies that is less than 30% of the human leukocyte antigen (HLA) Class II antibody concentration in donor apheresis plasma.

Embodiment 178 is the process of any one of embodiments 135-17, wherein the aqueous medium has a concentration of human neutrophil antigen (HNA) antibodies that is less than 30% of the HNA antibody concentration in donor apheresis plasma.

Embodiment 179 is the process of any one of embodiments 135-178, wherein the protein concentration is less than or equal to 10% of the protein concentration of donor apheresis plasma.

Embodiment 180 is the process of any one of embodiments 135-179, wherein the aqueous medium has a concentration of human HLA Class I antibodies that is less than 10% of the HLA Class I antibody concentration in donor apheresis plasma.

Embodiment 181 is the process of any one of embodiments 135-180, wherein the aqueous medium has a concentration of human HLA Class II antibodies that is less than 10% of the HLA Class II antibody concentration in donor apheresis plasma.

Embodiment 182 is the process of any one of embodiments 135-181, wherein the aqueous medium has a concentration of human HNA antibodies that is less than 10% of the HNA antibody concentration in donor apheresis plasma.

Embodiment 183 is the process of any one of embodiments 135-182, wherein the protein concentration is less than or equal to 5% of the protein concentration of donor apheresis plasma.

Embodiment 184 is the process of any one of embodiments 135-183, wherein the aqueous medium has a concentration of human HLA Class I antibodies that is less than 5% of the HLA Class I antibody concentration in donor apheresis plasma.

Embodiment 185 is the process of any one of embodiments 135-184, wherein the aqueous medium has a concentration of human HLA Class II antibodies that is less than 5% of the HLA Class II antibody concentration in donor apheresis plasma.

Embodiment 186 is the process of any one of embodiments 135-185, wherein the aqueous medium has a concentration of human HNA antibodies that is less than 5% of the HNA antibody concentration in donor apheresis plasma.

Embodiment 187 is the process of any one of embodiments 135-186, wherein the protein concentration is less than or equal to 3% of the protein concentration of donor apheresis plasma.

Embodiment 188 is the process of any one of embodiments 135-187, wherein the aqueous medium has a concentration of human HLA Class I antibodies that is less than 3% of the HLA Class I antibody concentration in donor apheresis plasma.

Embodiment 189 is the process of any one of embodiments 135-188, wherein the aqueous medium has a concentration of human HLA Class II antibodies that is less than 3% of the HLA Class II antibody concentration in donor apheresis plasma.

Embodiment 190 is the process of any one of embodiments 135-189, wherein the aqueous medium has a concentration of human HNA antibodies that is less than 3% of the HNA antibody concentration in donor apheresis plasma.

Embodiment 191 is the process of any one of embodiments 135-190, wherein the protein concentration is less than or equal to 1% of the protein concentration of donor apheresis plasma.

Embodiment 192 is the process of any one of embodiments 135-191, wherein the aqueous medium has a concentration of human HLA Class I antibodies that is less than 1% of the HLA Class I antibody concentration in donor apheresis plasma.

Embodiment 193 is the process of any one of embodiments 135-192, wherein the aqueous medium has a concentration of human HLA Class II antibodies that is less than 1% of the HLA Class II antibody concentration in donor apheresis plasma.

Embodiment 194 is the process of any one of embodiments 135-193, wherein the aqueous medium has a concentration of human HNA antibodies that is less than 1% of the HNA antibody concentration in donor apheresis plasma.

Embodiment 195 is the process of any one of embodiments 135-194, wherein the composition is negative for HLA Class I antibodies based on a regulatory agency approved test.

Embodiment 196 is the process of any one of embodiments 135-195, wherein the composition is negative for HLA Class II antibodies based on a regulatory agency approved test.

Embodiment 197 is the process of any one of embodiments 135-196, wherein the composition is negative for HNA antibodies based on a regulatory agency approved test.

Embodiment 198 is the process of any one of embodiments 135-197, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 5%.

Embodiment 199 is the process of any one of embodiments 135-198, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 3%.

Embodiment 200 is the process of any one of embodiments 135-199, wherein a percentage of beads positive for an antibody selected from the group consisting of HLA Class I antibodies, HLA Class II antibodies, and HNA antibodies, as determined for the composition by flow cytometry using beads coated with Class I HLAs, Class II HLAs, or HNAs, respectively, is less than 1%.

Embodiment 201 is the process of any one of embodiments 135-200, wherein a percentage of beads positive for HLA Class I antibodies, as determined for the composition by flow cytometry using beads coated with Class I HLAs, is less than 5%.

Embodiment 202 is the process of any one of embodiments 135-201, wherein a percentage of beads positive for HLA Class I antibodies, as determined for the composition by flow cytometry using beads coated with Class I HLAs, is less than 3%.

Embodiment 203 is the process of any one of embodiments 135-202, wherein a percentage of beads positive for HLA Class I antibodies, as determined for the composition by flow cytometry using beads coated with Class I HLAs, is less than 1%.

Embodiment 204 is the process of any one of embodiments 135-203, wherein a percentage of beads positive for HLA Class II antibodies, as determined for the composition by flow cytometry using beads coated with Class II HLAs is less than 5%.

Embodiment 205 is the process of any one of embodiments 135-204, wherein a percentage of beads positive for HLA Class II antibodies, as determined for the composition by flow cytometry using beads coated with Class II HLAs, is less than 3%.

Embodiment 206 is the process of any one of embodiments 135-205, wherein a percentage of beads positive for HLA Class II antibodies, as determined for the composition by flow cytometry using beads coated with Class II HLAs, is less than 1%.

Embodiment 207 is the process of any one of embodiments 135-206, wherein a percentage of beads positive for HNA antibodies, as determined for the composition by flow cytometry using beads coated with HNAs is less than 5%.

Embodiment 208 is the process of any one of embodiments 135-207, wherein a percentage of beads positive for HNA antibodies, as determined for the composition by flow cytometry using beads coated with HNAs, is less than 3%.

Embodiment 209 is the process of any one of embodiments 135-208, wherein a percentage of beads positive for HNAs, as determined for the composition by flow cytometry using beads coated with HNAs, is less than 1%.

Embodiment 210 is the process of any one of embodiments 135-209, wherein the composition comprises less than 5.0% (by scattering intensity) microparticles.

Embodiment 211 is the process of any one of embodiments 135-209, wherein the composition comprises less than 4.5% (by scattering intensity) microparticles.

Embodiment 212 is the process of any one of embodiments 135-209, wherein the composition comprises less than 4.0% (by scattering intensity) microparticles.

Embodiment 213 is the process of any one of embodiments 135-209, wherein the composition comprises less than 3.5% (by scattering intensity) microparticles.

Embodiment 214 is the process of any one of embodiments 135-213, wherein the platelets or platelet derivatives have a CD41 percent positivity of at least 55%.

Embodiment 215 is the process of any one of embodiments 135-213, wherein the platelets or platelet derivatives have a CD41 percent positivity of at least 60%.

Embodiment 216 is the process of any one of embodiments 135-213, wherein the platelets or platelet derivatives have a CD41 percent positivity of at least 65%.

Embodiment 217 is the process of any one of embodiments 135-216, wherein the platelets or platelet derivatives have a CD42 percent positivity of at least 65%.

Embodiment 218 is the process of any one of embodiments 135-216, wherein the platelets or platelet derivatives have a CD42 percent positivity of at least 80%.

Embodiment 219 is the process of any one of embodiments 135-216, wherein the platelets or platelet derivatives have a CD42 percent positivity of at least 90%.

Embodiment 220 is the process of any one of embodiments 135-219, wherein the platelets or platelet derivatives retain at least about 10% of the lactate dehydrogenase activity of donor apheresis platelets.

Embodiment 221 is the process of any one of embodiments 135-219, wherein the platelets or platelet derivatives retain at least about 15% of the lactate dehydrogenase activity of donor apheresis platelets.

Embodiment 222 is the process of any one of embodiments 135-219, wherein the platelets or platelet derivatives retain at least about 20% of the lactate dehydrogenase activity of donor apheresis platelets.

Embodiment 223 is the process of any one of embodiments 135-222, wherein the platelets or platelet derivatives have an annexin V percent positivity of at least 25%.

Embodiment 224 is the process of any one of embodiments 135-222, wherein the platelets or platelet derivatives have an annexin V percent positivity of at least 50%.

Embodiment 225 is the process of any one of embodiments 135-222, wherein the platelets or platelet derivatives have an annexin V percent positivity of at least 75%.

Embodiment 226 is the process of any one of embodiments 135-225, wherein the platelets or platelet derivatives have CD47 percent positivity of at least 8%.

Embodiment 227 is the process of any one of embodiments 135-225, wherein the platelets or platelet derivatives have CD47 percent positivity of at least 10%.

Embodiment 228 is the process of any one of embodiments 135-225, wherein the platelets or platelet derivatives have CD47 percent positivity of at least 15%.

Embodiment 229 is the process of any one of embodiments 135-225, wherein the platelets or platelet derivatives have CD47 percent positivity of at least 20%.

Embodiment 230 is the process of any one of embodiments 135-229, wherein the platelets or platelet derivatives have CD62 percent positivity of at least 10%.

Embodiment 231 is the process of any one of embodiments 135-229, wherein the platelets or platelet derivatives have CD62 percent positivity of at least 50%.

Embodiment 232 is the process of any one of embodiments 135-229, wherein the platelets or platelet derivatives have CD62 percent positivity of at least 80%.

Embodiment 233 is the process of any one of embodiments 135-229, wherein the platelets or platelet derivatives have CD62 percent positivity of at least 90%.

Embodiment 234 is the process of any one of embodiments 135-233, wherein the platelets or platelet derivatives have fibrinogen associated with the cell membrane.

Embodiment 235 is the process of any one of embodiments 135-234, wherein the aqueous medium has a lactate concentration of less than 2.0 mmol/L.

Embodiment 236 is the process of any one of embodiments 135-234, wherein the aqueous medium has a lactate concentration of less than 1.5 mmol/L.

Embodiment 237 is the process of any one of embodiments 135-236, wherein the aqueous medium has a lactate concentration of about 0.4 to about 1.3 mmol/L.

Embodiment 238 is the process of any one of embodiments 135-236, wherein the aqueous medium has a lactate concentration of about 0.5 to about 1.0 mmol/L.

Embodiment 239 is the process of any one of embodiments 135-238, wherein the platelet derivatives comprise thrombosomes.

Embodiment 240 is the process of any one of embodiments 135-239, further comprising a pathogen reduction step.

Embodiment 241 is the process of embodiment 240, wherein the pathogen reduction step precedes TFF.

Embodiment 242 is the process of any one of embodiments 135-241, further comprising lyophilizing the composition comprising platelets or platelet derivatives.

Embodiment 243 is the process of any one of embodiments 135-241, further comprising cryopreserving the composition comprising platelets or platelet derivatives.

Embodiment 244 is the process of any one of embodiments 135-243, further comprising thermally treating the composition comprising platelets or platelet derivatives.

Embodiment 245 is the process of any one of embodiments 135-148, 154-174, or 195-244, wherein the protein concentration is about 5% to about 50% of the protein concentration of donor apheresis plasma.

Embodiment 246 is the process of any one of embodiments 135-149, 154-178, or 195-245, wherein the protein concentration is about 5% to about 30% of the protein concentration of donor apheresis plasma.

Embodiment 247 is the process of any one of embodiments 135-148, 154-178, or 195-246, wherein the protein concentration is about 5% to about 15% of the protein concentration of donor apheresis plasma.

Embodiment 248 is the process of any one of embodiments 135-148, 154-182, or 195-247, wherein the protein concentration is about 8% to about 10% of the protein concentration of donor apheresis plasma.

Embodiment 249 is the process of any one of embodiments 135-148, 154-182, or 195-248, wherein the protein concentration is about 7% to about 10% of the protein concentration of donor apheresis plasma.

Embodiment 250 is the process of any one of embodiments 135-249, wherein the platelets or platelet derivatives, when at a concentration of about $4.8 \times 10^3$ particles/µL generate a thrombin peak height (TPH) of at least 25 nM when in the presence of a reagent containing tissue factor and phospholipids.

Embodiment 251 is the process of any one of embodiments 135-249, wherein the platelets or platelet derivatives, when at a concentration of about $4.8 \times 10^3$ particles/µL generate a thrombin peak height (TPH) of at least 50 nM when in the presence of a reagent containing tissue factor and phospholipids.

Embodiment 252 is the process of any one of embodiments 135-249, wherein the platelets or platelet derivatives have a potency of at least 1.5 thrombin generation potency units (TGPU) per $10^6$ particles.

Embodiment 253 is the process of any one of embodiments 135-249, wherein the platelets or platelet derivatives, when at a concentration of at least about $70 \times 10^3$ particles/µL, produce an occlusion time of less than 14 minutes in a total thrombus-formation analysis system (T-TAS) assay.

Embodiment 254 is the process of any one of embodiments 135-249, wherein the platelets or platelet derivatives, when at a concentration of at least about $70 \times 10^3$ particles/µL, produce an occlusion time of less than 12 minutes in a total thrombus-formation analysis system (T-TAS) assay.

Embodiment 255 is a composition comprising platelets or platelet derivatives and an aqueous medium prepared by the process of any one of embodiments 135-254.

Embodiment 256 is a process for preparing freeze-dried platelets, comprising: a) preparing a composition comprising platelets and an aqueous medium using the process of any one of embodiments 135-254; and b) freeze-drying the composition comprising platelets and the aqueous medium.

Embodiment 257 is a composition comprising freeze-dried platelets, prepared by the process of embodiment 235.

Embodiment 258 is a method for preparing a composition comprising platelets or platelet derivatives and an aqueous medium, the method comprising: diluting a starting material comprising platelets to form a diluted starting material; concentrating the diluted starting material such that the platelets have a concentration of about 2250×10³ cells/μL (±250×10³) to form a concentrated platelet composition; and washing the concentrated platelet composition with at least 2 diavolumes (DV) of a preparation agent to form a TFF-treated composition.

Embodiment 259 is the method of embodiment 258, wherein diluting comprises diluting with an approximately equal weight (±10%) of the preparation agent.

Embodiment 260 is the method of any one of embodiments 258-259, further comprising a pathogen reduction step.

Embodiment 261 is the method of embodiment 260, wherein the pathogen reduction step occurs before diluting the starting material.

Embodiment 262 is the method of any one of embodiments 258-261, wherein residual plasma percentage is less than or equal to about 15% relative plasma (as determined by plasma protein content).

Embodiment 263 is the method of any one of embodiments 258-262, wherein following washing, if the concentration of the cells in the TFF-treated composition is not about 2000×10³ cells/μL (±300×10³), diluting the preparation agent or can be concentrated to fall within this range.

Embodiment 264 is the method of any one of embodiments 258-263, further comprising lyophilizing the TFF-treated composition to form a lyophilized composition.

Embodiment 265 is the method of embodiment 264, further comprising treating the lyophilized composition at about 80° C. for about 24 hours.

Embodiment 266 is a composition comprising platelets or platelet derivatives prepared by the method of any one of embodiments 258-265.

Embodiment 267 is a method of treating a clotting-related disease or condition in a subject in need thereof, comprising administering to the subject a therapeutically effective amount of the composition of any of embodiments 1 to 134, 255 or 266.

Embodiment 268 is the method of embodiment 267, wherein the clotting-related disease or condition is selected from the group consisting of Von Willebrand Disease, a hemophilia, thrombasthenia, thrombocytopenia, thrombocytopenic purpura, trauma, or a combination thereof.

Embodiment 269 is a method of treating a clotting-related disease or condition in a subject in need thereof, comprising administering to the subject a therapeutically effective amount of a composition prepared by the process of any of embodiments 135 to 254.

Embodiment 270 is the method of embodiment 269, wherein the clotting-related disease or condition is selected from the group consisting of Von Willebrand Disease, a hemophilia, thrombasthenia, thrombocytopenia, thrombocytopenic purpura, trauma, or a combination thereof.

Embodiment 271 is a method of treating a clotting-related treating a disease or condition subject in need thereof, comprising administering to the subject a therapeutically effective amount of a composition prepared by the process of any of embodiments 258 to 266.

Embodiment 272 is the method of embodiment 271, wherein the clotting-related disease or condition is selected from the group consisting of Von Willebrand Disease, a hemophilia, thrombasthenia, thrombocytopenia, thrombocytopenic purpura, trauma, or a combination thereof.

EXAMPLES

Example 1. Tangential Flow Filtration (TFF) Method

Apheresis platelets underwent tangential flow filtration in accordance with a standard operating procedure, including the following process steps: platelet dilution, platelet concentration and platelet washing.

The platelet donor units are initially pooled into a common vessel. The platelets may or may not be initially diluted with an acidified washing buffer (e.g., a control buffer) to reduce platelet activation during processing. The platelets can undergo two processing pathways; either washed with control buffer until a desired residual component is reached (e.g., donor plasma) before being concentrated to a final product concentration or the platelets are concentrated to a final product concentration before being washed with control buffer until a desired residual component is reached (e.g., donor plasma). TFF processed platelets are then filled into vials, lyophilized and thermally treated.

One particular protocol follows.

For all steps of the TFF process in this Example, Buffer A was used. The process was carried out at a temperature of 18-24° C.

| Buffer A | |
|---|---|
| Component | Value (±1%) |
| HEPES | 7.6 mM |
| NaCl | 60 mM |
| KCl | 3.84 mM |
| Dextrose | 2.4 mM |
| NaHCO$_3$ | 9.6 mM |
| Trehalose | 80 mM |
| Ethanol | 0.8% |
| Polysucrose | 6% (w/v) |
| pH | 6.6-6.8 |

Platelets were loaded onto the TFF (PendoTECH controller system), which was prepared with a Repligen TFF Cassette (XPM45L01E). The platelets were diluted with an equal weight (±10%) of Buffer A. The platelets were concentrated to about 2250×10³ cells/μL (+250×10³) and then washed with approximately 2 diavolumes (DV) of Buffer A. The target plasma percentage was typically less than 15% relative plasma (as determined by plasma protein content). Removal of plasma proteins was monitored through 280 nm UV absorbance against known correlations. Following washing, if the concentration of the cells was not 2000×10³ cells/μL (±300×10³), the cells were either diluted with Buffer A or were concentrated to fall within this range. The cells were typically then lyophilized and subsequently thermally treated at 80° C. for 24 hours, thereby forming thrombosomes, but sometimes the cells were used before lyophilization (sometimes called thrombosomes 'pre-lyo'). Thrombosomes were typically rehydrated with water over 10 minutes at room temperature. In general, the rehydration volume is equal to the volume used to fill each vial of thrombosomes prior to drying.

In some cases, samples were drawn at UV readings correlating to about 51% relative plasma volume, about 8.1% relative plasma volume, about 6.0% relative plasma volume, and about 1.3% relative plasma readings. Low volume aliquots were sampled throughout each processing step with about 6.0% and under samples.

Example 2. Testing Plan and Assay Protocol

Testing Plan:
Thrombosomes Batch A was produced by the TFF method described in Example 1 using apheresis platelets collected from high-αHLA titer donors as reported by a platelet supplier.

Individual donor units, the donor pool, and timepoints along the TFF process were collected for αHLA testing. Plasma was added to HLA beads (One Lambda FLOW-PRA™ Screen Test), stained with an αIgG secondary antibody, and evaluated for αHLA-IgG binding by flow cytometry (Novocyte 3005 configuration)

Two bead types were evaluated: one coated with HLA Class I antigens and the other coated with HLA Class II antigens. Bead gating was performed as described in the FLOWPRA™ Screen Test instructions. "αHLA Positive" populations are gated on the basis of a George King (GK) PPP (platelet-poor plasma) negative control and a single-donor fresh-drawn negative control. Additional negative controls are collected following production to confirm ideal placement of these positivity gates.

Compensation settings were established using FITC- and PE-conjugated mouse IgG on Spherotech COMPtrol compensation beads. The HLA Class II beads fluoresce in PE and the secondary antibody used for IgG detection is FITC-conjugated.

Assay Protocol:
1. Thaw the One Lambda FLOWPRA™ Screen Test kit components to 4° C.
2. Obtain approximately 1 mL aliquots of 0.2 μm filtered PPP from each desired sample point.
3. To a 1.7 mL microcentrifuge tube, pipet 5 μL Class I HLA beads and 5 μL Class II HLA beads. Add 20 μL filtered test plasma. Vortex to mix.
4. Incubate plasma with HLA-coated beads for 30 minutes at room temperature in the dark with gentle rocking/agitation.
5. Dilute 10× wash buffer to the appropriate volume of 1× working stock with deionized water.
6. Wash the beads with 1 mL wash buffer. Vortex and centrifuge at 9,000 g×2 minutes to pellet the beads. Aspirate the supernatant.
7. Repeat step 6.
8. Dilute 100× αIgG-FITC to the appropriate volume of 1× working stock with wash buffer.
9. Add 100 μL 1× αIgG-FITC to the tube containing washed HLA beads. Vortex to mix.
10. Incubate HLA beads with αIgG-FITC for 30 minutes at room temperature in the dark with gentle rocking/agitation.
11. Repeat steps 6 and 7 to wash away unbound αIgG-FITC.
12. Resuspend the washed HLAbeads in 200 μL PBS. Vortex to mix.
13. Pipet approximately 100 μL of the HLA bead suspension to the appropriate well(s) of a 96-well U-bottom microplate and dock onto the NovoSampler.
14. Use the NovoCyte to collect events by flow cytometry.
    a. Slow collection of 10,000 events in the previously determined FLOWPRA™ Beads gate with FSC-H threshold 10,000.
    b. Secondary stop conditions were 2 minutes run time and 40 μL total sample volume.
    c. The SIP is washed between each sample to minimize carryover between wells. A well of PBS is run between each triplicate set to minimize carryover between testing points.

Results

Example 3. Gate Placement and Negative Controls

Initial gate placement for identification of Class I and Class II HLA beads is determined using FLOWPRA™ beads in PBS. (FIG. 1A and FIG. 1B)

Background/nonspecific binding is established using GK PPP and fresh donor PPP in triplicate. (Exemplary data is shown in FIG. 2A, FIG. 2B, FIG. 3A, and FIG. 3B) Note that GK PPP is shifted higher on FITC-H than the fresh donor plasma. This may be due to donor variability or freeze/thaw effects on the GK plasma. Additional sampling is necessary. Positivity gates are placed such that <1% of GK PPP returns FITC-positive.

Example 4. Single Donor Results

Representative FITC-H histograms from each HLA class are given for each sample. Positivity >1% is positive. Fluorescence ratios are reported against the GK PPP negative control (Class I and Class II bead FITC-H intensity). Fluorescence ratios >1.0 are positive. As additional negative controls are collected these positivity gates and fluorescence ratios will be updated.

Populations are negative for HLA Class I or Class II antibodies if both percent positivity and fluorescence ratio are <1 for that bead type.

Figure 4B:
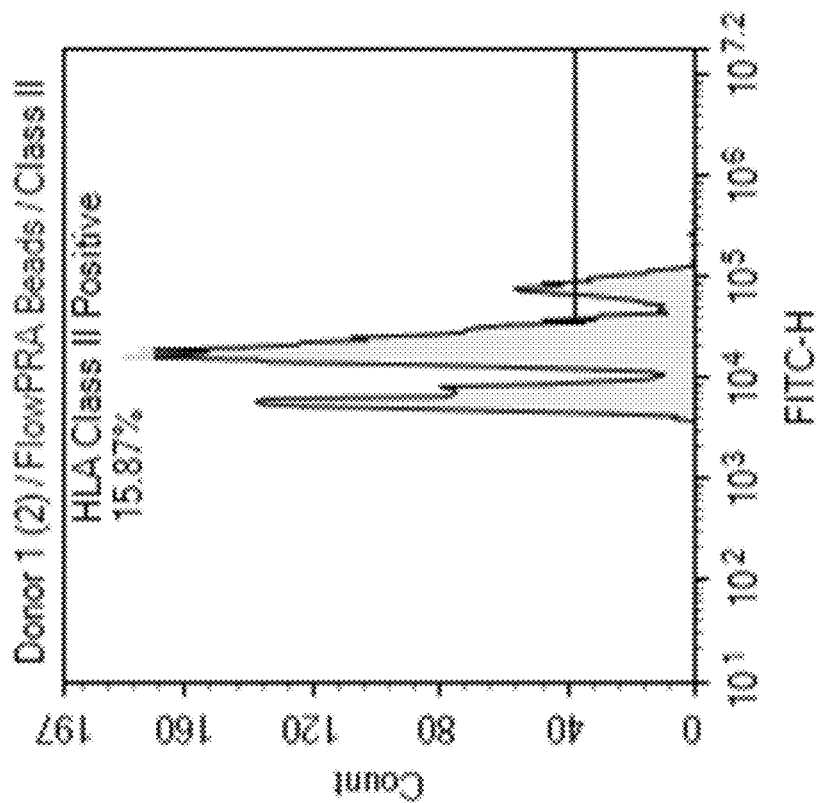
FIG. 4B shows an exemplary FITC-H histogram of FLOWPRA™ beads in Donor 1 PPP gated on Class II HLA.
Figure 4A:
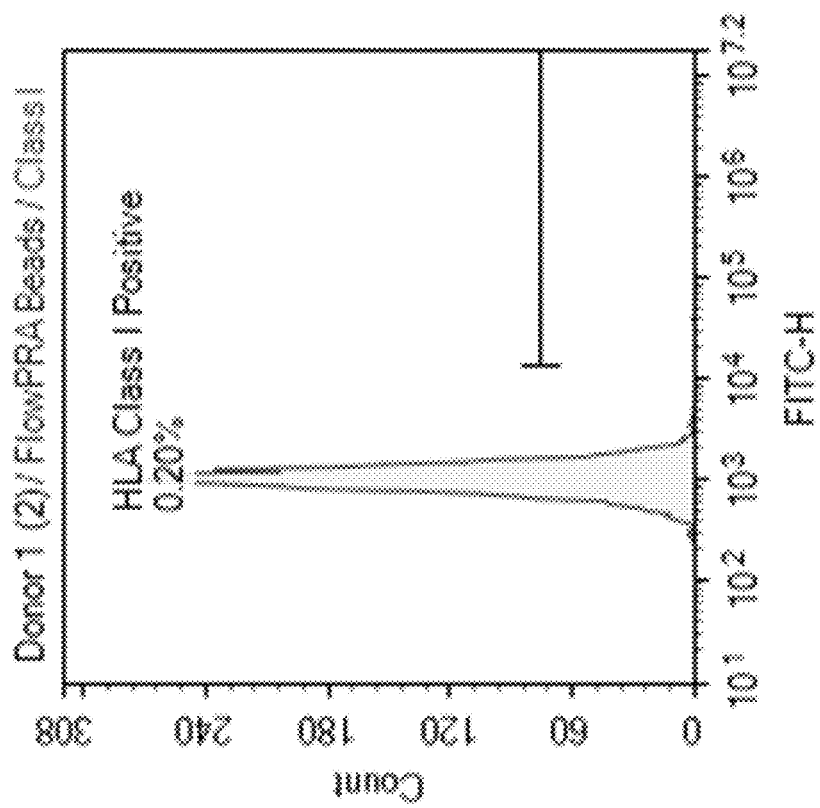
FIG. 4A shows an exemplary FITC-H histogram of FLOWPRA™ beads in Donor 1 PPP gated on Class I HLA.

Donor #1: HLA Class II Positive. Average positivity from triplicate data for Class I is 0.2% with fluorescence ratio 0.3; average positivity for Class II is 16.5% with fluorescence ratio 1.6. (Exemplary data is shown FIG. 4A and FIG. 4B).

Figure 5B:
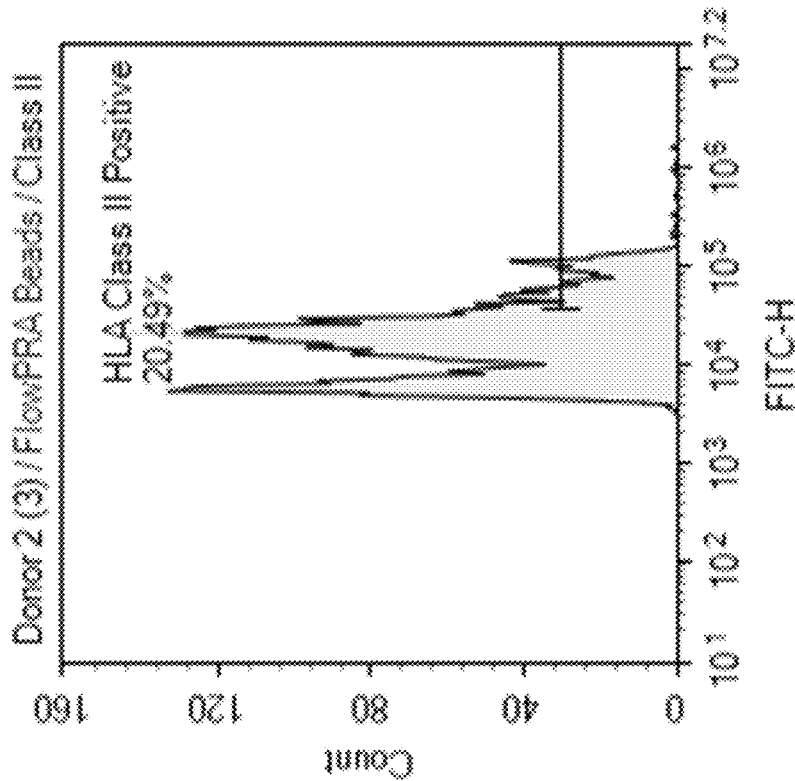
FIG. 5B shows an exemplary FITC-H histogram of FLOWPRA™ beads in Donor 2 PPP gated on Class II HLA.
Figure 5A:
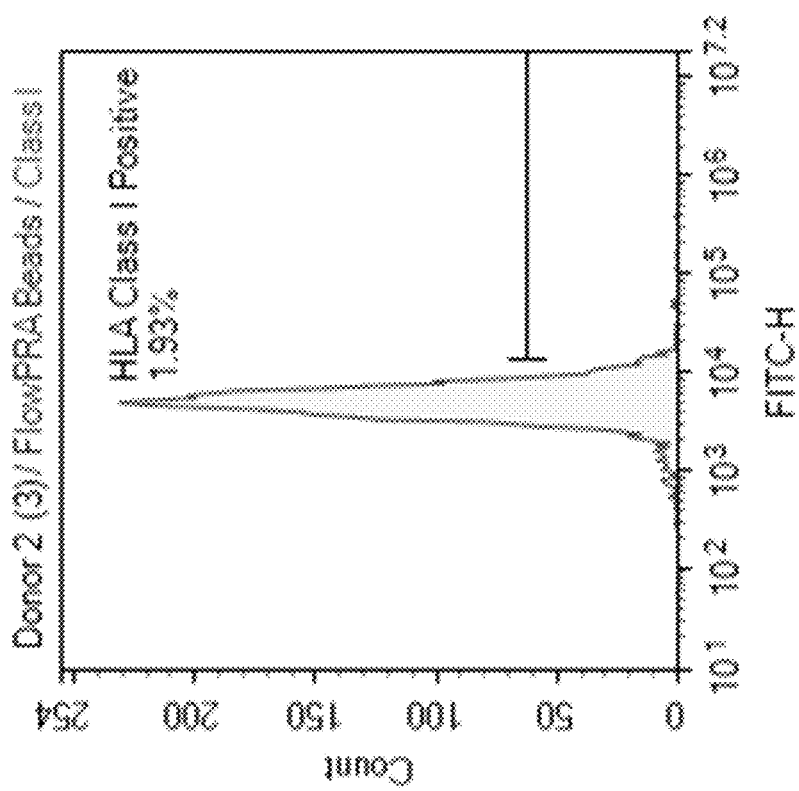
FIG. 5A shows an exemplary FITC-H histogram of FLOWPRA™ beads in Donor 2 PPP gated on Class I HLA.

Donor #2: HLA Class I and Class II Positive. Average positivity from triplicate data for Class I is 1.3% with fluorescence ratio 1.4; average positivity for Class II is 20.3% with fluorescence ratio 1.9. (Exemplary data is shown FIG. 5A and FIG. 5B).

Figure 6B:
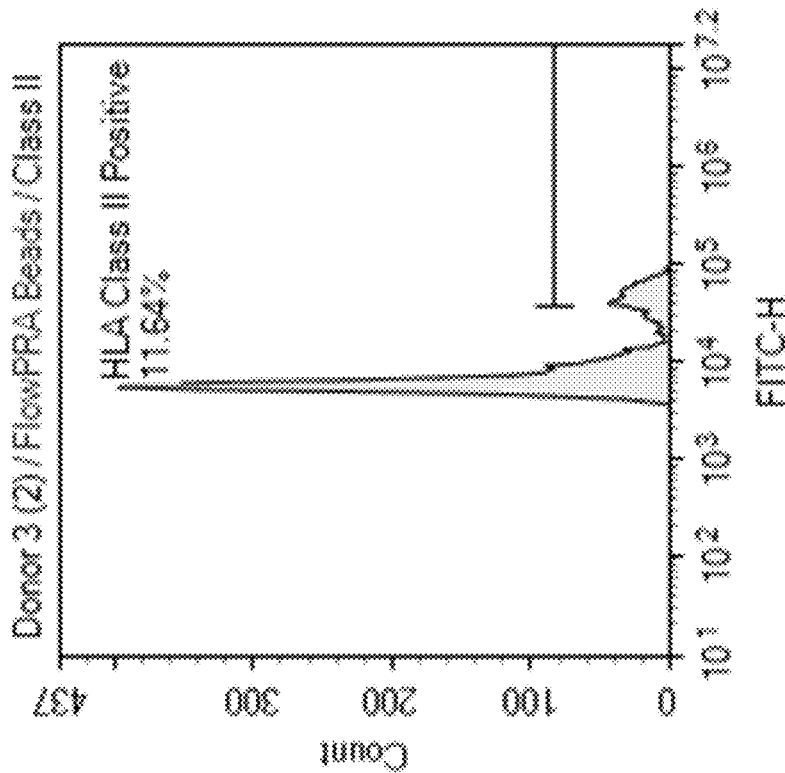
FIG. 6B shows an exemplary FITC-H histogram of FLOWPRA™ beads in Donor 3 PPP gated on Class II HLA.
Figure 6A:
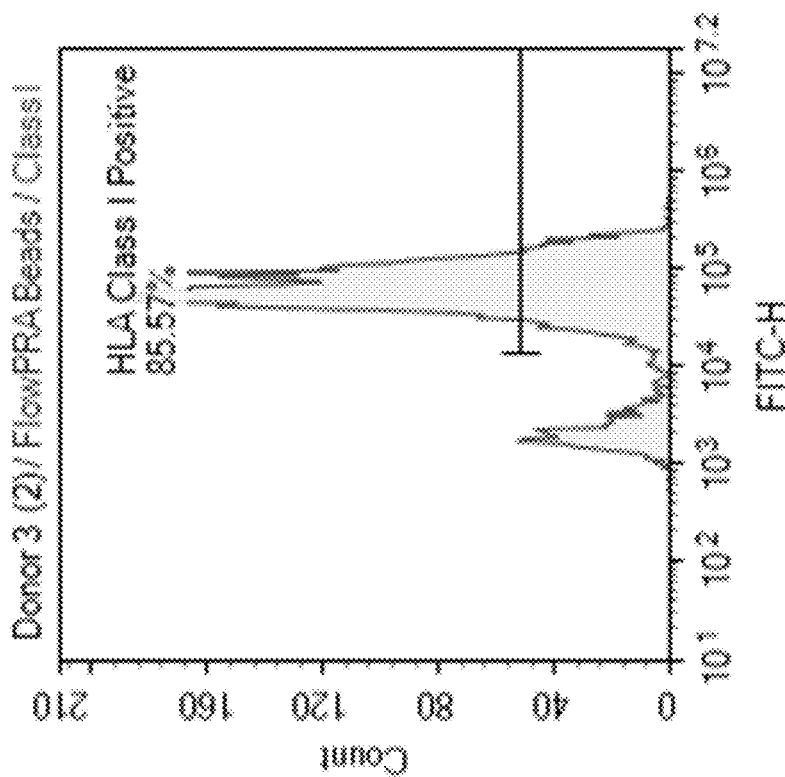
FIG. 6A shows an exemplary FITC-H histogram of FLOWPRA™ beads in Donor 3 PPP gated on Class I HLA.

Donor #3: HLA Class I and Class II Positive. Average positivity from triplicate data for Class I is 85.2% with fluorescence ratio 14.4. Average positivity for Class II is 12.0% with fluorescence ratio 0.8. (Exemplary data is shown FIG. 6A and FIG. 6B).

Donor #4: HLA Class I and Class II Positive. Average positivity from triplicate data for Class I is 83.5% with fluorescence ratio 14.5. Average positivity for Class II is 12.6% with fluorescence ratio 0.8. (Exemplary data is shown FIG. 7A and FIG. 7B).

Figure 8B:
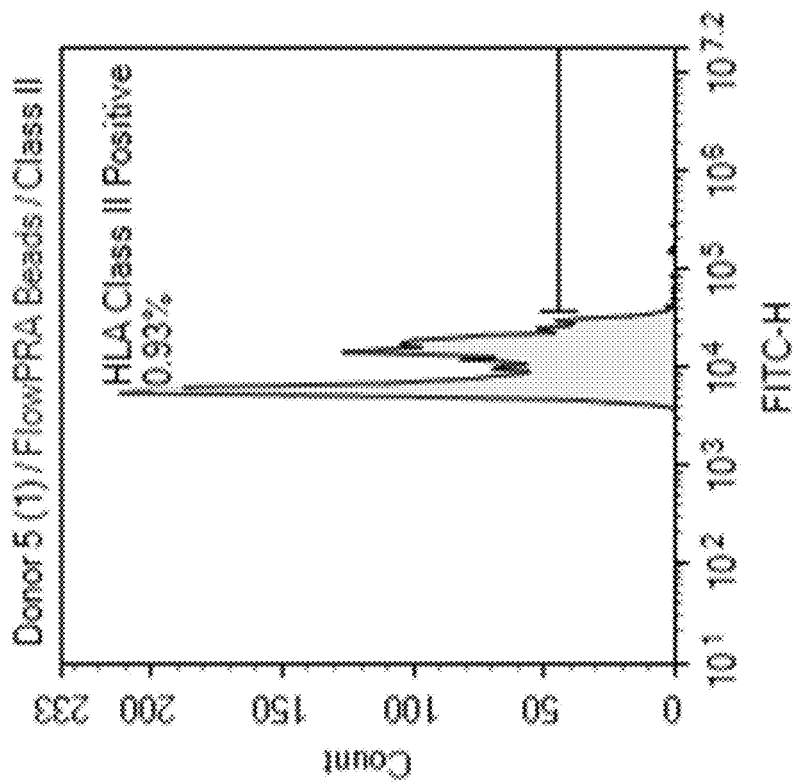
FIG. 8B shows an exemplary FITC-H histogram of FLOWPRA™ beads in Donor 5 PPP gated on Class II HLA.
Figure 8A:
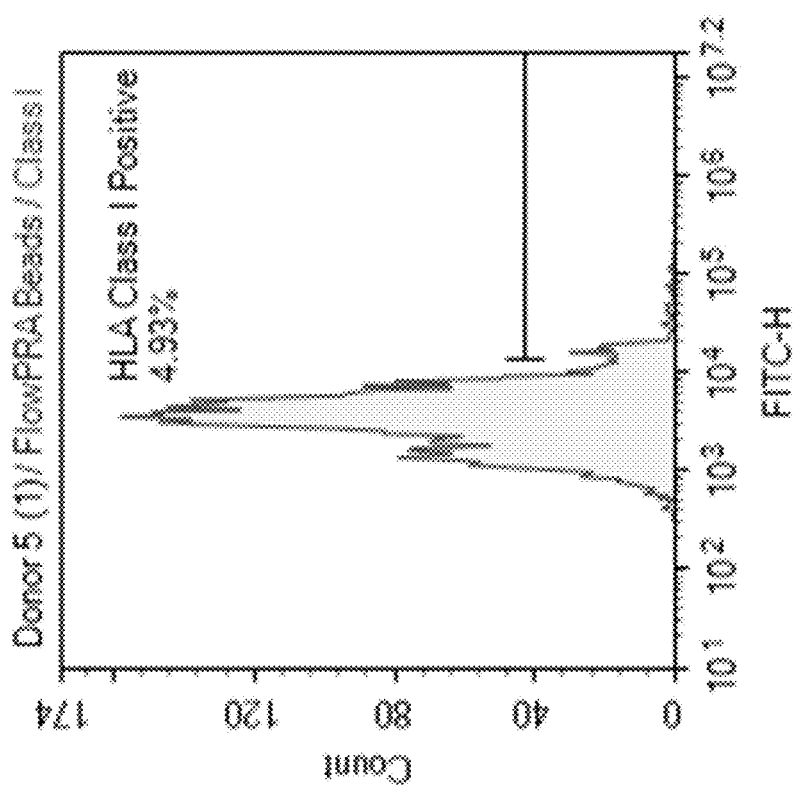
FIG. 8A shows an exemplary FITC-H histogram of FLOWPRA™ beads in Donor 5 PPP gated on Class I HLA.

Donor #5: HLA Class I and Class II Positive. Average positivity from triplicate data for Class I is 4.9% with fluorescence ratio 1.2. Average positivity for Class II is 1.3% with fluorescence ratio 0.8. (Exemplary data is shown FIG. 8A and FIG. 8B).

Figure 9B:
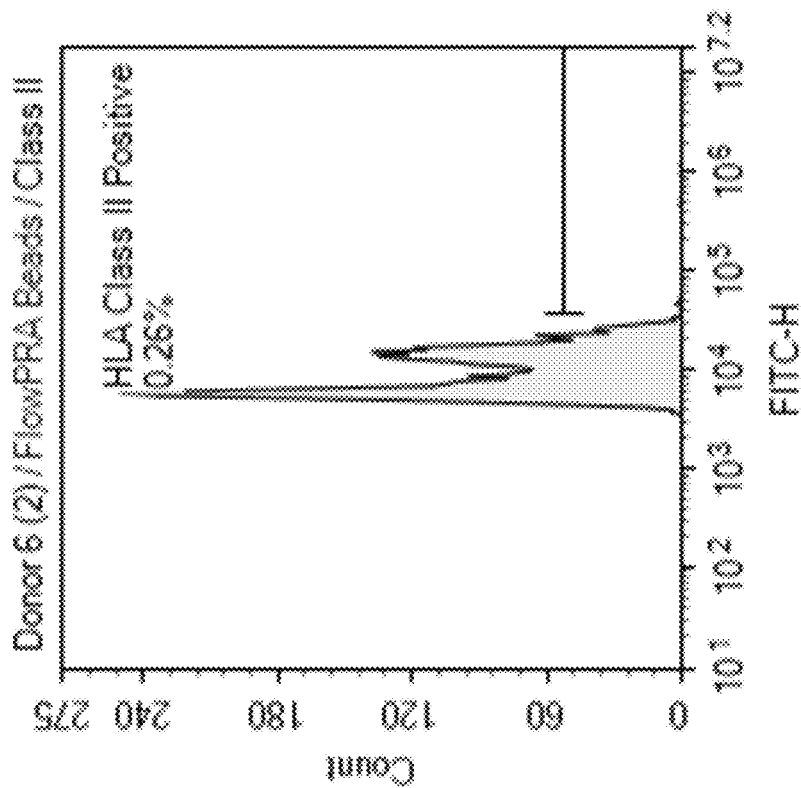
FIG. 9B shows an exemplary FITC-H histogram of FLOWPRA™ beads in Donor 6 PPP gated on Class II HLA.
Figure 9A:
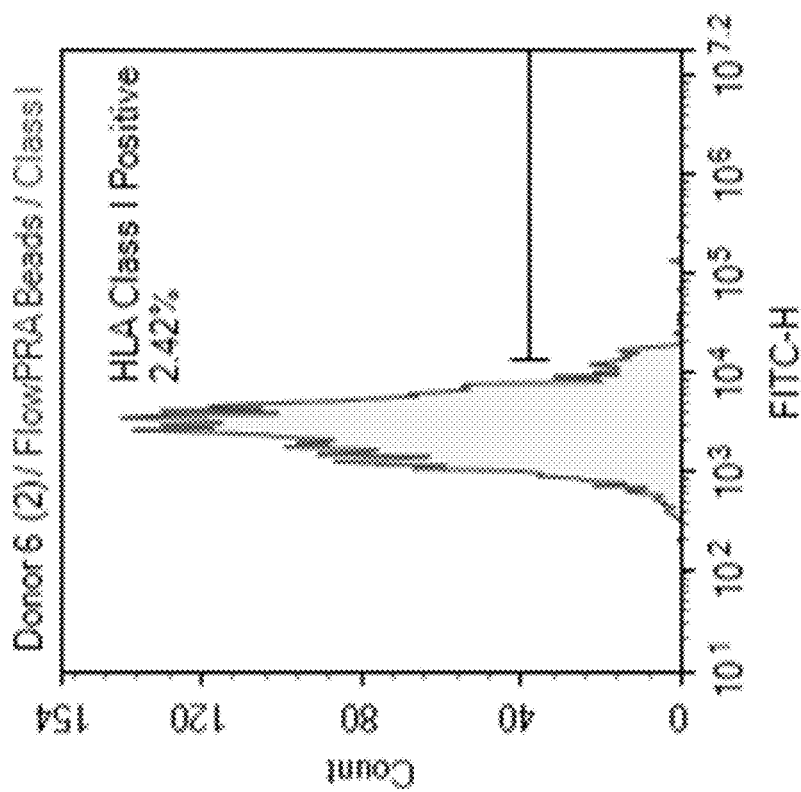
FIG. 9A shows an exemplary FITC-H histogram of FLOWPRA™ beads in Donor 6 PPP gated on Class I HLA.

Donor #6: HLA Class I Positive. Average positivity from triplicate data for Class I is 2.7% with fluorescence ratio 0.9. Average positivity for Class II is 0.3% with fluorescence ratio 0.7. (Exemplary data is shown FIG. 9A and FIG. 9B).

Donor #7: HLA Class II Positive. Average positivity for from triplicate data Class I is 0.7% with fluorescence ratio 0.5. Average positivity for Class II is 9.0% with fluorescence ratio 1.3. (Exemplary data is shown FIG. 10A and FIG. 10B).

The results for Donors 1-7 are also shown in Table 1.

TABLE 1

|  | Donor 1 | Donor 2 | Donor 3 | Donor 4 | Donor 5 | Donor 6 | Donor 7 |
|---|---|---|---|---|---|---|---|
| Average Percent Positivity Class I | 0.2 | 1.3 | 85.2 | 83.5 | 4.9 | 2.7 | 0.7 |
| Average Percent Positivity Class II | 16.5 | 20.3 | 12.0 | 12.6 | 1.3 | 0.3 | 9.0 |
| Average Fluorescence Ratio Class I | 0.3 | 1.4 | 14.4 | 14.5 | 1.2 | 0.9 | 0.5 |
| Average Fluorescence Ratio Class II | 1.6 | 1.9 | 0.8 | 0.8 | 0.8 | 0.7 | 1.3 |

Because there might be HLA-positive donors in the GK PNP pool, Table 2 displays results against an N=1 HLA-negative donor.

TABLE 2

|  | Donor 1 | Donor 2 | Donor 3 | Donor 4 | Donor 5 | Donor 6 | Donor 7 |
|---|---|---|---|---|---|---|---|
| AVERAGE PERCENT POSITIVITY CLASS I | 0.3 | 12.3 | 86.1 | 84.8 | 12.4 | 7.6 | 1.1 |
| AVERAGE PERCENT POSITIVITY CLASS II | 66.6 | 67.0 | 19.1 | 19.5 | 43.1 | 36.3 | 22.6 |
| AVERAGE FLUORESCENCE RATIO CLASS I | 0.9 | 4.2 | 44.4 | 44.6 | 3.8 | 2.9 | 1.6 |
| AVERAGE FLUORESCENCE RATIO CLASS II | 4.4 | 5.4 | 2.3 | 2.3 | 2.3 | 2.0 | 3.5 |

Example 5. Filtration Results

Figure 11B:
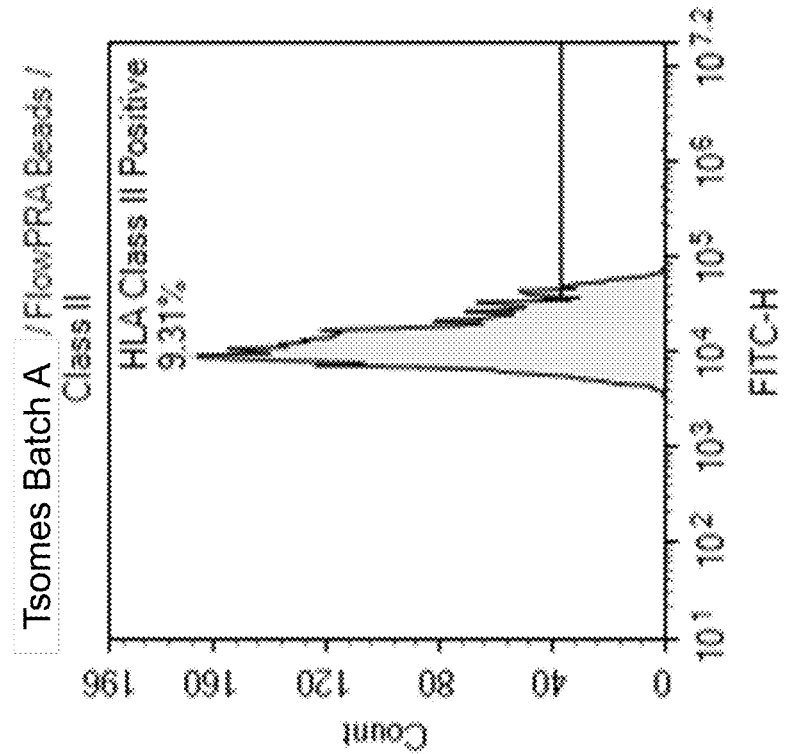
FIG. 11B shows an exemplary FITC-H histogram of FLOWPRA™ beads pooled Donor PPP gated on Class II HLA.
Figure 11A:
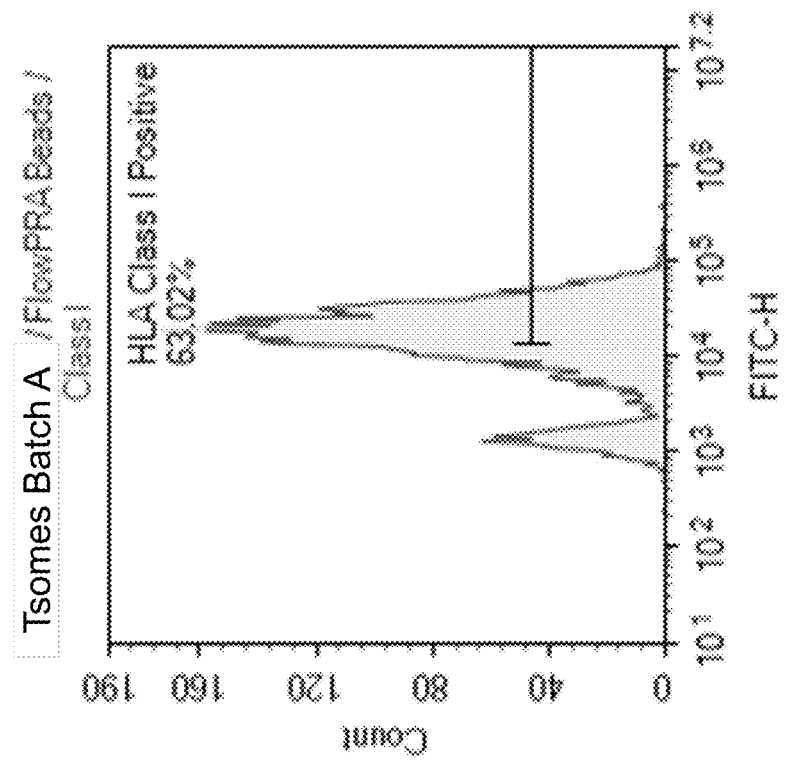
FIG. 11A shows an exemplary FITC-H histogram of FLOWPRA™ beads pooled Donor PPP gated on Class I HLA.

Pool: HLA Class I and Class II Positive. Average positivity from triplicate data for Class I is 61.1% with fluorescence ratio 4.6. Average positivity for Class II is 9.0% with fluorescence ratio 1.1. (Exemplary data is shown FIG. 11A and FIG. 11B).

Figure 12B:
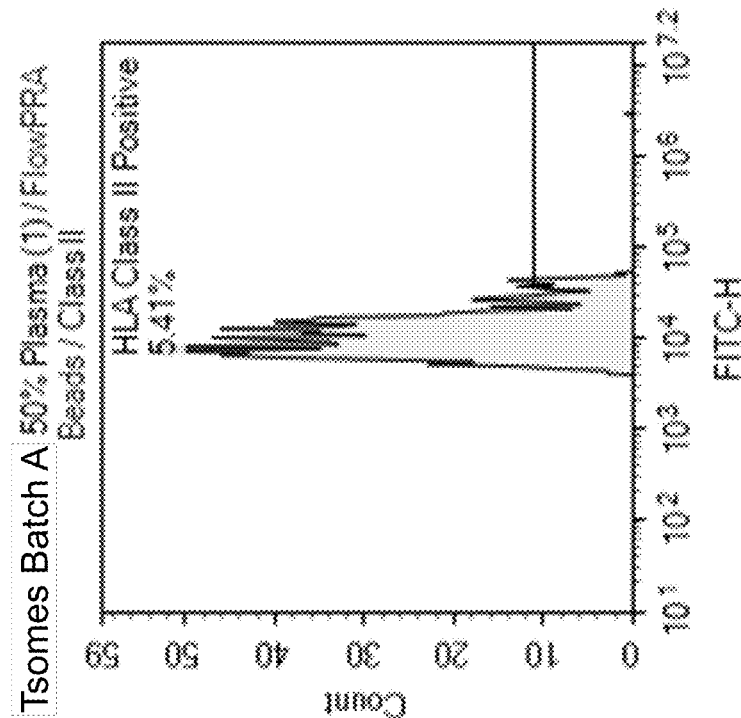
FIG. 12B shows an exemplary FITC-H histogram of FLOWPRA™ beads pooled Donor PPP gated on Class II HLA following tangential flow filtration (TFF) to 50% (by absorbance at 280 nm) retained plasma protein.
Figure 12A:
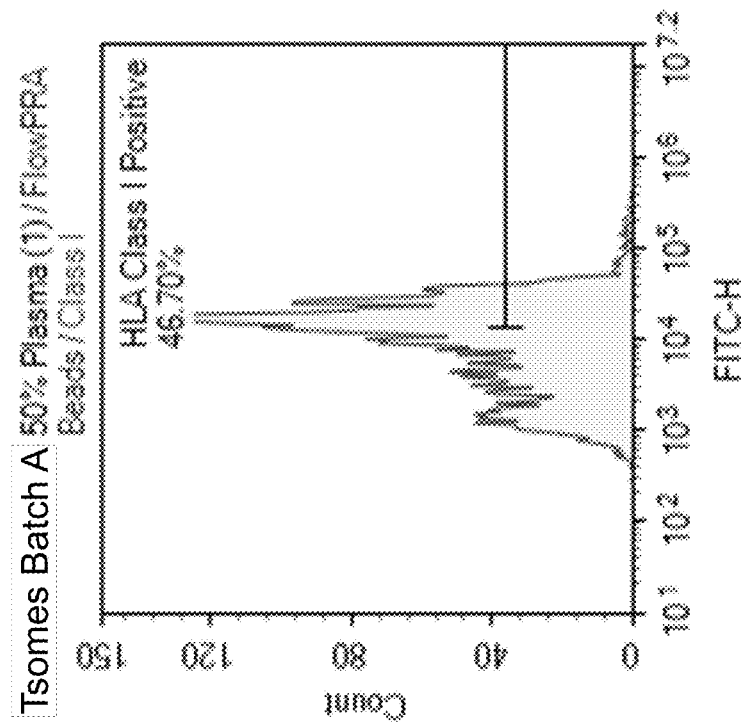
FIG. 12A shows an exemplary FITC-H histogram of FLOWPRA™ beads pooled Donor PPP gated on Class I HLA following tangential flow filtration (TFF) to 50% (by absorbance at 280 nm) retained plasma protein.

Initial Dilution (51%): HLA Class I and Class II Positive. Average positivity from triplicate data for Class I is 48.2% with fluorescence ratio 4.2. Average positivity for Class II is 5.9% with fluorescence ratio 0.9. (Exemplary data is shown FIG. 12A and FIG. 12B).

Figures 13A, 13B:
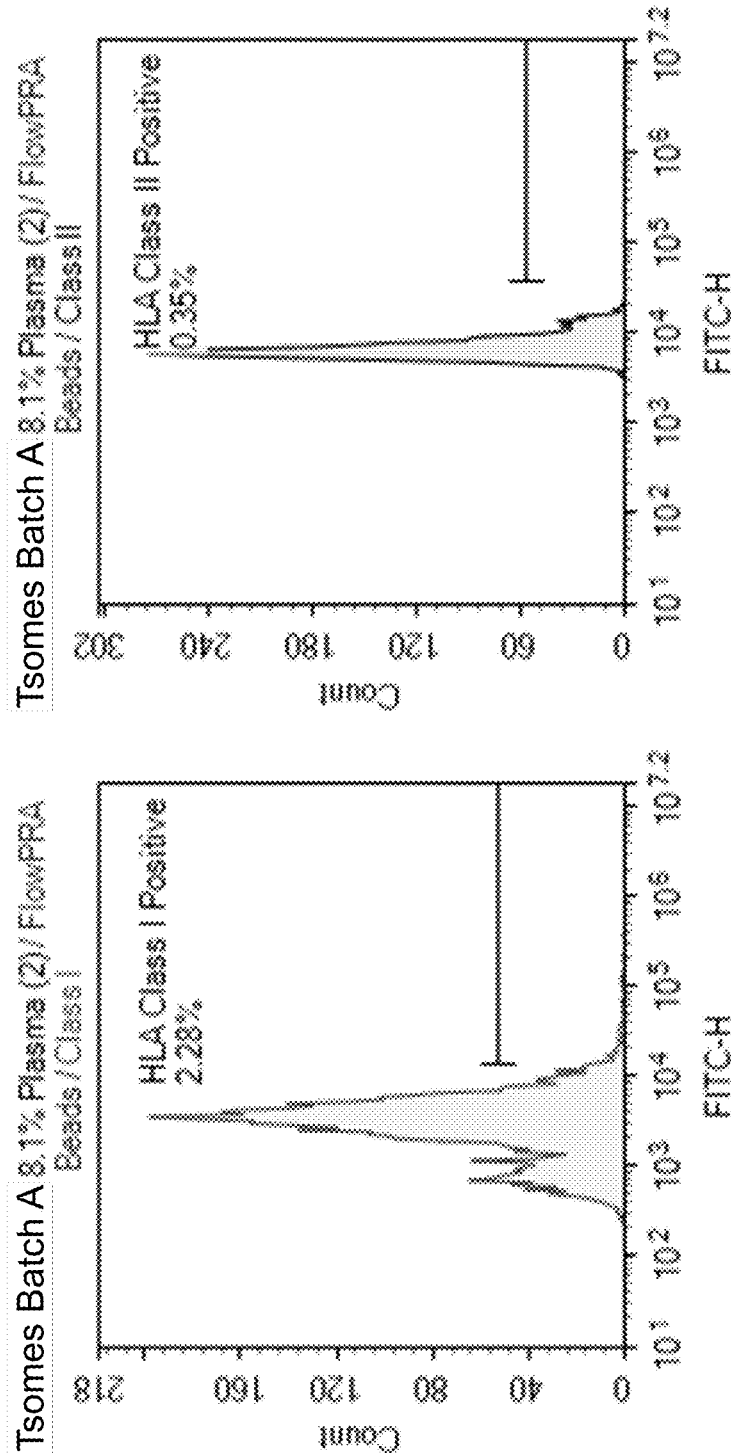
FIG. 13A shows an exemplary FITC-H histogram of FLOWPRA™ beads pooled Donor PPP gated on Class I HLA following tangential flow filtration (TFF) to about 8% (by absorbance at 280 nm) retained plasma protein.
FIG. 13B shows an exemplary FITC-H histogram of FLOWPRA™ beads pooled Donor PPP gated on Class II HLA following tangential flow filtration (TFF) to about 8% (by absorbance at 280 nm) retained plasma protein.

"20%" Plasma (8.1%): HLA Class I Positive. Average positivity from triplicate data for Class I is 2.4% with fluorescence ratio 1.0. Average positivity for Class II is 0.2% with fluorescence ratio 0.5. (Exemplary data is shown FIG. 13A and FIG. 13B).

Figure 14B:
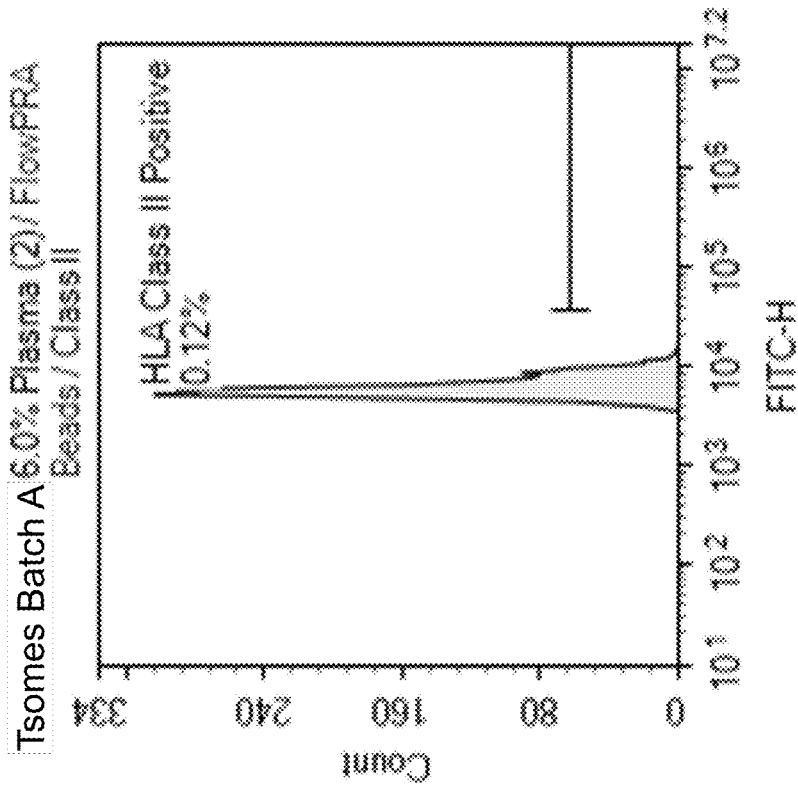
FIG. 14B shows an exemplary FITC-H histogram of FLOWPRA™ beads pooled Donor PPP gated on Class II HLA following tangential flow filtration (TFF) to about 6% (by absorbance at 280 nm) retained plasma protein.
Figure 14A:
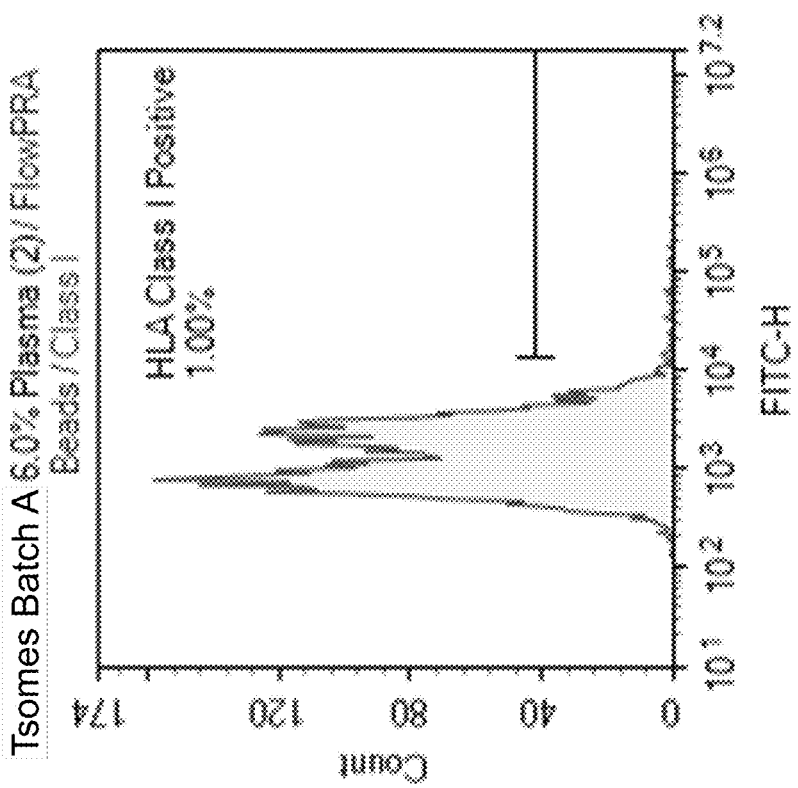
FIG. 14A shows an exemplary FITC-H histogram of FLOWPRA™ beads pooled Donor PPP gated on Class I HLA following tangential flow filtration (TFF) to about 6% (by absorbance at 280 nm) retained plasma protein.

"<10%" Plasma (6.0%): Borderline HLA Class I Positive. Average positivity from triplicate data for Class I is 1.1% with fluorescence ratio 1.0. Average positivity for Class II is 0.2% with fluorescence ratio 0.5. (Exemplary data is shown FIG. 14A and FIG. 14B).

Figures 15A, 15B:
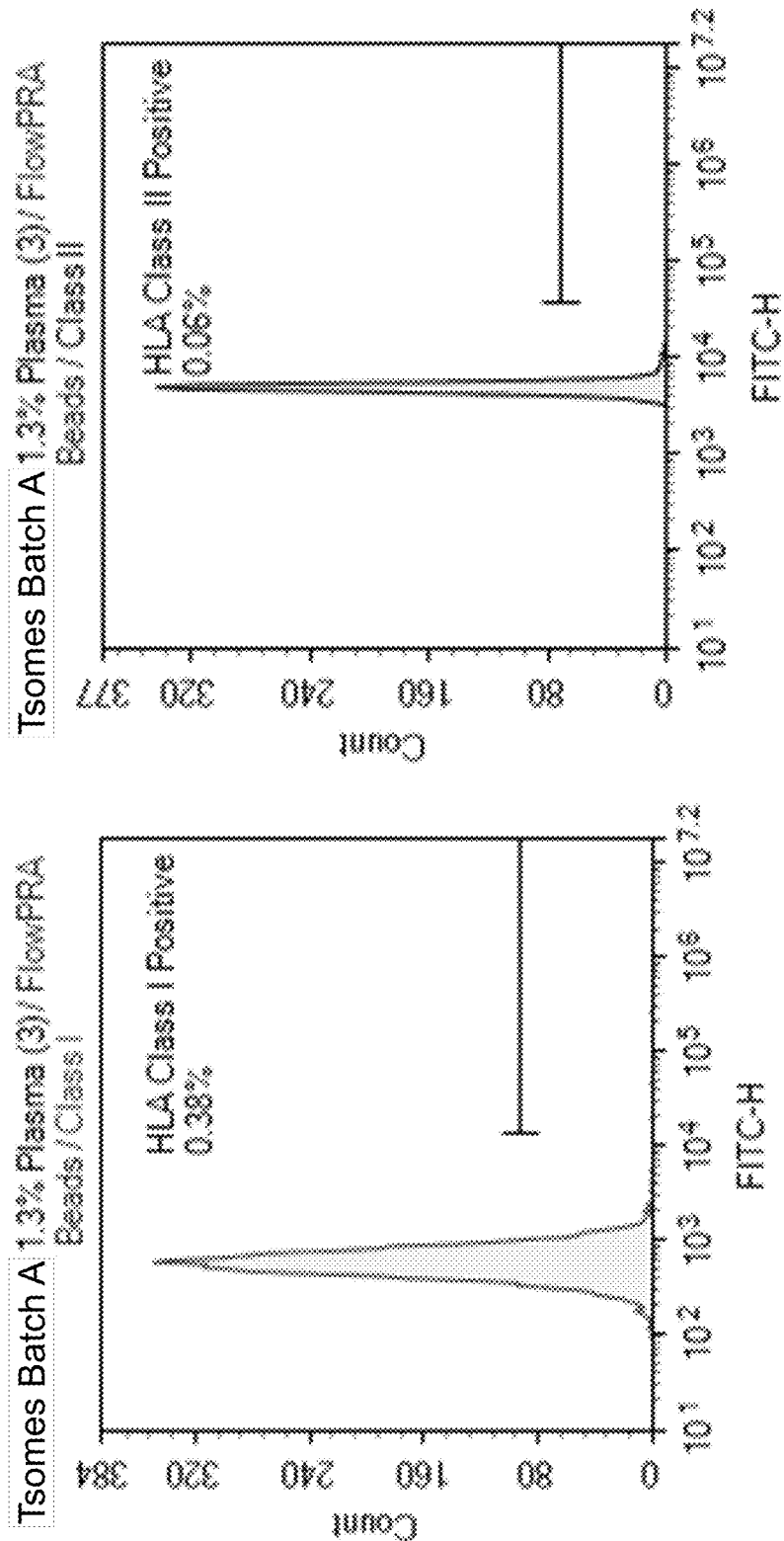
FIG. 15A shows an exemplary FITC-H histogram of FLOWPRA™ beads pooled Donor PPP gated on Class I HLA following tangential flow filtration (TFF) to about 1% (by absorbance at 280 nm) retained plasma protein.
FIG. 15B shows an exemplary FITC-H histogram of FLOWPRA™ beads pooled Donor PPP gated on Class II HLA following tangential flow filtration (TFF) to about 1% (by absorbance at 280 nm) retained plasma protein.

"<3%" Plasma (1.3%): HLA Negative. Average positivity from triplicate data for Class I is 0.4% with fluorescence ratio 0.2. Average positivity for Class II is 0.1% with fluorescence ratio 0.4. (Exemplary data is shown FIG. 15A and FIG. 15B).

The filtration results are also shown in Tables 3A and 3B.

TABLE 3A

|  | Pool | 51% Plasma | 8.1% Plasma | 6.0% Plasma | 1.3% Plasma |
|---|---|---|---|---|---|
| Average Percent Positivity Class I | 61.1 | 48.2 | 2.4 | 1.1 | 0.4 |
| Average Percent Positivity Class II | 9.0 | 5.9 | 0.2 | 0.2 | 0.1 |
| Average Fluorescence Ratio Class I | 4.6 | 4.2 | 1.0 | 0.7 | 0.2 |
| Average Fluorescence Ratio Class II | 1.1 | 0.9 | 0.5 | 0.5 | 0.4 |

TABLE 3B

Background fluorescence determined using HLA beads in PBS was subtracted from sample fluorescence prior to calculation of percent reduction in mean fluorescence intensity (a measure of reduction in antibody binding).

| Percent Reduction in Fluorescence Intensity | Class I HLA Beads With background subtraction from beads in PBS | Class II HLA Beads With background subtraction from beads in PBS |
|---|---|---|
| Pool | 0.0% | 0.0% |
| 51% Residual Plasma | 9.6% | 18.7% |
| 8.1% Residual Plasma | 80.8% | 74.8% |
| 6.0% Residual Plasma | 87.4% | 72.0% |
| 1.3% Residual Plasma | 97.3% | 83.8% |
| Thrombosomes 4.9% Residual Plasma Unbaked | 95.8% | 91.4% |

TABLE 3B-continued

Background fluorescence determined using HLA beads in PBS was
subtracted from sample fluorescence prior to calculation of percent reduction
in mean fluorescence intensity (a measure of reduction in antibody binding).

| Percent Reduction in Fluorescence Intensity | Class I HLA Beads With background subtraction from beads in PBS | Class II HLA Beads With background subtraction from beads in PBS |
|---|---|---|
| Thrombosomes 4.9% Residual Plasma Baked | 100.0% | 100.6% |
| Thrombosomes 1.3% Residual Plasma Unbaked | 100.0% | 100.9% |
| Thrombosomes 1.3% Residual Plasma Baked | 99.6% | 100.8% |

Values ≥100% indicate complete reduction in detectable HLA antibody binding to the indicated beads.

Because there might be HLA-positive donors in the GK PNP pool, Table 4 displays results against an N=HLA-negative donor.

TABLE 4

|  | Pool | 51% Plasma | 8% Plasma | 6% Plasma | <3% Plasma |
|---|---|---|---|---|---|
| AVERAGE PERCENT POSITIVITY CLASS I | 77.9 | 64.7 | 7.6 | 2.2 | 0.4 |
| AVERAGE PERCENT POSITIVITY CLASS II | 52.8 | 42.7 | 4.9 | 0.7 | 0.2 |
| AVERAGE FLUORESCENCE RATIO CLASS I | 14.3 | 12.9 | 3.0 | 2.1 | 0.7 |
| AVERAGE FLUORESCENCE RATIO CLASS II | 2.9 | 2.6 | 1.4 | 1.4 | 1.2 |

Example 6. Surface Markers and Thrombin Generation

Thrombosomes batch were produced by the TFF method described in Example 1 and assayed for cell surface marker expression using flow cytometry.

Flow cytometry was used to assess thrombosomes for expression of CD41, CD62, and phosphatidylserine (PS). Samples included approximately 270,000/µL thrombosomes during staining and were diluted approximately 1:34 before the sample was analyzed in the cytometer. Thrombosome samples were rehydrated and diluted 1:2 in deionized water. A stock of anti-CD41 was diluted by adding 47.6 µL of antibody to 52.4 µL of HMTA. Samples stained with anti-CD41 were made by adding 10 µL of diluted thrombosomes to 10 µL HMTA and 10 µL of diluted CD41 antibody. An anti-CD62 master mix was prepared by combining 12 µL anti-CD62 with 23.8 µL anti-CD41 and 64.2 µL of HMTA. An isotype control mix was made in the same manner. Samples stained with anti-CD62 were made by adding 10 µL of diluted thrombosomes to 20 µL of the anti-CD62 master. The isotype master mix was used to make isotype control samples in the same manner. An annexin V (AV) master mix was prepared by combining 11.7 µL of AV with 83.3 µL of anti-CD41 and 80 µL of HMTA. Sample stained with AV were made by adding 20 µL of diluted thrombosomes containing 50 mM GPRP to 20 µL of HMTA containing 15 mM $CaCl_2$) and 20 µL of the AV master mix. Negative gating control samples were made in the same manner using HMTA without calcium to prevent AV binding to PS. All samples were incubated at room temperature for 20 minutes. After incubation 1 mL HBS was added to all samples. HBS used to dilute AV test samples contained 5 mM $CaCl_2$).

Anti-CD41 binding was used to identify the population of interest. CD62 expression and PS expression was assessed by anti-CD62 and AV binding within the CD41 positive population.

Figure 16:
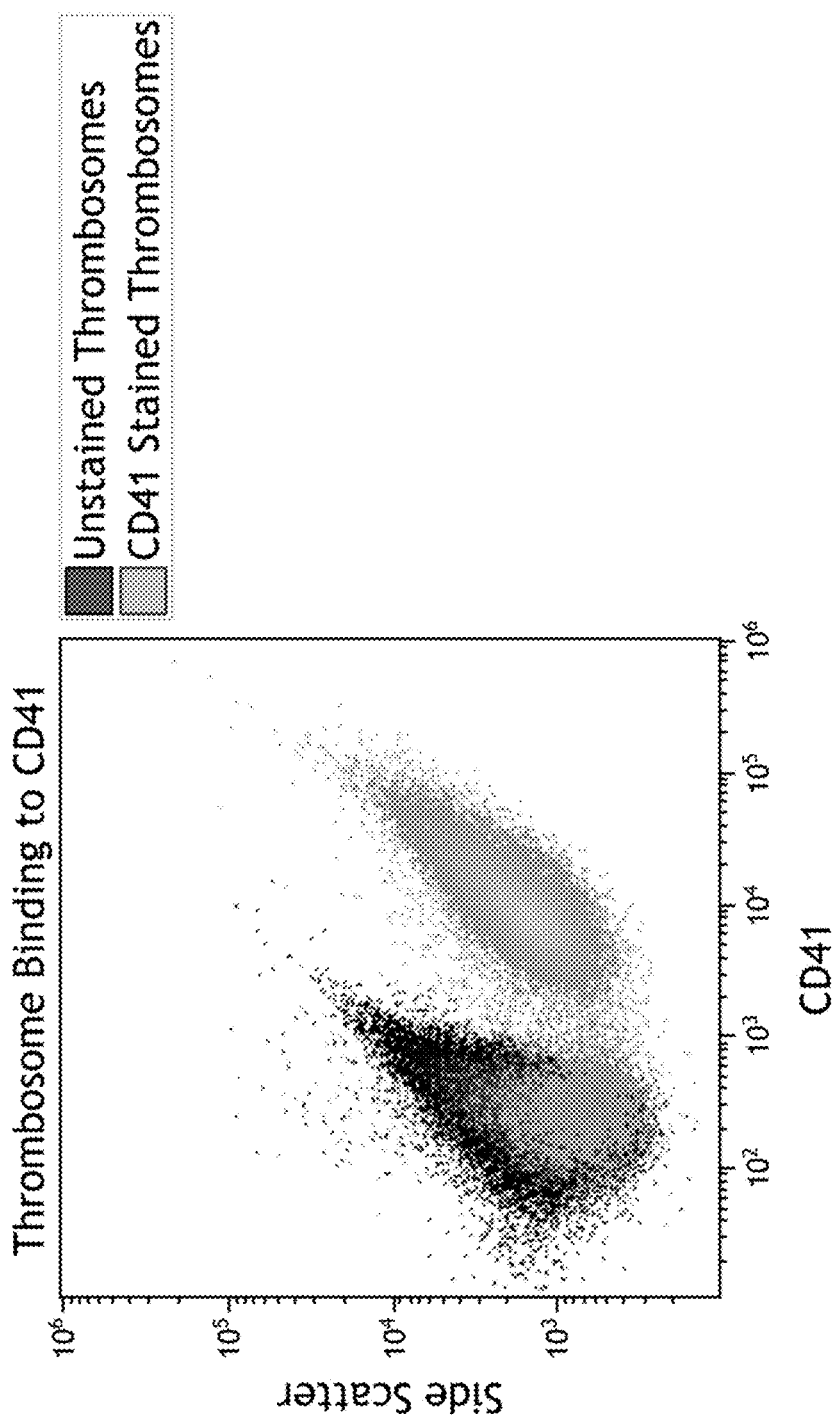
FIG. 16 shows exemplary flow cytometry data of thrombosomes unstained (dark data points) or stained (light data points) with an anti-CD-41 antibody.

Glycoprotein IIb (GPIIb, also known as antigen CD41) expression was assayed using an anti-CD41 antibody (4.8 µL, Beckman Coulter part #IM1416U). The assayed thrombosomes demonstrated CD41 positivity (Table 5; FIG. 16)

TABLE 5

| Batch | CD41 Positivity (%) |
|---|---|
| 1 | 81.5 |
| 2 | 79.4 |
| 3 | 85.7 |
| 4 | 78.2 |
| 5 | 81.5 |
| 6 | 84.0 |
| 7 | 78.5 |
| Mean | 81.3 |

Figure 17:
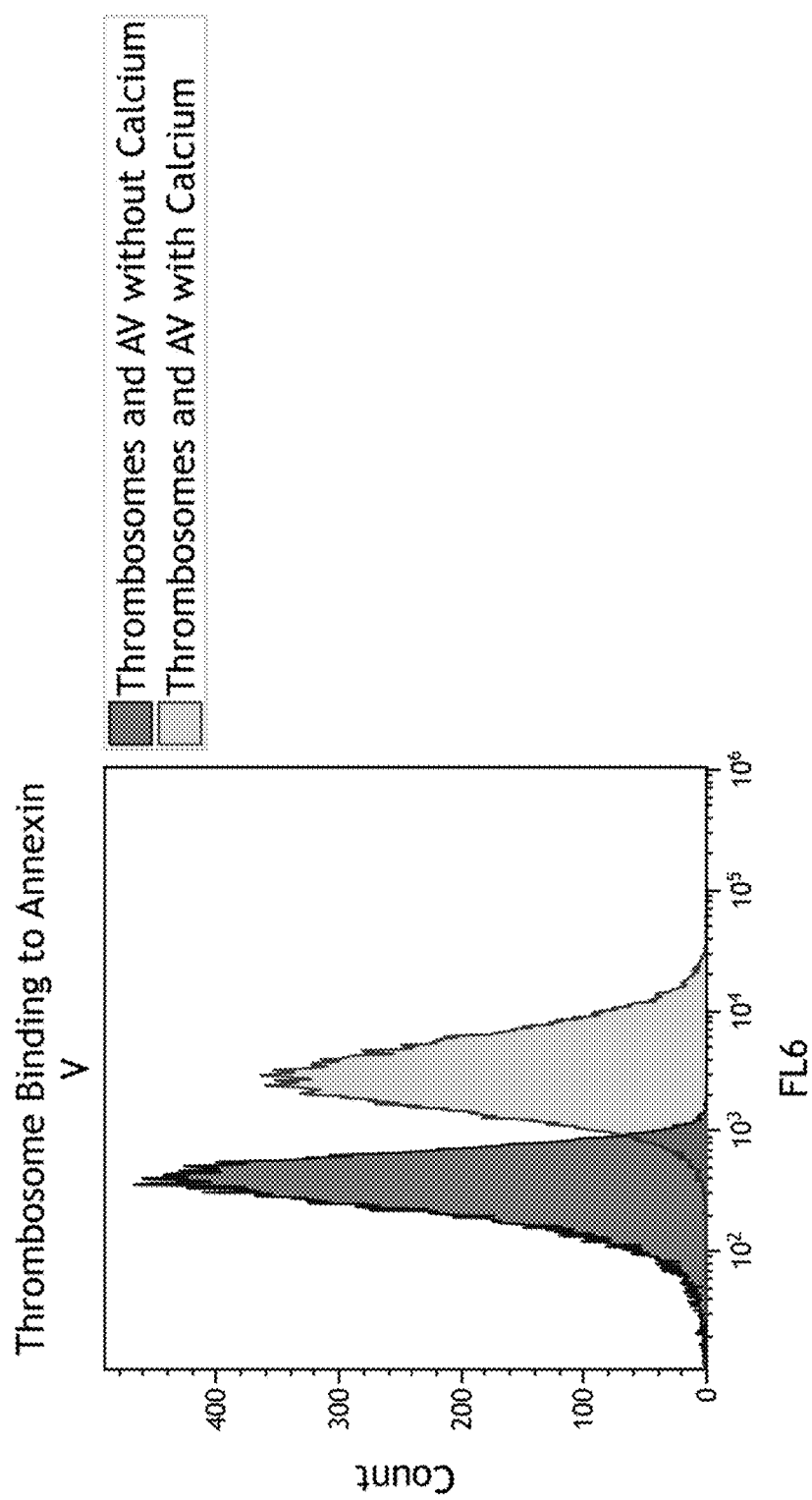
FIG. 17 shows an exemplary histogram of thrombosomes incubated with annexin V with (light data points) and without (dark data points) calcium.

Phosphatidylserine (PS) expression was assayed using annexin V (AV) (1.3 µL, BD Biosciences Cat. No. 550475). AV is a calcium-dependent phospholipid binding protein. The assayed thrombosomes demonstrated AV positivity (Table 6; FIG. 17).

TABLE 6

| Batch | AV Positivity (%) |
|---|---|
| 1 | 96.7 |
| 2 | 89.9 |
| 3 | 95.3 |
| 4 | 95.4 |
| 5 | 95.9 |
| 6 | 96.2 |
| 7 | 93.5 |
| Mean | 94.7 |

Figure 18:
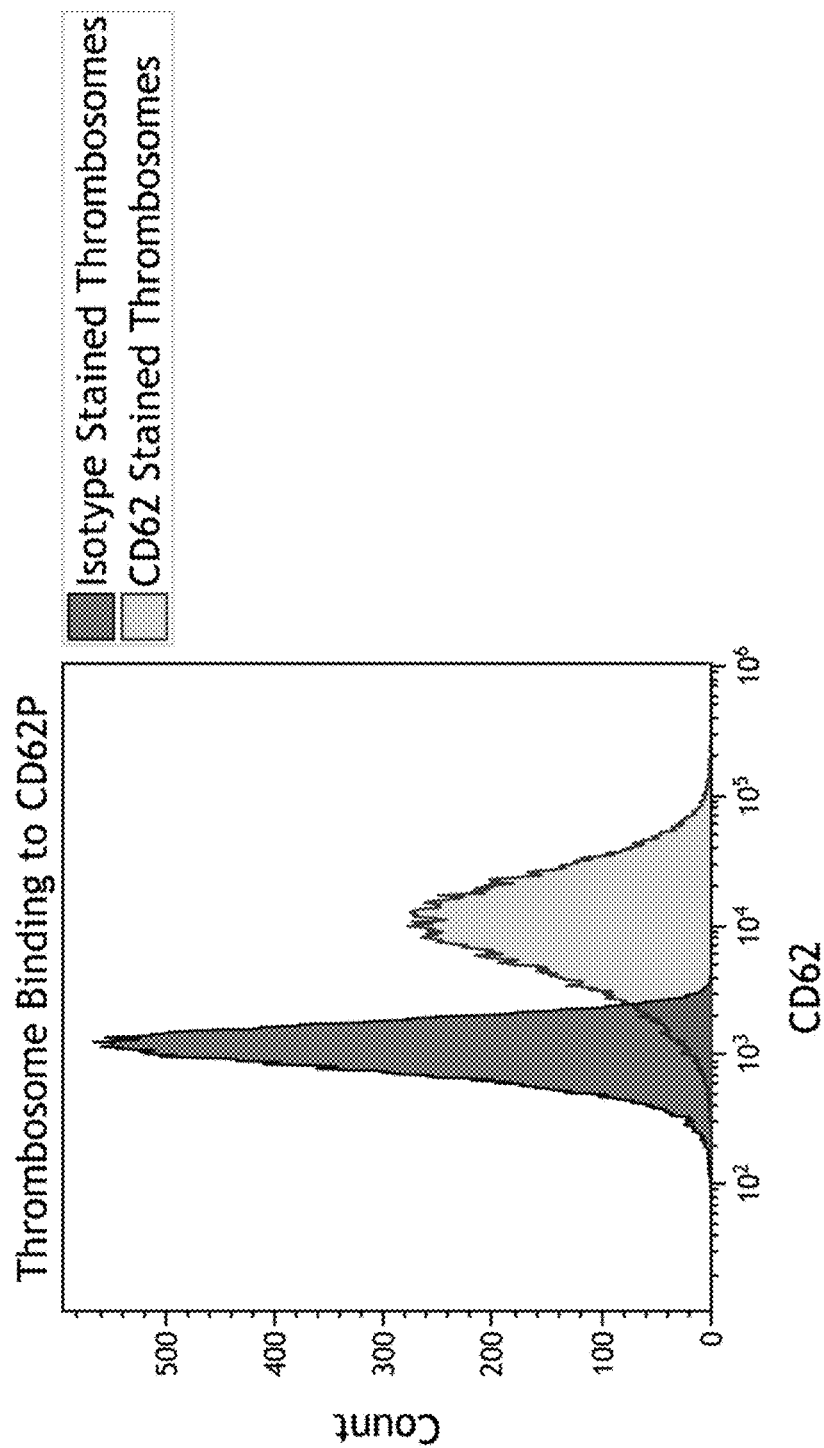
FIG. 18 shows an exemplary histogram of thrombosomes incubated with an anti-CD62 antibody (light data points) or with an isotype control (dark data points).

P-selectin (also called CD62P) expression was assayed using an anti-CD62P antibody (2.4 µL, BD Biosciences Cat. No. 550888). The assayed thrombosomes demonstrated CD62 positivity (Table 7, FIG. 18)

TABLE 7

| Batch | CD62 Positivity (%) |
|---|---|
| 1 | 94.2 |
| 2 | 93.1 |
| 3 | 89.8 |
| 4 | 92.4 |
| 5 | 92.5 |

TABLE 7-continued

| Batch | CD62 Positivity (%) |
|---|---|
| 6 | 87.3 |
| 7 | 90.7 |
| Mean | 91.4 |

Figure 19:
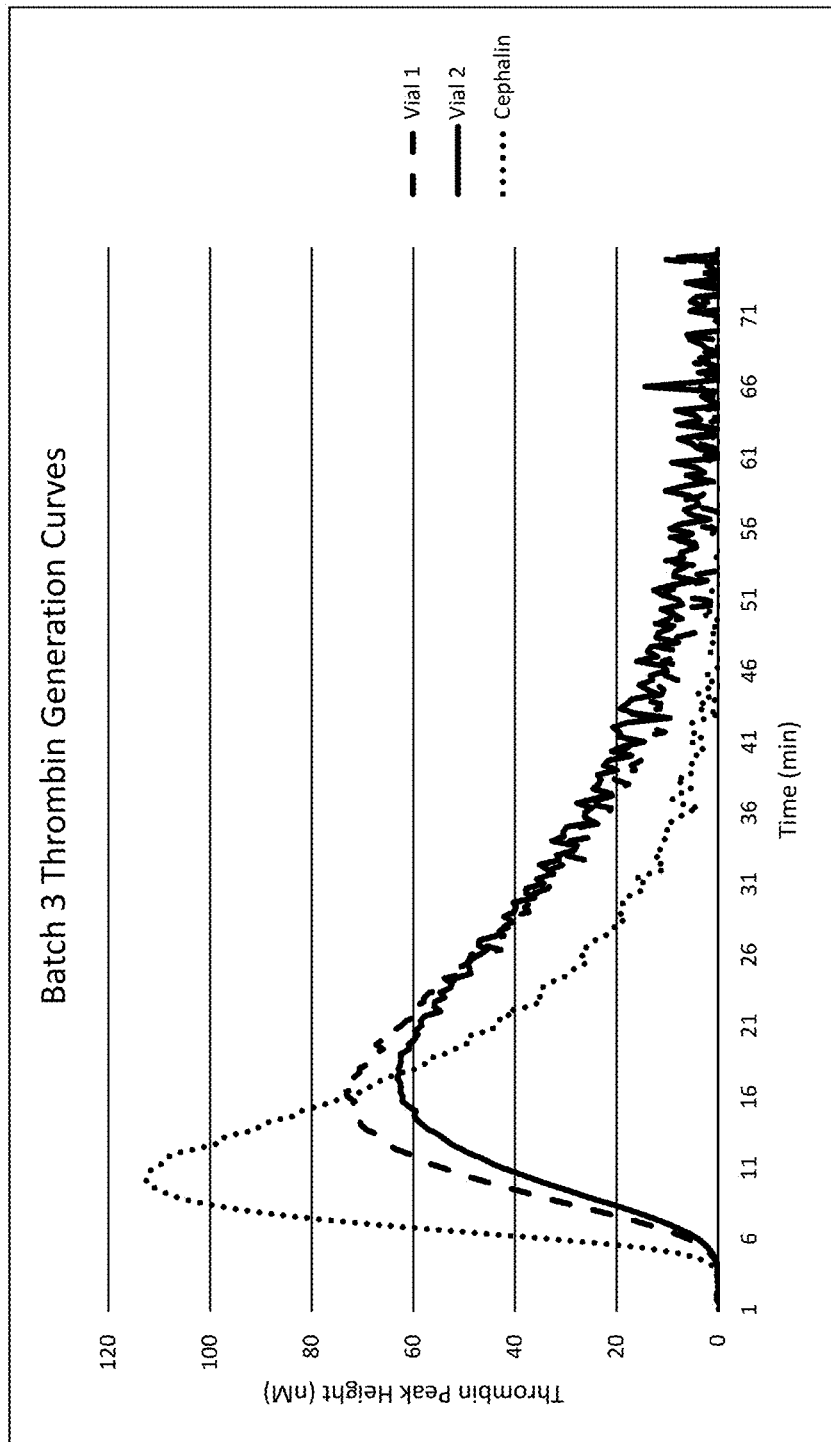
FIG. 19 shows a plot of thrombin peak height for thrombosomes in the presence of PRP Reagent containing tissue factor and phospholipids (solid line and long dashes) and control cephalin (dots).

Thrombin Generation was measured at $4.8 \times 10^3$ thrombosomes/µl in the presence of PRP Reagent containing tissue factor and phospholipids using the below protocol. On average, the Thrombin Peak Height (TPH) for a thrombosomes sample was 60.3 nM. Cephalin was used as a positive control. (Table 8; FIG. 19)

For each vial tested, a rehydrated sample of thrombosomes was diluted to 7,200 particles per µL based on the flow cytometry particle count using 30% solution of Octaplas in control buffer. In a 96 well plate, sample wells were generated by adding 20 µL of PRP reagent (Diagnostica Stago Catalog No. 86196) and 80 µL of diluted thrombosomes. Calibrator wells were generated by adding 20 µL of Thrombin Calibrator reagent (Diagnostica Stago Catalog No. 86197) to 80 µL of diluted thrombosomes. The plate was loaded into the plate reader and incubated in the dark at 40° C. for 10 minutes. During sample incubation, FluCa solution was prepared by adding 40 µL of FluCa substrate (Diagnostica Stago Catalog No. 86197) to 1.6 mL of Fluo-Buffer (Diagnostica Stago Catalog No. 86197) warmed to 37° C. and vortexed to mix. The FluCa solution was aspirated into the dispensing syringe and 20 µL was mechanically dispensed into each reaction well, bringing the final thrombosomes concentration in each well to 4,800 particles per µL and starting the thrombin generation reaction. Thrombin generation was measured via fluorescence in each well over the course of 75 minutes.

An exemplary step-by-step protocol follows:

1. Open CAT software; set up instrument; and prepare PRP reagent (including Tissue Factor and some phospholipids), calibrator, and fluo-buffer and fluo-substrate according to manufacturer guidelines.
2. Thaw Octaplas and TGA dilution buffer in 37° C. water bath for 10 minutes.
3. Add thawed Octaplas to TGA dilution buffer to create a buffer containing 30% Octaplas.
4. Use the 30% Octaplas mix to dilute reconstituted cephalin 1:50 to be used as a positive control.
5. Rehydrate thrombosomes with cell culture grade water for 10 minutes then dilute with 30% Octaplas to 7,200 thrombosomes/µL.
6. Using a multichannel pipette, add 20 µL of PRP reagent to each test well. Add 20 µL of Calibrator to each calibration well.
7. Add 80 µL of sample to each test and calibration well. Add 80 µL of 30% Octaplas to negative control wells and 1:50 cephalin to positive control wells.
8. Insert plate into tray and incubate for 10 minutes at 40° C. After incubation, dispense fluo-buffer and fluo-substrate mixture (including a fluorescent-labeled peptide, that when cleaved by thrombin, generates a fluorescent signal) into active wells.
9. Read plate for 75 minutes at 20 s intervals to capture full thrombin generation profile.

TABLE 8

| Batch | TPH (nM) |
|---|---|
| 1 | 61.5 |
| 2 | 71.4 |
| 3 | 67.8 |
| 4 | 52.0 |
| 5 | 60.2 |
| 6 | 54.7 |
| 7 | 54.4 |
| Mean | 60.3 |

Data from these assays is summarized in Table 9.

TABLE 9

| | TFF Batches | | | |
|---|---|---|---|---|
| Batch | Average TPH (nM) | Average CD41 Positivity | Average AV Positivity (0.5 µm-2.5 µm)[1] | Average CD62 Positivity (0.5 µm-2.5 µm)[1] |
| Batch B | 61.5 | 81.5 | 96.7 | 94.2 |
| Batch C | 71.4 | 79.4 | 89.9 | 93.1 |
| Batch D | 67.8 | 85.7 | 95.3 | 89.8 |
| Batch E | 52.0 | 78.2 | 95.4 | 92.4 |
| Batch F | 60.2 | 81.5 | 95.9 | 92.5 |
| Batch G | 54.7 | 84.0 | 96.2 | 87.3 |
| Batch H | 54.4 | 78.5 | 93.5 | 90.7 |
| Mean | 60.3 | 81.3 | 94.7 | 91.4 |

[1]Particle diameter as assessed using sizing beats on the flow cytometry forward scatter.

Example 7. 9F9 and PAC-1 Binding

Aggregation of activated platelets is mediated by the formation of the GPIIb/IIIa complex, which can bind to fibrinogen (also called Factor 1) and form a clot. GPIIb/IIIa is a platelet fibrinogen receptor also known as CD41/CD61 complex. In this process, ADP promotes the active form of the GPIIb/IIIa complex. Antibody 9F9 binds to fibrinogen associated with the cell membrane. The presence of fibrinogen on the cell membrane is thus indicative of thrombosomes capable of forming clots.

A vial of thrombosomes prepared according to Example 1 was rehydrated using 10 mL of deionized water. An aliquot of thrombosomes was diluted to a final concentration of $1 \times 10^5$ particles/µL using HMTA (HEPES Modified Tyrode's Albumin). Samples were prepared as shown in Table 11. Unstained samples were prepared by adding 10 µL of diluted thrombosomes to 20 µL of HMTA. FITC isotype control samples were prepared by adding 10 µL of diluted thrombosomes to 10 µL of the isotype control antibody (BD Biosciences Cat. No. 555748) and 10 µL of HMTA. Samples stained with 9F9 were prepared by adding 10 µL of diluted thrombosomes to 10 µL of the 9F9 antibody (BD Biosciences Cat. No. 340507 and 10 µL of HMTA. Samples stained with PAC-1 were prepared by adding 10 µL of diluted thrombosomes to 5 µL of the isotype control antibody and 15 µL of HMTA. All samples were prepared in duplicated using a total of $1 \times 10^6$ particles per reaction mixture. Samples were incubated at room temperature for 20 minutes away from open light. After incubation, all samples were diluted with 1 mL of HBS and acquired using the ACEANovoCyte flow cytometer. The fluorescent signal generated by PAC-1 was used to determine the expression of activated GPIIb/IIIa receptors without bound fibrinogen.

The fluorescent signal from 9F9 was used to determine binding of fibrinogen to the surface receptors on thrombosomes.

HTMA (HEPES Modified Tyrode's Albumin).

| Component | Concentration (mM, except where otherwise indicated) |
|---|---|
| HEPES | 9.5 |
| NaCl | 145.0 |
| KCl | 4.8 |
| NaHCO$_3$ | 12.0 |
| Dextrose | 5.0 |
| Bovine Serum Albumin | 0.35% w/v |

TABLE 10

| | Unstained | FITC Iso | 9F9 | PAC-1 |
|---|---|---|---|---|
| Cells (uL) | 10 | 10 | 10 | 10 |
| HMTA (uL) | 20 | 10 | 10 | 15 |
| Antibody (uL) | 0 | 10 | 10 | 5 |

Figure 20:
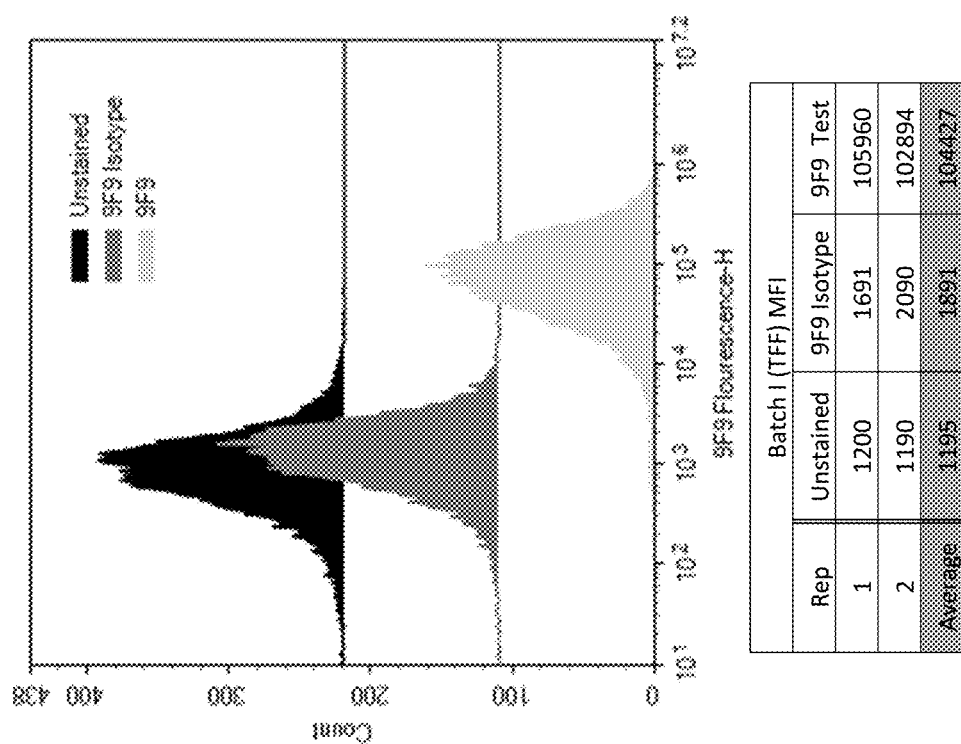
FIG. 20 is an exemplary histogram comparison of low-plasma thrombosomes unstained (black) or stained with an isotype control antibody (dark gray) or a FITC-labeled 9F9 antibody (light gray), and a table showing the mean fluorescence intensity for two replicates.
Figure 21:
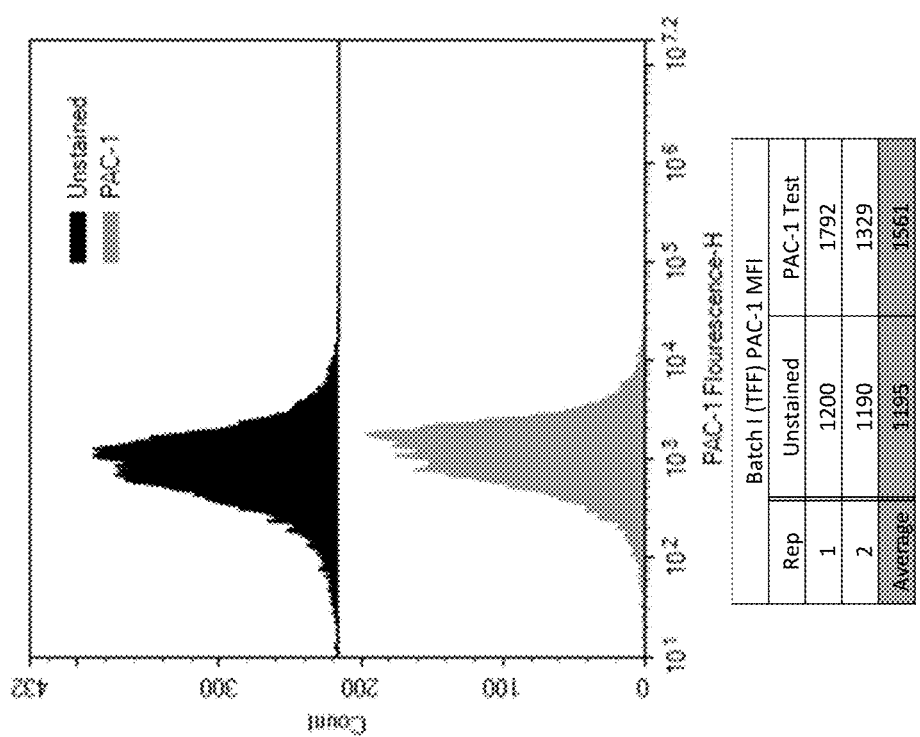
FIG. 21 is an exemplary histogram comparison of low-plasma thrombosomes unstained (black) or stained with an anti-PAC-1 antibody (light gray), and a table showing the mean fluorescence intensity for two replicates.

The samples were assayed by flow cytometry, and it was demonstrated that there is surface-bound fibrinogen post rehydration (FIG. 20), while the anti-PAC-1 antibody shows no significant binding (FIG. 21). This is further evidence that the thrombosomes prepared by TFF include fibrinogen bound to the active form of GPIIb/GPIIIa, as PAC-1 binds to the same complex.

Example 8. Evaluation of CD47 Binding

CD47 is a cell-surface marker used in self-recognition. Absence of this marker can, in some cases, lead to phagocytosis.

Figure 22A:
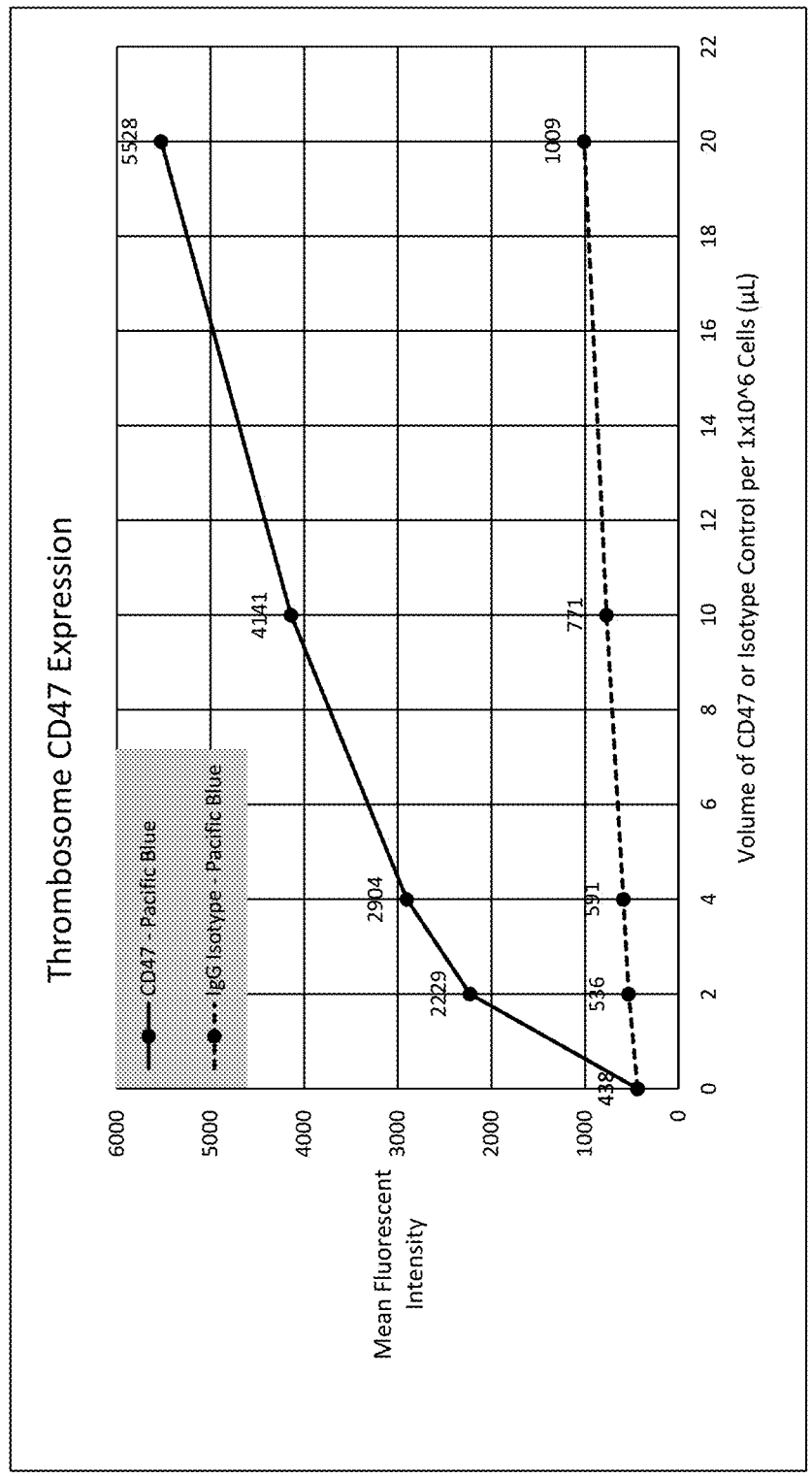
FIG. 22A is a plot of the mean fluorescence intensity of thrombosomes ($1\times10^6$ cells) treated with various concentrations of a labeled anti-CD47 antibody or an isotype control.
Figure 22B:
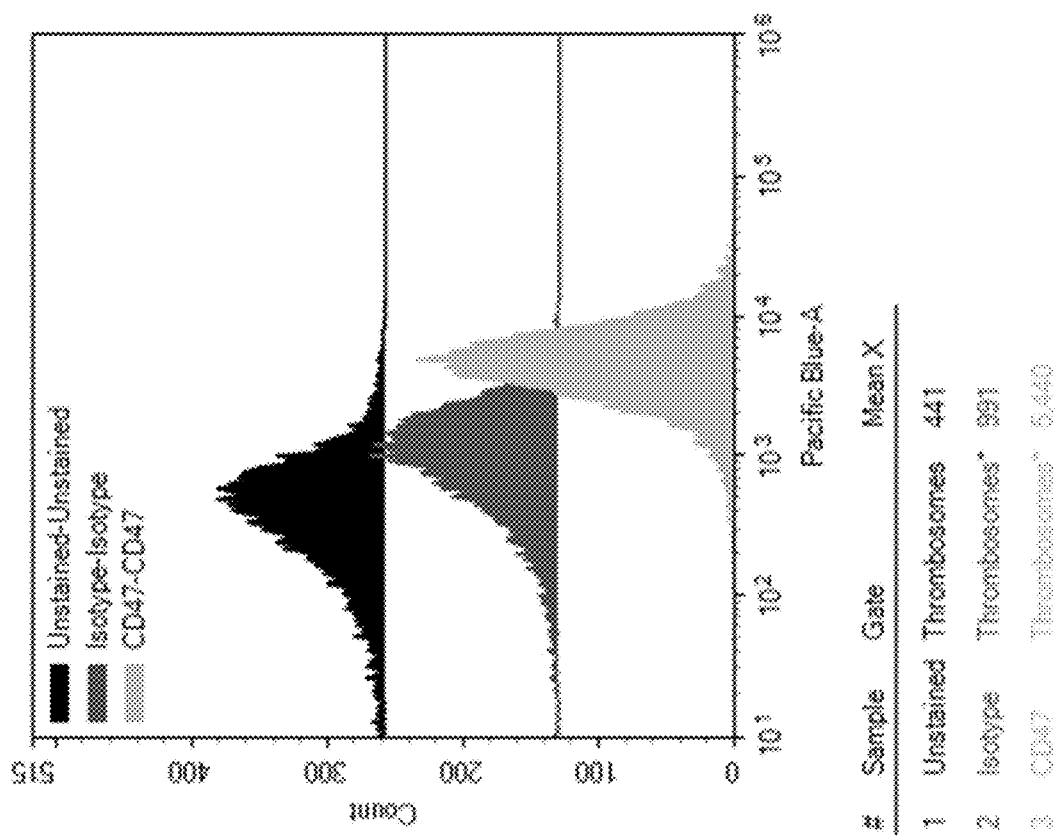
FIG. 22B is an exemplary histogram of thrombosomes that were unstained (black), stained with an isotype control antibody (dark gray), or stained with an anti-CD47 antibody (light gray).

One vial of thrombosomes prepared as described in Example 1 was rehydrated with 10 mL sterile water for injection and stained with increasing volumes of anti-CD47 antibody conjugated to Pacific Blue (BD Biosciences Cat. No. 561564) or a corresponding isotype control (BD Biosciences Cat. No. 560373). All samples contained 1 million cells. This titration resulted in a maximum fluorescent signal that was ~5× over background (FIG. 22A) and an overall CD47 positivity of ~40% (Table 12). An exemplary histogram is shown in FIG. 22B.

Aliquots of CD47 antibody conjugated to V450 were prepared at a 1:10, 1:5, and 1:2 dilution with HMTA. The initial concentration of a thrombosome sample was determined using the AcT diff 2 and the concentration of a 1 mL aliquot was adjusted to 100×10$^3$ per µL using HMTA. TFF thrombosomes were stained in duplicate at each antibody dilution by adding 10 µL of antibody to 10 µL of diluted thrombosomes. Samples stained with undiluted antibody were generated in the same manner. Unstained control samples were made by adding 10 µL of HMTA to 10 µL of diluted thrombosomes. This sample preparation was repeated using an isotype control antibody in place of the anti-CD47. All samples were incubated at room temperature away from light for 20 minutes. After incubation samples were diluted with 500 µL of HBS and 15,000 events were acquired for each sample using the ACEA NovoCyte flow cytometer. V450 fluorescence in the test samples was used to assess antibody binding to CD47 on the thrombosome surface. V450 fluorescence of the isotype control samples was used to monitor nonspecific binding.

Table 11 shows the mean fluorescence intensity of samples with various amounts of antibody (anti-CD47 or isotype control).

TABLE 11

| Mean CD47 MFI (Batch C) | | | | | |
|---|---|---|---|---|---|
| Volume Antibody (µL) | 0 | 2 | 4 | 10 | 20 |
| CD47 - Pacific Blue | 438 | 2229 | 2904 | 4141 | 5528 |
| IgG Isotype - Pacific Blue | 438 | 536 | 591 | 771 | 1009 |

Table 12 shows the CD47 percent positivity at various concentrations of anti-CD47 antibody.

TABLE 12

| CD47 Percent Positive (Batch C) | | | | | |
|---|---|---|---|---|---|
| Volume Antibody (µL) | 0 (Unstained) | 2 | 4 | 10 | 20 (Undiluted) |
| Rep 1 | 0.00% | 11.89% | 23.07% | 36.51% | 40.18% |
| Rep 2 | 0.00% | 9.39% | 18.24% | 33.28% | 38.43% |
| Average | 0.00% | 10.64% | 20.66% | 34.90% | 39.31% |

Figure 22C:
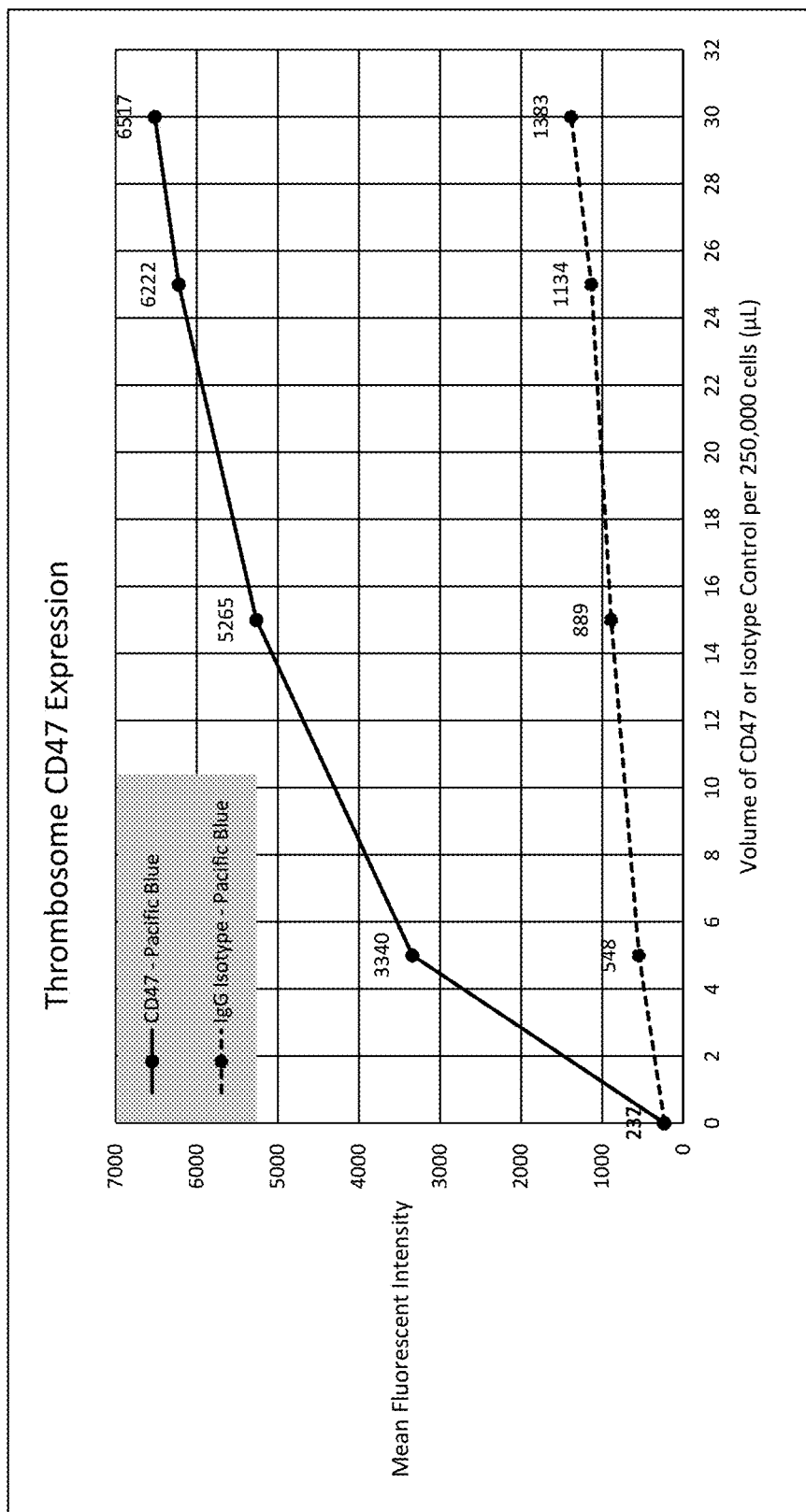
FIG. 22C is a plot of the mean fluorescence intensity of thrombosomes (250,000 cells) treated with various concentrations of a labeled anti-CD47 antibody or an isotype control.

A second vial of TFF thrombosomes from a different lot was rehydrated and stained with increasing volumes of anti-CD47 conjugated to Pacific Blue or a corresponding isotype control. All sampled contained 250,000 cells. Again, fluorescent signal that was ~5× to 6× over background (FIG. 22C) and an overall CD47 positivity of ~50% (Table 15). An exemplary histogram is shown in FIG. 22D.

A second round of testing was performed on a new TFF thrombosomes sample using an increased amount of antibody and decreased number of thrombosomes per sample in order to improve the intensity of the signal caused by anti-CD47 binding to the thrombosomes. The initial concentration of a thrombosome sample was determined using the AcT diff 2 and the concentration of a 1 mL aliquot was adjusted to 25×10$^3$ per µL using HMTA. Samples were stained in duplicate with increasing amounts of antibody according to Table 13 below. The final volume for each sample was held constant at 40 µL. The total number of thrombosomes in each sample was help constant at 250×10$^3$ per µL. This sample preparation was repeated using an isotype control antibody in place of the anti-CD47.

TABLE 13

| Volume Tsomes | Volume AB (µL) | Volume HMTA (µL) | Total |
|---|---|---|---|
| 10 | 0 | 30 | 40 |
| 10 | 5 | 25 | 40 |
| 10 | 15 | 15 | 40 |
| 10 | 25 | 5 | 40 |
| 10 | 30 | 0 | 40 |

All samples were incubated at room temperature away from light for 20 minutes. After incubation samples were diluted with 500 µL of HBS 15,000 events were acquired for each sample using the ACEA NovoCyte flow cytometer. V450 fluorescence in the test samples was used to assess antibody binding to CD47 on the thrombosome surface. V450 fluorescence of the isotype control samples was used to monitor nonspecific binding.

Table 14 shows the mean fluorescence intensity of samples with various amounts of antibody (anti-CD47 or isotype control).

TABLE 14

| Mean CD47 MFI (Batch D) | | | | | |
| --- | --- | --- | --- | --- | --- |
| Volume Antibody (µL) | 0 | 5 | 15 | 25 | 30 |
| Anti-CD47 - Pacific Blue | 237 | 3340 | 5265 | 6222 | 6517 |
| IgG Isotype - Pacific Blue | 232 | 548 | 889 | 1134 | 1383 |

Table 15 shows the CD47 percent positivity at various concentrations of anti-CD47 antibody.

TABLE 15

| CD47 Percent Positivity (Batch D) | | | | | |
| --- | --- | --- | --- | --- | --- |
| Sample | Unstained | 5 uL | 15 uL | 25 uL | 30 uL |
| Rep 1 | 0.00% | 48.79% | 49.73% | 41.23% | 38.21% |
| Rep 2 | 0.00% | 42.29% | 51.75% | 38.64% | 33.48% |
| Average | 0.00% | 45.54% | 50.74% | 39.94% | 35.85% |

Example 9. Microparticle Content Reduction

Figure 23A:
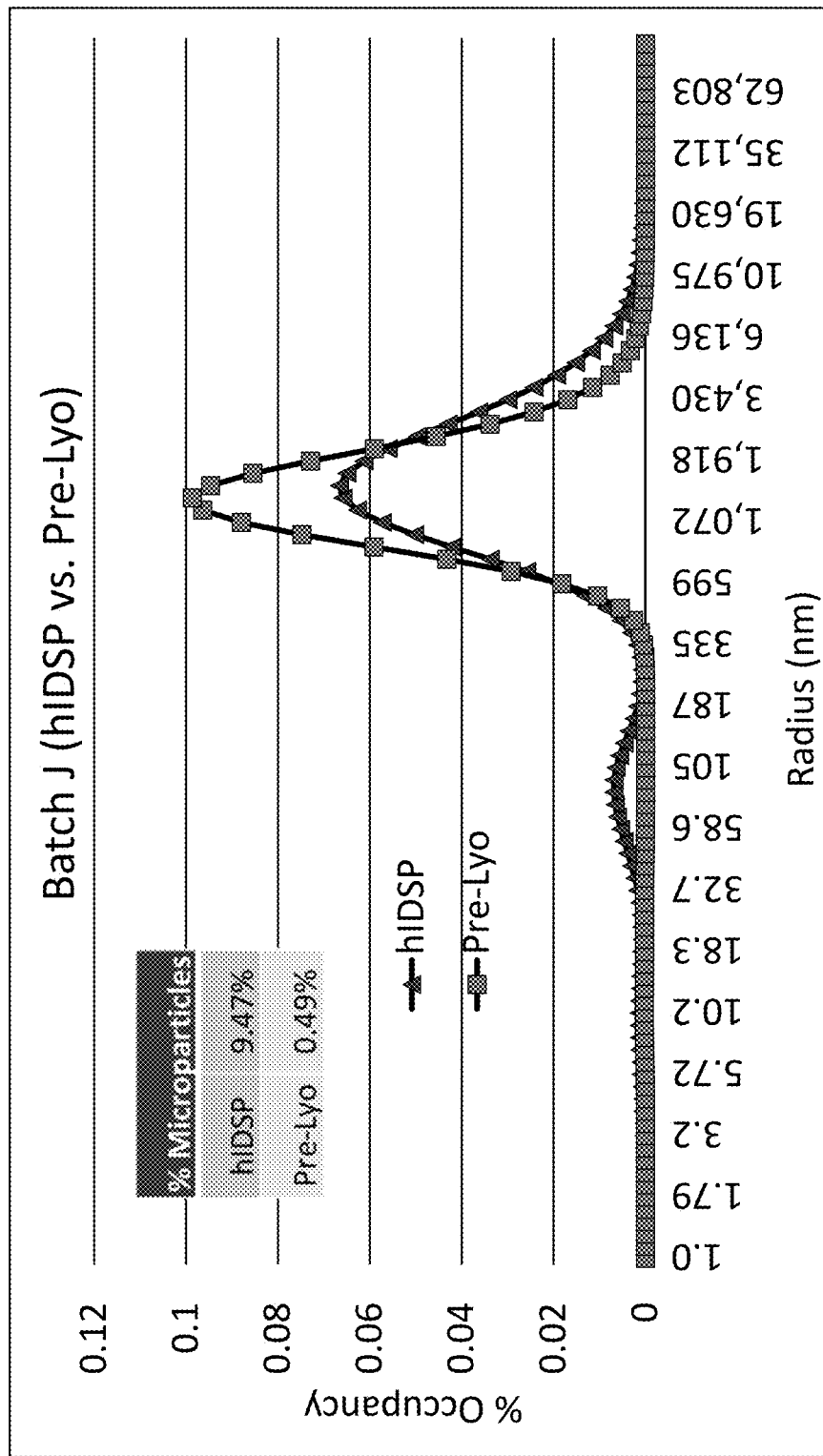
FIG. 23A is a plot of the percent occupancy of particles of different radii in human in-date stored platelets (Batch J) and platelet derivatives (pre-lyophilization) derived therefrom as determined by dynamic light scattering (DLS).
Figure 23B:
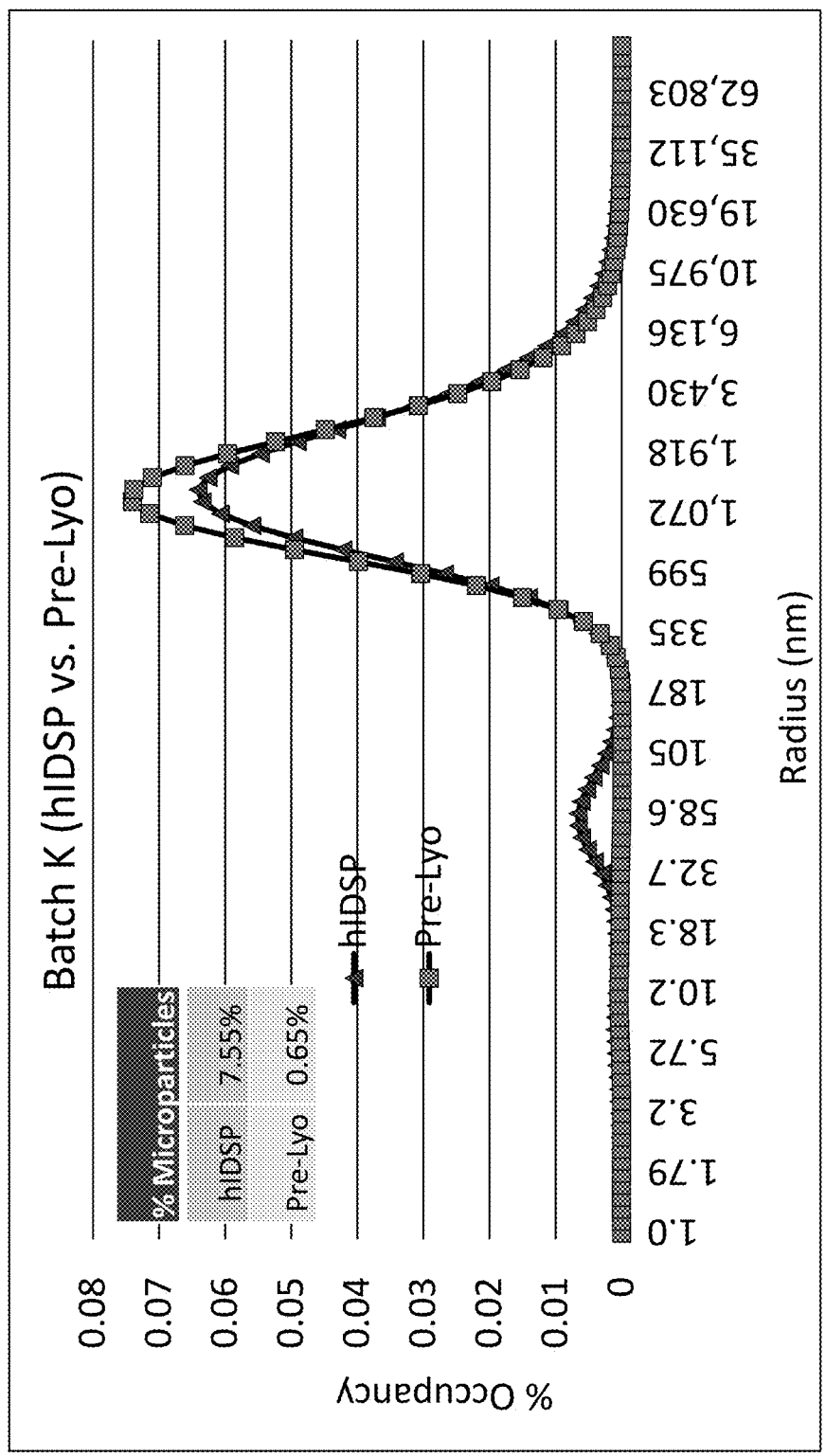
FIG. 23B is a plot of the percent occupancy of particles of different radii in human in-date stored platelets (Batch K) and platelet derivatives (pre-lyophilization) derived therefrom as determined by DLS.
Figure 23C:
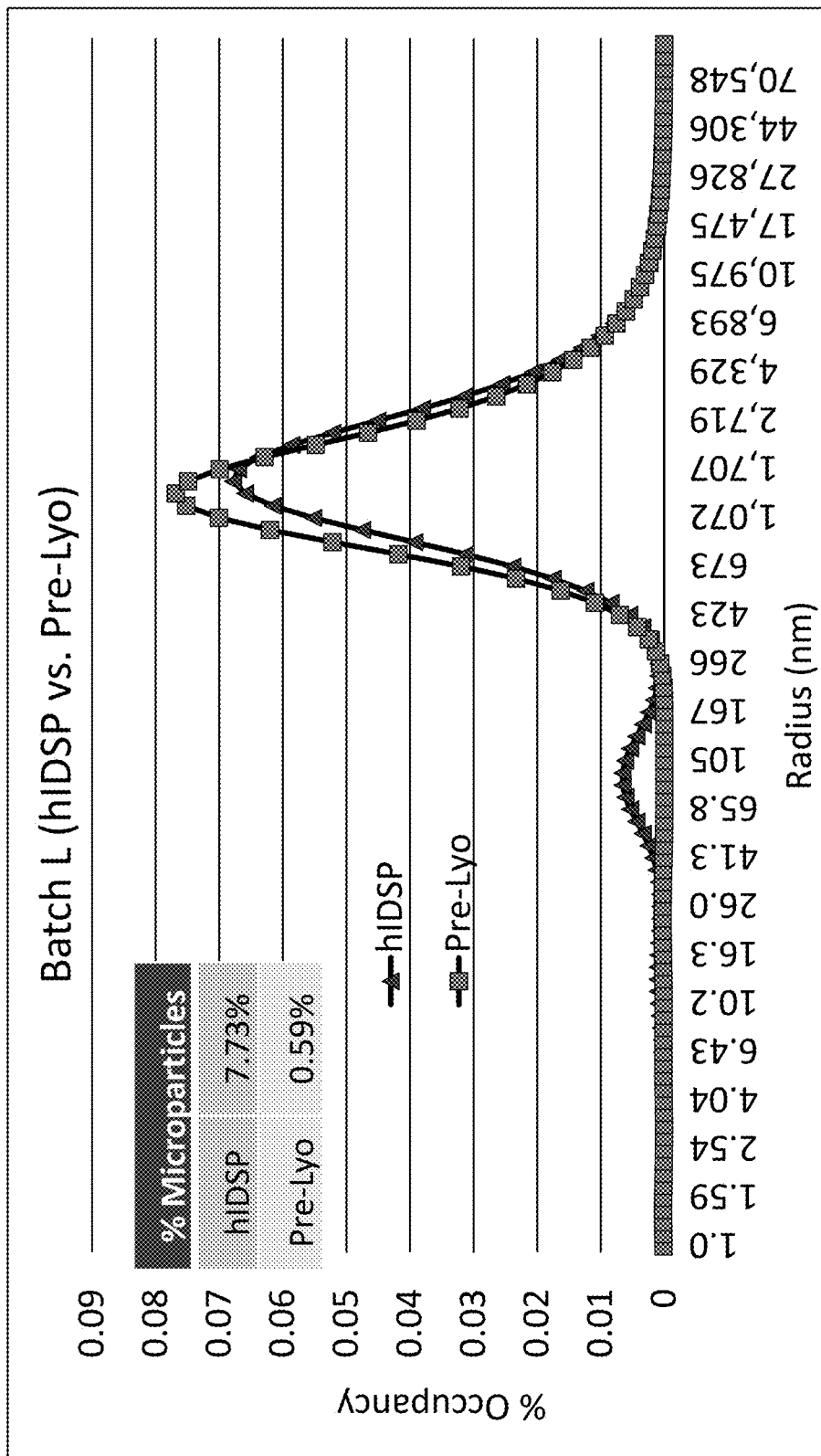
FIG. 23C is a plot of the percent occupancy of particles of different radii in human in-date stored platelets (Batch L) and platelet derivatives (pre-lyophilization) derived therefrom as determined by DLS.

The microparticle content of human in-date stored platelets (hIDSP) compared to thrombosomes prepared according to Example 1 (but not lyophilized) were compared using dynamic light scattering. The results are shown in FIGS. 23A-C and Table 16. FIGS. 23A-C are histograms that are normalized to a relative intensity so that the sum of the intensity of each data point equals 1.0. For example, if a particular data point has a y-axis value of 0.1 then it can be typically interpreted that the data point makes up 10% of the scattering intensity of the sample.

A pool of the apheresis units used to manufacture a batch of thrombosomes was made for analysis. This sample type is denoted as "hIDSP." A 1 mL aliquot of this hIDSP (human In-Date Stored Platelets) pool was taken for dynamic light scattering (DLS; Thrombolux—Light Integra) analysis. A sample from this aliquot was then drawn into a capillary and inserted into the DLS instrument. The capillary sat in the instrument for 1 minute to allow the temperature and movement to equilibrate. The internal temperature of the machine is 37° C. After 1 minute of equilibration, the viscosity setting for the sample was chosen. The DLS instrument has a built-in viscosity setting for samples that are in plasma, such as apheresis units. This viscosity setting was used for hIDSP samples. The viscosity of this setting is 1.060 cP (centipoise). After the plasma viscosity setting was selected, the sample was analyzed. From the same hIDSP aliquot, a $2^{nd}$ and $3^{rd}$ sample were drawn into a capillary and analyzed with this hIDSP protocol, for triplicate analysis. Microparticle percentage was then determined from the data.

"Pre-Lyo" samples are an in-process sample from the thrombosomes manufacturing process. This sample type is the material taken right before lyophilization. A viscosity measurement of the sample was taken in order to analysis these samples with DLS. The viscometer (Rheosense pVISC) has a built-in oven that is used to bring the sample to the temperature of the DLS instrument (37° C.). Prior to viscosity analysis of the sample the oven must be heated to 37° C. To determine the viscosity of the pre-lyo sample a 400-350 µL sample was drawn into a syringe and inserted into the viscometer. After inserting the sample into the viscometer, the instrument temperature needs to reach 37° C. again. After the oven reaches 37° C. the sample was analyzed with all settings on AUTO except for "Measurement Volume" which was set to 400 µL. This viscosity was used for the DLS measurement of the same sample. A 1 mL aliquot of this pre-lyo sample was taken for dynamic light scattering (DLS; Thrombolux—LightIntegra) analysis. A sample from this aliquot was then drawn into a capillary and inserted into the DLS instrument. The capillary sat in the instrument for 1 minute to allow the temperature and movement to equilibrate. The internal temperature of the machine is 37° C. After 1 minute of equilibration, the previously measured viscosity was put into the viscosity setting of the DLS instrument. After the viscosity was entered, the sample was analyzed. From the same pre-lyo aliquot, a $2^{nd}$ and $3^{rd}$ sample were drawn into a capillary and analyzed with this Pre-Lyo Protocol, for triplicate analysis. Microparticle percentage was then determined from the data.

Thrombosomes were rehydrated according to standard protocol and diluted 1:5 in a mixture of SeraSub (CST Technologies, Inc.) and ACD. The SeraSub/ACD diluent consists of a 1:9 dilution of ACD in SeraSub. 1 mL of the 1:5 dilution of thrombosomes was prepared for analysis by DLS. A sample of the thrombosomes dilution was drawn into the capillary and inserted into the DLS instrument. The capillary sat in the instrument for 1 minute to allow the temperature and movement to equilibrate. The internal temperature of the machine is 37° C. After 1 minute of equilibration, the viscosity setting for the sample was chosen. The viscosity used for the sample was 1.200 cP. After the viscosity was entered, the sample was analyzed. A $2^{nd}$, $3^{rd}$, and $4^{th}$ sample were drawn into a capillary and analyzed with this thrombosomes protocol, for quadruplicate analysis. Microparticle percentage was then determined from the data (and platelet radius where applicable).

TABLE 16

| Batch Number | hIDSP % MP | Pre-Lyo % MP |
| --- | --- | --- |
| Batch J | 9.47% | 0.49% |
| Batch K | 7.55% | 0.65% |
| Batch L | 7.73% | 0.59% |
| Average | 8.25% | 0.58% |

Figure 24A:
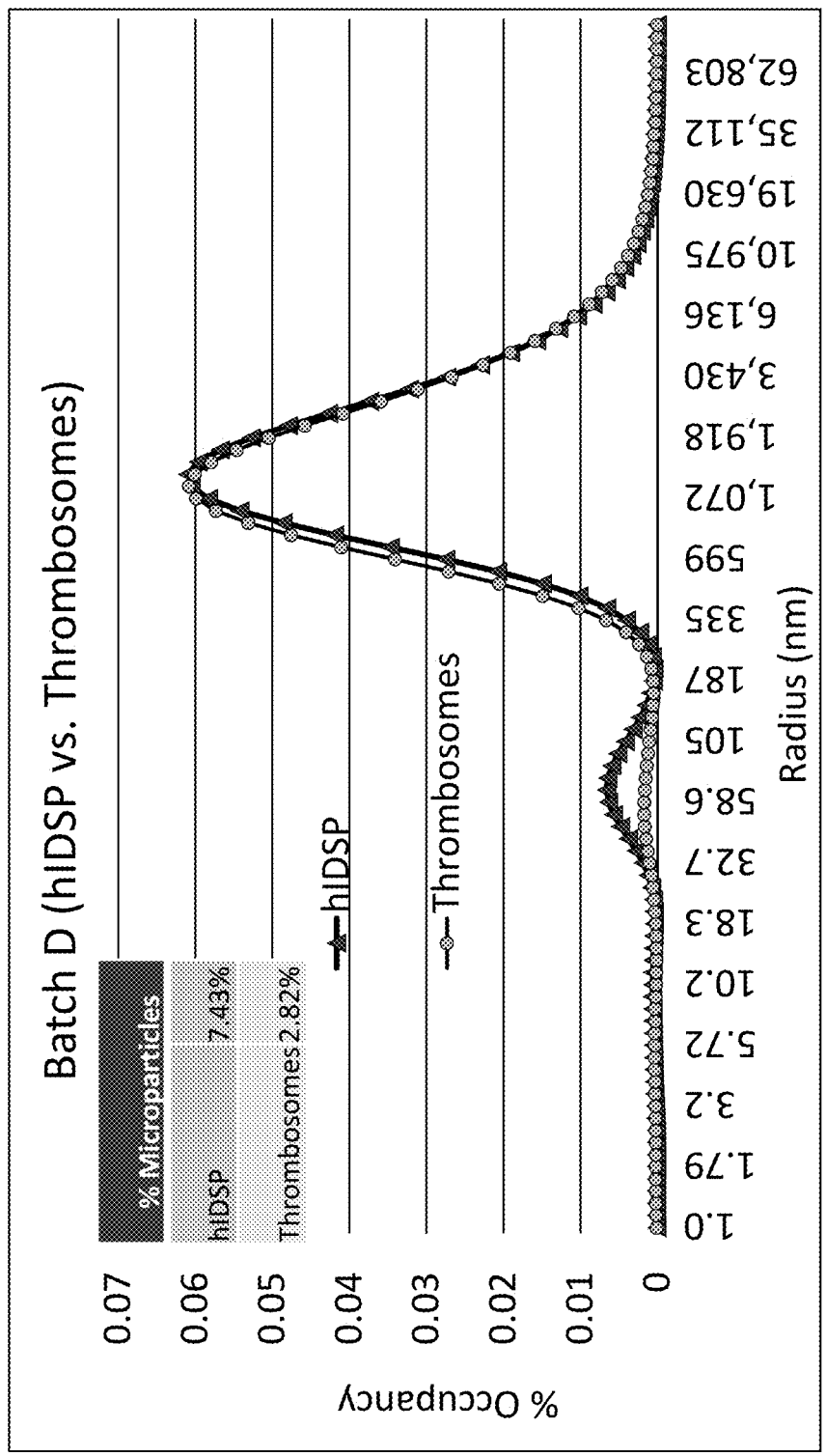
FIG. 24A is a plot of the percent occupancy of particles of different radii in human in-date stored platelets (Batch D) and platelet derivatives (pre-lyophilization) derived therefrom as determined by DLS.
Figure 24B:
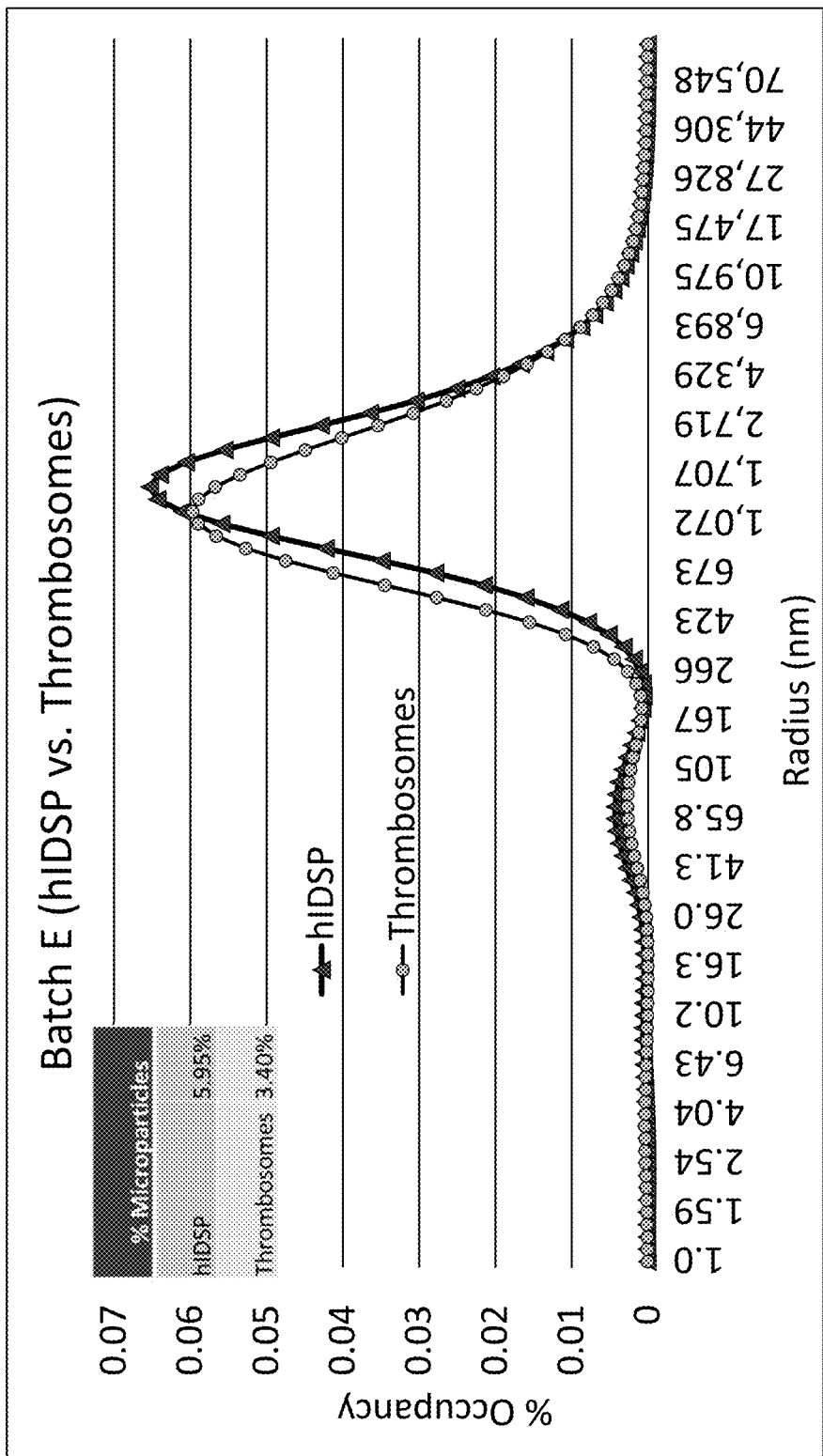
FIG. 24B is a plot of the percent occupancy of particles of different radii in human in-date stored platelets (Batch E) and platelet derivatives (pre-lyophilization) derived therefrom as determined by DLS.
Figure 24C:
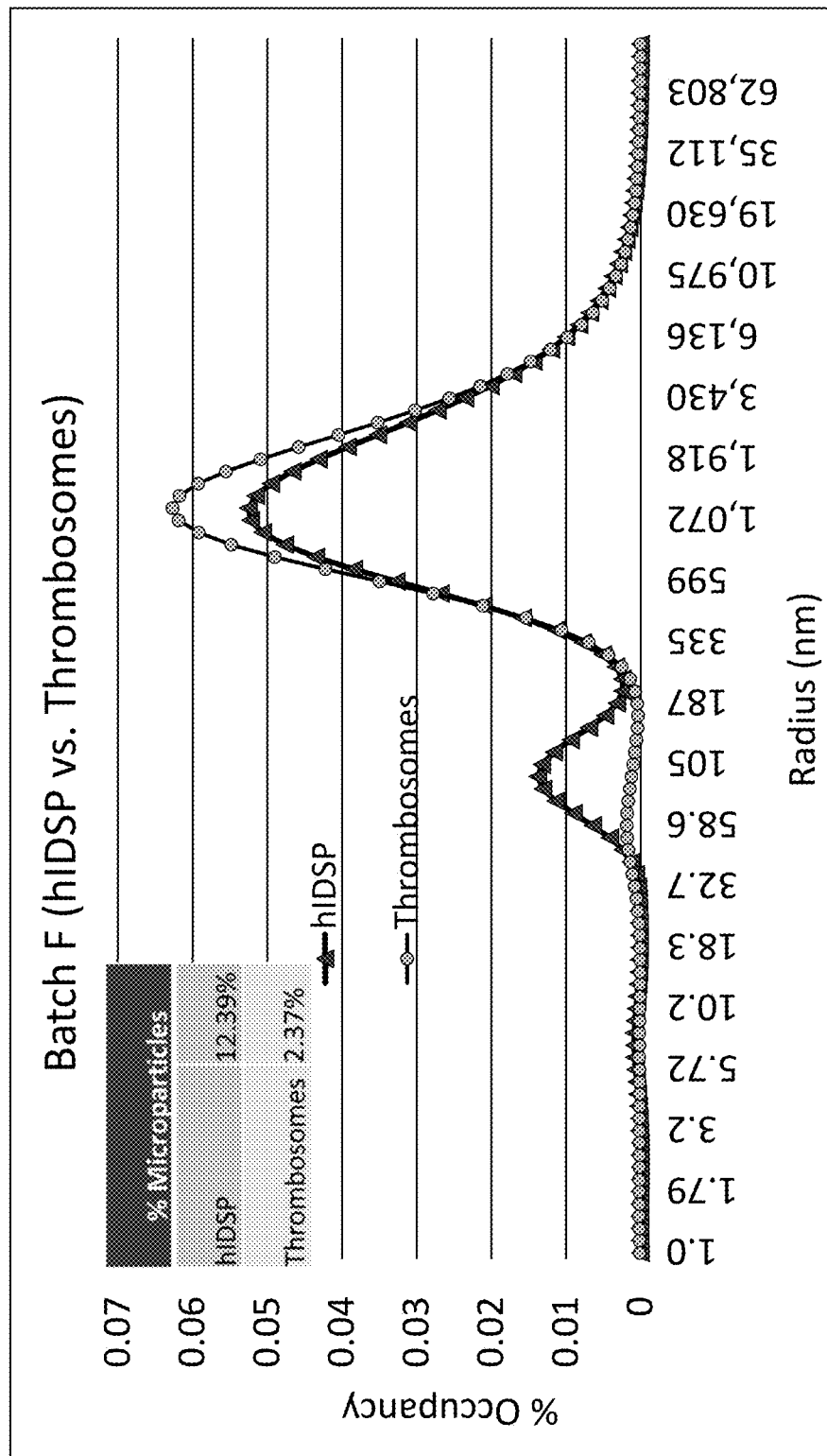
FIG. 24C is a plot of the percent occupancy of particles of different radii in human in-date stored platelets (Batch F) and platelet derivatives (pre-lyophilization) derived therefrom as determined by DLS.

In additional experiments, the microparticle content of human in-date stored platelets (hIDSP) compared to rehydrated thrombosomes prepared according to Example 1 were compared using dynamic light scattering (DLS). The results are shown in FIGS. 24A-C and Table 17.

TABLE 17

| Batch Number | hIDSP % MP | Thrombosomes % MP |
| --- | --- | --- |
| Batch D | 7.43% | 2.82% |
| Batch E | 5.95% | 3.40% |
| Batch F | 12.39% | 2.37% |
| Average | 8.59% | 2.86% |

Example 12. Metabolite Analysis

Table 18 shows an analysis of pH and metabolites present in the preparation of thrombosomes as described in Example 1, including analyses of the raw platelet material, after an initial dilution, after the platelet derivatives were concentrated, and after the end of the diafiltration process, as determined using an i-STAT handheld blood analyzer and CG4+ cartridges.

Platelet samples for iStat analysis were collected at different processing steps in small volumes (1 ml). The initial sample for iStat analysis named "Raw Material" was collected after the platelet donor units were pooled together but before any processing had occurred. Named "Initial Dilution", The pooled platelet units were 1:1 diluted with Control Buffer before subjecting the platelets to TFF processing. At the end of the concentration phase of TFF, the "End of Conc" sample was drawn from the platelet product. After washing the cells, the "End of DV (Pre-Lyo)" sample was drawn as a representation of the product as it enters the lyophilizer.

DLS was performed as described in Example 9.

TABLE 19

| Process Parameter | Specification |
|---|---|
| Feed Pump | 600 ml/min (3/8" Tube) |
| Retentate Pressure | Target = 4 to 6 PSI Criteria = 2 to 8 PSI |
| Buffer Pump | 100 ml/min (noncritical) |
| DiaVolumes | X2 DVs |
| Concentration Factor | ~4 (from initial dilution) |

Exemplary comparative data of pH and metabolites of thrombosomes prepared as in Example 1, with or without treatment with the INTERCEPT® system is shown in Table 20.

TABLE 20

| iSTAT CG4+ | Raw Material | | Initial Dilution | | End of Con | | End of DV (Pre-Lyo) | |
|---|---|---|---|---|---|---|---|---|
| | Control | Treated | Control | Treated | Control | Treated | Control | Treated |
| pH | 7.2 | 7.2 | 7.3 | 7.1 | 7.3 | 7.3 | 7.3 | 7.2 |
| pCO2 (mmHg) | 32.9 | 25.7 | 16.5 | 29.1 | 16.1 | 14.4 | 11.3 | 12.4 |
| pO2 (mmHg) | 67 | 149 | 167 | 150 | 142 | 155 | 145 | 153 |
| HCO3 (mmol/L) | 12.7 | 10.2 | 8.5 | 8.1 | 7.8 | 6.7 | 5.8 | 5.1 |
| TCO2 (mmol/L) | 14 | 11 | 9 | 9 | 8 | 7 | 6 | 5 |
| sO2 (%) | 89 | 99 | 99 | 98 | 99 | 99 | 99 | 99 |
| Lac (mmol/L) | 6.56 | 6.75 | 3.26 | 3.33 | 2.80 | 2.50 | 0.91 | 1.19 |

TABLE 18

| | Batch P | | | |
|---|---|---|---|---|
| iStat CG4+ | Raw Material | Initial Dilution | End of Conc | End of DV (Pre-Lyo) |
| pH | 7.6 | 7.5 | 7.4 | 7.1 |
| pCO2 (mmHg) | 14.9 | 12.5 | 14.7 | 18 |
| pO2 (mmHg) | 147 | 176 | 160 | 163 |
| HCO3 (mmol/L) | 14.7 | 10 | 9.3 | 5.9 |
| TCO2 (mmol/L) | 15 | 10 | 10 | 6 |
| sO2 (%) | 100 | 100 | 100 | 99 |
| Lac (mmol/L) | 6.14 | 2.97 | 2.6 | 0.55 |

Example 11. Pathogen Reduction

The reduction of pathogens is generally desirable in blood products. One method of pathogen reduction involves the use of a photosensitive nucleic acid-intercalating compound to alter the nucleic acids of pathogens upon illumination with an appropriate wavelength.

Figure 25A:
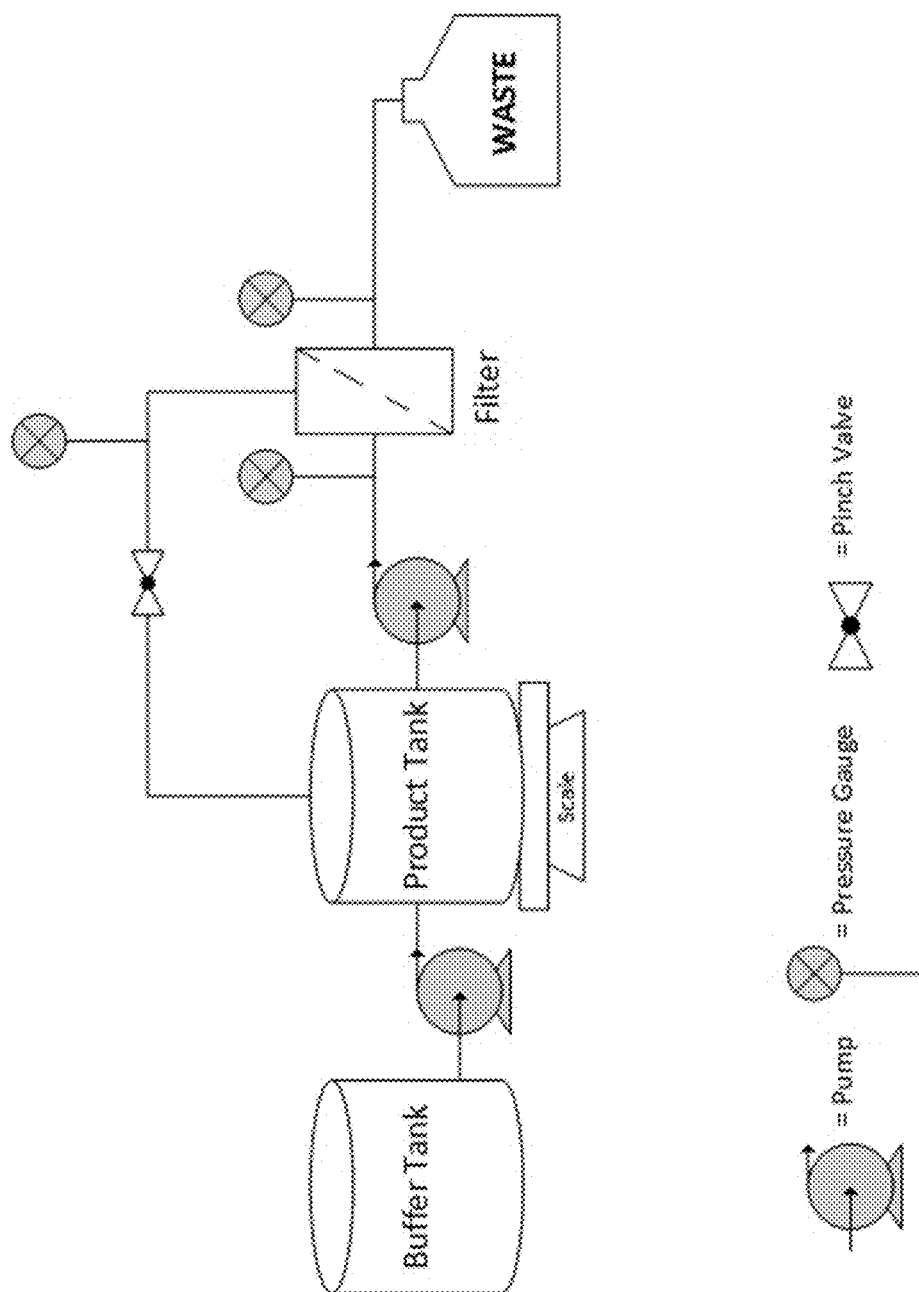
FIG. 25A is an exemplary schematic of a pathogen reduction system.
Figure 25B:
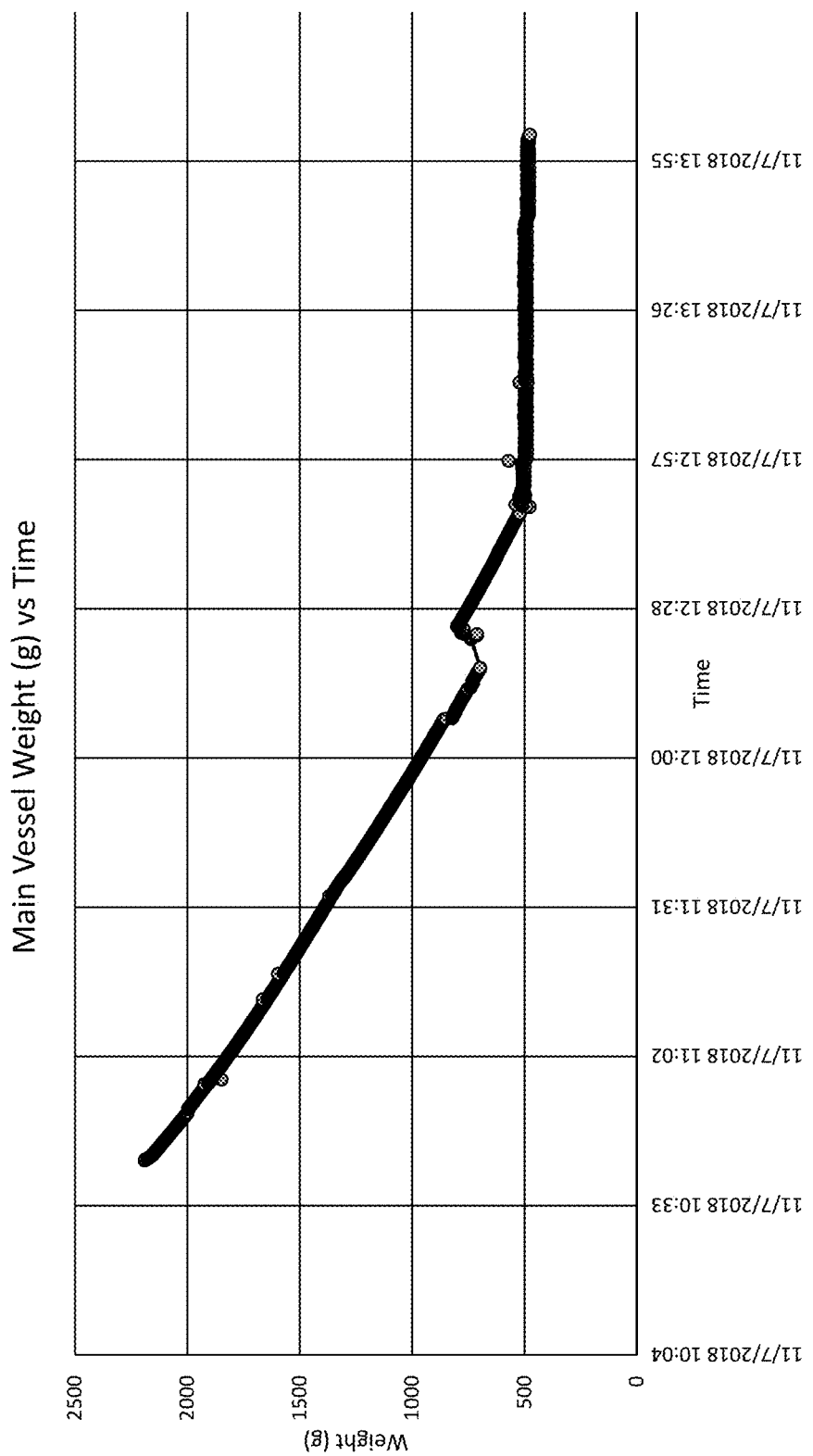
FIG. 25B is a plot of the weight of a reaction vessel over time.
Figure 25C:
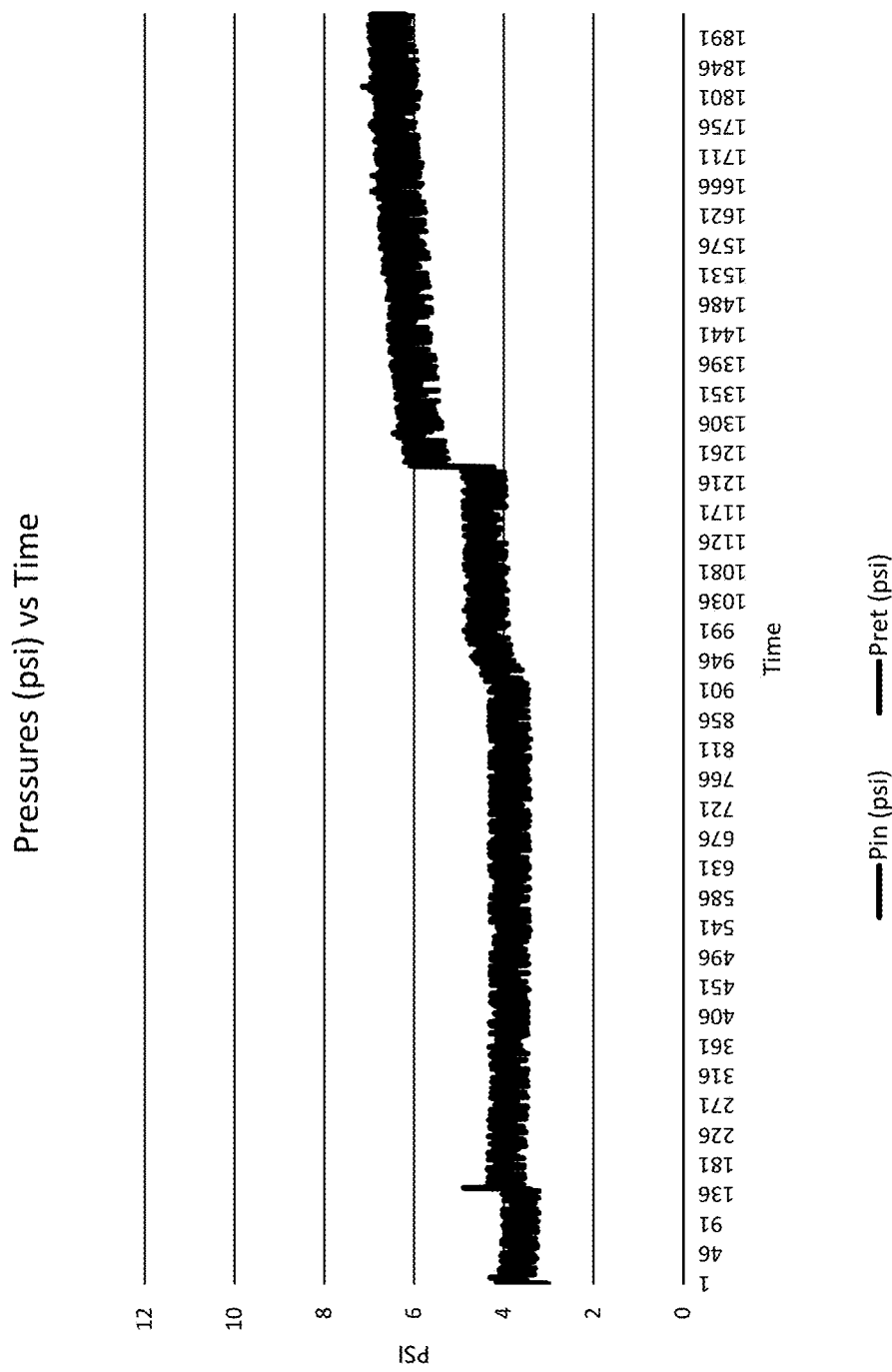
FIG. 25C is a plot of pressure in a reaction vessel over time.

The INTERCEPT® system (made by Cerus) uses amotosalen, a nucleic acid intercalating compound that forms cross-links in nucleic acid upon illumination with UVA. Exemplary parameters for use of this system are shown in Table 19, and a schematic of the system is shown in FIG. 25A, while exemplary process data are shown in FIGS. 25B-C for 2.6 L of processed material in 198 minutes (approx. 14/min average).

Exemplary comparative data of functional characterization (AcT count and aggregation parameters) and cell-surface markers are shown in Tables 21 (hIDSPs), 22 (prior to lyophilization) and Table 23 (following lyophilization and rehydration in 10 mL sterile water for injection to a concentration of approximately $1.8 \times 10^6/\mu L$ (individual sample counts are shown in Table 23).

TABLE 21

| | | Raw Material (hIDSP) | |
|---|---|---|---|
| | | Batch M "Control" | Batch N "Treated" |
| AcT Counts | AVG (×10^3) | 1212 | 1120 |
| Aggregation (%) | Collagen AVG | 22 | 21 |
| | Plasma - A. Acid AVG | 75 | 84 |
| | 250 k Thrombin AVG | 97 | 97 |
| | Buffer - A. Acid AVG | 94 | 92 |
| Flow (percent positivity) | CD41 | 93.5 | 97.6 |
| | CD42 | 91.4 | 95.8 |
| | Double Positive % | 92.0 | 95.6 |
| | CD62 | 23.9 | 42.5 |
| | AVS | 3.8 | 8.4 |

TABLE 22

|  |  | Pre-Lyophilization | |
|---|---|---|---|
|  |  | Batch M "Control" | Batch N "Treated" |
| AcT Counts | AVG (x10^3) | 1787 | 2057 |
| Aggregation (%) | Collagen AVG | 81 | 82 |
|  | Plasma - A. Acid AVG | 93 | 84 |
|  | 250 k Thrombin AVG | 97 | 90 |
|  | Buffer - A. Acid AVG | 89 | 95 |
| Flow (percent positivity) | CD41 | 98.4 | 97.0 |
|  | CD42 | 98.2 | 95.4 |
|  | Double Positive % | 97.5 | 94.3 |
|  | CD62 | 26.7 | 41.6 |
|  | AV5 | 10.6 | 13.7 |

TABLE 23

|  |  | Final Product QC | | |
|---|---|---|---|---|
|  |  | Batch M "Control" | | Batch N |
|  |  | V1 | V2 | V1 |
| AcT Counts | AVG (x10^3) | 1765 | 1767 | 1720 |
| Aggregation (%) | 375K Thrombin | 84 | 66 | 74 |
| Flow (percent positivity) | CD41 | 85.5 | 79.5 | 91.2 |
|  | CD42 | 85.1 | 79.2 | 90.6 |
|  | Double Positive % | 84.6 | 78.8 | 90.1 |
|  | CD62 | 87.0 | 93.2 | 87.1 |
|  | AV5 | 95.4 | 95.0 | 92.6 |
| TGA | 4.8K TPH | 72.3 | 71.5 | 74.8 |
| Residual Plasma % |  | 7.0% |  | 8.4% |

Figure 26A:
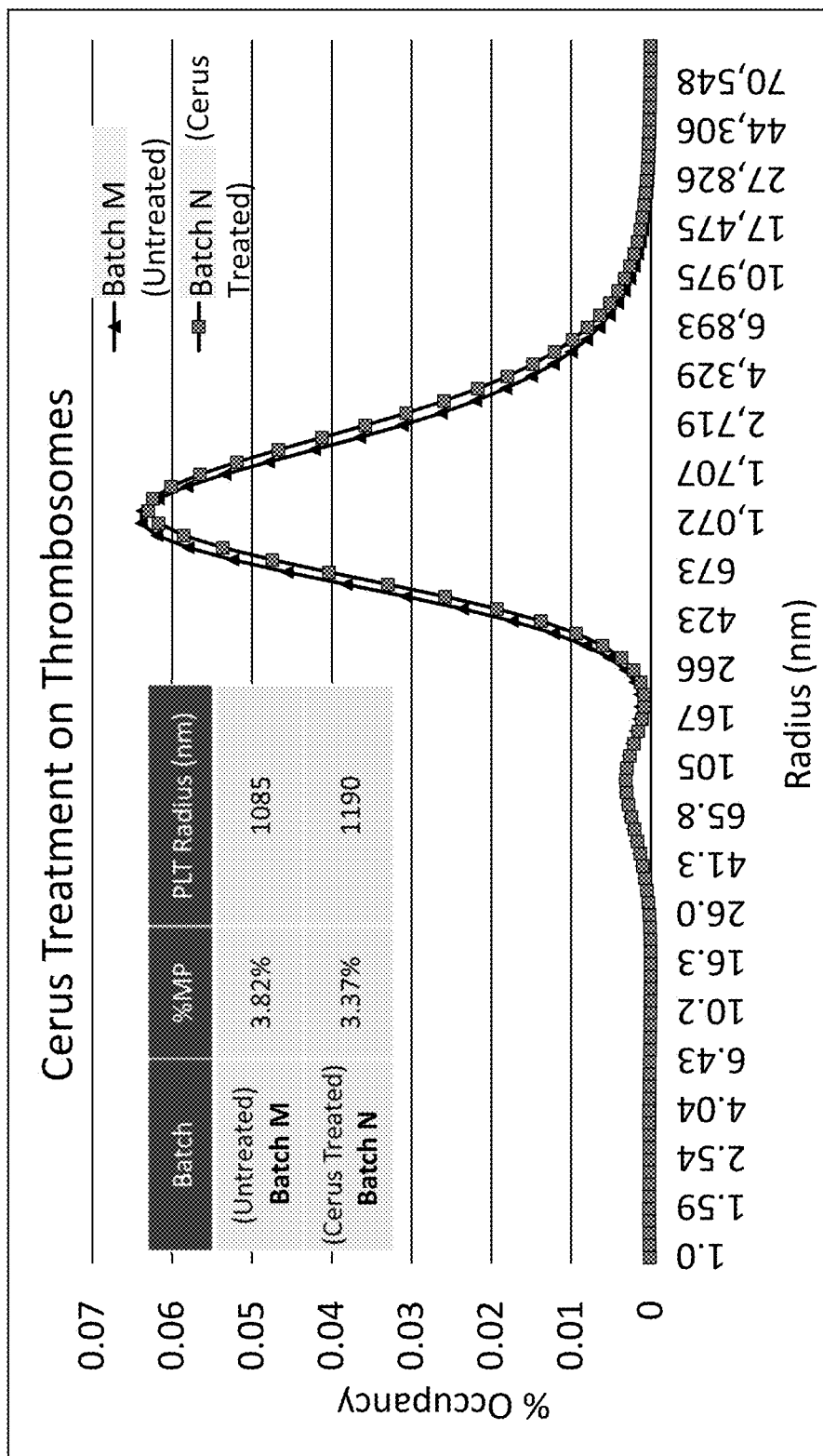
FIG. 26A is a plot of the percent occupancy of particles of different radii in rehydrated thrombosomes that were (Batch N) or were not (Batch M) treated to remove pathogens, as determined by DLS.
Figure 26B:
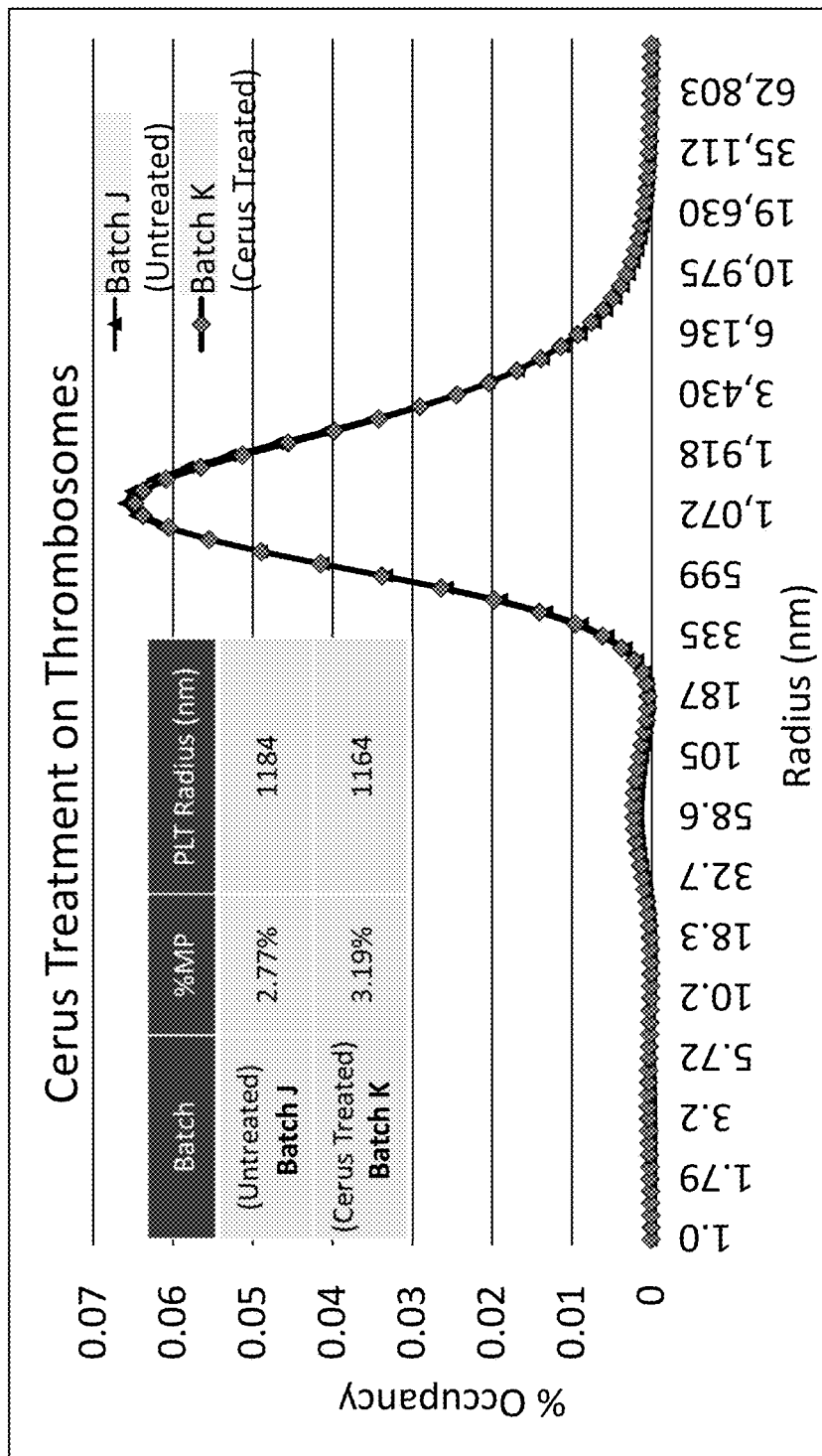
FIG. 26B is a plot of the percent occupancy of particles of different radii in rehydrated thrombosomes that were (Batch K) or were not (Batch J) treated to remove pathogens, as determined by DLS.
Figure 27A:
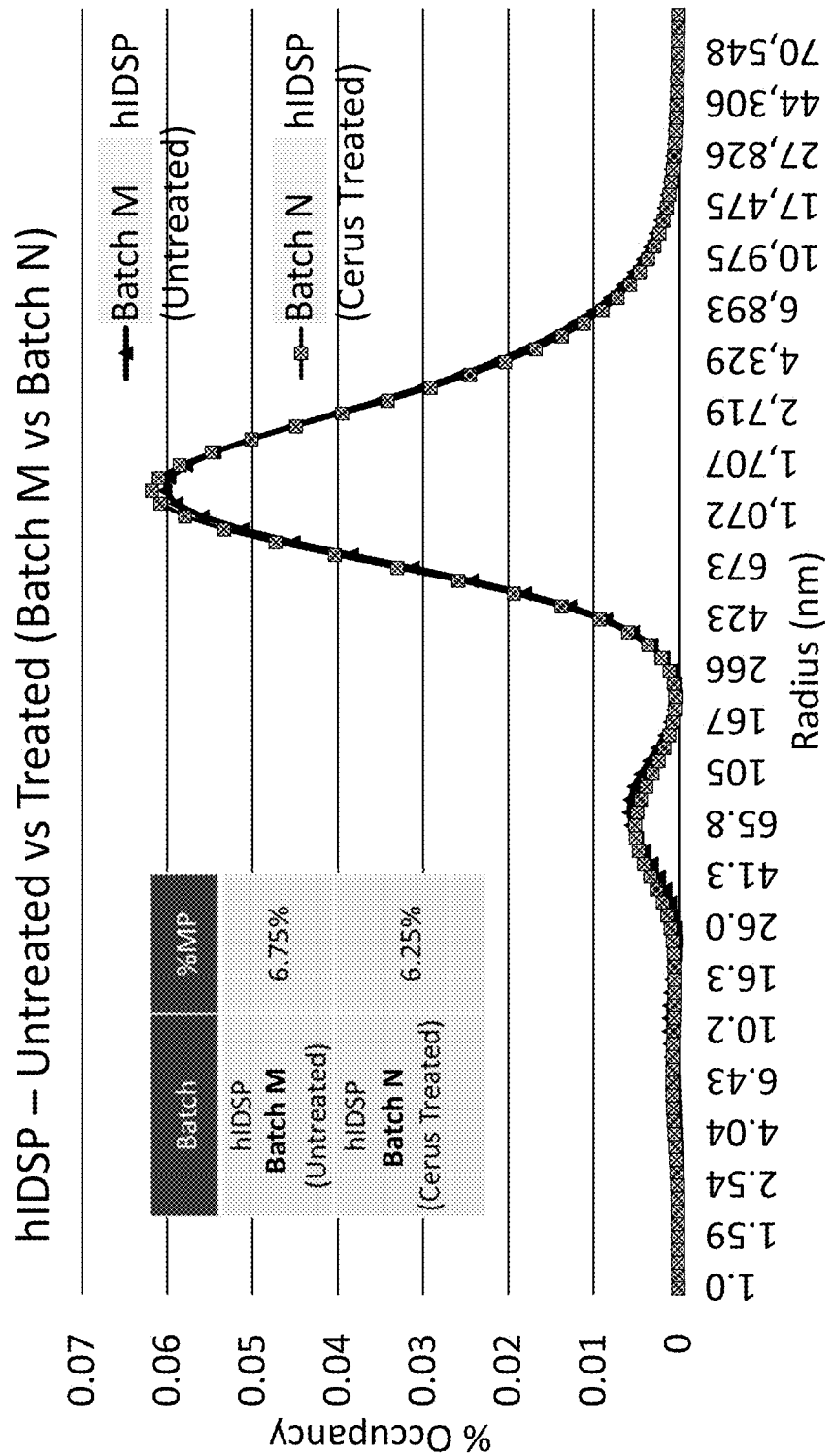
FIG. 27A is a plot of the percent occupancy of particles of different radii in hIDSPs that were (Batch N) or were not (Batch M) treated to remove pathogens, as determined by DLS.
Figure 27B:
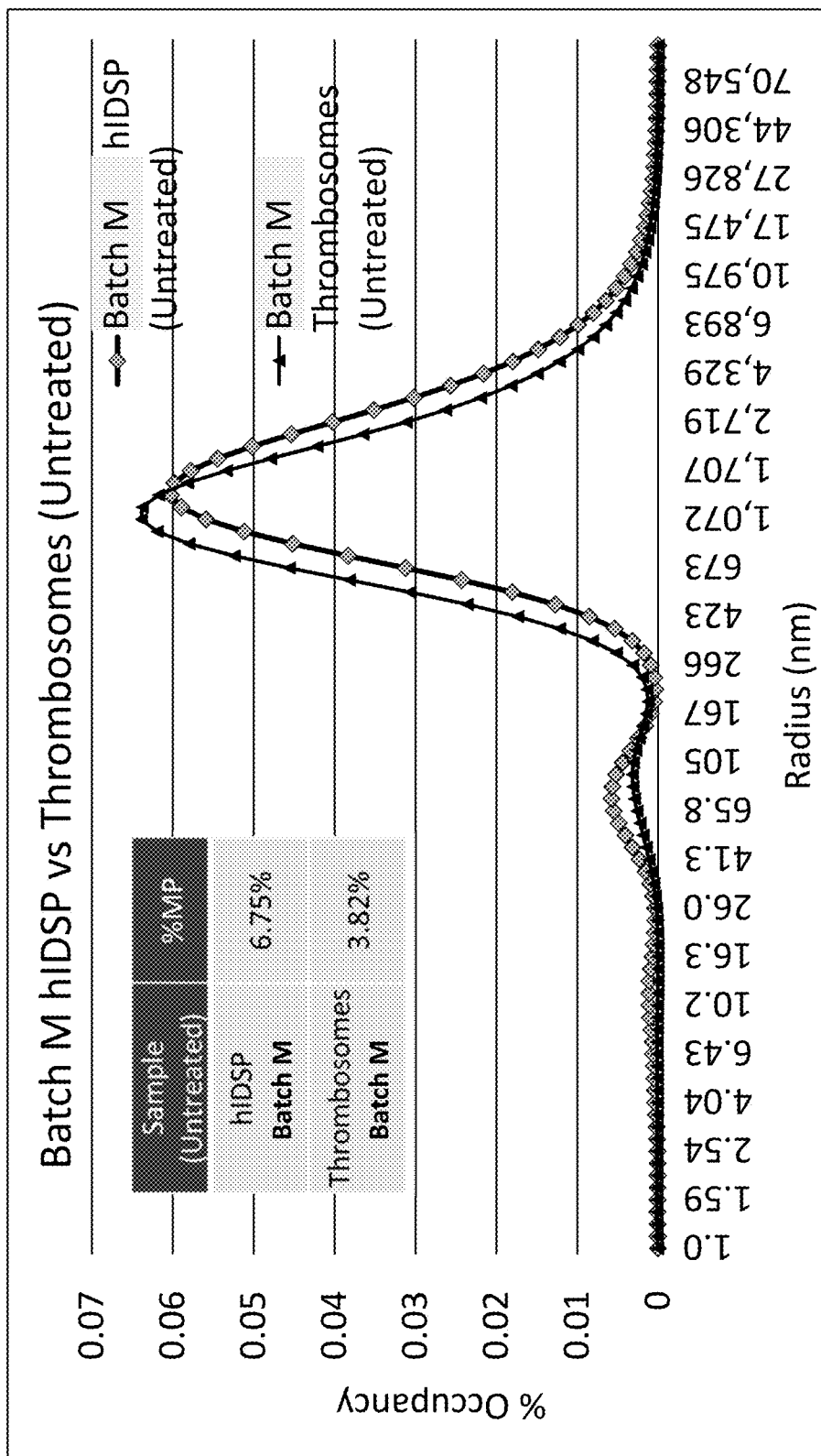
FIG. 27B is a plot of the percent occupancy of particles of different radii in hIDSPs and thrombosomes derived therefrom (Batch M) that were not treated to remove pathogens, as determined by DLS.
Figure 27C:
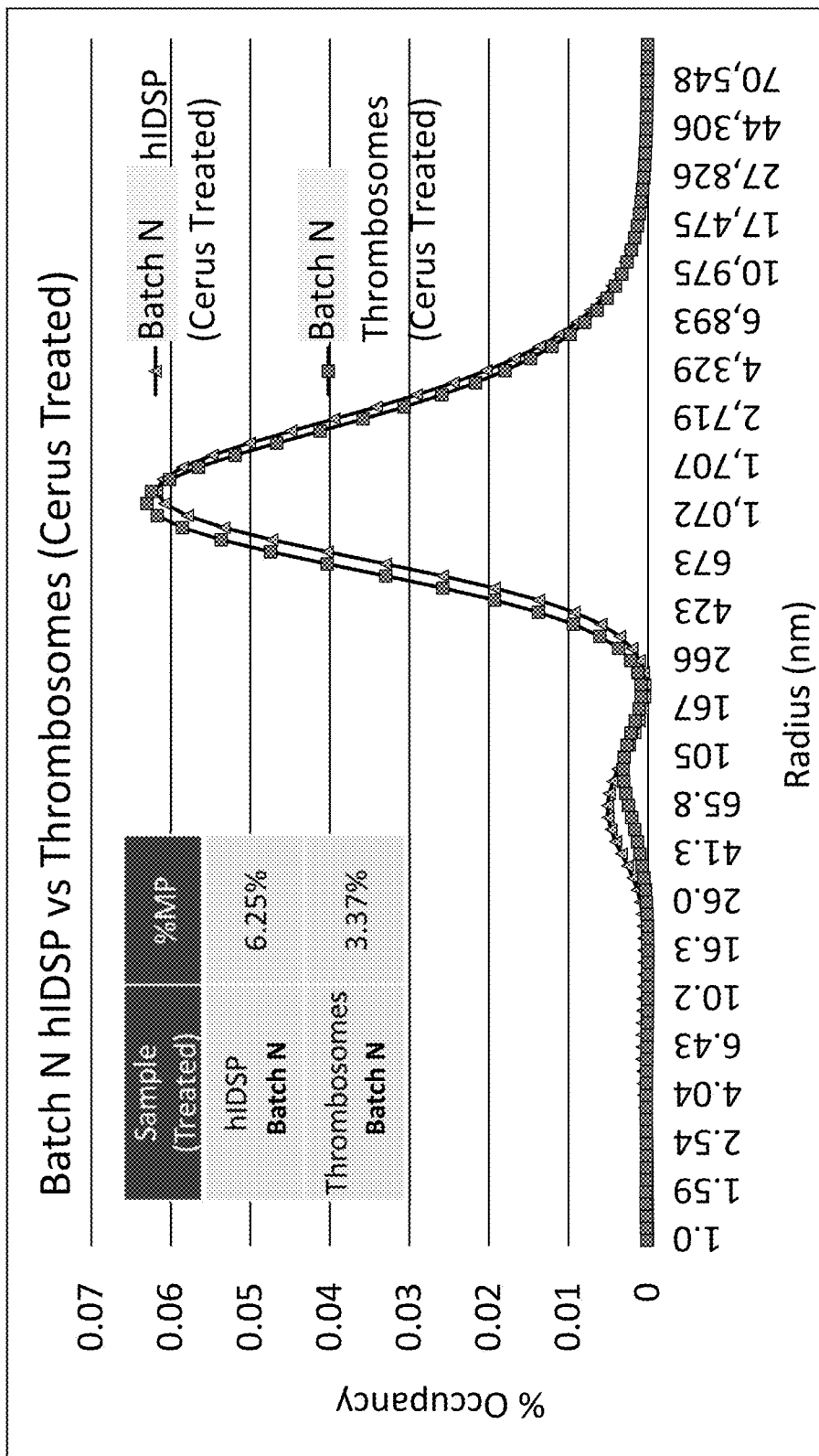
FIG. 27C is a plot of the percent occupancy of particles of different radii in hIDSPs and thrombosomes derived therefrom (Batch N) that were treated to remove pathogens, as determined by DLS.
Figure 28A:
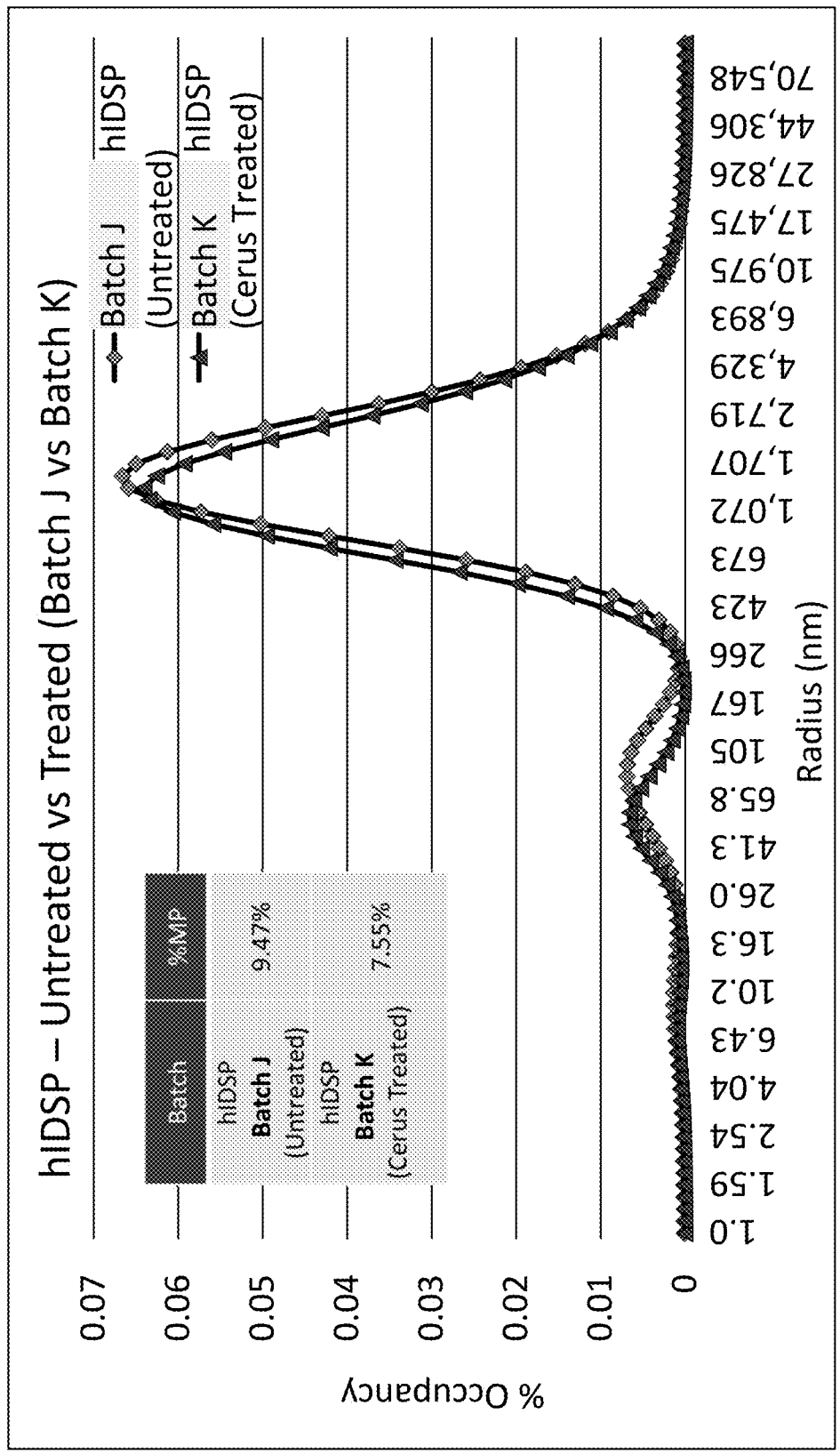
FIG. 28A is a plot of the percent occupancy of particles of different radii in hIDSPs that were (Batch K) or were not (Batch J) treated to remove pathogens, as determined by DLS.
Figure 28B:
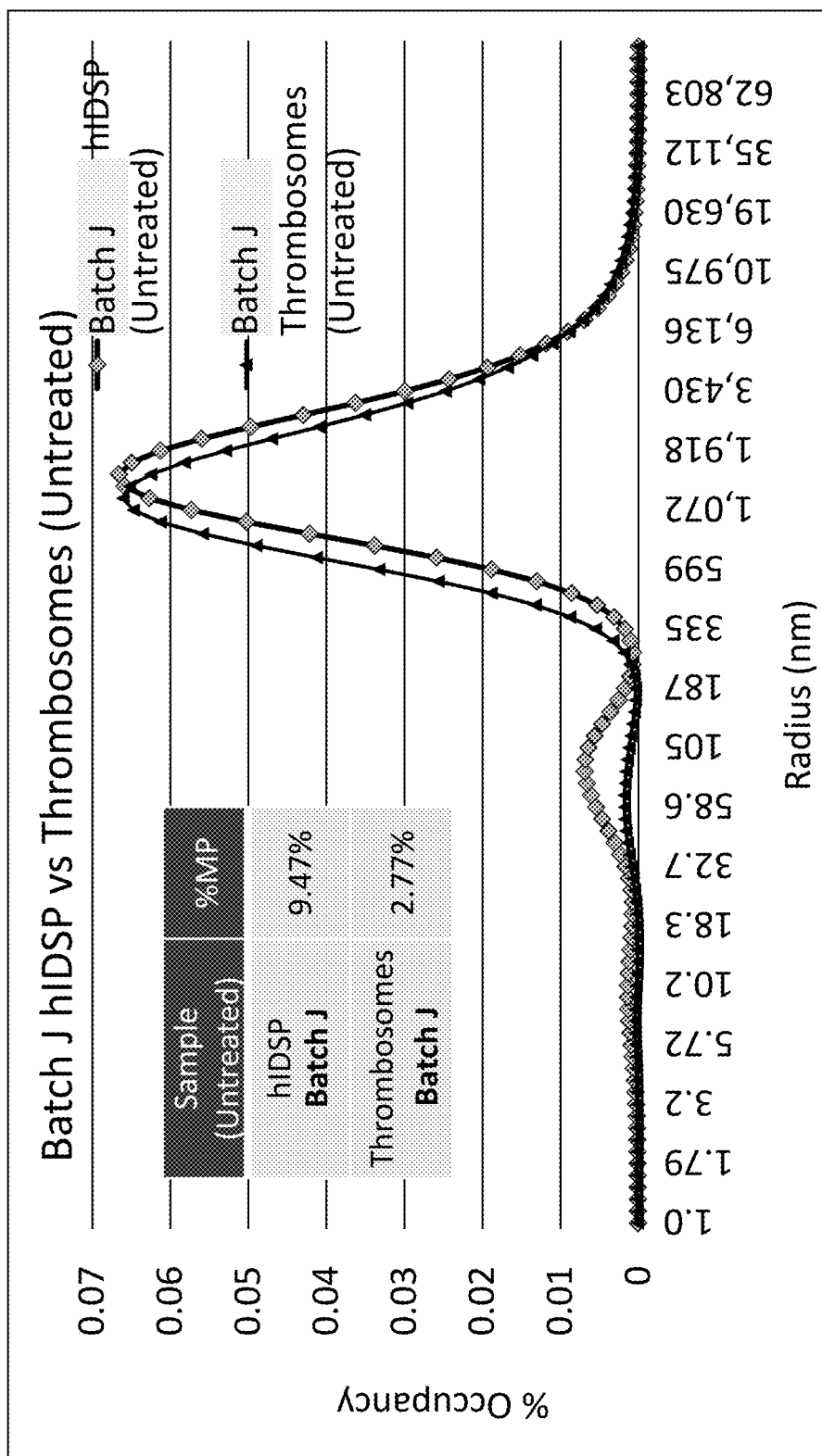
FIG. 28B is a plot of the percent occupancy of particles of different radii in hIDSPs and thrombosomes derived therefrom (Batch J) that were not treated to remove pathogens, as determined by DLS.
Figure 28C:
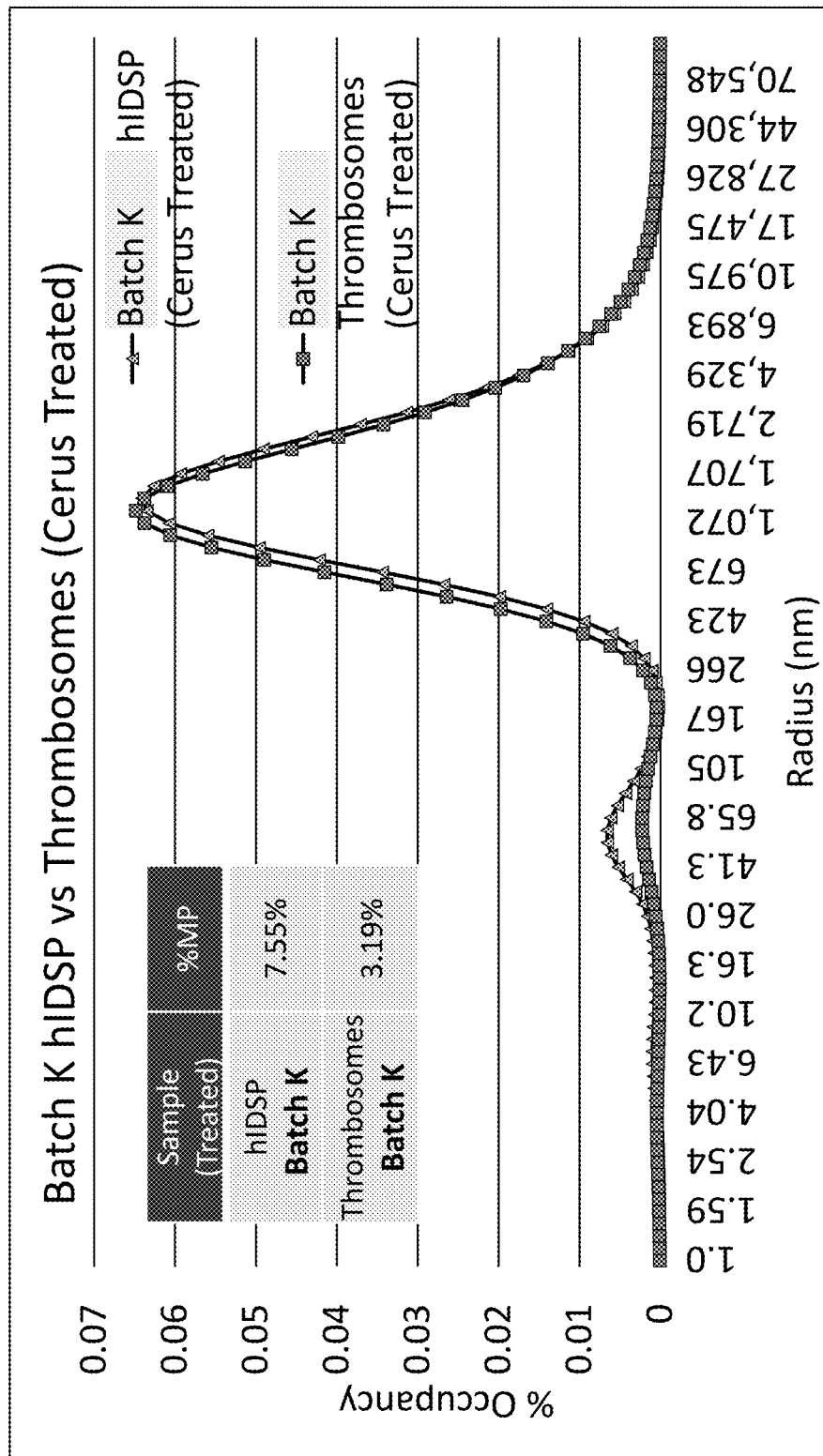
FIG. 28C is a plot of the percent occupancy of particles of different radii in hIDSPs and thrombosomes derived therefrom (Batch K) that were treated to remove pathogens, as determined by DLS.

The microparticle content at various stages of the preparation of thrombosomes was also determined as described in Example 9. FIGS. 26A-B show the similarity of rehydrated thrombosomes prepared with and without pathogen reduction treatment. A summary of these data is shown in Table 24. FIG. 27A shows the microparticle content of hiDSPs with or without pathogen reduction treatment. FIGS. 27B-C compare the microparticle content of the hiDSPs shown in FIG. 29A and rehydrated thrombosomes prepared therefrom. A summary of these data is shown in Table 25. FIG. 28A shows the microparticle content of hiDSPs with or without pathogen reduction treatment. FIGS. 28B-C compare the microparticle content of the hiDSPs shown in FIG. 28A and rehydrated thrombosomes prepared therefrom. A summary of these data is shown in Table 26.

TABLE 24

| Batch | % MP | Particle Radius (nm) |
|---|---|---|
| (Untreated) Batch M | 3.82% | 1085 |
| (Cerus Treated) Batch N | 3.37% | 1190 |
| (Untreated) Batch J | 2.77% | 1184 |
| (Cerus Treated) Batch K | 3.19% | 1164 |

TABLE 25

| Batch | % MP |
|---|---|
| hIDSP Batch M (Untreated) | 6.75% |
| Thrombosomes Batch M (Untreated) | 3.82% |
| hIDSP Batch N (Treated) | 6.25% |
| Thrombosomes Batch N (Treated) | 3.37% |

TABLE 26

| Batch | % MP |
|---|---|
| hIDSP Batch J (Untreated) | 9.47% |
| Thrombosomes Batch J (Untreated) | 2.77% |
| hIDSP Batch K (Treated) | 7.55% |
| Thrombosomes Batch K (Treated) | 3.19% |

Example 12. Interactions Between Platelets and Thrombosomes

In this Example, 'platelets' are platelets isolated from citrated whole blood approximately 3 hours post-collection. The thrombosomes are Batch D, prepared by the method described in Example 1. Table 27 is a sample layout for the experiments in this Example.

TABLE 27

|  | Volume Platelets (µL) | Volume Tsomes (µL) | Portion of Count Platelets (*10^3/µL) | Portion of Count Tsomes (*10^3/µL) | Total Count (*10^3/µL) |
|---|---|---|---|---|---|
| Platelets Only | 600 | 0 | 237 | 0 | 237 |
| Tsomes Only | 0 | 600 | 0 | 204 | 204 |
| 9:1 | 540 | 60 | 213 | 20 | 233 |
| 4:1 | 480 | 120 | 190 | 41 | 231 |
| 2:1 | 400 | 200 | 158 | 68 | 226 |
| 1:1 | 300 | 300 | 119 | 102 | 221 |
| 1:2 | 200 | 400 | 79 | 136 | 215 |
| 1:4 | 120 | 480 | 47 | 163 | 210 |

Platelet and thrombosome co-aggregation was evaluated by light transmission aggregometry. Platelets and thrombosomes were coincubated and evaluated by aggregometry+/− platelet activation with 40-Phorbol-12-myristate-13-acetate (PMA). For fresh-drawn platelets isolated from whole blood, 100 ng/mL PMA was used. For stored platelets (i.e. apheresis platelets) 1000 ng/mL PMA was used.

Fresh platelets were isolated from ACD anticoagulated whole blood, washed, and diluted to 250,000 cells/µL in HMTA. Thrombosomes were rehydrated according to standard protocol and diluted to 250,000 cells/µL in HMTA. An aliquot each of platelets in HMTA and Thrombosomes in HMTA were mixed in equal proportions. Platelets, Thrombosomes, and the mixed sample were evaluated by light transmission aggregometry (Helena AggRAM) in response to phorbol-myristate-acetate (PMA; 100 ng/mL) activation. The mixed samples were evaluated with and without a stir bar to assess the effect of stirring-induced shear on observed platelet-Thrombosomes coaggregation.

Figures 29A, 29B:
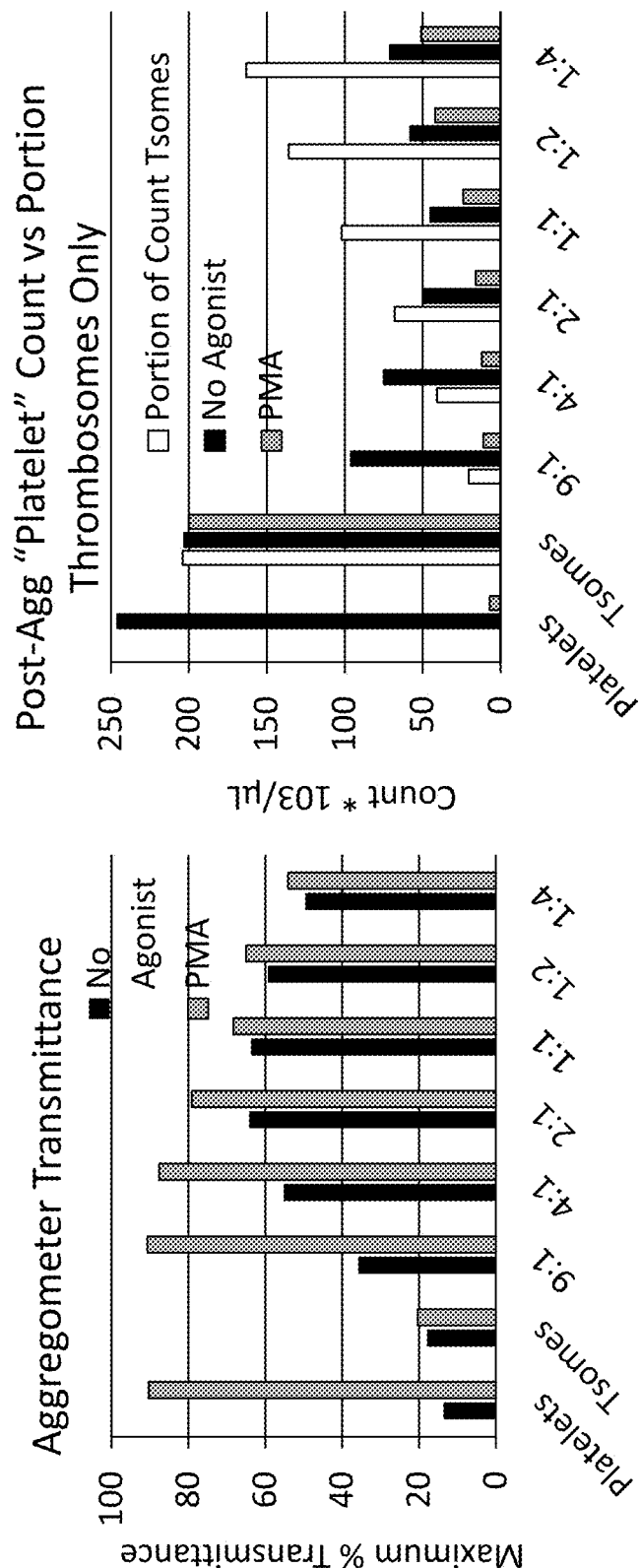
FIG. 29A is a bar plot of the transmittance of platelets, thrombosomes, and combinations thereof using light transmission aggregometry.
FIG. 29B is a bar plot of the platelet (and/or thrombosome) count of platelets, thrombosomes, and combinations thereof following aggregation.

FIG. 29A shows the transmittance of the samples in Table 27, with and without agonist. Plus shear and minus agonist (black) mixing, thrombosomes and fresh-drawn platelets induced platelet activation and aggregation. PMA (gray) activated platelets and the magnitude of Δtransmittance suggests mixed aggregation with thrombosomes. Without shear there is either no activation or co-aggregation to less than the magnitude observed in FIG. 29A.

The platelet and thrombosomes AcT counts pre- and post-aggregometry were also evaluated. FIG. 29B shows the post-aggregation counts. Cases for which the white bar is greater than the other(s) suggest incorporation of thrombosomes into platelet aggregates. The absolute decrease in particle count for the no agonist cases (black) is especially dramatic and unexpected.

Figure 29C:
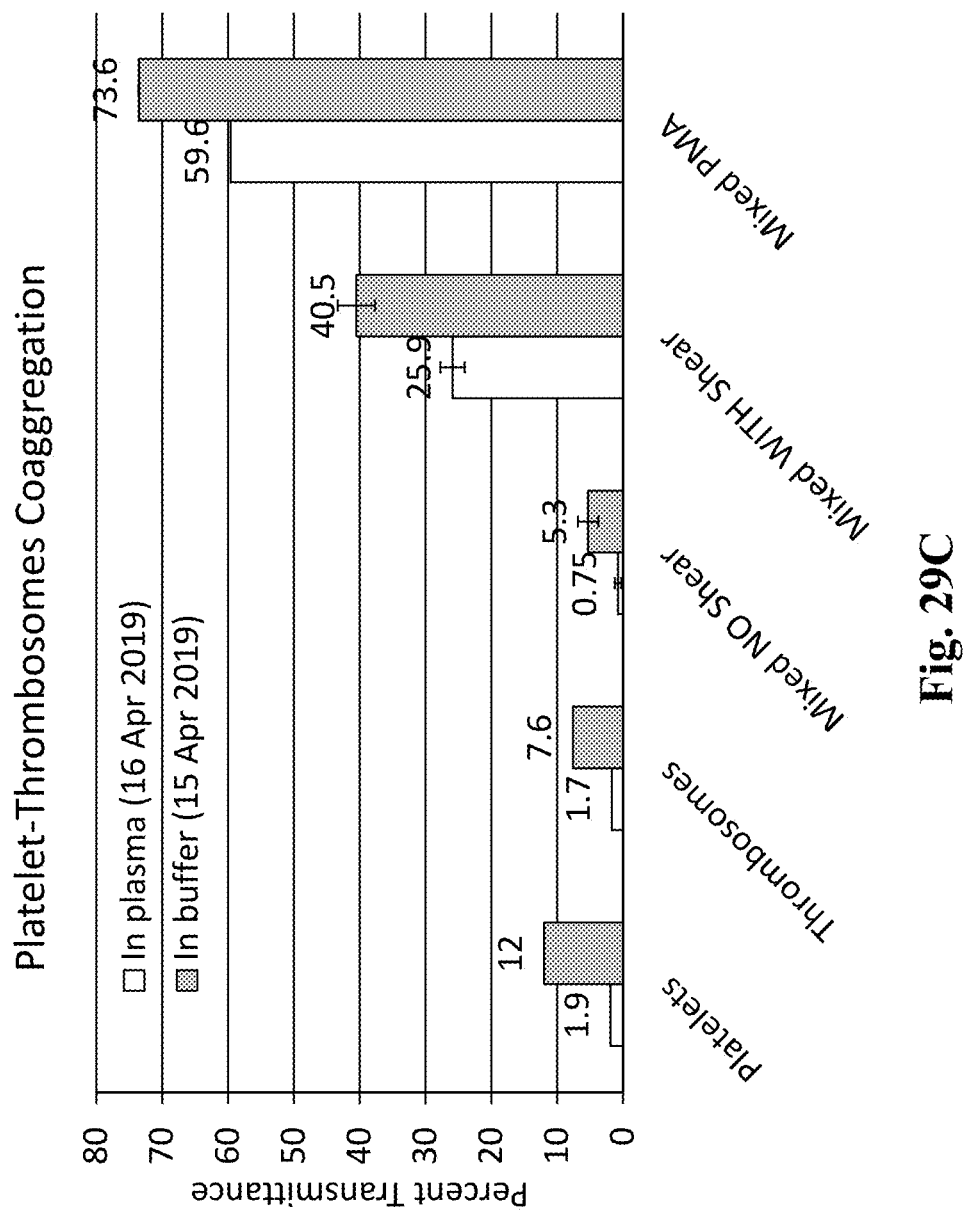
FIG. 29C is a bar plot of the transmittance of platelets, thrombosomes, and combinations thereof in light transmission aggregometry.

The effect of shear on aggregation was also evaluated. Mixed aggregometry (1:1 platelets:thrombosomes by count) was repeated with and without stir bars. Results are shown in FIG. 29C. These results show that shear is necessary for observable coaggregation in the absence of a platelet agonist. The magnitude of measured counts and co-aggregation+/−agonist is slightly decreased in plasma vs buffer.

Example 13. Inhibition of Fibrin Trapping with GPRP

In this Example, 'platelets' are isolated from whole blood approximately 1 hour post-collection. The thrombosomes are Batch H, prepared by the method described in Example 1.

Fresh platelets were isolated from ACD anticoagulated whole blood, washed, and diluted to 250,000 cells/µL in HMTA. Thrombosomes were rehydrated according to standard protocol and diluted to 250,000 cells/µL in HMTA. An aliquot each of platelets in HMTA and thrombosomes in HMTA were mixed in equal proportions. Each group of platelets, thrombosomes, or mixed suspensions were divided equally; one group was treated with 1 mM GPRP to inhibit fibrin polymerization and one group remained untreated. The peptide Gly-Pro-Arg-Pro (GPRP; Sigma-Aldrich item G1895) is a peptide that prevents fibrin polymerization. Platelets, thrombosomes, and the mixed samples were evaluated by light transmission aggregometry (Helena AggRAM) in response to thrombin (2.5 U/mL) activation.

Figures 30, 31:
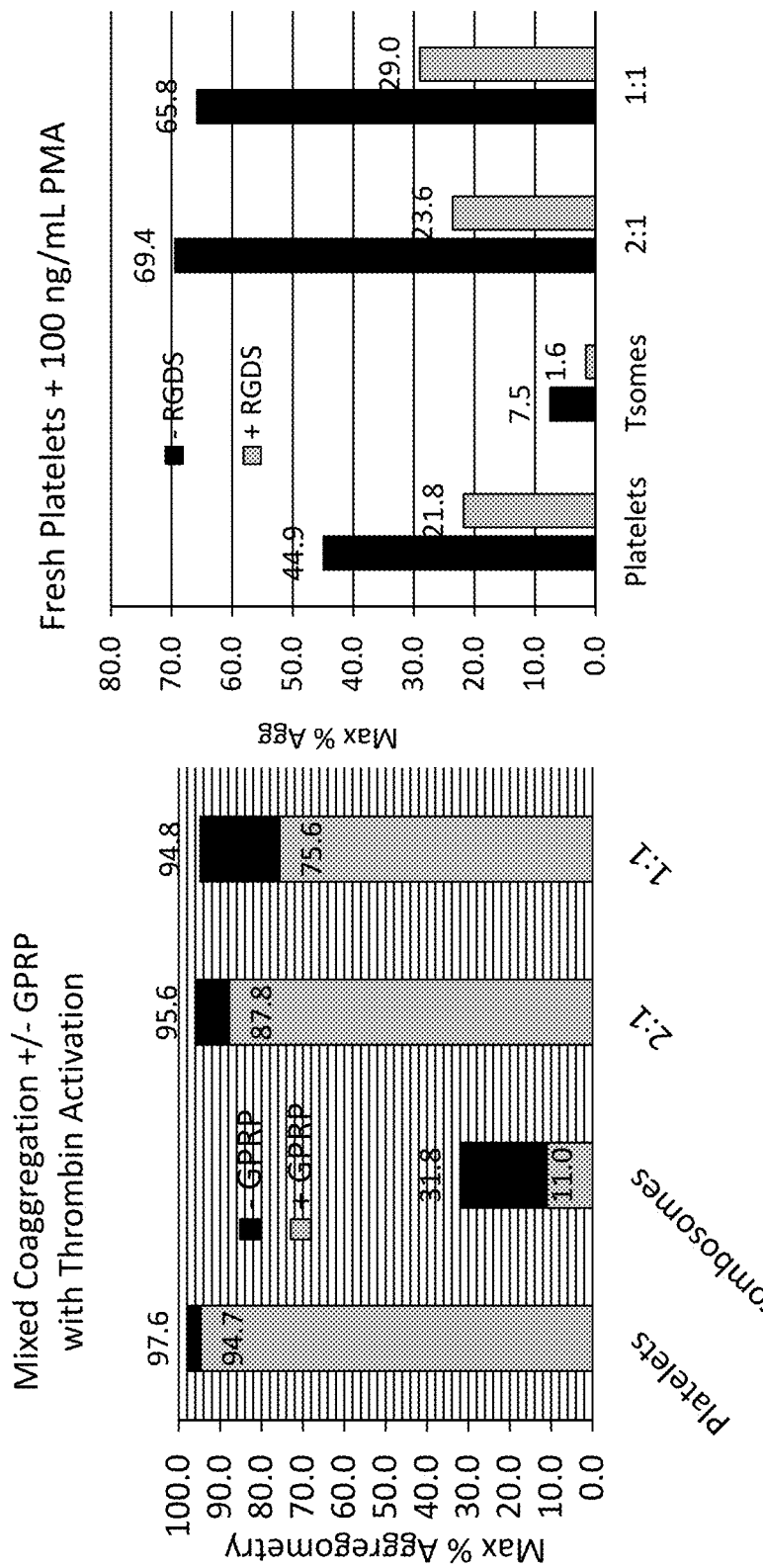
FIG. 30 is a bar plot of the transmittance of thrombin-activated platelets, thrombosomes, and combinations thereof in the presence and absence of GPRP.
FIG. 31 is a bar plot of the percent aggregation of PMA-activated platelets, thrombosomes, and combinations thereof in the presence and absence of RGDS.

FIG. 30 shows the results of co-aggregation experiments using platelets, thrombosomes, and 2:1 and 1:1 mixtures of platelets and thrombosomes, all activated with thrombin, either in the presence or absence of GPRP (1 mM). In the mixed cases, total measured aggregation decreased as the thrombosome population increased, suggesting that the interaction of platelets and thrombosomes is partly caused by fibrin trapping. However, the bulk of the co-aggregation interaction was platelet-mediated, and not reliant on fibrin trapping as evidenced by high measured aggregation even with GPRP.

Examples 12-13 show that platelets and thrombosomes co-aggregated under shear with (and to a lesser extent, without) platelet activation. The fibrin polymerization inhibitor GPRP only slightly inhibited platelet-thrombosomes co-aggregation following thrombin activation.

Example 14. RGDS Inhibition of Co-aggregation

In this Example, 'platelets' are isolated from whole blood approximately 1 hour post-collection. The thrombosomes are Batch H, prepared by the method described in Example 1.

Fresh platelets were isolated from ACD anticoagulated whole blood, washed, and diluted to 250,000 cells/µL in HMTA. Thrombosomes were rehydrated according to standard protocol and diluted to 250,000 cells/µL in HMTA. An aliquot each of platelets in HMTA and thrombosomes in HMTA were mixed in equal proportions. Each group of platelets, thrombosomes, or mixed suspensions were divided equally; one group was treated with 100 µM RGDS to inhibit fibrinogen binding to platelets and one group remained untreated. RGDS (Arg-Gly-Asp-Ser; Cayman Chemical item 15359) is a peptide sequence that binds platelet surface integrins, particularly GPIIb/IIIa. It inhibits platelet binding to fibrinogen and other adhesive proteins. Platelets, thrombosomes, and the mixed samples were evaluated by light transmission aggregometry in response to phorbol myristate-acetate (PMA; 100 ng/mL) activation.

Co-aggregation experiments were performed with 100 µM RGDS and activation with PMA to investigate whether the interaction is caused by fibrinogen bridging between platelets and thrombosomes. Results are shown in FIG. 31. RGDS blocks >50% of measured co-aggregation, suggesting the interaction between platelets and thrombosomes may be caused in a large part by fibrinogen binding.

Examples 12-14 show that thrombosomes readily co-aggregate with activated platelets (e.g., as evidenced by light transmission aggregometry). Spontaneous co-aggregation is induced by shear. Platelet-thrombosomes interactions are apparent in both buffer and plasma. While co-aggregation is not substantially inhibited by GPRP, co-aggregation is substantially inhibited by RGDS. This suggests a key role for active platelet-fibrinogen binding in the co-aggregation mechanism and that co-aggregation is not caused only by passive fibrin trapping.

Example 15. Scanning Electron Microscopy (SEM)

A 10 mL aliquot of rehydrated thrombosomes were centrifuged at 2000 RPM for 30 minutes. The supernatant of the centrifuges sample was removed down to 1 mL and discarded. The sample was gently agitated to resuspend the Thrombosomes. The concentrated thrombosomes were treated with 3% glutaraldehyde in 0.1 M cacodylate buffer at a pH of 7.4 for 2 hours with agitation every 15 minutes. The thrombosomes were rinsed with sterile water three times and transferred to a 1% solution of osmium tetroxide for 1 hour with agitation every 15 minutes. The sample was then rinsed three more times with sterile water and a 0.5 mL droplet was transferred to a polysulfone filter membrane. The mounted sample was frozen with liquid nitrogen and dried under vacuum before being gold sputtered and imaged using scanning electron microscopy.

Figure 32A:
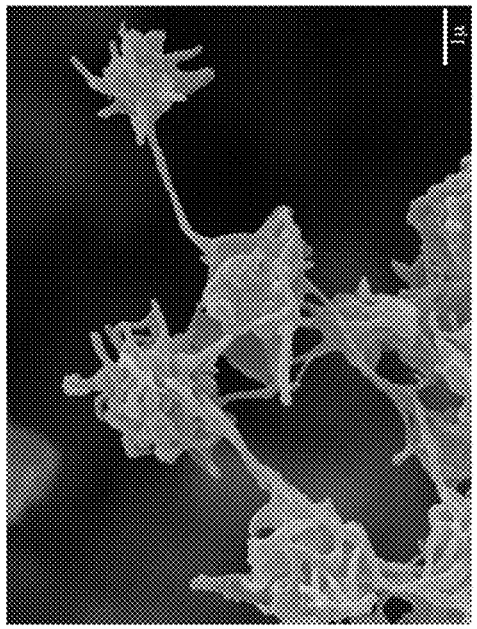
FIG. 32A shows SEM of activated platelets (scale bar=2 μm).
Figure 32B:
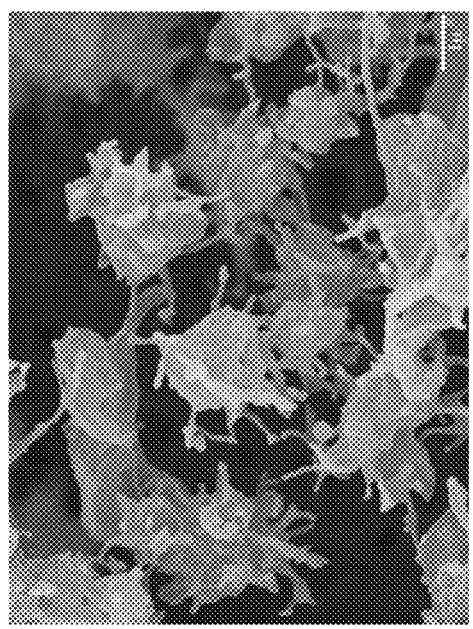
FIG. 32B shows SEM of activated platelets (scale bar=1 μm).
Figure 32C:
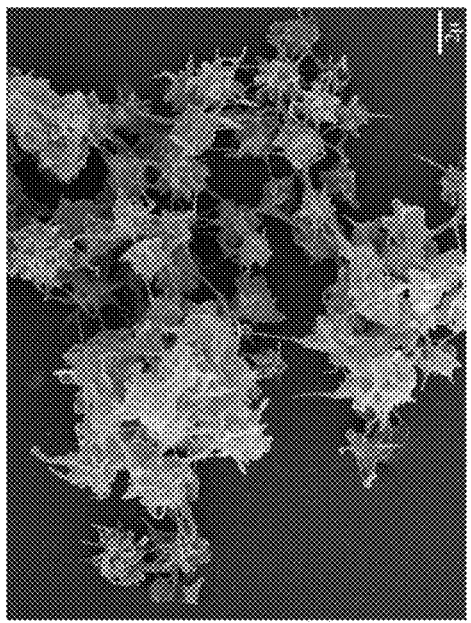
FIG. 32C shows SEM of rehydrated human thrombosomes (scale bar=2 μm).
Figure 32D:
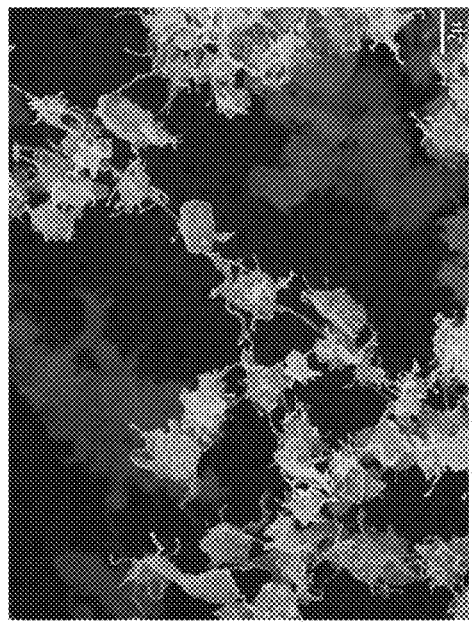
FIG. 32D shows SEM of rehydrated human thrombosomes (scale bar=1 μm).

FIGS. 32A-D show SEM of platelets and human thrombosomes. Fresh activated platelets are shown in FIG. 32A (scale bar=2 µm) and FIG. 32B (scale bar=1 µm). Rehydrated human thrombosomes prepared as in Example 1 are shown in FIG. 32C (scale bar=2 µm) and FIG. 32D (scale bar=1 µm).

Example 16. T-TAS® Thrombosome Data

In the Total Thrombus-formation Analysis System (T-TAS®, FUJIMORI KOGYO CO., LTD), the sample is forced through collagen-coated microchannels using mineral oil. Changes in pressure are used to assess thrombus formation. The Occlusion Start Time is time it takes to reach A10 kPa, and the Occlusion Time=time it takes to each A80 kPa using an AR chip (Zacros Item No, TC0101).

According to FUJIMORI KOGYO CO., LTD, an AR chip can be used for analyzing the formation of a mixed white thrombus consisting chiefly of fibrin and activated platelets. It has a flow path (300 μm wide by 50 μm high) coated with collagen and tissue factors and can be used to analyze the clotting function and platelet function. In comparison, a PL chip can be used for analyzing the formation of a platelet thrombus consisting chiefly of activated platelets. A PL chip has a flow path coated with collagen only and can be used to analyze the platelet function.

T-TAS® reagents (CaCTI, AR Chip) were warmed to 37° C. and Thrombosomes were rehydrated according to standard protocol. An aliquot of the rehydrated Thrombosomes was washed by centrifugation at 3900 g×10 minutes and resuspended to approximately 300,000 cells/μL in sodium citrate anticoagulated platelet-poor plasma (PPP). CaCTI (20 μL) was mixed with Thrombosomes in PPP (480 μL) and run through the T-TAS AR Chip under high shear. Pressure in the system was monitored over 30 minutes or until the maximum backpressure in the channel was achieved.

The T-TAS® instrument was prepared for use according to the manufacturer's instructions. AR Chips (Diapharma Cat. #TC0101) and AR Chip Calcium Corn Trypsin Inhibitor (CaCTI; Diapharma Cat. #TR0101) were warmed to room temperature. 300 uL of rehydrated thrombosomes were transferred to a 1.7 mL microcentrifuge tube and centrifuged at 3900 g×10 minutes to pellet. The thrombosomes pellet was resuspended in George King (GK) pooled normal human plasma or autologous plasma with or without autologous platelets to a concentration of approximately 100,000-450,000/uL, as determined by AcT counts (Beckman Coulter AcT Diff 2 Cell Counter). 20 uL of CaCTI with 480 uL of thrombosomes sample in GK plasma were mixed with gentle pipetting. The sample was loaded and run on the T-TAS® according to the manufacturer's instructions.

Table 28 shows T-TAS® results from citrated whole blood, platelet-reduced citrated whole blood supplemented with varying concentrations of thrombosomes as prepared in Example 1, and George King Platelet Poor Plasma (GK PPP) supplemented with varying concentrations of thrombosomes as prepared in Example 1 in experiments run according to the manufacturer's instructions using the AR chip and High Shear instrument settings.

TABLE 28

T-TAS AR Chip Results

| Sample Type | Actual Tsome Concentration (×10^3/μL) | Base Pressure (kPa) | Occlusion Start Time (hh:mm:ss) | Occlusion Time (hh:mm:ss) | Occlusion Speed (kPa/min) | Area Under Curve |
|---|---|---|---|---|---|---|
| Citrated Whole Blood | 0 | 3.2 | 0:11:19 | 0:14:03 | 25.6 | 1393.9 |
| Platelet Reduced Citrated Whole Blood | 0 | 3.3 | 0:12:41 | 0:16:57 | 16.4 | 1180.6 |
| | 73 | 3.2 | 0:11:11 | 0:13:47 | 26.9 | 1380.9 |
| | 173 | 3.4 | 0:09:37 | 0:13:22 | 18.7 | 1498.5 |
| | 255 | 3.4 | 0:08:36 | 0:10:40 | 33.9 | 1653.1 |
| GK PPP | 0 | 2.7 | 0:25:34 | 0:00:00† | 0 | 138.8 |
| | 45 | 2.8 | 0:27:22 | 0:28:48 | 48.8 | 190.6 |
| | 193* | 2.9 | 0:12:41 | 0:00:00† | 0 | 775.3 |
| | 384 | 2.8 | 0:10:54 | 0:12:20 | 48.8 | 1479.8 |

*Test peaked at ~75 kPa before rapidly dropping off. Possible erroneous result.
†Test timed out.

Figure 33A:
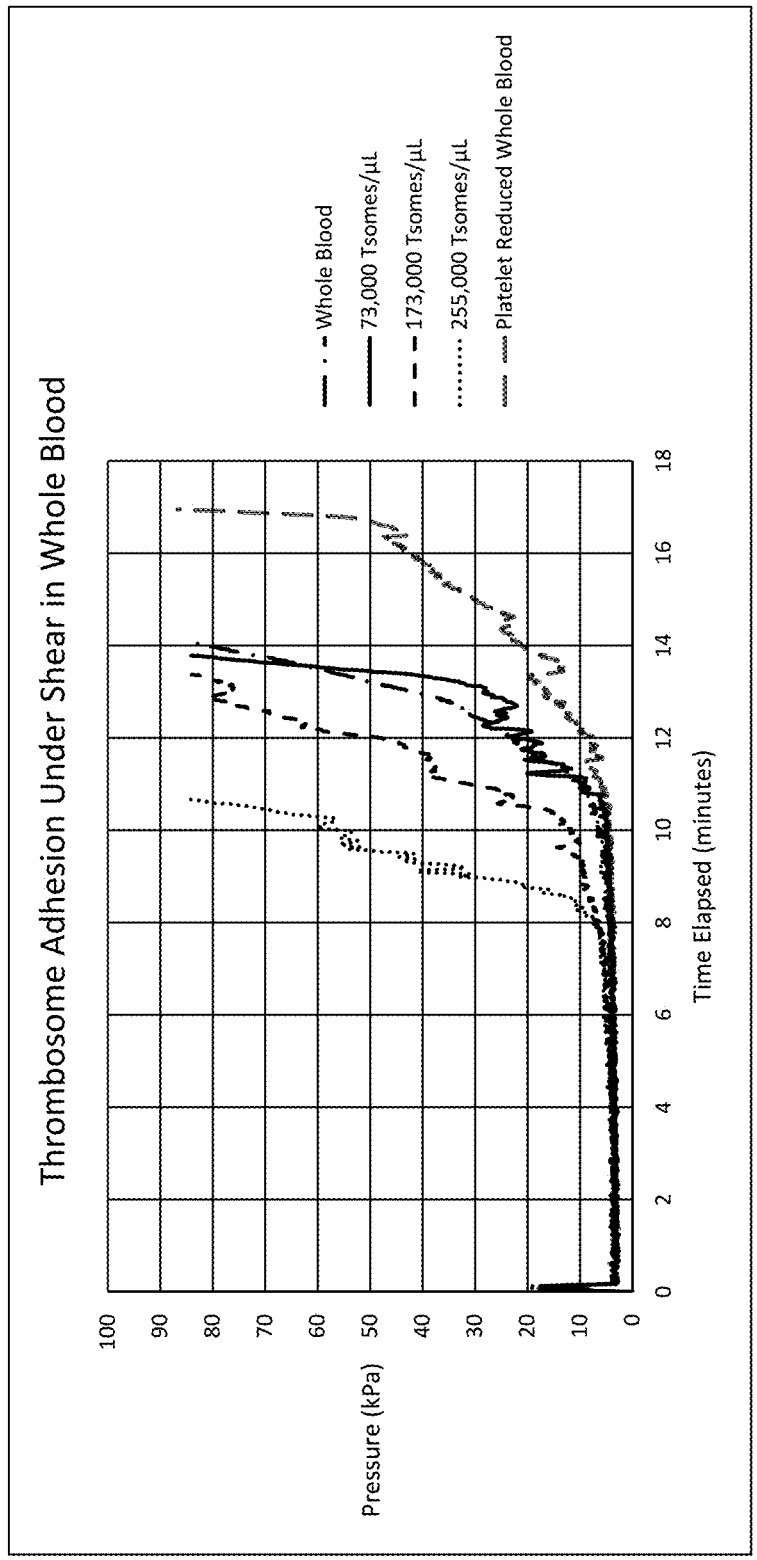
FIG. 33A is a plot of thrombosome adhesion under shear in whole blood.
Figure 33B:
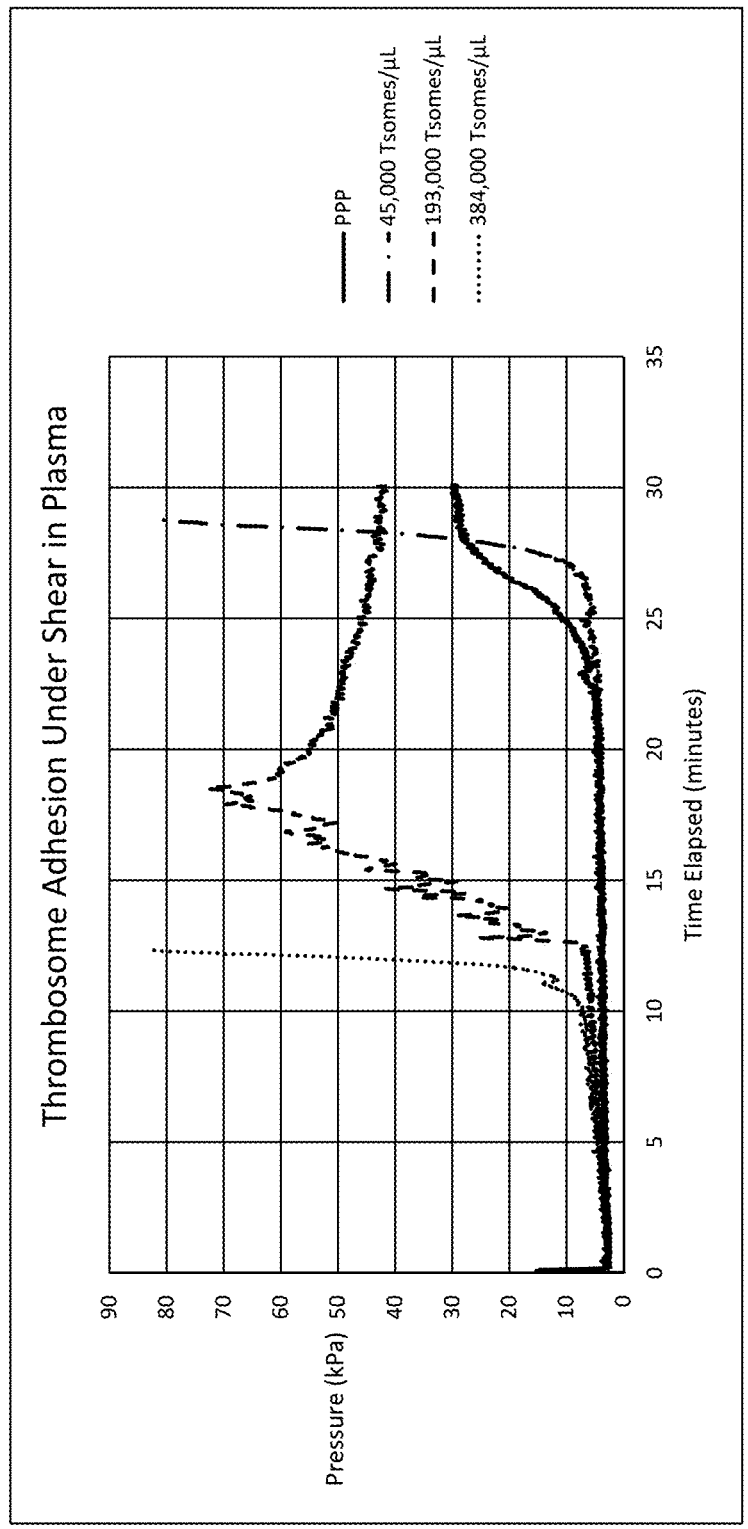
FIG. 33B is a plot of thrombosome adhesion under shear in plasma.

Time-elapsed results are shown in FIGS. 33A-B. Increasing the concentration of thrombosomes in platelet-reduced whole blood promoted more robust thrombus formation as measured by shortened occlusion times (FIG. 33A). Increasing the concentration of Thrombosomes in platelet poor plasma (PPP) promoted more robust thrombus formation as measured by shortened occlusion times (FIG. 33B).

Figure 33C:
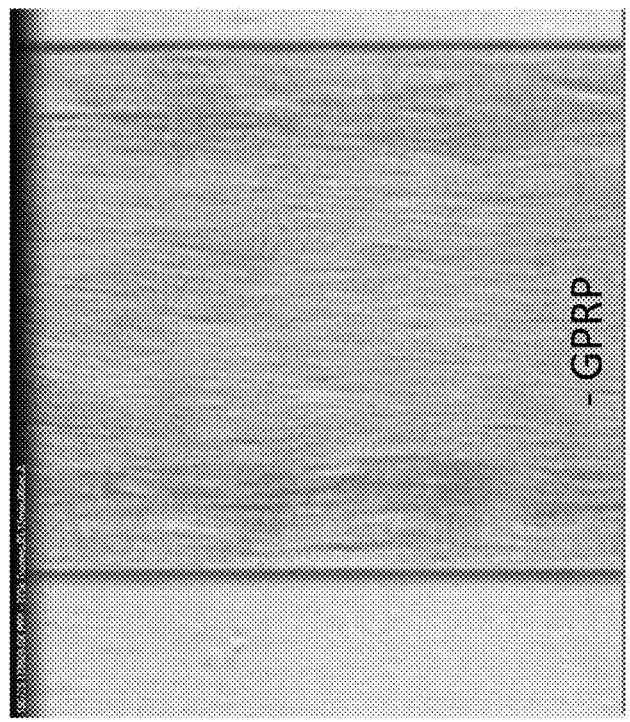
FIG. 33C shows formation of fibrin in a microcapillary channel in the absence of GPRP.
Figure 33D:
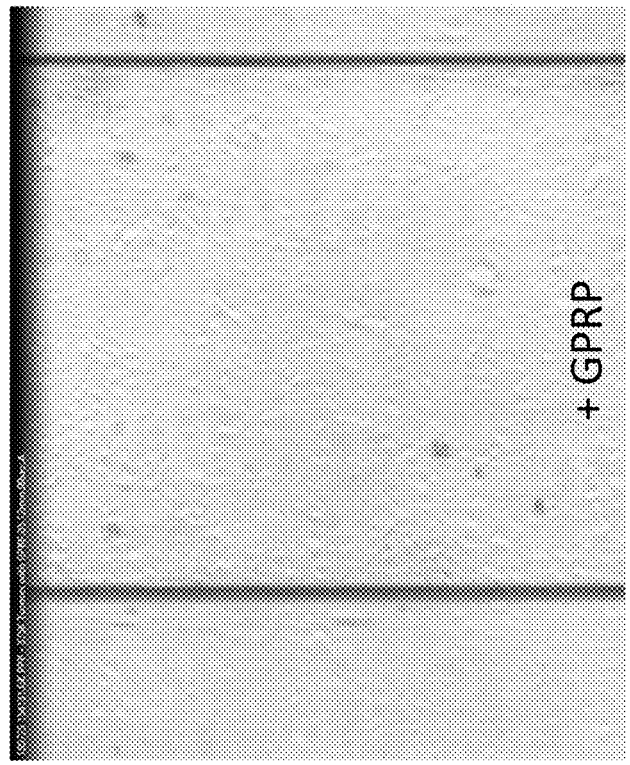
FIG. 33D shows a lack of formation of fibrin in a microcapillary channel in the presence of GPRP.
Figure 33E:
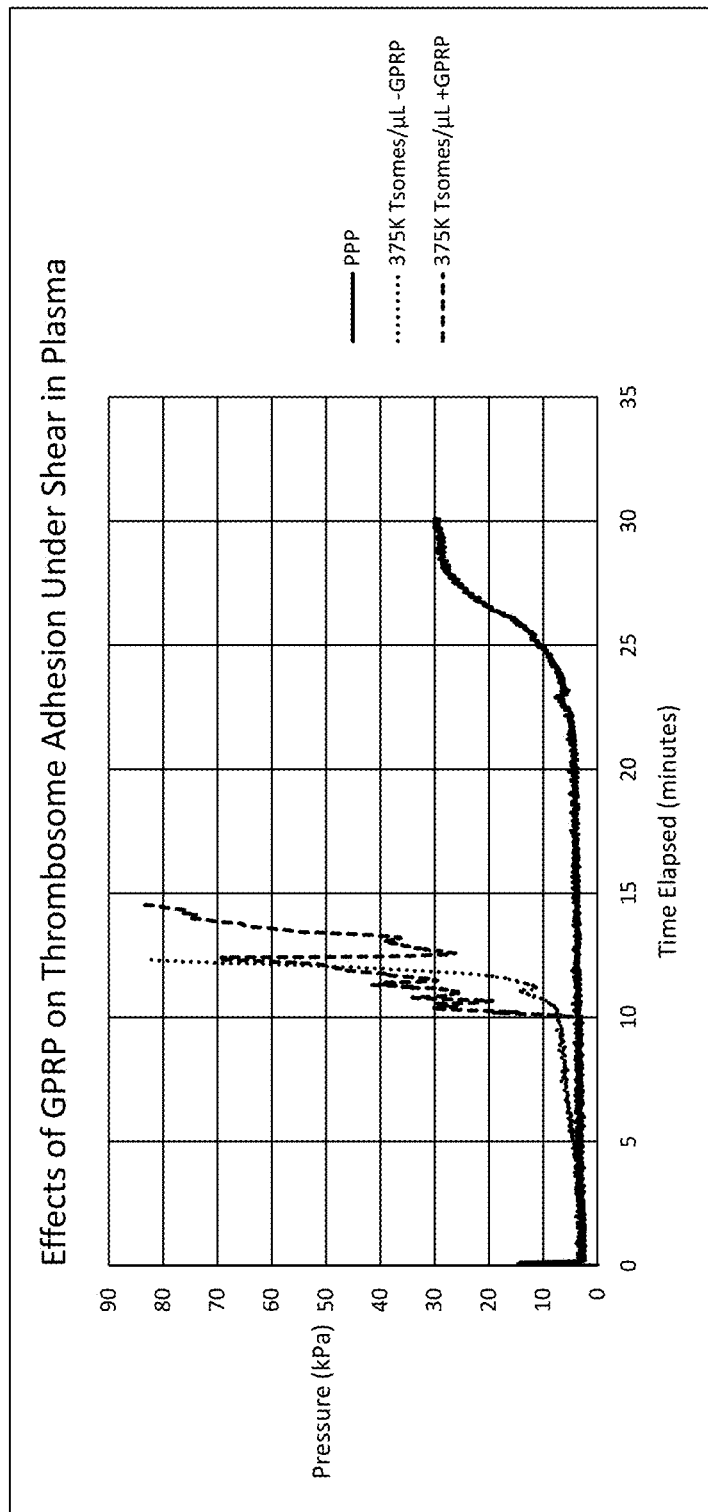
FIG. 33E is a plot of the effect of GPRP on thrombosome adhesion under shear in plasma.

The effect of GPRP (1 mM) on occlusion activity was also assayed. Table 29 shows T-TAS® results for platelet-poor plasma, with and without thrombosomes in the presence and absence of GPRP. Adding GPRP to prevent fibrinogen formation did not prevent the thrombosome-containing sample from reaching occlusion pressure. While the addition of GPRP to thrombosome samples in plasma prevents the formation of fibrin in the microcapillary channel (FIGS. 33C (no GPRP) and 33D (GPRP), both in GK PPP), the addition of GPRP to thrombosomes (PPP) did not prevent thrombus formation (FIG. 33E).

TABLE 29

AR Chip: GPRP Comparison

| Sample Type | Actual Tsome Concentration (×10^3/μL) | Base Pressure (kPa) | Occlusion Start Time (hh:mm:ss) | Occlusion Time (hh:mm:ss) | Occlusion Speed (kPa/min) | Area Under Curve |
|---|---|---|---|---|---|---|
| GK PPP (No Tsomes) | 0 | 2.7 | 0:25:34 | 0:00:00† | 0 | 138.8 |
| GK PPP + 1 mM GPRP (No Tsomes) | 0 | 3.5 | 0:00:00 | 0:00:00† | 0 | 52.43 |

TABLE 29-continued

AR Chip: GPRP Comparison

| Sample Type | Actual Tsome Concentration (×10^3/μL) | Base Pressure (kPa) | Occlusion Start Time (hh:mm:ss) | Occlusion Time (hh:mm:ss) | Occlusion Speed (kPa/min) | Area Under Curve |
|---|---|---|---|---|---|---|
| GK PPP + 375k Tsomes | 384 | 2.8 | 0:10:54 | 0:12:20 | 48.8 | 1479.8 |
| GK PPP + 375k Tsomes with 1 mM GPRP | 380 | 3.2 | 0:10:09 | 0:14:32 | 16 | 1426.9 |

†Test timed out

While the embodiments of the invention are amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

What is claimed is:

1. A process for preparing a thermally-treated platelet composition, the process comprising:
    performing tangential flow filtration (TFF) of a platelet composition comprising platelets in a preparation agent comprising a buffering agent, between 10 mM and 1000 mM of saccharides comprising a monosaccharide and/or a disaccharide, and polysucrose in an amount in the range of 3% to 7%, wherein the TFF is performed until a particular residual plasma protein endpoint is reached, thereby preparing a TFF-treated composition comprising at least 1000×10³ platelets/μl in an aqueous medium having less than or equal to 15% plasma protein and having less than 5.0% microparticles by scattering intensity;
    freeze drying the TFF-treated composition comprising platelets in the aqueous medium to form a freeze-dried platelet composition; and
    heating the freeze-dried platelet composition at a temperature in the range of 60° C. to 85° C. for at least 1 hour to not more than 36 hours to thermally treat the freeze-dried platelets in the freeze-dried platelet composition to form the thermally-treated platelet composition,
    wherein the thermally-treated platelets in the thermally-treated platelet composition are capable of generating thrombin in an in vitro thrombin formation assay.

2. The process of claim 1, wherein at least 79% of the thermally-treated platelets in the thermally-treated platelet composition are CD42 positive.

3. The process of claim 1, wherein the particular residual plasma protein endpoint is set at less than or equal to 7.5% residual plasma protein.

4. The process of claim 1, wherein the particular residual plasma protein endpoint is set at less than or equal to 5% residual plasma protein.

5. The process of claim 1, wherein an absorbance at 280 nm (A280) of the aqueous medium is measured to determine that the particular residual plasma protein endpoint is reached.

6. The process of claim 2, wherein between 79% and 95% of the thermally-treated platelets in the thermally-treated platelet composition are CD42 positive, and at least 78% of the thermally-treated platelets in the thermally-treated platelet composition are CD41 positive.

7. The process of claim 2, wherein at least 80% of the thermally-treated platelets in the thermally-treated platelet composition are CD42 positive, and at least 80% of the thermally-treated platelets in the thermally-treated platelet composition are CD41 positive.

8. The process of claim 2, wherein the saccharides comprise the monosaccharide and the disaccharide, and wherein the disaccharide is selected from the group consisting of trehalose, sucrose, maltose, and combinations thereof, and the monosaccharide is selected from the group consisting of glucose, mannose, dextrose, xylose, and combinations thereof.

9. The process of claim 8, wherein the disaccharide comprises trehalose in an amount in the range of 10 mM to 500 mM, and the monosaccharide comprises dextrose.

10. The process of claim 2, wherein the saccharides comprise a disaccharide selected from the group consisting of trehalose, sucrose, maltose, and combinations thereof, and wherein the disaccharide is in an amount in the range of 10 mM to 500 mM.

11. The process of claim 10, wherein the disaccharide is trehalose in an amount in the range of 50 mM to 500 mM.

12. The process of claim 2, wherein the thermally-treated platelets in the thermally-treated platelet composition are capable of generating clots in an in vitro clotting assay, and promoting aggregation or co-aggregation in an in vitro aggregation or co-aggregation assay.

13. The process of claim 12, wherein the thermally-treated platelets in the thermally-treated platelet composition when at a concentration of at least about 70×10³ particles/μL, produce an occlusion time of less than 14 minutes in a total thrombus-formation analysis system (T-TAS) assay.

14. The process of claim 2, wherein the TFF is performed using a membrane with a pore size in the range of 0.45 to 0.65 μm, and wherein the TFF-treated composition has less than 3.0% microparticles by scattering intensity.

15. The process of claim 1, wherein the TFF-treated composition comprises microparticles in an amount below 3.0% by scattering intensity and wherein at least 80% of the thermally-treated platelets in the thermally-treated platelet composition are CD42 positive.

16. The process of claim 1, wherein the thermally-treated platelet composition is:
    a) negative for HLA Class I antibodies based on a regulatory agency approved test for HLA Class I antibodies;
    b) negative for HLA Class II antibodies based on a regulatory agency approved test for HLA Class II antibodies;

c) negative for HNA antibodies based on a regulatory agency approved test for HNA antibodies;
or d) two or more of a), b), and c).

17. The process of claim 1, wherein the thermally-treated platelet composition is:
  a) negative for HLA Class I antibodies based on a regulatory agency approved test for HLA Class I antibodies;
  b) negative for HLA Class II antibodies based on a regulatory agency approved test for HLA Class II antibodies; and
  c) negative for HNA antibodies based on a regulatory agency approved test for HNA antibodies.

18. The process of claim 7, wherein the TFF is performed using a membrane with a pore size in the range of 0.45 to 0.65 µm, and wherein the TFF-treated composition has less than 3.0% microparticles by scattering intensity, and wherein the thermally-treated platelets in the thermally-treated platelet composition are capable of generating clots in an in vitro clotting assay.

19. The process of claim 7, wherein the thermally-treated platelets in the thermally-treated platelet composition:
  a) when at a concentration of about $4.8 \times 10^3$ particles/µL generate a thrombin peak height (TPH) of at least 25 nM when in the presence of a reagent containing tissue factor and phospholipids;
  b) when at a concentration of at least about $70 \times 10^3$ particles/µL, produce an occlusion time of less than 14 minutes in a total thrombus-formation analysis system (T-TAS) assay; or
  c) both a) and b).

20. The process of claim 15, wherein the thermally-treated platelets in the thermally-treated platelet composition:
  a) when at a concentration of about $4.8 \times 10^3$ particles/µL generate a thrombin peak height (TPH) of at least 25 nM when in the presence of a reagent containing tissue factor and phospholipids; and
  b) when at a concentration of at least about $70 \times 10^3$ particles/µL, produce an occlusion time of less than 14 minutes in a total thrombus-formation analysis system (T-TAS) assay.

21. The process of claim 15, wherein the thermally-treated platelets in the thermally-treated platelet composition comprises:
  a) at least 55% thermally-treated freeze-dried platelets positive for CD41;
  b) at least 70% thermally-treated freeze-dried platelets positive for annexin V;
  c) at least 8% thermally-treated freeze-dried platelets positive for CD47;
  d) at least 80% thermally-treated freeze-dried platelets positive for CD62; or
  e) two or more of a), b), c), and d).

22. The process of claim 21, wherein the thermally-treated platelets in the thermally-treated platelet composition comprises:
  b) at least 85% thermally-treated freeze-dried platelets positive for annexin V; and
  d) at least 85% thermally-treated freeze-dried platelets positive for CD62 positive.

23. The process of claim 21, wherein the thermally-treated platelets in the thermally-treated platelet composition comprises:
  a) at least 75% thermally-treated freeze-dried platelets positive for CD41;
  b) at least 85% thermally-treated freeze-dried platelets positive for annexin V; and
  d) at least 85% thermally-treated freeze-dried platelets positive for CD62.

24. The process of claim 1, wherein the buffering agent comprising comprises HEPES (4-(2-hydroxyethyl)-1-piperazineethanesulfonic acid, and the preparation agent further comprises an organic solvent comprising ethanol in the range of 0.10% to 5.0%, and has a pH in the range of 6.0 to 7.4.

25. The process of claim 1, wherein the process does not comprise centrifugation of the platelet composition, and wherein the TFF-treated composition comprises at least $2000 \times 10^3$ platelets/µl in the aqueous medium, and wherein the process does not comprise treatment of the platelet composition with an agent capable of altering nucleic acids of a pathogen prior to performing the TFF.

* * * * *